US012778926B2

(12) United States Patent
Minakar et al.

(10) Patent No.: US 12,778,926 B2
(45) Date of Patent: Nov. 3, 2026

(54) COOLING AGENTS AND PREPARATIONS CONTAINING THEM

(71) Applicant: Symrise AG, Holzminden (DE)

(72) Inventors: Judith Minakar, Holzminden (DE); Benoit Join, Holzminden (DE); Michael Backes, Holzminden (DE); Saskia Hupe, Holzminden (DE); Dominik Stuhlmann, Holzminden (DE); Joachim Hans, Holzminden (DE); Gabriela Matuszko, Braunschweig (DE)

(73) Assignee: Symrise AG, Holzminden (DE)

( * ) Notice: Subject to any disclaimer, the term of this patent is extended or adjusted under 35 U.S.C. 154(b) by 460 days.

(21) Appl. No.: 18/253,022

(22) PCT Filed: Nov. 17, 2021

(86) PCT No.: PCT/EP2021/081954
§ 371 (c)(1),
(2) Date: May 15, 2023

(87) PCT Pub. No.: WO2022/106452
PCT Pub. Date: May 27, 2022

(65) Prior Publication Data

US 2024/0000746 A1 Jan. 4, 2024

(30) Foreign Application Priority Data

Nov. 17, 2020 (WO) ................. PCT/EP2020/082410

(51) Int. Cl.

| | |
|---|---|
| *A61K 31/357* | (2006.01) |
| *A61K 8/41* | (2006.01) |
| *A61K 31/341* | (2006.01) |
| *A61K 31/4155* | (2006.01) |
| *A61K 31/443* | (2006.01) |
| *A61K 31/4436* | (2006.01) |
| *A61K 31/444* | (2006.01) |
| *A61Q 5/00* | (2006.01) |
| *A61Q 11/00* | (2006.01) |
| *A61Q 17/00* | (2006.01) |
| *A61Q 19/00* | (2006.01) |

(52) U.S. Cl.
CPC .............. *A61K 31/357* (2013.01); *A61K 8/41* (2013.01); *A61K 31/341* (2013.01); *A61K 31/4155* (2013.01); *A61K 31/443* (2013.01); *A61K 31/4436* (2013.01); *A61K 31/444* (2013.01); *A61Q 5/00* (2013.01); *A61Q 11/00* (2013.01); *A61Q 17/00* (2013.01); *A61Q 19/00* (2013.01); *A61K 2800/244* (2013.01)

(58) Field of Classification Search
CPC .................................................... C07D 401/04
See application file for complete search history.

(56) References Cited

U.S. PATENT DOCUMENTS

| | | | | |
|---|---|---|---|---|
| 5,330,740 A * | 7/1994 | Illig | A61K 49/0404 | 564/442 |
| 8,927,605 B2 * | 1/2015 | Subkowski | A61K 31/36 | 514/617 |
| 11,434,220 B2 * | 9/2022 | Join | C07D 213/75 | |
| 2002/0090445 A1 * | 7/2002 | Alani | A61K 47/12 | 426/534 |
| 2016/0115119 A1 * | 4/2016 | Hirasawa | A61P 25/22 | 514/355 |

FOREIGN PATENT DOCUMENTS

| | | |
|---|---|---|
| EP | 2614860 A2 | 7/2013 |
| EP | 2995611 A1 | 3/2016 |
| JP | 2004059474 A | 2/2004 |
| JP | 2013136532 A | 7/2013 |
| JP | 2009507778 A | 1/2014 |
| JP | 2014503486 A | 2/2014 |
| KR | 100220266 B1 | 10/1999 |
| WO | 2012061698 A2 | 5/2012 |
| WO | 2012120398 A1 | 9/2012 |

OTHER PUBLICATIONS

Molander et al., "Synthesis of Amidomethyltrifluoroborates and Their Use in Cross-Coupling Reactions", 2010, Organic Letters, vol. 12, No. 21, pp. 4876-4879. (Year: 2010).*
PubChem CID 38049971, 2022, "[(3,4-dimethoxyphenyl)methyl]({[2-(1H-pyrazol1-yl)pyridin-4-yl]methyl}". 11 Pages.
PubChem CID 45899061, 2021, "[(2H-1,3-Benzodioxol-4-yl)methyl]({[2-(morpholin-4-yl)pyridin-4-yl]methyl})amine hydrochloride", 9 pages.
PubChem CID 47038827, 2021, "[(2H-1,3-benzodioxol-4-yl)methyl]({[6-(pyrrolidin-1-yl)pyridin-3-yl]methyl})amine hydrochloride", 8 pages.
PubChem CID 47038849, 2021, "N-[(2H-1,3-benzodioxol-4-yl)methyl]-1-(pyridin-2-yl)piperidin-4-amine hydrochloride", 8 pages.
PubChem CID 47039111, 2021, "1-[6-(azepan-1-yl)pyridin-3-yl]-n-(1,3-benzodioxol-4-ylmethyl)methanamine", 7 pages.
PubChem CID 47052493, 2021, [(3,4-dimethoxyphenyl)methyl]({[2-(piperidin-1-yl)pyridin-4-yl]methyl})amine., 10 pages.
PubChem CID 53538800, 2021, "[(2h-1,3-benzodioxol-4-yl)methyl]({[2-(piperidin-1-yl)pyridin-3-yl]methyl})amine hydrochloride", 8 pages.
PubChem CID 56809181, 2021, "[(2h-1,3-benzodioxol-4-yl)methyl]({[6-(piperidin-1-yl)pyridin-3-yl]methyl})amine hydrochloride", 8 pages.

(Continued)

*Primary Examiner* — Michael B. Pallay
(74) *Attorney, Agent, or Firm* — McDonnell Boehnen Hulbert & Berghoff LLP

(57) ABSTRACT

The present invention relates to novel physiological cooling agents, cooling agent mixtures containing said novel agents, mixtures of said cooling agents with flavourings, the use of said cooling agents, and articles and final consumer preparations containing said physiological cooling agents or cooling agent mixtures.

20 Claims, No Drawings

(56) References Cited

OTHER PUBLICATIONS

PubChem CID 121695261, 2022, "N-(furan-2-ylmethyl)-1-(2-piperidin-1-ylpyridin4-yl)methanamine", 11 pages.
PubChem CID 126802055, "[(2h-1,3-benzodioxol-4-yl)methyl}{{[2-(piperidin-1-yl)pyridin-4-yl]methyl})amine", 8 pages.
Qian Zhang, et al., (2020) "An unprecedented cobalt-catalyzed selective aroylation of primary amines with aroyl peroxides", Tetrahedron Letters 61, 152399, 5 pages.
Kazuhiko Orito, et al., (2006) "Pd(OAc)2-Catalyzed Carbonylation of Amines", J. Org. Chem, 71 pp. 5951-5958.
Collection of well-known and conventional technologies (Fragrance) Part 1 Fragrance general, Japan Patent Office, 1999, pp. 211-213.

* cited by examiner

COOLING AGENTS AND PREPARATIONS CONTAINING THEM

CROSS-REFERENCE TO RELATED APPLICATIONS

This application is the US national phase under 35 U.S.C. § 371 of International Application No. PCT/EP2021/081954, filed Nov. 17, 2021, which claims priority to of International Application No. PCT/EP2020/082410, filed Nov. 17, 2020, the contents of each of which are hereby incorporated by reference in their entirety.

FIELD OF THE INVENTION

The present invention is in the field of physiological cooling agents and relates to new representatives of this group, the use of these cooling agents and articles and preparations comprising these cooling agents.

TECHNOLOGICAL BACKGROUND

Physiological cooling agents are regularly used to produce a cool sensory impression on the skin or mucous membrane, for example on the mucous membrane in the mouth, nose and/or throat, although no physical cooling actually takes place, as for example in the evaporation of solvents. Both individual components and mixtures can be used as physiological cooling agents. It must be taken into account that not all compounds that influence receptors in vitro that are (also) involved in mediating a physiological cooling effect actually produce such an effect in vivo on the skin or mucous membranes. In particular, such an effect will not always be identical. This means, for example, that the strength of the mediated physiological cooling effect as well as the course of the strength of the cooling effect against time cannot be concluded solely from the fact that a certain compound is an agonist of a receptor involved in mediating a cooling impression.

TRP channels play an important role in the perception of temperature (hot-cold). TRP channels (transient receptor potential channels) are an extensive family of cellular ion channels that can be divided into seven subfamilies.

The cold-menthol receptor TRPM8 (also called cold-membrane receptor (CMR1)) belongs to the family of "transient receptor potential ion channels", is specifically expressed in a special group of neurons and forms pores in the cell membrane (four units each form a tetramer), which selectively allow $Ca^{2+}$ ions to pass. The protein has six transmembrane domains and a cytoplasmic C- and N-terminus. Low temperatures (preferably 10 to 25° C.) stimulate this receptor, resulting in a signal transduction that is interpreted by the nervous system as a feeling of cold.

For several TRP channels, there is evidence that they are important for growth control. Changes in the expression of some of these channels may contribute to the development of cancer. For example, the expression of the TRPM8 gene is upregulated in prostate carcinomas. Accordingly, TRPM8 are also attractive targets for the treatment of prostate or bladder carcinoma.

STATE OF THE ART

Cooling compounds, such as menthol, have long played an important role in the flavour and fragrance industry to create an association with freshness and cleanliness.

The best-known physiologically effective cooling agent is L-menthol. The compound menthol has been shown to act as a natural modulator of the receptor TRPM8. The application of menthol activates TRPM8, which causes a $Ca^2$ influx into the cold-sensitive neurons. The electrical signal generated by this is ultimately perceived as a feeling of cold.

However, menthol has some disadvantages, such as a strong odour, a high volatility and, in higher concentrations, a bitter and/or pungent taste and an irritating effect on the skin. Excessive menthol concentrations can also cause irritation and an anaesthetic effect on the skin or mucous membrane.

Strong cooling agents that do not have the adverse properties of L-menthol have been sought before.

For example, lactic acid esters of menthol(s) according to DE 2608226 A1 and mixed carbonates with menthol(s) and polyols according to DE 4226043 A1 and menthone ketals according to EP 0507190 B1 have been described.

In addition, menthol derivatives with similar effects have been described in various publications.

Menthyl monoesters of diacids according to U.S. Pat. Nos. 5,725,865 and 5,843,466 are interesting naturally occurring alternatives but cannot reach the strength of the previously described cooling agents in sensory tests.

It was found that the compounds L-menthanecarboxylic acid-N-ethylamide ("WS-3") and especially Nα-(L-menthanecarbonyl)glycine ethyl ester ("WS-5") are strong cooling agents. Although having a strong effect, the latter, however, has the disadvantage of being sensitive to hydrolysis and thereby forming the corresponding free acid Nα-(L-menthancarbonyl)glycine, which itself only shows a very weak cooling effect. Despite the detailed investigations described, a systematic prediction on the properties of potential cooling agents, especially on their bitterness and/or their other trigeminal effects is not possible and also not described. Thus, even many molecules falling under the class of the menthancarboxylic acid amides are strongly cooling, but often show pronounced bitter notes at the same time, e.g. the menthanecarboxylic acid N-(alkyloxyalkyl) amides according to JP 2004 059474 A2 or are additionally strongly irritant, such as the N-[[5-methyl-2-(1-methylethyl) cyclohexyl]carbonyl]glycine ethyl ester also designated as WS-5 according to US 2005 0222256 A1, so that such compounds are not suitable for use in food preparations or the like.

Nα-(menthancarbonyl)alkyloxyalkylamides were described in JP 2004 059474 A2. However, with a strong cooling effect and high hydrolysis stability, these have the disadvantage of being very bitter and are therefore not suitable for use in foodstuffs and also in cosmetic products used for facial care.

Furthermore, menthyl glyoxylates and their hydrates have been described as cooling substances in JP 2005 343795 A2.

Overviews of the cooling agents produced and used so far are known to the skilled person.

There are also isolated compounds structurally unrelated to menthol that cause significant TRPM8 modulation, such as the cooling agent WS-23 or the compounds listed in patent application WO 2007 019719 A1.

However, many of the modulators of TRPM8 found so far have deficiencies in terms of potency, duration of action, skin/mucous membrane irritation, odour, taste, solubility as well as volatility.

WO 2010 026094 A1 discloses individual compounds for modulating the TRPM8 receptor.

Further compounds for modulating the TRPM8 receptor are also proposed in WO 2011 061330 A2.

Special cooling agents with the carboxamide structure (I)

(I)

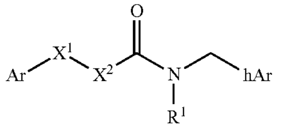

are also known from WO 2012 061698 A1.

On the oral mucosa, many to all of the above-mentioned conventional and prior art cooling substances show a more or less identical cooling behaviour. The cooling sensation of freshness they impart starts after about 0.5 minutes, but then levels off again relatively quickly after a peak at 3 to 5 minutes, whereby the cooling is clearly perceptible for a maximum of 30 minutes overall and, according to experience, can only be influenced to a small extent in terms of intensity and duration by changing the dosage. On the part of the consumer, however, there is a desire for a particularly long-lasting cooling effect, which is associated with a corresponding feeling of freshness and well-being for the user.

Task of the Invention

The primary task of the present invention was therefore to identify new substances that have a particular physiological cooling effect, preferably those that lead to a modulation of the TRPM8 receptor (so-called modulators), which can be used as alternatives, preferably as more suitable agents, to the modulators known to date. Such compounds should also be particularly suitable for applications in the field of cosmetics, nutrition, textiles, OTC products (e.g. burn ointments), pharmaceuticals (e.g. in the field of tumour treatment, bladder weakness) or packaging. The compounds or mixtures of compounds to be indicated should preferably have as weak an inherent taste as possible, in particular little or no bitter taste, and should preferably be non-irritant.

For the solution of the task according to the invention, the search was primarily for active substances which can impart a particularly long-lasting cooling sensation. Preferably, these active substances should also be able to impart particularly intense and/or fast-onset cooling sensations. The cooling agents should be efficient, i.e. they should develop a high cooling effect or sensation even at low concentrations.

Another task has been to compensate for off-flavours that many flavourings, especially sweeteners such as representatives of the stevioside group, exhibit. This concerns in particular their bitter, astringent and metallic aftertaste.

The problem is solved by the objects of the independent patent claims. Further aspects of the present invention are apparent from the wording of the dependent patent claims, the following description and the examples.

DETAILED DESCRIPTION OF THE INVENTION

According to the invention, the primary task of the present invention is solved by a physiological cooling agent selected from the group consisting of compounds represented by the general formula (I)

Formula (I)

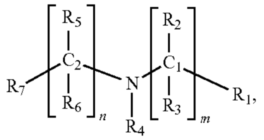

in which the residues R1 to R7 can each be identical or different and have the following meanings independently of one another:

R1 optionally substituted linear or branched alkyl group or
optionally substituted linear or branched alkenyl group or
optionally substituted linear or branched alkynyl group or
optionally substituted linear or branched alkoxy group or
optionally substituted acyl group R(C═O)— or
optionally substituted cycloalkyl group or
optionally substituted aryl group or
optionally substituted heterocycloalkyl group or
is an optionally substituted heteroaryl group;

R2 H or
$SiR_3$ or
a group Q or
optionally substituted linear or branched alkyl group or
optionally substituted linear or branched alkenyl group or
optionally substituted linear or branched alkynyl group, or
optionally substituted linear or branched alkoxy group or
optionally substituted linear or branched alkylthio group or
optionally substituted acyl group R(C═O)— or
optionally substituted cycloalkyl group or
optionally substituted aryl group or
optionally substituted heterocycloalkyl group or
is an optionally substituted heteroaryl group;

R3 H or
$SiR_3$ or
a group Q or
optionally substituted linear or branched alkyl group or
optionally substituted linear or branched alkenyl group or
optionally substituted linear or branched alkynyl group or
optionally substituted linear or branched alkoxy group or
optionally substituted linear or branched alkylthio group or
optionally substituted acyl group R(C═O)— or
optionally substituted cycloalkyl group or
optionally substituted aryl group or
optionally substituted heterocycloalkyl group or
is an optionally substituted heteroaryl group;

R4 H or
optionally substituted linear or branched alkyl group or
optionally substituted linear or branched alkenyl group or
optionally substituted linear or branched alkynyl group, or
optionally substituted acyl group R(C═O)— or
optionally substituted cycloalkyl group or optionally substituted aryl group or
optionally substituted heterocycloalkyl group or
is an optionally substituted heteroaryl group;

R5 H or
$SiR_3$ or
a group Q or
optionally substituted linear or branched alkyl group or
optionally substituted linear or branched alkenyl group or
optionally substituted linear or branched alkynyl group, or
optionally substituted linear or branched alkoxy group or
optionally substituted linear or branched alkylthio group or
optionally substituted acyl group R(C═O)— or
optionally substituted cycloalkyl group or
optionally substituted aryl group or
optionally substituted heterocycloalkyl group or
is an optionally substituted heteroaryl group or
R2 and R5 together with the $C_1$ and $C_2$ atom to which they are attached and the N atom between the $C_1$ and $C_2$ atom, form an optionally substituted heterocycloalkyl ring or optionally substituted heteroaryl ring;

R6 H or
$SiR_3$ or
a group Q or
optionally substituted linear or branched alkyl group or
optionally substituted linear or branched alkenyl group or
optionally substituted linear or branched alkynyl group, or
optionally substituted linear or branched alkoxy group or
optionally substituted linear or branched alkylthio group or
optionally substituted acyl group R(C═O)— or
optionally substituted cycloalkyl group or
optionally substituted aryl group or
optionally substituted heterocycloalkyl group or
is an optionally substituted heteroaryl group or
R3 and R6 together with the $C_1$ and $C_2$ atom to which they are attached and the N atom between the $C_1$ and $C_2$ atom, form an optionally substituted heterocycloalkyl ring or optionally substituted heteroaryl ring;

R7 optionally substituted linear or branched alkyl group or
optionally substituted linear or branched alkenyl group or
optionally substituted linear or branched alkynyl group or
optionally substituted linear or branched alkoxy group or
optionally substituted acyl group R(C═O)— or
optionally substituted cycloalkyl group or
optionally substituted aryl group or
optionally substituted heterocycloalkyl group or
is an optionally substituted heteroaryl group;

m is 0 to 4; provided that
if m=0, $C_1$, R2 and R3 are omitted;
if m=1, $C_1$, R2 and R3 each occur once;
if m=2, $C_1$, R2 and R3 each occur twice;
if m=3, $C_1$, R2 and R3 each occur three times; and
if m=4, $C_1$, R2 and R3 each occur four times;
with the proviso that when m=2, 3 or 4, the bond between the $C_1$ atoms may be a single bond or a double bond and when the bond between the C atoms is a double bond, either R2 or R3 is absent at the corresponding C atoms; and
where R2 and R3 can each be selected independently of each other;

n is 0 to 4; provided that
if n=0, $C_2$, R5 and R6 are omitted;
if n=1, $C_2$, R5 and R6 each occur once;
if n=2, $C_2$, R5 and R6 each occur twice;
if n=3, $C_2$, R5 and R6 each occur three times; and
if n=4, $C_2$, R5 and R6 each occur four times;
with the proviso that when n=2, 3 or 4, the bond between the $C_2$ atoms may be a single bond or a double bond and when the bond between the C atoms is a double bond, either R5 or R6 is absent at the corresponding C atoms; and
where R5 and R6 can each be selected independently of each other;

where
the group Q is a residue selected from the group consisting of: halogen, ═O, —OY, —SY, ═S, —NZZ, ═NY, ═N—OY, trihalomethyl, —$CF_3$, —CN, —OCN, —SCN, —NO, —$NO_2$, ═$N_2$, —$N_3$, —$S(O)_2Y$, —$S(O)_2OY$, —$OS(O)_2Y$, —$OS(O)_2OY$, —$P(O)(OY)_2$, —P(O)(OY)(OY), —C(O)Y, —C(S)Y, —C(NY)Y, —C(O)OY, —C(S)OY, —C(O)NZZ, —C(NY)NZZ, —OC(O)Y, —OC(S)Y, —OC(O)OY, —OC(S)OY, —NYC(O)Y, —NYC(S)Y, —NYC(O)OY, —NYC(S)OY, —NYC(O)NZZ, —NYC(NY)Y or —NYC(NY)NZZ;

where
Y is selected from the group consisting of hydrogen,
optionally substituted alkyl group, in particular optionally substituted $C_1$- to $C_{10}$-alkyl group, in particular optionally substituted $C_1$- to $C_6$-alkyl group, in particular optionally substituted $C_1$-, $C_2$-, $C_3$- or $C_4$-alkyl group,
optionally substituted alkoxy group, in particular optionally substituted $C_1$-$C_6$-alkoxy group, in particular optionally substituted $C_1$-, $C_2$-, $C_3$- or $C_4$-alkoxy group,
optionally substituted alkylthio group, in particular optionally substituted $C_1$- to $C_6$-alkylthio group, in particular optionally substituted $C_1$-, $C_2$-, $C_3$- or $C_4$-alkylthio group,
optionally substituted cycloalkyl group,
optionally substituted aryl group,
optionally substituted heterocycloalkyl group,
optionally substituted heteroaryl group; and/or
Z represents Y or alternatively, two Z's together with the nitrogen atom to which they are attached represent a four, five, six or seven membered heterocycloalkyl ring or heteroaryl ring, wherein the heterocycloalkyl ring or heteroaryl ring may comprise one, two, three or four of the same or different heteroatoms selected from the group consisting of nitrogen, oxygen and sulphur;
the optionally substituted alkyl group is an optionally substituted $C_1$- to $C_{10}$-alkyl group, in particular an optionally substituted $C_1$- to $C_6$-alkyl group, in particular an optionally substituted $C_1$-, $C_2$-, $C_3$- or $C_4$-alkyl group;
the optionally substituted alkenyl group is an optionally substituted $C_1$- to $C_{10}$-alkenyl group,
in particular an optionally substituted $C_1$- to $C_6$-alkenyl group,
in particular an optionally substituted $C_1$-, $C_2$-, $C_3$- or $C_4$-alkenyl group;

the optionally substituted alkynyl group is an optionally substituted $C_1$- to $C_{10}$-alkynyl group, in particular an optionally substituted $C_1$- to $C_6$-alkynyl group, in particular an optionally substituted $C_1$-, $C_2$-, $C_3$- or $C_4$-alkynyl group;

the optionally substituted alkoxy group is an optionally substituted $C_1$- to $C_{10}$-alkoxy group, in particular an optionally substituted $C_1$- to $C_6$-alkoxy group, in particular an optionally substituted $C_1$-, $C_2$-, $C_3$- or $C_4$-alkoxy group;

the optionally substituted alkylthio group is an optionally substituted $C_1$- to $C_{10}$-alkylthio group, in particular an optionally substituted $C_1$- to $C_6$-alkylthio group, in particular an optionally substituted $C_1$-, $C_2$-, $C_3$- or $C_4$-alkylthio group;

in the acyl group R—(C═O)— the residue R represents hydrogen or an optionally substituted $C_1$- to $C_{10}$-alkyl group, in particular an optionally substituted $C_1$- to $C_6$-alkyl group, in particular an optionally substituted $C_1$-, $C_2$-, $C_3$- or $C_4$-acyl group; in the group $SiR_3$ the residue R represents hydrogen or an optionally substituted $C_1$- to $C_{10}$-alkyl group, in particular an optionally substituted $C_1$- to $C_6$-alkyl group, in particular an optionally substituted $C_1$-, $C_2$-, $C_3$- or $C_4$-alkyl group;

the optionally substituted cycloalkyl group is an optionally substituted four- to ten-membered, in particular five-, six- or seven-membered, monocyclic cycloalkyl group or an optionally substituted nine- to twelve-membered polycyclic, in particular bicyclic, cycloalkyl group;

the optionally substituted aryl group is an optionally substituted four- to ten-membered, in particular five-, six- or seven-membered, monocyclic aryl group or an optionally substituted nine- to twelve-membered polycyclic, in particular bicyclic aryl group;

the optionally substituted heterocycloalkyl group is an optionally substituted four-, five-, six- or seven-membered monocyclic heterocycloalkyl group or an optionally substituted nine- to twelve-membered polycyclic, in particular bicyclic, heterocycloalkyl group, wherein the heterocycloalkyl group may comprise one, two, three or four identical or different heteroatoms selected from the group consisting of nitrogen, oxygen and sulphur;

the optionally substituted heteroaryl group is an optionally substituted four-, five-, six- or seven-membered monocyclic heteroaryl group or an optionally substituted nine- to twelve-membered polycyclic, in particular bicyclic, heteroaryl group, wherein the heteroaryl group may comprise one, two, three or four identical or different heteroatoms selected from the group consisting of nitrogen, oxygen and sulphur;

wherein the substituents are each independently selected; and their salts.

For example, if R1 and R7 are the same and R2 and R5 are the same or R3 and R6 are the same, symmetrical amines can be represented, which are also suitable cooling agents in the context of the present invention.

The cooling agents of the invention according to formula (I) can be present both in stereoisomerically pure form or as mixtures of different stereoisomers.

In a preferred embodiment according to the first aspect of the present invention, it is a physiological cooling agent selected from the group consisting of compounds represented by the general formula (II)

Formula (II)

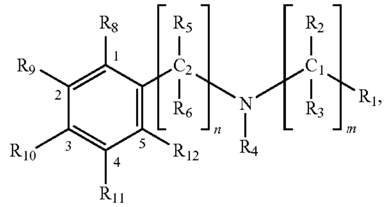

in which the residues R1 to R6 and R8 to R12 can each be identical or different and can have the following meanings independently of one another:

R1 as defined in claim 1;
R2 as defined in claim 1;
R3 as defined in claim 1;
R4 as defined in claim 1;
R5 as defined in claim 1;
R6 as defined in claim 1;
R8 H or
$SiR_3$ or
a group Q or
optionally substituted linear or branched alkyl group or
optionally substituted linear or branched alkenyl group or
optionally substituted linear or branched alkynyl group, or
optionally substituted linear or branched alkoxy group or
optionally substituted linear or branched alkylthio group or
optionally substituted acyl group R(C═O)— or
optionally substituted cycloalkyl group or
optionally substituted aryl group or
optionally substituted heterocycloalkyl group or
is an optionally substituted heteroaryl group or
R8 with the adjacent R9, together with the carbon atoms to which they are attached, forms an optionally substituted four, five, six or seven membered cycloalkyl or aryl ring or forms an optionally substituted four, five, six or seven membered heterocycloalkyl or heteroaryl ring, wherein the heterocycloalkyl or heteroaryl ring may comprise one, two, three or four identical or different heteroatoms selected from the group consisting of nitrogen, oxygen and sulphur;
R9 H or
$SiR_3$ or
a group Q or
optionally substituted linear or branched alkyl group or
optionally substituted linear or branched alkenyl group or
optionally substituted linear or branched alkynyl group or
optionally substituted linear or branched alkoxy group or
optionally substituted linear or branched alkylthio group or
optionally substituted acyl group R(C═O)— or
optionally substituted cycloalkyl group or
optionally substituted aryl group or
optionally substituted heterocycloalkyl group or
is an optionally substituted heteroaryl group or R9 with the adjacent R8 or R10, together with the carbon atoms to which they are attached, forms an optionally substituted four, five, six or seven membered cycloalkyl or aryl ring or forms an optionally substituted four, five, six or seven membered heterocycloalkyl or heteroaryl ring, wherein the heterocycloalkyl or heteroaryl ring may comprise one, two, three or four identical or different heteroatoms selected from the group consisting of nitrogen, oxygen and sulphur;

R10 H or
$SiR_3$ or
a group Q or
optionally substituted linear or branched alkyl group or
optionally substituted linear or branched alkenyl group or
optionally substituted linear or branched alkynyl group or
optionally substituted linear or branched alkoxy group or
optionally substituted linear or branched alkylthio group or
optionally substituted acyl group R(C═O)— or
optionally substituted cycloalkyl group or
optionally substituted aryl group or
optionally substituted heterocycloalkyl group or
is an optionally substituted heteroaryl group or
R10 with the adjacent R9 or R11, together with the carbon atoms to which they are attached, forms an optionally substituted four-, five-, six- or seven-membered cycloalkyl or aryl ring, or forms an optionally substituted four-, five-, six- or seven-membered heterocycloalkyl or heteroaryl ring, wherein the heterocycloalkyl or heteroaryl ring may comprise one, two, three or four identical or different heteroatoms selected from the group consisting of nitrogen, oxygen and sulfur;

R11 H or
$SiR_3$ or
a group Q or
optionally substituted linear or branched alkyl group or
optionally substituted linear or branched alkenyl group or
optionally substituted linear or branched alkynyl group or
optionally substituted linear or branched alkoxy group or
optionally substituted linear or branched alkylthio group or
optionally substituted acyl group R(C═O)— or
optionally substituted cycloalkyl group or
optionally substituted aryl group or
optionally substituted heterocycloalkyl group or
is an optionally substituted heteroaryl group or
R11 with the adjacent R10 or R12, together with the carbon atoms to which they are attached, forms an optionally substituted four-, five-, six- or seven-membered cycloalkyl or aryl ring, or forms an optionally substituted four-, five-, six- or seven-membered heterocycloalkyl or heteroaryl ring, wherein the heterocycloalkyl or heteroaryl ring may comprise one, two, three or four identical or different heteroatoms selected from the group consisting of nitrogen, oxygen and sulfur;

R12 H or
$SiR_3$ or
a group Q or
optionally substituted linear or branched alkyl group or
optionally substituted linear or branched alkenyl group or
optionally substituted linear or branched alkynyl group, or
optionally substituted linear or branched alkoxy group or
optionally substituted linear or branched alkylthio group or
optionally substituted acyl group R(C═O)— or
optionally substituted cycloalkyl group or
optionally substituted aryl group or
optionally substituted heterocycloalkyl group or
is an optionally substituted heteroaryl group or
R12 with the adjacent R11, together with the carbon atoms to which they are attached, forms an optionally substituted four, five, six or seven membered cycloalkyl or aryl ring or forms an optionally substituted four, five, six or seven membered heterocycloalkyl or heteroaryl ring, wherein the heterocycloalkyl or heteroaryl ring may comprise one, two, three or four identical or different heteroatoms selected from the group consisting of nitrogen, oxygen and sulphur;

m as defined in claim 1;
n as defined in claim 1;
where
the group Q is a residue selected from the group consisting of: halogen, ═O, —OY, —SY, ═S, —NZZ, ═NY, ═N—OY, trihalomethyl, $—CF_3$, —CN, —OCN, —SCN, —NO, $—NO_2$, $═N_2$, $—N_3$, $—S(O)_2Y$, $—S(O)_2OY$, $—OS(O)_2Y$, $—OS(O)_2OY$, $—P(O)(OY)_2$, —P(O)(OY)(OY), —C(O)Y, —C(S)Y, —C(NY)Y, —C(O)OY, —C(S)OY, —C(O)NZZ, —C(NY)NZZ, —OC(O)Y, —OC(S)Y, —OC(O)OY, —OC(S)OY, —NYC(O)Y, —NYC(S)Y, —NYC(O)OY, —NYC(S)OY, —NYC(O)NZZ, —NYC(NY)Y or —NYC(NY)NZZ;
where
Y is selected from the group consisting of hydrogen,
optionally substituted alkyl group, in particular optionally substituted $C_1$- to $C_{10}$-alkyl group,
in particular optionally substituted $C_1$- to $C_6$-alkyl group, in particular optionally substituted $C_1$-, $C_2$-, $C_3$- or $C_4$-alkyl group, optionally substituted alkoxy group, in particular optionally substituted $C_1$-$C_6$-alkoxy group,
in particular optionally substituted $C_1$-, $C_2$-, $C_3$- or $C_4$-alkoxy group, optionally substituted alkylthio group, in particular optionally substituted $C_1$- to $C_6$-alkylthio group, in particular optionally substituted $C_1$-, $C_2$-, $C_3$- or $C_4$-alkylthio group,
optionally substituted cycloalkyl group,
optionally substituted aryl group,
optionally substituted heterocycloalkyl group,
optionally substituted heteroaryl group; and/or
Z represents Y or alternatively, two Z's together with the nitrogen atom to which they are attached represent a four, five, six or seven membered heterocycloalkyl ring or heteroaryl ring, wherein the heterocycloalkyl ring or heteroaryl ring may comprise one, two, three or four of the same or different heteroatoms selected from the group consisting of nitrogen, oxygen and sulphur;
the optionally substituted alkyl group is an optionally substituted $C_1$- to $C_{10}$-alkyl group, in particular an optionally substituted $C_1$- to $C_6$-alkyl group,
in particular an optionally substituted $C_1$-, $C_2$-, $C_3$- or $C_4$-alkyl group;

the optionally substituted alkenyl group is an optionally substituted $C_1$- to $C_{10}$-alkenyl group, in particular an optionally substituted $C_1$- to $C_6$-alkenyl group, in particular an optionally substituted $C_1$-, $C_2$-, $C_3$- or $C_4$-alkenyl group;

the optionally substituted alkynyl group is an optionally substituted $C_1$- to $C_{10}$-alkynyl group, in particular an optionally substituted $C_1$- to $C_6$-alkynyl group, in particular an optionally substituted $C_1$-, $C_2$-, $C_3$- or $C_4$-alkynyl group;

the optionally substituted alkoxy group is an optionally substituted $C_1$- to $C_{IO}$-alkoxy group, in particular an optionally substituted $C_1$- to $C_6$-alkoxy group, in particular an optionally substituted $C_1$-, $C_2$-, $C_3$- or $C_4$-alkoxy group;

the optionally substituted alkylthio group is an optionally substituted $C_1$- to $C_{10}$-alkylthio group, in particular an optionally substituted $C_1$- to $C_6$-alkylthio group, in particular an optionally substituted $C_1$-, $C_2$-, $C_3$- or $C_4$-alkylthio group; in the acyl group R—(C═O)— the residue R represents hydrogen or an optionally substituted $C_1$- to $C_{10}$-alkyl group, in particular an optionally substituted $C_1$- to $C_6$-alkyl group, in particular an optionally substituted $C_1$-, $C_2$-, $C_3$- or $C_4$-acyl group; in the group $SiR_3$ the residue R represents hydrogen or an optionally substituted $C_1$- to $C_{10}$-alkyl group, in particular an optionally substituted $C_1$- to $C_6$-alkyl group, in particular an optionally substituted $C_1$-, $C_2$-, $C_3$- or $C_4$-alkyl group;

the optionally substituted cycloalkyl group is an optionally substituted four- to ten-membered, in particular five-, six- or seven-membered, monocyclic cycloalkyl group or an optionally substituted nine- to twelve-membered polycyclic, in particular bicyclic, cycloalkyl group;

the optionally substituted aryl group is an optionally substituted four- to ten-membered, in particular five-, six- or seven-membered, monocyclic aryl group or an optionally substituted nine- to twelve-membered polycyclic, in particular bicyclic aryl group;

the optionally substituted heterocycloalkyl group is an optionally substituted four-, five-, six- or seven-membered monocyclic heterocycloalkyl group or an optionally substituted nine- to twelve-membered polycyclic, in particular bicyclic, heterocycloalkyl group, wherein the heterocycloalkyl group may comprise one, two, three or four identical or different heteroatoms selected from the group consisting of nitrogen, oxygen and sulphur;

the optionally substituted heteroaryl group is an optionally substituted four-, five-, six- or seven-membered monocyclic heteroaryl group or an optionally substituted nine- to twelve-membered polycyclic, in particular bicyclic, heteroaryl group, wherein the heteroaryl group may comprise one, two, three or four identical or different heteroatoms selected from the group consisting of nitrogen, oxygen and sulphur;

wherein the substituents are each independently selected;

wherein optionally one, two, three, four or five carbon atom(s) in position 1, 2, 3, 4 or 5 of the benzene ring at the $C_2$ atom of the general formula (II) is/are each replaced by a nitrogen atom;

and their salts.

The cooling agents according to formula (II) of the invention can also be present both in stereoisomerically pure form or as mixtures of different stereoisomers.

In the context of the present invention, in particular for the definition of the general formula (I) and formula (II), the following general meanings apply:

The term "or" or "and/or" is used as a function word to indicate that two words or phrases are to be taken together or separately.

The terms "comprising", "with", "including" and "containing" are to be understood as open terms, i.e. "comprising", "including" or "containing", but not "limited to".

The endpoints of all ranges directed to the same component or property are inclusive and independently combinable.

The term "compound(s)" or "compound(s) of the present invention" refers to all compounds encompassed by the structural formulae Formula (I) and/or Formula (II) disclosed herein and includes any subgenus and any specific compounds within the formula whose structure is disclosed herein. The compounds may be identified by either their chemical structure and/or their chemical name. When the chemical structure and chemical name are in conflict, the chemical structure determines the identity of the compound. The compounds described herein may contain one or more chiral centres and/or double bonds and may therefore exist as stereoisomers, such as double bond isomers, i.e. geometric isomers, enantiomers or diastereomers. Accordingly, the chemical structures of the general formula (I) and/or formula (II) shown here include all possible enantiomers and diastereomers or stereoisomers.

The term "alkyl" alone or as part of another substituent according to the present invention refers to a saturated or mono- or polyunsaturated linear or branched monovalent hydrocarbon radical obtained by removing a hydrogen atom from a single carbon atom of a corresponding parent alkane.

In a preferred variant, the term "alkyl" also includes any alkyl moieties in residues derived therefrom, such as alkoxy, alkylthio, alkylsulphonyl saturated linear or branched hydrocarbon residues having 1 to 10, 1 to 8, 1 to 6 or 1 to 4 carbon atoms.

If the alkyl radical is further bonded to another atom, it becomes an alkylene residue or an alkylene group. In other words, the term "alkylene" also refers to a divalent alkyl. For example, $—CH_2CH_3$ is an ethyl, while $—CH_2CH_2—$ is an ethylene.

The term "alkylene" alone or as part of another substituent refers to a saturated linear or branched divalent hydrocarbon radical obtained by removing two hydrogen atoms from a single carbon atom or two different carbon atoms of a starting alkane.

In preferred variants according to the present invention, an alkyl group or an alkylene group comprises 1 to 10 carbon atoms. In other still more preferred variants, an alkyl group or alkylene group comprises 1 to 6 carbon atoms. Most preferred are alkyl groups or alkylene groups with 1 to 4 carbon atoms.

Preferred alkyl residues or alkyl groups comprise, but are not limited to: $C_1$- to $C_6$-alkyl, comprising methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl; $C_1$- to $C_6$-alkoxy, comprising $C_1$- to $C_4$-alkoxy, such as e.g. methoxy, ethoxy, n-propoxy, 1-methylethoxy, butoxy, 1-methylpropoxy, 2-methylpropoxy or 1,1-dimethylethoxy; as well as pentoxy, 1-methylbutoxy, 2-methylbutoxy, 3-methylbutoxy, 1,1-dimethylpropoxy, 1,2-dimethylpropoxy, 2,2-dimethylpropoxy, 1-ethylpropoxy, hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy or 1-ethyl-2-methylpropoxy.

Most preferred according to the invention are saturated linear or branched $C_1$- to $C_6$-alkyl groups or saturated linear or branched $C_1$- to $C_6$-alkylene groups.

The term "alkyl" or "alkylene" further includes residues or groups with any degree of saturation, i.e. groups with only single carbon-carbon bonds ("alkyl" or "alkylene"), groups with one or more double carbon-carbon bonds ("alkenyl"), residue with one or more triple carbon-carbon bonds ("alkynyl") and groups with a mixture of single, double and/or triple carbon-carbon bonds.

The term "alkenyl" alone or as part of another substituent according to the present invention refers to an unsaturated linear or branched monovalent hydrocarbon radical having at least one carbon-carbon double bond (C═C double bond). The residue may be in either the cis or trans conformation around the double bond(s). So that the term "alkenyl" also comprises the corresponding cis/trans isomers.

Typical alkenyl residues or alkenyl groups comprise, but are not limited to, ethenyl; propenyls such as prop-1-en-1-yl, prop-1-en-2-yl, prop-2-en-1-yl (allyl), prop-2-en-2-yl, cycloprop-1-en-1-yl, cycloprop-2-en-1-yl; butenyls such as but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl and the like.

In preferred variants according to the present invention, an alkenyl group comprises 2 to 10 carbon atoms. In other preferred variants, an alkenyl group comprises 2 to 6 carbon atoms. In still further preferred variants, an alkenyl group comprises 2 to 4 carbon atoms.

Most preferred according to the invention are mono- or diunsaturated linear or branched $C_1$- to $C_6$-alkenyl groups.

The term "alkynyl" alone or as part of another substituent according to the present invention refers to an unsaturated linear or branched monovalent hydrocarbon radical having at least one carbon-carbon triple bond (C≡C triple bond).

Typical alkynyl residues or alkynyl groups comprise, but are not limited to, ethynyl; propynyls such as prop-1-yn-1-yl, prop-2-yn-1-yl, etc.; butynyls such as but-1-yn-1-yl, but-1-yn-3-yl, but-3-yn-1-yl and the like.

In preferred variants according to the present invention, an alkynyl group comprises 2 to 10 carbon atoms. In other preferred variants, an alkynyl group comprises 2 to 6 carbon atoms. In still further preferred variants, an alkynyl group comprises 2 to 4 carbon atoms.

The term "alkoxy" alone or as part of another substituent according to the present invention refers to a radical of the formula —O—R, where R is alkyl or substituted alkyl as defined herein.

The term "alkylthio" or "thioalkoxy" alone or as part of another substituent according to the present invention refers to a radical of the formula —S—R, wherein R is alkyl or substituted alkyl as defined herein.

According to the invention, the term "alkyl" or "alkylene" also comprises heteroalkyl residues or heteroalkyl groups. The term "heteroalkyl" by itself or as part of other substituents refers to alkyl groups in which one or more of the carbon atom(s) is/are independently replaced by the same or another heteroatom or by the same or another heteroatomic group(s). Typical heteroatoms or heteroatomic groups that may replace the carbon atoms comprise, but are not limited to, —O—, —S—, —N—, —Si—, —NH—, —S(O)—, —$S(O)_2$—, —S(O)NH—, —$S(O)_2$NH— and the like and combinations thereof. The heteroatoms or heteroatomic groups may be located at any internal position of the alkyl group. Typical heteroatomic groups that may be included in said groups comprise, but are not limited to, —O—, —S—, —O—O—, —S—S—, —O—S—, —NRR—, =NN=, —N═N—, —N═N—NRR, —PR—, —$P(O)_2$—, —POR—, —O—$P(O)_2$—, —SO—, —$SO_2$—, —$SR_2$OR—, and the like, wherein R is independently hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl or substituted heteroarylalkyl as defined herein.

The alkyl group or the alkylene group as defined above may furthermore be substituted.

The term "acyl" alone or as part of another substituent according to the present invention refers to a radical —R(C═O)—, wherein R is hydrogen, alkyl, substituted alkyl, cycloalkyl, substituted cycloalkyl, aryl, substituted aryl, arylalkyl, substituted arylalkyl, heteroalkyl, substituted heteroalkyl, heteroarylalkyl or substituted heteroarylalkyl as defined herein.

Representative examples comprise, but are not limited to, formyl, acetyl, propionyl, butyryl, valeryl, benzoyl, cyclohexylcarbonyl, cyclohexylmethylcarbonyl, benzylcarbonyl and the like.

The term "cycloalkyl" alone or as part of another substituent according to the present invention refers to a saturated or mono- or polyunsaturated, non-aromatic, cyclic monovalent hydrocarbon radical in which the carbon atoms are linked together in a ring and which has no heteroatom.

The carbon ring can occur as a monocyclic compound, which has only a single ring, or as a polycyclic compound, which has two or more rings.

In a preferred variant, the term "cycloalkyl" comprises a three to ten membered monocyclic cycloalkyl residue or cycloalkyl group or a nine to twelve membered polycyclic cycloalkyl residue or cycloalkyl group. In other still more preferred variants, the cycloalkyl residue comprises a five-, six- or seven-membered monocyclic cycloalkyl residue or a nine- to twelve-membered bicyclic cycloalkyl moiety.

In a preferred variant according to the present invention, a cycloalkyl residue or group comprises 3 to 20 carbon atoms. In a still more preferred variant, a cycloalkyl radical comprises 6 to 15 carbon atoms. In a most preferred variant, a cycloalkyl radical comprises 6 to 10 carbon atoms. Most preferred are monocyclic $C_3$- to $C_7$-cycloalkyl groups.

Typical cycloalkyl groups comprise, but are not limited to, saturated carbocyclic residues having 3 to 20 carbon atoms, such as $C_3$- to $C_{12}$-carbocyclyl, comprising cyclopropyl, cyclobutyl, cyclopentyl, cyclohexyl, cycloheptyl, cyclooctyl, cyclononyl, cyclodecyl, cycloundecyl and cyclododecyl; preferably cyclopentyl, cyclohexyl, cycloheptyl, as well as cyclopropyl-methyl, cyclopropyl-ethyl, cyclobutyl-methyl, cyclobutyl-ethyl, cyclopentyl-methyl, cyclopentyl-ethyl, cyclohexyl-methyl, or $C_3$- to $C_7$-carbocyclyl, comprising cyclopropyl, cyclobutyl, cyclopentyl, cyclohexyl, cycloheptyl, cydopropyl-methyl, cyclopropyl-ethyl, cyclobutyl-methyl, cyclopentyl-ethyl, cyclohexyl-methyl, cydobut-1-en-1-yl, cyclobut-1-en-3-yl, cyclobuta-1, 3-dien-1-yl and the like.

Saturated polycyclic cycloalkyl radicals or cycloalkyl groups preferred according to the invention comprise, but are not limited to, for example adamantyl groups and the like.

According to the invention, the term "cycloalkyl" also comprises cycloalkenyls, i.e. unsaturated cyclic hydrocarbon radicals containing C═C double bonds between two carbon atoms of the ring molecule. In a broader sense, cydoalkenyls are compounds with one, two or more double bond(s), whereby the number of possible, mostly conjugated double bonds in the molecule depends on the ring size.

Typical cycloalkenyls comprise, but are not limited to, cyclopropenyl, cyclopentenyl, cyclohexenyl, cyclopentadienyl and the like.

According to the invention, the term "cycloalkyl" also includes cycloalkynyls, i.e. unsaturated, cyclic hydrocarbon radicals containing —C≡C-triple bonds between two carbon atoms of the ring molecule, the triple bond being dependent on the ring size for reasons of ring tension.

Typical cycloalkynes include cyclooctyne.

The cycloalkyl residue or the cycloalkyl group can be attached to the residue of the molecule of formula (I) and/or formula (II) via any suitable C atom.

The cycloalkyl residue or the cycloalkyl group, as defined above, may furthermore be substituted.

The term "aryl" alone or as part of another substituent according to the present invention refers to a monovalent aromatic hydrocarbon radical derived by removing a hydrogen atom from a single carbon atom of an aromatic ring system.

In a preferred variant, the term "aryl" comprises a three to ten membered monocyclic aryl moiety or group or a nine to twelve membered polycyclic aryl moiety or group. In other still more preferred variants, the carboaryl moiety comprises a five-, six- or seven-membered monocyclic carboaryl moiety or a nine- to twelve-membered bicyclic carboaryl moiety.

In a preferred variant according to the present invention, the aryl moiety comprises 3 to 20 carbon atoms. In an even more preferred variant, an aryl moiety comprises 6 to 15 carbon atoms. In a most preferred variant, an aryl residue comprises 6 to 10 carbon atoms. Most preferred according to the invention are monocyclic $C_3$- to $C_{12}$-aryl groups. Most preferred are monocyclic $C_3$- to $C_7$-aryl groups.

Typical aryl residues comprise, but are not limited to, benzene, phenyl, biphenyl, naphthyl such as 1- or 2-naphthyl, tetrahydronaphthyl, fluorenyl, indenyl and phenanthrenyl. Typical carboaryl moieties further comprise, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, S-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like.

Aromatic polycyclic aryl residues or aryl groups preferred according to the invention comprise, but are not limited to, naphthalene, biphenyl and the like.

The attachment of the aryl residue or the aryl group to the residue of the molecule of formula (I) or formula (II) can take place via any suitable C atom.

The aryl residue or the aryl group, as defined above, may furthermore be substituted. For example, the aryl residue forms an anisole group.

The term "arylalkyl" alone or as part of another substituent according to the present invention refers to an acyclic alkyl group in which one of the hydrogen atoms attached to a carbon atom, typically a terminal or sp carbon atom, is replaced by an aryl group as defined herein. In other words, arylalkyl may also be considered as alkyl substituted by aryl. Typical arylalkyl groups comprise, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like.

The term "heteroarylalkyl" alone or as part of another substituent refers to a cyclic alkyl group in which one of the hydrogen atoms attached to a carbon atom is replaced by a heteroaryl group. In a preferred embodiment according to the present invention, the heteroarylalkyl group is a 6- to 20-membered heteroarylalkyl, e.g. the alkanyl, alkenyl or alkynyl group of the heteroarylalkyl is a $C_1$- to $C_6$-alkyl and the heteroaryl group is a 5- to 15-membered heteroaryl group. In other embodiments, the heteroarylalkyl is a 6- to 13-membered heteroarylalkyl, e.g., the alkanyl, alkenyl or alkynyl group is a $C_1$- to $C_6$-alkyl and the heteroaryl group is a 5- to 10-membered heteroaryl.

The term "heterocycloalkyl" alone or as part of another substituent according to the present invention refers to a saturated, non-aromatic, cyclic monovalent hydrocarbon radical in which one or more carbon atom(s) is/are independently replaced by the same or a different heteroatom. Typical heteroatoms to replace the carbon atom(s) comprise, but are not limited to, N, P, O, S, Si, etc. Typical heterocycloalkyl groups comprise, but are not limited to, groups derived from epoxides, azirines, thiiranes, imidazolidine, morpholine, piperazine, piperidine, pyrazolidine, pyrrolidone, quinuclidine and the like.

The heterocycloalkyl moiety may occur as a monocyclic compound having only a single ring or as a polycyclic compound having two or more rings.

Preferably, the term "heterocycloalkyl" comprises three- to seven-membered, saturated or mono- or polyunsaturated heterocycloalkyl residues comprising one, two, three or four heteroatoms selected from the group consisting of O, N and S. The heteroatom or heteroatoms may occupy any position in the heterocycloalkyl ring.

In one preferred variant, the term "heterocycloalkyl" comprises a three- to ten-membered monocyclic heterocycloalkyl radical or a nine- to twelve-membered polycyclic heterocycloalkyl residue. In other still more preferred variants, the heterocycloalkyl residue comprises a five-, six- or seven-membered monocyclic heterocycloalkyl residue or a nine- to twelve-membered bicyclic heterocycloalkyl residue.

In a preferred variant according to the present invention, the "heterocycloalkyl" residue or heterocycloalkyl group comprises 3 to 20 ring atoms. In a preferred variant, the heterocycloalkyl residue comprises 6 to 15 ring atoms. In a still more preferred variant, the heterocycloalkyl residue comprises 6 to 10 carbon atoms. Most preferred according to the invention are monocyclic heterocycloalkyl residues comprising 3 to 12 carbon atoms. Most preferred are monocyclic heterocycloalkyl residues having 5 to 7 ring atoms.

Typical heterocycloalkyl residues comprise, but are not limited to: five- or six-membered, saturated or monounsaturated heterocycloalkyl containing one or two nitrogen atoms and/or one oxygen or sulfur atom or one or two oxygen and/or sulfur atoms as ring members, comprising 2-tetrahydrofuranyl, 3-tetrahydrofuranyl, 2-tetrahydrothienyl, 3-tetrahydrothienyl, 1-pyrrolidinyl, 2-pyrrolidinyl, 3-pyrrolidinyl, 3-isoxazolidinyl, 4-isoxazolidinyl, 5-isoxazolidinyl, 3-isothiazolidinyl, 4-isothiazolidinyl, 5-isothiazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 2-imidazolidinyl, 4-imidazolidinyl, 2-pyrrolin-2-yl, 2-pyrrolin-3-yl, 3-pyrrolin-2-yl, 3-pyrrolin-3-yl, 1-piperidinyl, 2-piperidinyl, 3-piperidinyl, 4-piperidinyl, 1,3-dioxan-5-yl, 2-tetrahydropyranyl, 4-tetrahydropyranyl, 2-tetrahydrothienyl, 3-hexahydropyridazinyl, 4-hexahydropyridazinyl, 2-hexahydropyrimidinyl, 4-hexahydropyrimidinyl, 5-hexahydropyrimidinyl, 2-piperazinyl and the like.

The heterocycloalkyl residue or the heterocycloalkyl group, as defined above, may furthermore be substituted.

The heterocycloalkyl radical or the heterocycloalkyl group may be bonded to the residue of the molecule of formula (I) or formula (II) via a ring carbon atom or a ring heteroatom.

The term "heteroaryl" by itself or as part of another substituent according to the present invention refers to a monovalent heteroaromatic radical obtained by removing a hydrogen atom from a single atom of a heteroaromatic ring system. Typical heteroaryl residues or heteroaryl groups comprise, but are not limited to, those groups derived from acridine, β-carboline, chroman, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, thiazole, thiophene, triazole, xanthene and the like.

The heteroaryl residue can occur as a monocyclic compound, which has only a single ring, or as a polycyclic compound, which has two or more rings.

In a preferred variant, the term "heteroaryl" comprises a three- to ten-membered monocyclic heteroaryl residue or a nine- to twelve-membered polycyclic heteroaryl residue. In other still more preferred variants, the heteroaryl moiety comprises a five-, six- or seven-membered monocyclic heteroaryl moiety or a nine- to twelve-membered bicyclic heteroaryl moiety.

Preferably, the term "heteroaryl" comprises three- to seven-membered monocyclic heteroaryl residues comprising one, two, three or four heteroatoms selected from the group consisting of O, N and S. The heteroatom or heteroatoms may occupy any position in the heteroaryl ring.

In a preferred variant according to the present invention, the heteroaryl moiety or group comprises 3 to 20 ring atoms. In an even more preferred variant, the heteroaryl moiety comprises 6 to 15 ring atoms. In a most preferred variant, the heteroaryl group comprises 6 to 10 ring atoms. Most preferred according to the invention are monocyclic $C_3$- to $C_7$-heteroaryl groups.

Particularly preferred heteroaryl residues or heteroaryl groups comprise, but are not limited to, those derived from furan, thiophene, pyrrole, benzothiophene, benzofuran, benzimidazole, indole, pyridine, pyrazole, quinoline, imidazole, oxazole, isoxazole and pyrazine.

Five-membered aromatic heteroaryl residues containing, in addition to carbon atoms, one, two or three nitrogen atoms or one or two nitrogen atoms and one sulphur or oxygen atom as ring atoms comprise 2-furyl, 3-furyl, 2-thienyl, 3-thienyl, 2-pyrrolyl, 3-pyrrolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-Imidazolyl, 4-Imidazolyl, and 1,3,4-triazol-2-yl.

Five-membered aromatic heteroaryl residues containing one, two, three or four nitrogen atoms as ring atoms comprise 1-, 2- or 3-pyrrolyl, 1-, 3- or 4-pyrazolyl, 1-, 2- or 4-Imidazolyl, 1,2,3-[1H]-triazol-1-yl, 1,2,3-[2H]-triazol-2-yl, 1,2,3-[1H]-triazol-4-yl, 1,2,3-[1H]-triazol-5-yl, 1,2,3-[2H]-triazol-4-yl, 1,2,4-[1H]-triazol-1-yl, 1,2,4-[1H]-triazol-3-yl, 1,2,4-[1H]-triazol-5-yl, 1,2,4-[4H]-triazol-4-yl, 1,2,4-[4H]-triazol-3-yl, [1H]-tetrazol-1-yl, [1H]-tetrazol-5-yl, [2H]-tetrazol-2-yl, [2H]-tetrazol-5-yl and the like.

Five-membered aromatic heteroaryl residues containing a heteroatom selected from oxygen or sulfur and optionally one, two or three nitrogen atoms as ring atoms comprise 2-furyl, 3-furyl, 2-thienyl, 3-thienyl, 3- or 4-Isoxazolyl, 3- or 4-isothiazolyl, 2-, 4- or 5-oxazolyl, 2-, 4- or 5-thiazolyl, 1,2,4-thiadiazol-3-yl, 1,2,4-thiadiazol-5-yl, 1,3,4-thiadiazol-2-yl, 1,2,4-oxadiazol-3-yl, 1,2,4-oxadiazol-5-yl and 1,3,4-oxadiazol-2-yl.

Six-membered heteroaryl residues containing, in addition to carbon atoms, one or two or one, two or three nitrogen atoms as ring atoms and comprise, for example 2-pyridinyl, 3-pyridinyl, 4-pyridinyl, 3-pyridazinyl, 4-pyridazinyl, 2-pyrimidinyl, 4-pyrimidinyl, 5-pyrimidinyl, 2-pyrazinyl, 1,2,4-triazin-3-yl; 1,2,4-triazin-5-yl, 1,2,4-triazin-6-yl and 1,3,5-triazin-2-yl.

The heteroaryl residue or the heteroaryl group, as defined above, can furthermore be substituted.

The heteroaryl residue or group may be attached to the residue of the molecule of formula (I) or formula (II) via a ring carbon atom or a ring heteroatom.

Of the monocyclic heteroaryl residues mentioned above, particularly preferred in the context of the present invention are those heteroaryl residues derived from the five- or six-membered saturated compounds comprising pyrrolidone, tetrahydrofuran, tetrahydrothiophene, piperidine, tetrahydropyran, tetrahydrothipyran or from the five- or six-membered aromatic compounds comprising pyrrole, furan, thiophene, pyridine, pyrylium ion and thiopyrylium ion, pyrazole, imidazole, imidazoline, pyrimidine, oxazole, thiazole and 1,4-thiazine.

Of the above-mentioned polycyclic heterocycloalkyl ring systems, benzimidazole, benzoxazole, quinoline, or benzoxazine, 1,3-benzodioxole and benzodioxane are particularly preferred in the context of the present invention.

Of the above-mentioned polycyclic cycloalkyl ring systems, 1,3-benzodioxole is particularly preferred in the context of the present invention.

Of the polycyclic heteroaryl ring systems mentioned above, those which can be derived from benzothiophene, benzofuran, indole (benzopyrrole), and quinoline, such as quinazoline, quinoxaline, are particularly preferred in the context of the present invention.

The term "substituted" in the context of the present invention means that one or more hydrogen atoms of the indicated residue or radical are independently replaced by the same or a different substituent.

Substituents or substituent groups useful for substituting saturated carbon atoms in the indicated group or residue comprise, but are not limited to, —X, halo, =O, —OY, —$SiR_3$, —SY, =S, —NZZ, =NY, =N—OY, trihalomethyl, —$CF_3$, —CN, —OCN, —SCN, —NO, —$NO_2$, =$N_2$, —$N_3$, —$S(O)_2Y$, —$S(O)_2OY$, —$OS(O)_2Y$, —$OS(O)_2OY$, —$P(O)(OY)_2$, —P(O)(OY)(OY), —C(O)Y, —C(S)Y, —C(NY)Y, —C(O)OY, —C(S)OY, —C(O)NZZ, —C(NY)NZZ, —OC(O)Y, —OC(S)Y, —OC(O)OY, —OC(S)OY, —NYC(O)Y, —NYC(S)Y, —NYC(O)OY, —NYC(S)OY, —NYC(O)NZZ, —NYC(NY)Y or —NYC(NY)NZZ; wherein X is selected from the group consisting of optionally substituted alkyl, in particular optionally substituted $C_1$- to $C_{10}$-alkyl, in particular optionally substituted $C_1$-$C_6$-alkyl, in particular optionally substituted $C_1$-, $C_2$-, $C_3$- or $C_4$-alkyl group, optionally substituted alkoxy residue, in particular optionally substituted $C_1$-$C_6$-alkoxy residue, in particular optionally substituted $C_1$-, $C_2$-, $C_3$- or $C_4$-alkoxy group, optionally substituted alkylthio residue, in particular optionally substituted $C_1$-$C_6$-alkylthio residue, in particular optionally substituted $C_1$-, $C_2$-, $C_3$- or $C_4$-alkylthio group, optionally substituted cycloalkyl residue, optionally substituted aryl residue, optionally substituted carboaryl residue, optionally substituted carboarylalkyl residue, optionally substituted heteroalkyl residue, optionally substituted heterocycloalkyl residue, optionally substituted heteroaryl residue and optionally substituted heteroarylalkyl residue, and as defined above; and/or Y denotes hydrogen or X; and/or Z is Y or alternatively two Z's together with the nitrogen atom to which they are attached form a four, five, six or seven membered heterocycloalkyl or heteroaryl ring, wherein the heterocycloalkyl or heteroaryl ring may comprise one, two, three or four of the same or different heteroatoms selected from the group consisting of nitrogen, oxygen and sulphur.

For example, R2 can also represent an oxygen atom that is bonded to the corresponding C1 atom via a double bond and can consequently form a keto group with the C1 atom. The same applies with regard to R3, R5 and R6 and the C1 or C2 atom.

As specific examples, —NZZ shall comprise —$NH_2$, —NH-alkyl, N-pyrrolidinyl and N-morpholinyl. As further specific examples of substitution shall comprise -alkylene-O-alkyl, -alkylene-heteroaryl, -alkylene-cycloheteroalkyl, -alkylene-C(O)OY, -alkylene-C(O)NYY and —$CH_2$—$CH_2$—C(O)—$CH_3$ wherein Y has the above-mentioned meaning.

In a further variant, the one or more substituent group(s) together with the atoms to which they are attached may form a cyclic ring, including cycloalkyl or heterocycloalkyl.

Similarly, substituent groups useful for substituting unsaturated carbon atoms in the indicated group or radical comprise, but are not limited to, —X, halo, =O, —OY, —$SiR_3$, —SY, =S, —NZZ, =NY, =N—OY, trihalomethyl, —$CF_3$, —CN, —OCN, —SCN, —NO, —$NO_2$, =$N_2$, —$N_3$, —$S(O)_2Y$, —$S(O)_2OY$, —$OS(O)_2Y$, —$OS(O)_2OY$, —$P(O)(OY)_2$, —P(O)(OY)(OY), —C(O)Y, —C(S)Y, —C(NY)Y, —C(O)OY, —C(S)OY, —C(O)NZZ, —C(NY)NZZ, —OC(O)Y, —OC(S)Y, —OC(O)OY, —OC(S)OY, —NYC(O)Y, —NYC(S)Y, —NYC(O)OY, —NYC(S)OY, —NYC(O)NZZ, —NYC(NY)Y and —NYC(NY)NZZ, where X, Y and Z have the same meaning as defined above.

Substituents or substituent groups for the substitution of nitrogen atoms in heteroalkyl and heterocycloalkyl residues comprise, without being limited to, —X, —OY, —$SiR_3$, —SY, —NZZ, trihalomethyl, —$CF_3$, —CN, —OCN, —SCN, —NO, —$NO_2$, =$N_2$, —$N_3$, —$S(O)_2Y$, —$S(O)_2OY$, —$OS(O)_2Y$, —$OS(O)_2OY$, —$P(O)(OY)_2$, —P(O)(OY)(OY), —C(O)Y, —C(S)Y, —C(NY)Y, —C(O)OY, —C(S)OY, —C(O)NZZ, —C(NY)NZZ, —OC(O)Y, —OC(S)Y, —OC(O)OY, —OC(S)OY, —NYC(O)Y, —NYC(S)Y, —NYC(O)OY, —NYC(S)OY, —NYC(O)NZZ, —NYC(NY)Y and —NYC(NY)NZZ, where X, Y and Z also have the same meaning as defined above.

The term "substituted" specifically provides for one or more, i.e. two, three, four, five, six or more, substitutions that are common in the art. However, it is generally known to those skilled in the art that substituents should be selected so that they do not adversely affect the useful properties of the compound or its function.

Suitable substituents in the context of the present invention preferably include halogen groups, perfluoroalkyl groups, perfluoroalkoxy groups, alkyl groups, alkenyl groups, alkynyl groups, hydroxy groups, oxo groups, mercapto groups, alkylthio groups, alkoxy groups, aryl or heteroaryl groups, aryloxy groups or heteroaryloxy groups, arylalkyl or heteroarylalkyl groups, arylalkoxy or heteroarylalkoxy groups, amino groups, alkyl and dialkylamino groups, carbamoyl groups, alkylcarbonyl groups, carboxyl groups, alkoxycarbonyl groups, alkylaminocarbonyl groups, dialkylaminocarbonyl groups, arylcarbonyl groups, aryloxycarbonyl groups, alkylsulfonyl groups, arylsulfonyl groups, cycloalkyl groups, cyano groups, $C_1$- to $C_6$-alkylthio groups, arylthio groups, nitro groups, keto groups, acyl groups, boronate or boronyl groups, phosphate or phosphonyl groups, sulfamyl groups, sulfonyl groups, sulfinyl groups and combinations thereof. In the case of substituted combinations such as substituted arylalkyl, either the aryl or the alkyl group may be substituted, or both the aryl and the alkyl group may be substituted with one or more substituents.

Preferred substituents for the above-mentioned groups or residues are in particular selected from COOH, COO-alkyl, $NH_2$, $NO_2$, OH, SH, CN, Si, halogens, linear or branched $C_1$- to $C_6$-alkyl groups, linear or branched $C_1$- to $C_6$-alkoxy groups or linear or branched $C_1$- to $C_6$-alkylthio groups, wherein one or more H atoms in the alkyl groups may be replaced by halogen.

Additionally, in some cases, suitable substituents may be combined to form one or more rings as known to those skilled in the art.

The term "optionally substituted" in the context of the present invention means the presence or absence of the substituent group(s), i.e. means "substituted" or "unsubstituted". For example, the term "optionally substituted alkyl" comprises both unsubstituted alkyl and substituted alkyl.

According to the invention, the substituents used to replace a particular residue or radical may in turn be further substituted, typically with one or more identical or different residues selected from the various groups indicated above and as defined in detail above.

The physiological cooling agents according to the general formula (I) or (II) are present either in neutral, i.e. uncharged form, or in the form of their salts, such as acid addition salts, with inorganic or organic, mono- or polyvalent carboxylic acids.

The term "salt" in the context of the present invention refers to a salt of a compound that has the desired effect or pharmacological activity of the parent compound. Such salts comprise:

(1) Acid addition salts formed with inorganic acids, or formed with organic acids, preferably monovalent or polyvalent carboxylic acids; or (2) Salts formed when an acidic proton present in the parent compound is replaced by a metal ion, e.g. an alkali metal ion, an alkaline earth ion or an aluminium ion; or coordinated with an organic base.

Among the salts, acid addition salts are again particularly preferred, since the physiological cooling agent according to the general formula (I) or (II) comprises a protonatable N atom in its $C_1$—N—$C_2$-linker group.

The inorganic acids which form acid addition salts with the physiological cooling agents of the present invention are preferably selected from the group consisting of hydrochloric acid, hydrobromic acid, sulphuric acid, nitric acid, phosphoric acid and the like. Among the salts most preferred are the hydrochlorides or sulphates. Particularly preferred is the hydrochloride salt or the sulphate salt at the central nitrogen atom of the C1-N—$C_2$ linker group.

Even more preferred are acid addition salts with organic mono- or polycarboxylic acids. Further preferred are acid addition salts with organic mono- or polycarboxylic acids, wherein the carboxylic acid is selected from saturated or mono- or polyunsaturated C1- to C30-monocarboxylic acids, saturated or mono- or polyunsaturated C3- to 10-di- or tricarboxylic acids. The carboxylic acid may be mono- or polysubstituted with hydroxy groups, preferably α-hydroxycarboxylic acids in which the hydroxy group is located on the carbon atom adjacent to the carboxy group. Many representatives occur naturally as so-called fruit acids. Preferred α-hydroxycarboxylic acids are: malic acid, citric acid, 2-hydroxy-4-methylmercaptobutyric acid, glycolic acid, isocitric acid, mandelic acid, lactic acid, tartronic acid or tartaric acid.

The organic acids which form acid addition salts with the physiological cooling agents according to the present invention are preferably selected from the group consisting of amino acids, acetic acid, trifluoroacetic acid, propionic acid, hexanoic acid, cyclopentane propionic acid, glycolic acid, pyruvic acid, lactic acid, malonic acid, oxalic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tert.butylacetic acid, laurylsulphuric acid, gluconic acid, glutamic acid, hydroxynaphthoic acid, salicylic acid, stearic acid, muconic acid, 4-hydroxybutanoic acid, and the like.

Among the organic acids that form acid addition salts with the physiological cooling agents of the present invention, acetic acid, lactic acid, malonic acid, succinic acid, malic acid, citric acid or tartaric acid are most preferred.

The metal ions for salt formation which replace an acidic proton present in the starting compound are selected from the group consisting of alkali metal ions, preferably Na+ or K+, alkaline earth metal ions, preferably Ca++, Mg++, and aluminium+++.

The coordinating organic base for salt formation is selected from the group consisting of ethanolamine, diethanolamine, triethanolamine, N-methylglucamine and the like.

In the following description and in the patent claims, the terms "physiological cooling agent" or "compound" comprise both the neutral, uncharged form of the cooling agent/compound and equally the salt form of the cooling agent/compound.

Because of their better solubility, the salts of the physiological cooling agents according to the present invention are particularly preferred. The better solubility in water also means that the cooling agents or compounds are more readily available for use.

Surprisingly, it was found that the compounds according to the invention or their salts have the common property of producing a particularly long and intensive cooling effect on the skin or mucous membrane in vivo even at low dosage. This means that in the final preparation, a lower dosage of the cooling compound according to the invention or its salt or of the cooling mixture according to the invention is required in order to bring about an intensive cooling effect. Thus, the compounds described herein are particularly efficient cooling substances. This was not predictable for the TRPM8 modulators mentioned in this application, nor is it true for all of these modulators.

Moreover, the cooling agents according to the invention or the cooling agent mixtures according to the invention are colourless and non-discolouring, which is very advantageous in particular for their storage and/or application in the end product. Consequently, the compounds described herein stand out as particularly suitable additives in various preparations. In addition, the compounds according to the present invention are largely neutral in taste and odour, so that they are also excellently suited for incorporation into neutral and/or flavoured preparations without creating a taste impression that is perceived as negative, for example as bitter, or without adversely affecting the intended taste or odour impression.

The salts of the cooling agents according to the invention show a better effect in vitro than their neutral, uncharged equivalents, which is particularly advantageous when they are used in the oral care sector. In vitro tests have also shown that the salts of the compound according to the invention exhibit better TRPM8 activities and consequently show more intense and at the same time more efficient cooling effects than their uncharged equivalents. Therefore, only small amounts of the compound according to the invention are necessary to produce an intensive cooling effect (low EC50 values).

As illustrated below in the experimental section, the acid addition salt of compound 87 has a TRPM8 activation of 133% and has an EC value of 0.00695 μM. The counterpart, namely the neutral, uncharged compound 27, has a TRPM8 activation of the same order of magnitude, namely 129.7%, while its EC value is 0.1 μM. Consequently, the salt compound shows more intense and at the same time more efficient cooling effects than its uncharged equivalent at the same concentration. Therefore, in order to produce an intensive cooling effect, lower amounts are necessary for compound 87 (low EC50 values) than for compound 27.

Up to now, there has been no evidence in the prior art that in particular the compounds to be used according to the invention or their salts can have any cooling effect at all and certainly not a particularly long-lasting cooling effect.

Equally surprising was the fact that the cooling agents of the invention or their salts are able to mask the known taste disadvantages of flavourings, especially of sweeteners such as steviosides. In particular, the pungent, bitter and metallic aftertaste is effectively masked even when small amounts are added.

Thus, the compounds described herein are suitable as particularly efficient cooling substances, which can be incorporated particularly well into a variety of formulations. Because of their better solubility, the salts, and even more preferably the acid addition salts, of the compounds according to the invention are particularly advantageous for use in the oral care sector.

Cooling agents of the formula (I) with particularly advantageous properties, i.e. a particularly intensive and effective and preferably simultaneously long-lasting cooling effect and/or optionally a particularly efficient masking of undesirable taste impressions, are regularly found in structures in which R1 represents an optionally substituted phenyl group, optionally substituted benzyl group, optionally substituted tolyl group, optionally substituted xylolyl group, optionally substituted phenol group, optionally substituted dihydroxybenzene group, optionally substituted pyridinyl group, optionally substituted piperidinyl group, optionally substituted tetrahydropyranyl group, optionally substituted pyrollyl group, optionally substituted imidazolyl group, optionally substituted pyrimidinyl group, optionally substituted oxazolyl group, optionally substituted indolyl group, optionally substituted benzothiophenyl group, optionally substituted furanyl group, optionally substituted benzofuranyl group, optionally substituted thiophenyl group, optionally substituted 1,3-benzodioxolyl group, optionally substituted benzodioxanyl group, optionally substituted morpholinyl group or optionally substituted quinolinyl group, and/or R7 represents an optionally substituted phenyl group, optionally substituted tolyl group, optionally substituted xylolyl group, optionally substituted phenol group, optionally substituted dihydroxybenzene group, optionally substituted pyridinyl group, optionally substituted piperidinyl group, optionally substituted tetrahydropyranyl group, optionally substituted pyrollyl group, optionally substituted imidazolyl group, optionally substituted pyrimidinyl group, optionally substituted oxazolyl group, optionally substituted indolyl group, optionally substituted benzothiophenyl group, optionally substituted furanyl group, optionally substituted benzofuranyl group, optionally substituted thiophenyl group, optionally substituted benzodioxolyl group, optionally substituted benzodioxanyl group, optionally substituted morpholinyl group or optionally substituted quinolinyl group.

Further preferred are compounds wherein R1 represents an optionally substituted pyridinyl group, optionally substituted 1,3-benzodioxolyl group, optionally substituted indolyl group, optionally substituted furanyl group, optionally substituted quinolinyl group, optionally substituted benzofuranyl group, optionally substituted benzyl group, optionally substituted phenyl group, optionally substituted thiophenyl group, optionally substituted benzothiophenyl group, and/or R7 represents an optionally substituted pyridinyl group, optionally substituted piperidinyl group, optionally substituted 1,3-benzodioxolyl group, optionally substituted dihydroxybenzene group, optionally substituted benzodioxanyl group, optionally substituted phenol group, optionally substituted phenyl group, optionally substituted thiophenyl group and optionally substituted tolyl group.

In this context, R1 and R7 can each be selected independently of one another, but can also represent the same groups, whereby preferably R1 and R7 each represent an optionally substituted phenyl group and/or an optionally substituted pyridinyl group and/or an optionally substituted thiophenyl group and/or an optionally substituted 1,3-benzodioxolyl group. It has been shown that these compounds in particular exhibit excellent TRPM8 activities and are capable of producing sensory cooling effects of extraordinary intensity even in small application quantities.

Also preferred according to the invention are those cooling agents of the formula (I) in which R1 represents an optionally substituted phenyl group, optionally substituted pyridinyl group, optionally substituted piperidinyl group, optionally substituted 1,3-benzodioxolyl group, optionally substituted benzodioxanyl group or optionally substituted thiophenyl group and/or in which R7 represents an optionally substituted phenyl group, optionally substituted pyridinyl group, optionally substituted 1,3-benzodioxolyl group, optionally substituted indolyl group, optionally substituted furanyl group, optionally substituted benzofuranyl group, optionally substituted thiophenyl group, optionally substituted benzothiophenyl group or optionally substituted quinolinyl group.

Particularly preferred are also those cooling agents of formula (I) which have the following structures:

R1=optionally substituted phenyl group and R7=optionally substituted phenyl group or optionally substituted pyridinyl group or optionally substituted benzodioxolyl group or optionally substituted indolyl group or optionally substituted furanyl group or optionally substituted benzofuranyl group or optionally substituted thiophenyl group or optionally substituted benzothiophenyl group or optionally substituted quinolinyl group; or R1=optionally substituted pyridinyl group and R7=optionally substituted phenyl group or optionally substituted pyridinyl group or optionally substituted benzodioxolyl group or optionally substituted indolyl group or optionally substituted furanyl group or optionally substituted benzofuranyl group or optionally substituted thiophenyl group or optionally substituted benzothiophenyl group or optionally substituted quinolinyl group; or R1=optionally substituted piperidinyl group and R7=optionally substituted phenyl group or optionally substituted pyridinyl group or optionally substituted benzodioxolyl group or optionally substituted indolyl group or optionally substituted furanyl group or optionally substituted benzofuranyl group or optionally substituted thiophenyl group or optionally substituted benzothiophenyl group or optionally substituted quinolinyl group; or R1=optionally substituted benzodioxolyl group and R7=optionally substituted phenyl group or optionally substituted pyridinyl group or optionally substituted benzodioxolyl group or optionally substituted indolyl group or optionally substituted furanyl group or optionally substituted benzofuranyl group or optionally substituted thiophenyl group or optionally substituted benzothiophenyl group or optionally substituted quinolinyl group; or R1=optionally substituted benzodioxanyl group and R7=optionally substituted phenyl group or optionally substituted pyridinyl group or optionally substituted benzodioxolyl group or optionally substituted indolyl group or optionally substituted furanyl group or optionally substituted benzofuranyl group or optionally substituted thiophenyl group or optionally substituted benzothiophenyl group or optionally substituted quinolinyl group; or R1=optionally substituted thiophenyl group and R7=optionally substituted phenyl group or optionally substituted pyridinyl group or optionally substituted benzodioxolyl group or optionally substituted indolyl group or optionally substituted furanyl group or optionally substituted benzofuranyl group or optionally substituted thiophenyl group or optionally substituted benzothiophenyl group or optionally substituted quinolinyl group; or R7=optionally substituted phenyl group and R1=optionally substituted phenyl group or optionally substituted pyridinyl group or optionally substituted piperidinyl group or optionally substituted benzodioxolyl group or optionally substituted benzodioxanyl group or optionally substituted thiophenyl group; or R7=optionally substituted pyridinyl group and R1=optionally substituted phenyl group or optionally substituted pyridinyl group or optionally substituted piperidinyl group or optionally substituted benzodioxolyl group or optionally substituted benzodioxanyl group or optionally substituted thiophenyl group; or R7=optionally substituted benzodioxolyl group and R1=optionally substituted phenyl group or optionally substituted pyridinyl group or optionally substituted piperidinyl group or optionally substituted benzodioxolyl group or optionally substituted benzodioxanyl group or optionally substituted thiophenyl group; or R7=optionally substituted indolyl group and R1=optionally substituted phenyl group or optionally substituted pyridinyl group or optionally substituted piperidinyl group or optionally substituted benzodioxolyl group or optionally substituted benzodioxanyl group or optionally substituted thiophenyl group; or R7=optionally substituted furanyl group and R1=optionally substituted phenyl group or optionally substituted pyridinyl group or optionally substituted piperidinyl group or optionally substituted benzodioxolyl group or optionally substituted benzodioxanyl group or optionally substituted thiophenyl group; or R7=optionally substituted benzofuranyl group and R1=optionally substituted phenyl group or optionally substituted pyridinyl group or optionally substituted piperidinyl group or optionally substituted benzodioxolyl group or optionally substituted benzodioxanyl group or optionally substituted thiophenyl group; or R7=optionally substituted thiophenyl group and R1=optionally substituted phenyl group or optionally substituted pyridinyl group or optionally substituted piperidinyl group or optionally substituted benzodioxolyl group or optionally substituted benzodioxanyl group or optionally substituted thiophenyl group; or R7=optionally substituted benzothiophenyl group and R1=optionally substituted phenyl group or optionally substituted pyridinyl group or optionally substituted piperidinyl group or optionally substituted benzodioxolyl group or optionally substituted benzodioxanyl group or optionally substituted thiophenyl group; or R7=optionally substituted quinolinyl group and R1=optionally substituted phenyl group or optionally substituted pyridinyl group or optionally substituted piperidinyl group or optionally substituted benzodioxolyl group or optionally substituted benzodioxanyl group or optionally substituted thiophenyl group.

In a further variant, the present invention relates to compounds of the general formula (I) wherein R1 and R7 are the same or different. Preferably, R1 and R7 are different.

In a further preferred variant, therefore, in the general formula (I) R1 and R7 are the same or R1 and R7 each independently represent an optionally substituted phenyl group and/or an optionally substituted pyridinyl group and/or an optionally substituted thiophenyl group and/or an optionally substituted 1,3-benzodioxolyl group. Particularly intensive TRPM8 activities were observed for different residues R1 and R2.

Particularly preferred according to the invention are those cooling agents of the formula (II) in which R1 represents an optionally substituted phenyl group, optionally substituted pyridinyl group, optionally substituted piperidinyl group, optionally substituted 1,3-benzodioxolyl group, optionally substituted benzodioxanyl group or optionally substituted thiophenyl group, even more preferably those cooling agents of formula (II) in which R1 represents an optionally substituted phenyl group, optionally substituted pyridinyl group or optionally substituted 1,3-benzodioxolyl group or thiophenyl group, the said phenyl, pyridinyl and 1,3-benzodioxolyl groups being particularly preferable. Such substances have proven to be particularly effective cooling substances, especially in sensory investigations, and show markedly high cooling intensities and TRPM8 activations.

In an even more preferred variant, in the general formula (I), R1 and R7, R2 and R5 and R3 and R6 are each the same, preferably forming a symmetrical amine compound.

In a particularly preferred variant of the present invention, at least one aromatic structure is contained in the general formula (I), for example at least one aromatic substituent R1 to R7, for example an optionally substituted phenyl group and/or an optionally substituted pyridinyl group and/or an optionally substituted thiophenyl group. Surprisingly, it has been shown that these compounds lead to particularly intense and at the same time efficient cooling effects, which are due to a strong TRPM8 activation, whereby already a low concentration of substance according to the invention is necessary to evoke a strong and efficient cooling sensation.

Furthermore, it is further preferred that the aforementioned optionally substituted groups R1 and/or R7 optionally themselves have one or more substituents selected from the group consisting of: optionally substituted piperdinyl group, optionally substituted morpholinyl group, optionally substituted hexamethyleneiminyl group, optionally substituted pyridinyl group, optionally substituted tetrahydropyrrolyl group, optionally substituted alkyl-piperidinyl group, optionally substituted thiomorpholinyl group, optionally substituted pyrollyl group, optionally substituted thioalkoxy group, optionally substituted alkoxy group and optionally substituted phenyl group. Particularly preferred substituents are optionally substituted pyridinyl groups and/or optionally substituted alkoxy groups as substituents.

A substitution of the residues R1 and/or R7 with an optionally substituted piperidinyl group is particularly preferred in order to achieve especially high TRPM8 activations or efficient cooling effects.

Of the physiological cooling agents as defined by general formula (I) or formula (II), the compounds having the following structure are explicitly excluded:

(1)

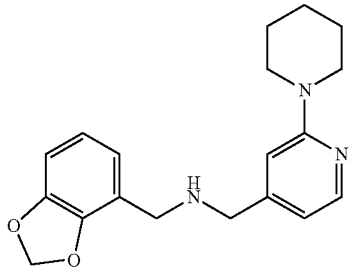 [SMILES: c1cc(CNCc2ccnc(N3CCCCC3)c2)c2c(c1)OCO2]

(2)

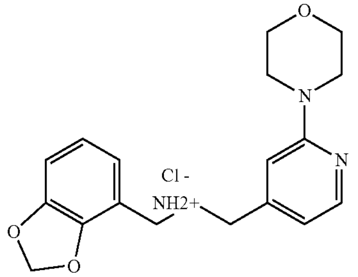

-continued (3)

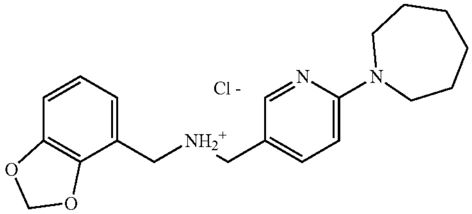

(4)

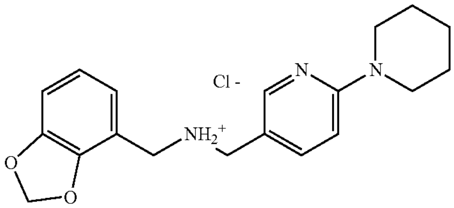

(5)

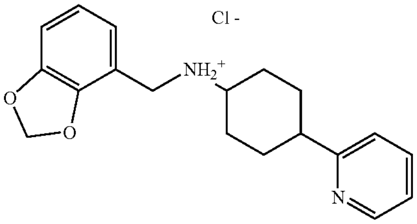

-continued (6)

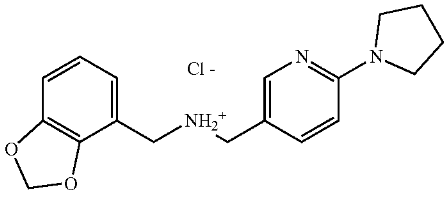

(7)

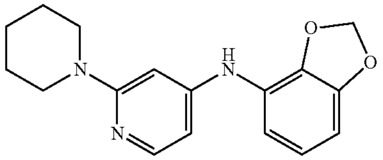

(8)

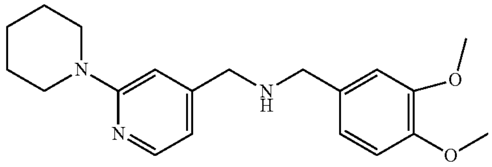

However, this disclaimer does not apply insofar as it relates to the uses of these specific compounds as described in detail below.

Particularly preferred are the physiological cooling agents of the general formula (I) or formula (II) selected from the group consisting of the compounds shown in Table 1.

TABLE 1

Structures according to the invention with relative TRPM8 activation in %.

| Structure | Relative TRPM8 activation (%) | Compound |
|---|---|---|
| 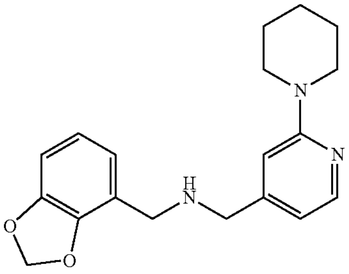 | 158 | Compound 1 |
| 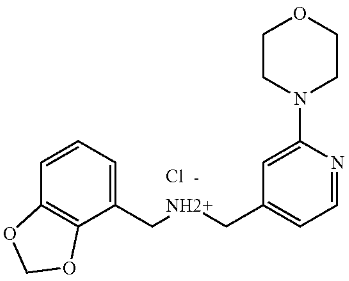 | 82 | Compound 2 |

TABLE 1-continued
Structures according to the invention with relative TRPM8 activation in %.
| Structure | Relative TRPM8 activation (%) | Compound |
|---|---|---|
| 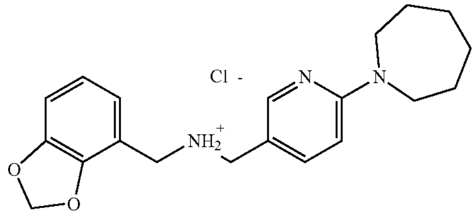 [SMILES: c1cc(CNCc2ccc(N3CCCCCC3)nc2)c2c(c1)OCO2 ; Cl] | 18.1 | Compound 3 |
| 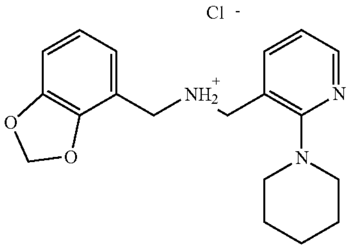 [SMILES: Cl ; c1cnc(N2CCCCC2)c(CNCc2cccc3c2OCO3)c1] | 69.8 | Compound 4 |
| 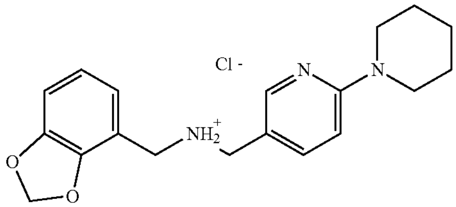 [SMILES: c1cc(CNCc2ccc(N3CCCCC3)nc2)c2c(c1)OCO2 ; Cl] | 8.5 | Compound 5 |
| 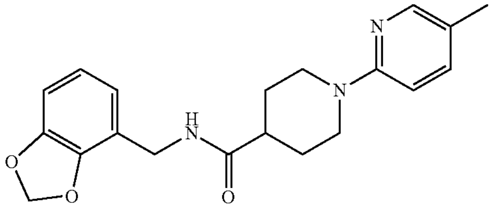 [SMILES: Cc1ccc(N2CCC(C(=O)NCc3cccc4c3OCO4)CC2)nc1] | 2.4 | Compound 5 a |
| 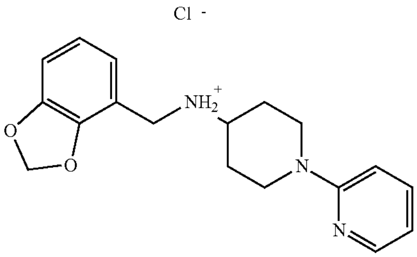 [SMILES: Cl ; c1ccc(N2CCC(NCc3cccc4c3OCO4)CC2)nc1] | 20.8 | Compound 6 |
| 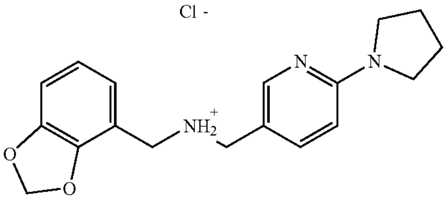 [SMILES: c1cc(CNCc2ccc(N3CCCC3)nc2)c2c(c1)OCO2 ; Cl] | 5.5 | Compound 7 |

TABLE 1-continued
Structures according to the invention with relative TRPM8 activation in %.
| Structure | Relative TRPM8 activation (%) | Compound |
|---|---|---|
| 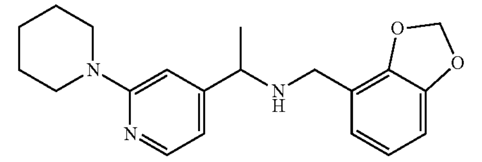 [SMILES: CC(NCc1cccc2c1OCO2)c1ccnc(N2CCCCC2)c1] | 174.6 | Compound 8 |
| 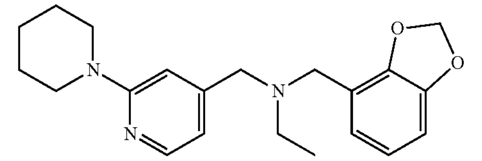 [SMILES: CCN(Cc1ccnc(N2CCCCC2)c1)Cc1cccc2c1OCO2] | — | Compound 9 |
| 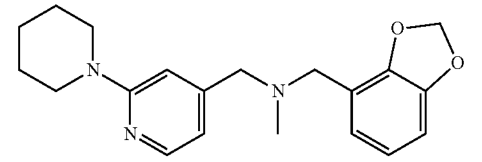 [SMILES: CN(Cc1ccnc(N2CCCCC2)c1)Cc1cccc2c1OCO2] | 22 | Compound 10 |
| 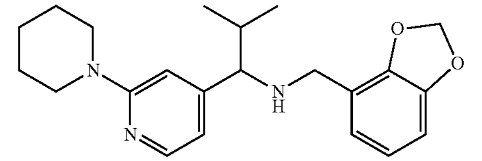 | 110 | Compound 11 |
| 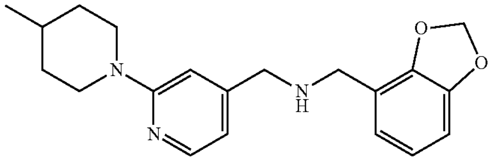 [SMILES: CC1CCN(c2cc(CNCc3cccc4c3OCO4)ccn2)CC1] | 104 | Compound 12 |
| 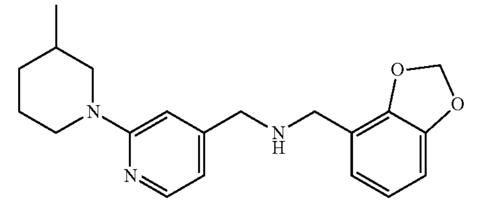 [SMILES: CC1CCCN(c2cc(CNCc3cccc4c3OCO4)ccn2)C1] | 112 | Compound 13 |
| 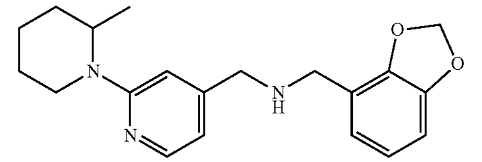 [SMILES: CC1CCCCN1c1cc(CNCc2cccc3c2OCO3)ccn1] | 137.5 | Compound 14 |
| 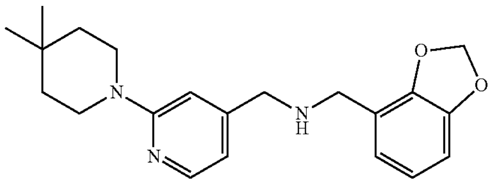 [SMILES: CC1(C)CCN(c2cc(CNCc3cccc4c3OCO4)ccn2)CC1] | 107 | Compound 15 |

TABLE 1-continued
| Structures according to the invention with relative TRPM8 activation in %. | | |
|---|---|---|
| Structure | Relative TRPM8 activation (%) | Compound |
| 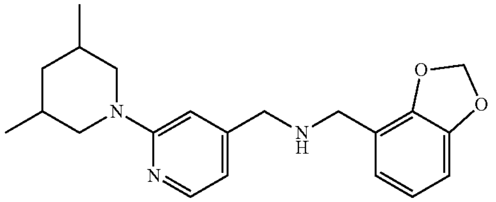 [SMILES: CC1CC(C)CN(c2cc(CNCc3cccc4c3OCO4)ccn2)C1] | 132.7 | Compound 16 |
| 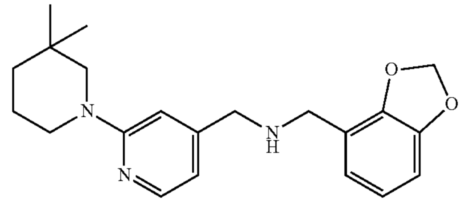 [SMILES: CC1(C)CCCN(c2cc(CNCc3cccc4c3OCO4)ccn2)C1] | 149.5 | Compound 17 |
| 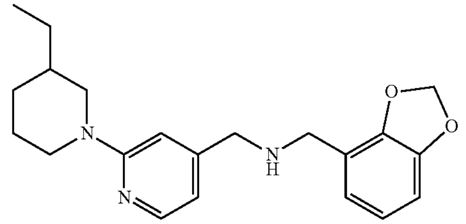 [SMILES: CCC1CCCN(c2cc(CNCc3cccc4c3OCO4)ccn2)C1] | 123.9 | Compound 18 |
| 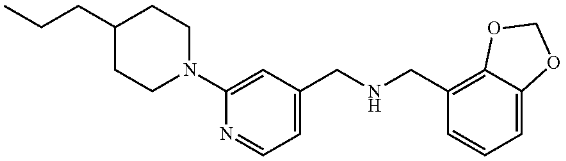 [SMILES: CCCC1CCN(c2cc(CNCc3cccc4c3OCO4)ccn2)CC1] | −0.8 | Compound 18 a |
| 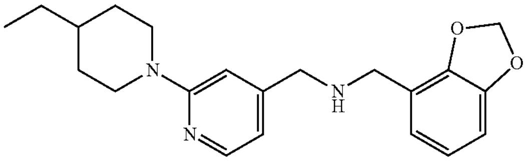 [SMILES: CCC1CCN(c2cc(CNCc3cccc4c3OCO4)ccn2)CC1] | 16 | Compound 19 |
| 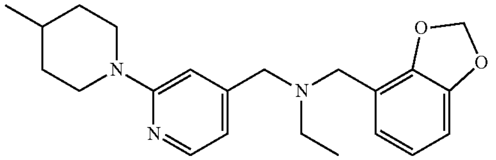 [SMILES: CCN(Cc1ccnc(N2CCC(C)CC2)c1)Cc1cccc2c1OCO2] | 3.4 | Compound 19 a |
| 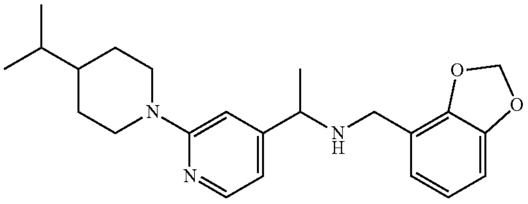 [SMILES: CC(NCc1cccc2c1OCO2)c1ccnc(N2CCC(C(C)C)CC2)c1] | 25.8 | Compound 20 |

TABLE 1-continued
Structures according to the invention with relative TRPM8 activation in %.
| Structure | Relative TRPM8 activation (%) | Compound |
|---|---|---|
| 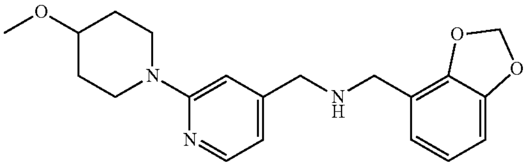 [SMILES: COC1CCN(c2cc(CNCc3cccc4c3OCO4)ccn2)CC1] | 43.1 | Compound 21 |
| 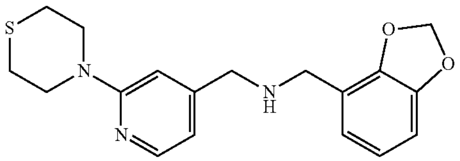 [SMILES: c1cc(CNCc2ccnc(N3CCSCC3)c2)c2c(c1)OCO2] | 155.4 | Compound 22 |
| 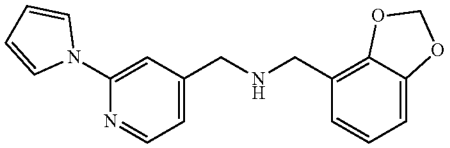 [SMILES: c1cc(CNCc2ccnc(-n3cccc3)c2)c2c(c1)OCO2] | 3 | Compound 22 a |
| 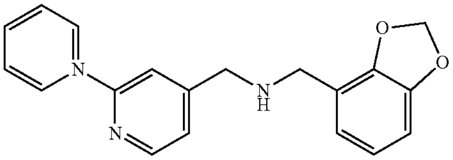 | −1.9 | Compound 22 b |
| 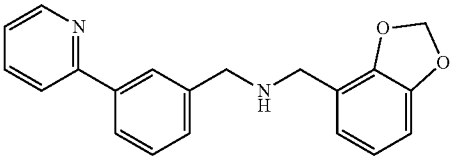 | 3.6 | Compound 22 c |
| 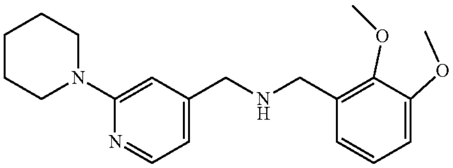 [SMILES: COc1cccc(CNCc2ccnc(N3CCCCC3)c2)c1OC] | 120.8 | Compound 23 |
| 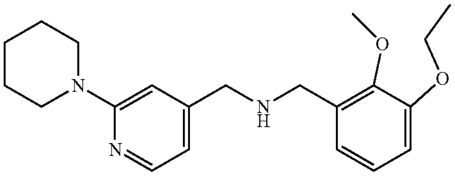 [SMILES: CCOc1cccc(CNCc2ccnc(N3CCCCC3)c2)c1OC] | 112.7 | Compound 24 |
| 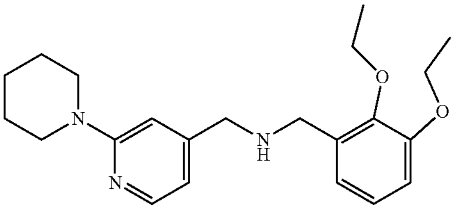 [SMILES: CCOc1cccc(CNCc2ccnc(N3CCCCC3)c2)c1OCC] | 82 | Compound 25 |

TABLE 1-continued
Structures according to the invention with relative TRPM8 activation in %.
| Structure | Relative TRPM8 activation (%) | Compound |
|---|---|---|
| 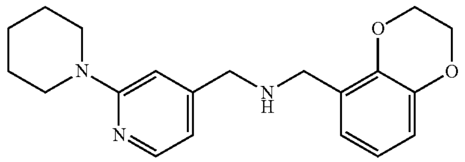 [SMILES: c1cc(CNCc2ccnc(N3CCCCC3)c2)c2c(c1)OCCO2] | 92.7 | Compound 26 |
| 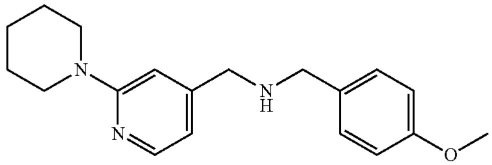 [SMILES: COc1ccc(CNCc2ccnc(N3CCCCC3)c2)cc1] | 129.7 | Compound 27 |
| 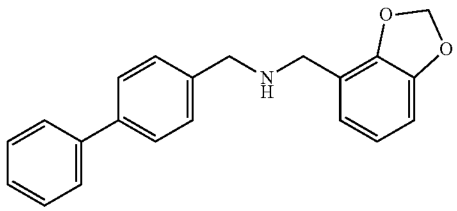 [SMILES: c1ccc(-c2ccc(CNCc3cccc4c3OCO4)cc2)cc1] | 5.4 | Compound 28 |
| 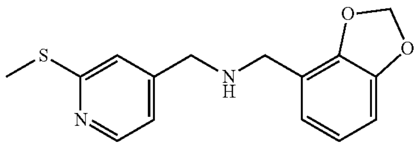 [SMILES: CSc1cc(CNCc2cccc3c2OCO3)ccn1] | 73 | Compound 29 |
| 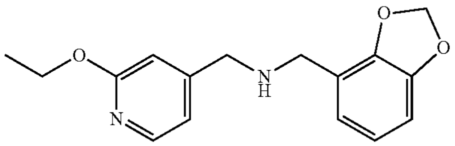 [SMILES: CCOc1cc(CNCc2cccc3c2OCO3)ccn1] | 9 | Compound 30 |
| 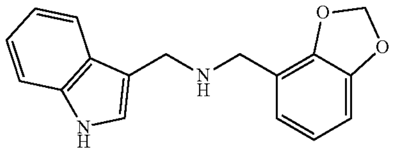 [SMILES: c1cc(CNCc2c[nH]c3ccccc23)c2c(c1)OCO2] | 0 | Compound 31 |
| 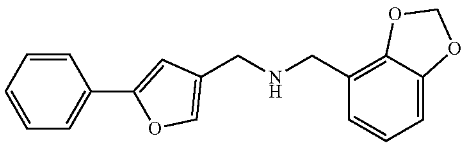 | 0 | Compound 31 a |
| 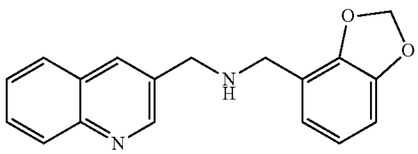 [SMILES: c1cc(CNCc2cnc3ccccc3c2)c2c(c1)OCO2] | 27.7 | Compound 32 |

TABLE 1-continued
Structures according to the invention with relative TRPM8 activation in %.
| Structure | Relative TRPM8 activation (%) | Compound |
|---|---|---|
| 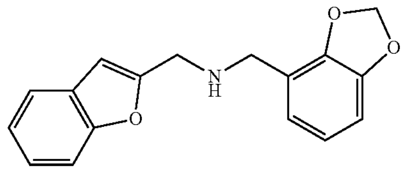 | 1.3 | Compound 32 a |
| 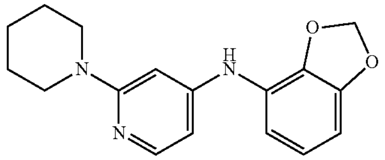 [SMILES: c1cc(Nc2ccnc(N3CCCCC3)c2)c2c(c1)OCO2] | 9.4 | Compound 33 |
| 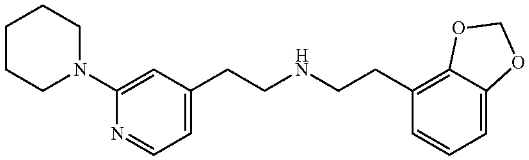 [SMILES: c1cc(CCNCCc2ccnc(N3CCCCC3)c2)c2c(c1)OCO2] | 6.49 | Compound 34 |
| 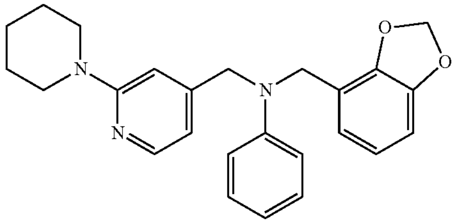 [SMILES: c1ccc(N(Cc2ccnc(N3CCCCC3)c2)Cc2cccc3c2OCO3)cc1] | 0 | Compound 35 |
| 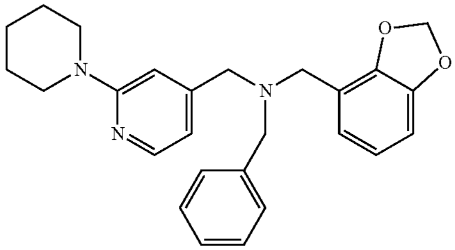 [SMILES: c1ccc(CN(Cc2ccnc(N3CCCCC3)c2)Cc2cccc3c2OCO3)cc1] | 2 | Compound 36 |
| 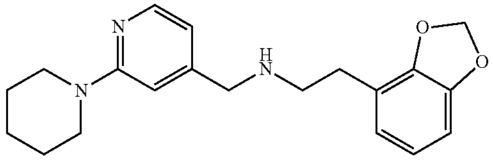 [SMILES: c1cc(CCNCc2ccnc(N3CCCCC3)c2)c2c(c1)OCO2] | 18.2 | Compound 37 |
| 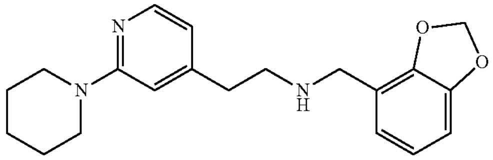 [SMILES: c1cc(CNCCc2ccnc(N3CCCCC3)c2)c2c(c1)OCO2] | 15.8 | Compound 38 |

TABLE 1-continued
| Structures according to the invention with relative TRPM8 activation in %. | | |
|---|---|---|
| Structure | Relative TRPM8 activation (%) | Compound |
| 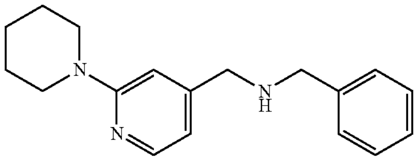 [SMILES: c1ccc(CNCc2ccnc(N3CCCCC3)c2)cc1] | 116.4 | Compound 39 |
| 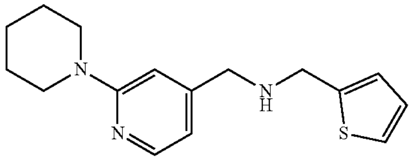 | 112.4 | Compound 40 |
| 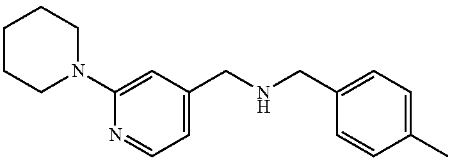 [SMILES: Cc1ccc(CNCc2ccnc(N3CCCCC3)c2)cc1] | 117.9 | Compound 41 |
| 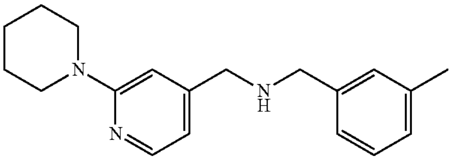 [SMILES: Cc1cccc(CNCc2ccnc(N3CCCCC3)c2)c1] | 107.3 | Compound 42 |
| 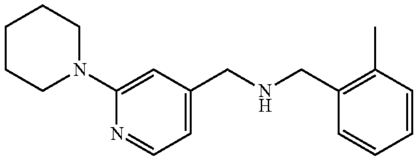 [SMILES: Cc1ccccc1CNCc1ccnc(N2CCCCC2)c1] | 100.9 | Compound 43 |
| 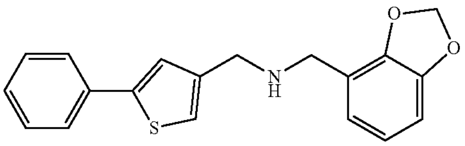 | 0 | Compound 43 a |
| 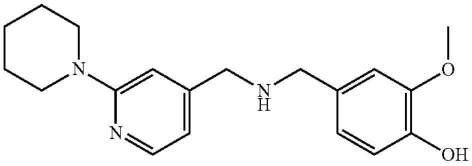 [SMILES: COc1cc(CNCc2ccnc(N3CCCCC3)c2)ccc1O] | 42 | Compound 44 |
| 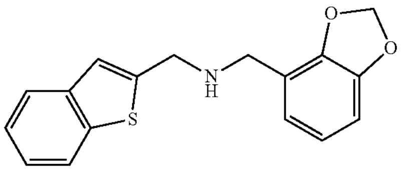 [SMILES: c1cc(CNCc2cc3ccccc3s2)c2c(c1)OCO2] | 10.7 | Compound 45 |

TABLE 1-continued
| Structure | Relative TRPM8 activation (%) | Compound |
|---|---|---|
| 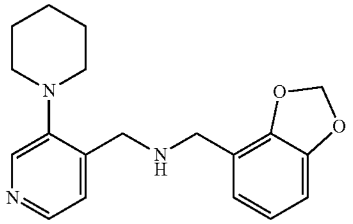 [SMILES: c1cc(CNCc2ccncc2N2CCCCC2)c2c(c1)OCO2] | 3 | Compound 46 |
| 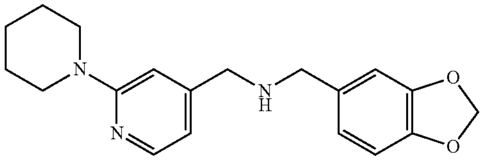 [SMILES: c1cc(CNCc2ccc3c(c2)OCO3)cc(N2CCCCC2)n1] | 102.5 | Compound 47 |
| 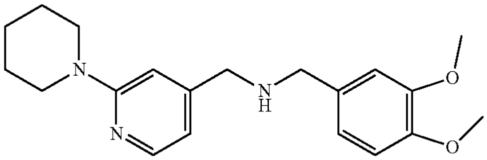 [SMILES: COc1ccc(CNCc2ccnc(N3CCCCC3)c2)cc1OC] | 84.7 | Compound 48 |
| 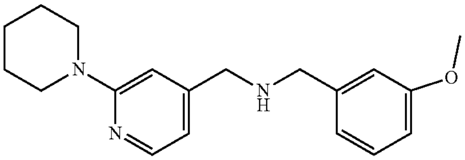 [SMILES: COc1cccc(CNCc2ccnc(N3CCCCC3)c2)c1] | 113.3 | Compound 49 |
| 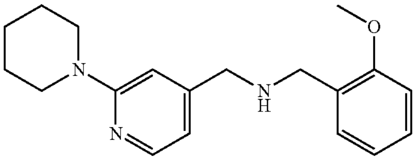 [SMILES: COc1ccccc1CNCc1ccnc(N2CCCCC2)c1] | 97.1 | Compound 50 |
| 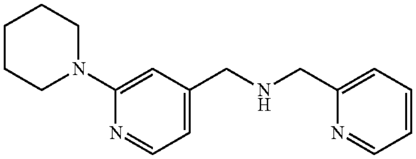 [SMILES: c1ccc(CNCc2ccnc(N3CCCCC3)c2)nc1] | 102.6 | Compound 51 |
| 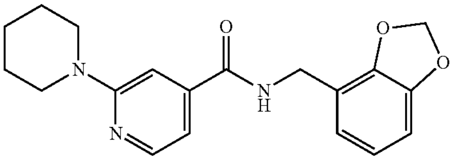 [SMILES: O=C(NCc1cccc2c1OCO2)c1ccnc(N2CCCCC2)c1] | 0 | Compound 51 a |
| 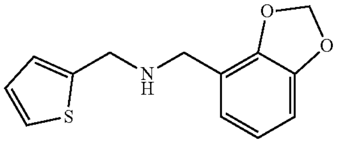 [SMILES: c1csc(CNCc2cccc3c2OCO3)c1] | 0 | Compound 52 |
Structures according to the invention with relative TRPM8 activation in %.

TABLE 1-continued
| Structure | Relative TRPM8 activation (%) | Compound |
|---|---|---|
| 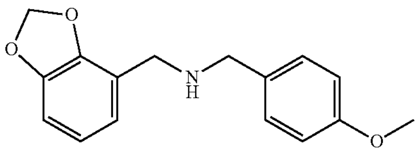 [SMILES: COc1ccc(CNCc2cccc3c2OCO3)cc1] | 2 | Compound 53 |
| 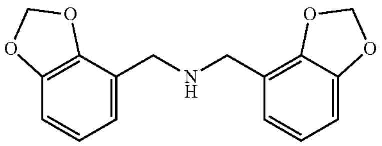 [SMILES: c1cc(CNCc2cccc3c2OCO3)c2c(c1)OCO2] | 3 | Compound 54 |
| 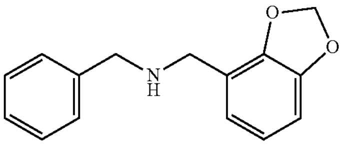 [SMILES: c1ccc(CNCc2cccc3c2OCO3)cc1] | 1 | Compound 55 |
| 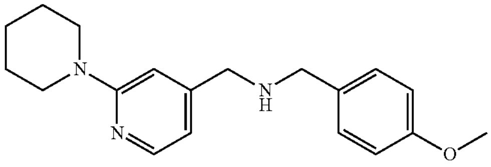 [SMILES: COc1ccc(CNCc2ccnc(N3CCCCC3)c2)cc1] | 120 | Compound 56 |
| 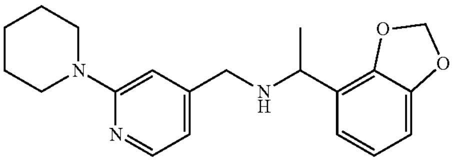 | 8 | Compound 57 |
| 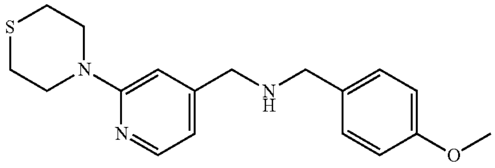 [SMILES: COc1ccc(CNCc2ccnc(N3CCSCC3)c2)cc1] | 131 | Compound 58 |
| 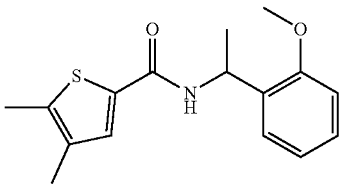 [SMILES: COc1ccccc1C(C)NC(=O)c1cc(C)c(C)s1] | −4 | Compound 59 |
| 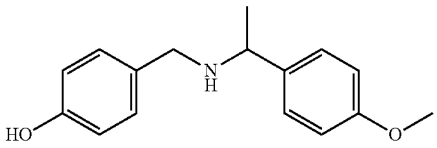 [SMILES: COc1ccc(C(C)NCc2ccc(O)cc2)cc1] | 6 | Compound 60 |
Structures according to the invention with relative TRPM8 activation in %.

TABLE 1-continued
Structures according to the invention with relative TRPM8 activation in %.
| Structure | Relative TRPM8 activation (%) | Compound |
|---|---|---|
| 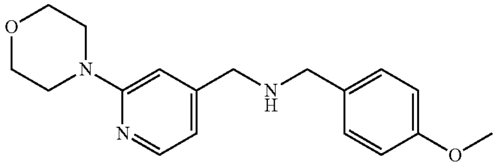 [SMILES: COc1ccc(CNCc2ccnc(N3CCOCC3)c2)cc1] | 114 | Compound 61 |
| 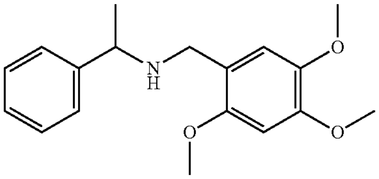 [SMILES: COc1cc(OC)c(OC)cc1CNC(C)c1ccccc1] | 14 | Compound 62 |
| 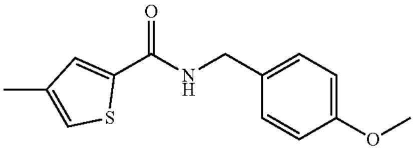 | −1 | Compound 63 |
| 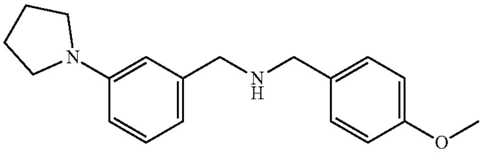 [SMILES: COc1ccc(CNCc2cccc(N3CCCC3)c2)cc1] | 108 | Compound 64 |
| 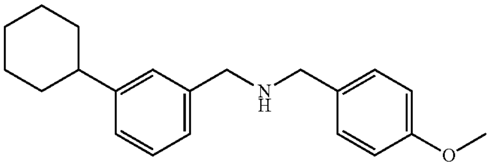 [SMILES: COc1ccc(CNCc2cccc(C3CCCCC3)c2)cc1] | 75 | Compound 65 |
| 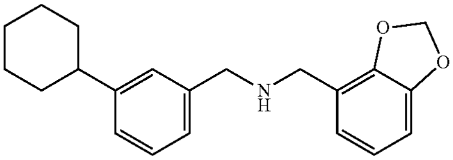 [SMILES: c1cc(CNCc2cccc3c2OCO3)cc(C2CCCCC2)c1] | 2 | Compound 66 |
| 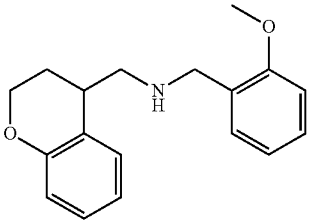 [SMILES: COc1ccccc1CNCC1CCOc2ccccc21] | −1 | Compound 67 |
| 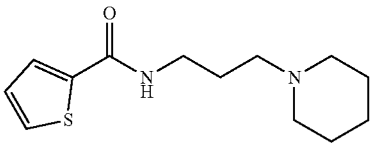 [SMILES: O=C(NCCCN1CCCCC1)c1cccs1] | 0 | Compound 68 |

TABLE 1-continued
| Structures according to the invention with relative TRPM8 activation in %. | | |
|---|---|---|
| Structure | Relative TRPM8 activation (%) | Compound |
| 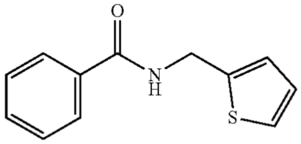 [SMILES: O=C(NCc1cccs1)c1ccccc1] | 0 | Compound 69 |
| 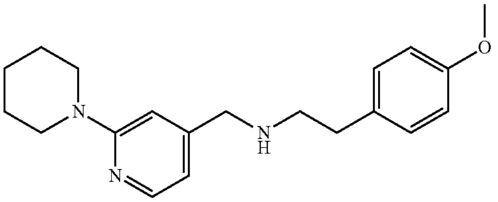 [SMILES: COc1ccc(CCNCc2ccnc(N3CCCCC3)c2)cc1] | — | Compound 70 |
| 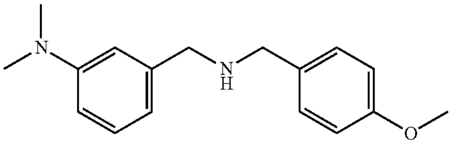 | 67 | Compound 71 |
| 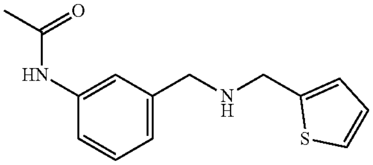 [SMILES: CC(=O)Nc1cccc(CNCc2cccs2)c1] | 2 | Compound 72 |
| 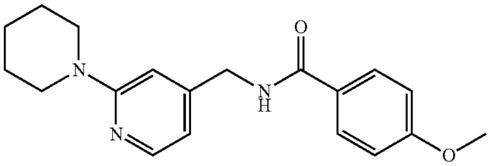 | −3 | Compound 73 |
| 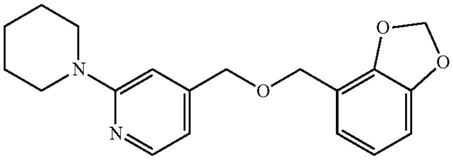 | 1 | Compound 74 |
| 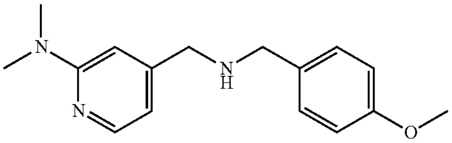 | 113 | Compound 75 |
| 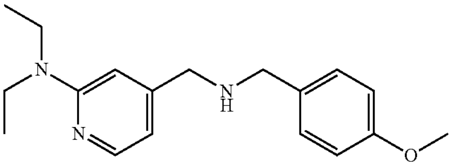 [SMILES: CCN(CC)c1cc(CNCc2ccc(OC)cc2)ccn1] | 114 | Compound 76 |

TABLE 1-continued
Structures according to the invention with relative TRPM8 activation in %.
| Structure | Relative TRPM8 activation (%) | Compound |
|---|---|---|
| 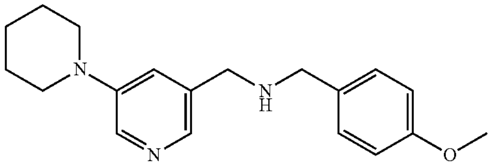 [SMILES: COc1ccc(CNCc2cncc(N3CCCCC3)c2)cc1] | — | Compound 77 |
| 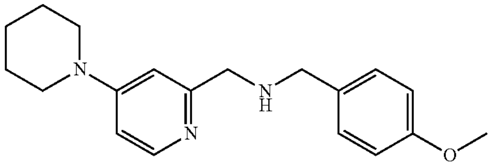 [SMILES: COc1ccc(CNCc2cc(N3CCCCC3)ccn2)cc1] | — | Compound 79 |
| 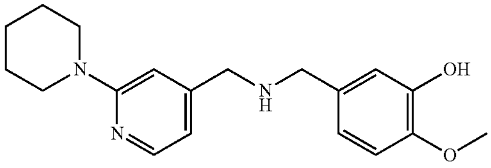 [SMILES: COc1ccc(CNCc2ccnc(N3CCCCC3)c2)cc1O] | 113 | Compound 80 |
| 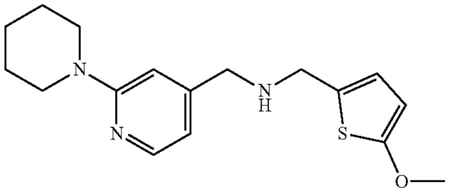 [SMILES: COc1ccc(CNCc2ccnc(N3CCCCC3)c2)s1] | — | Compound 81 |
| 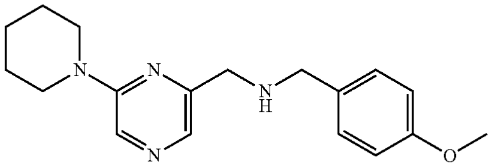 [SMILES: COc1ccc(CNCc2cncc(N3CCCCC3)n2)cc1] | — | Compound 82 |
| 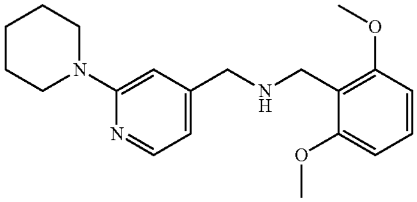 [SMILES: COc1cccc(OC)c1CNCc1ccnc(N2CCCCC2)c1] | 86 | Compound 83 |
| 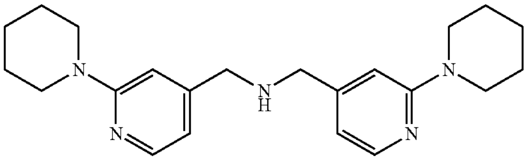 [SMILES: c1cc(CNCc2ccnc(N3CCCCC3)c2)cc(N2CCCCC2)n1] | 57 | Compound 84 |
| 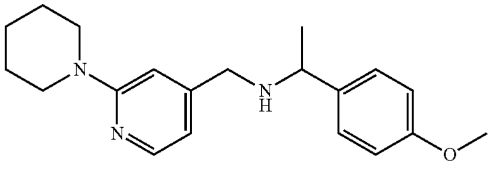 [SMILES: COc1ccc(C(C)NCc2ccnc(N3CCCCC3)c2)cc1] | 118 | Compound 85 |

TABLE 1-continued

Structures according to the invention with relative TRPM8 activation in %.

| Structure | Relative TRPM8 activation (%) | Compound |
|---|---|---|
| 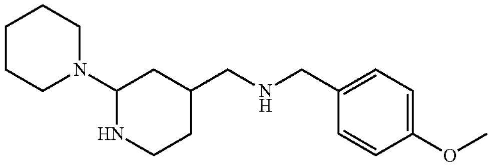 [SMILES: COc1ccc(CNCC2CCNC(N3CCCCC3)C2)cc1] | — | Compound 86 |
| 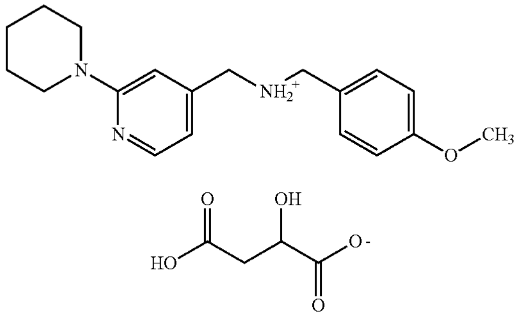 | 133 | Compound 87 |
| 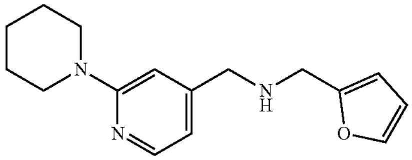 [SMILES: c1coc(CNCc2ccnc(N3CCCCC3)c2)c1] | — | Compound 88 |
| 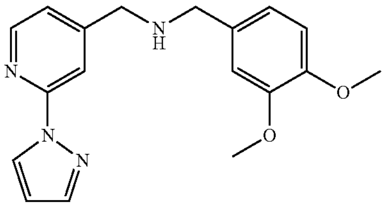 [SMILES: COc1ccc(CNCc2ccnc(-n3cccn3)c2)cc1OC] | — | Compound 89 |
| 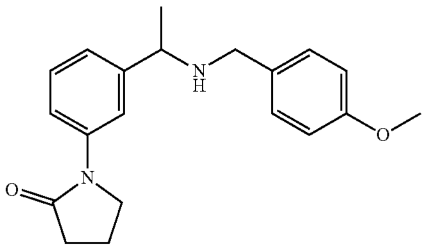 [SMILES: COc1ccc(CNC(C)c2cccc(N3CCCC3=O)c2)cc1] | — | Compound 90 |

in particular compounds 1, 2, 4, 8, 11, 12, 13, 14, 15, 16, 17, 18, 22, 23, 24, 25, 26, 27, 29, 39, 40, 41, 42, 43, 47, 48, 49, 50, 51, 56, 58, 61, 64, 65, 71, 75, 76, 80, 83, 84, 85 and 87 and further preferably compounds 1, 8, 11, 12, 13, 14, 15, 16, 17, 18, 22, 23, 24, 27, 39, 40, 41, 42, 43, 47, 49, 51, 56, 58, 61, 64, 75, 76, 80, 85 and 87 and particularly preferably compounds 1, 8, 11, 13, 14, 16, 17, 18, 22, 23, 24, 27, 39, 40, 41, 49, 56, 58, 61, 75, 76, 80, 85 and 87.

The cooling agents according to the general formula (I) or (II) listed in Table 1 are either present in neutral, uncharged form or are present in the form of their salts, such as an acid addition salt, with inorganic or organic, monovalent or polyvalent carboxylic acids, as described in detail above. In this respect, what has been said above also applies equally here.

The cooling agents according to Table 1 can be present in stereoisomer-pure form or as mixtures of different stereoisomers and consequently can also be used in formulations in this way.

Surprisingly, it has been shown that the compounds of the invention exhibit particularly high TRPM8 activations and are thus excellently suited as cooling agents.

The most preferred cooling agents, i.e. cooling agents with a particularly efficient and strong TRPM8 activation, i.e. efficient and intensive cooling effect at a low application rate, are the compounds 1, 2, 4, 8, 11, 12, 13, 14, 15, 16, 17, 18, 22, 23, 24, 25, 26, 27, 29, 39, 40, 41, 42, 43, 47, 48, 49, 50, 51, 56, 58, 61, 64, 65, 71, 75, 76, 80, 83, 84, 85 and 87 (TRPM8 activation a 50%) and in particular compounds 1, 8, 11, 12, 13, 14, 15, 16, 17, 18, 22, 23, 24, 27, 39, 40, 41, 42, 43, 47, 49, 51, 56, 58, 61, 64, 75, 76, 80, 85 and 87 (TRPM8 activation a 100%). Particularly preferred are compounds 1, 8, 11, 13, 14, 16, 17, 18, 22, 23, 24, 27, 39, 40, 41, 49, 56, 58, 61, 75, 76, 80, 85 and 87, which show exceptionally high TRPM8 activity (TRPM8 activation a 110%).

Because of their outstanding relative TRPM8 activation, compounds 8 (TRPM8 activation of 174.6%), 27 (TRPM8 activation of 129.7%) and 39 (TRPM8 activation of 116.4) are the most preferred.

In addition, compounds of the formulae (I) and (II) in which n and m are both 1 appear to be preferred with regard to the determined TRPM8 activity.

Even more preferred are the physiological cooling agents of the general formula (I) or formula (II) selected from the group consisting of the compounds shown in Table 2:

TABLE 2

Structures according to the invention with relative TRPM8 activation in %.

| Structure | Relative TRPM8 activation (%) | Compound |
|---|---|---|
| 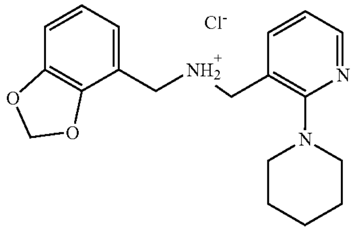 [SMILES: c1cnc(N2CCCCC2)c(CNCc2cccc3c2OCO3)c1 ; [Cl-]] | 69.8 | Compound 4 |
| 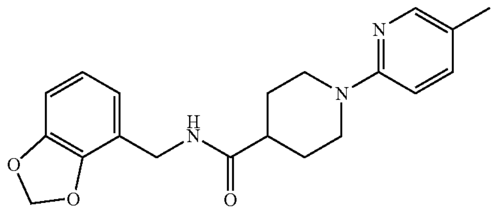 [SMILES: Cc1ccc(N2CCC(C(=O)NCc3cccc4c3OCO4)CC2)nc1] | 2.4 | Compound 5 a |
| 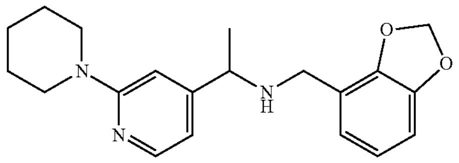 [SMILES: CC(NCc1cccc2c1OCO2)c1ccnc(N2CCCCC2)c1] | 174.6 | Compound 8 |
| 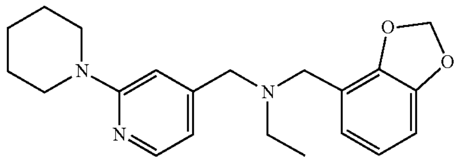 [SMILES: CCN(Cc1ccnc(N2CCCCC2)c1)Cc1cccc2c1OCO2] | — | Compound 9 |
| 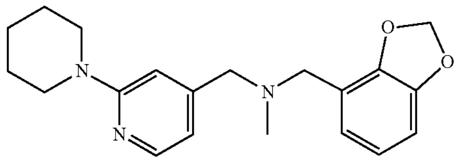 [SMILES: CN(Cc1ccnc(N2CCCCC2)c1)Cc1cccc2c1OCO2] | 22 | Compound 10 |
| 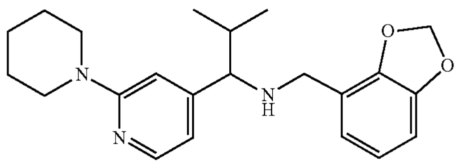 [SMILES: CC(C)C(NCc1cccc2c1OCO2)c1ccnc(N2CCCCC2)c1] | 110 | Compound 11 |

TABLE 2-continued
Structures according to the invention with relative TRPM8 activation in %.
| Structure | Relative TRPM8 activation (%) | Compound |
|---|---|---|
| 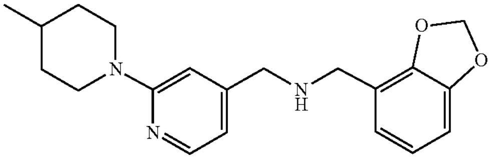 [SMILES: CC1CCN(c2cc(CNCc3cccc4c3OCO4)ccn2)CC1] | 104 | Compound 12 |
| 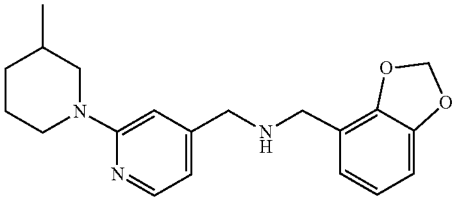 [SMILES: CC1CCCN(c2cc(CNCc3cccc4c3OCO4)ccn2)C1] | 112 | Compound 13 |
| 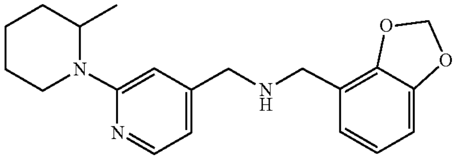 [SMILES: CC1CCCCN1c1cc(CNCc2cccc3c2OCO3)ccn1] | 137.5 | Compound 14 |
| 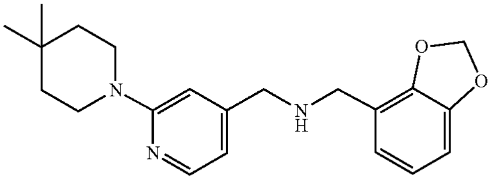 [SMILES: CC1(C)CCN(c2cc(CNCc3cccc4c3OCO4)ccn2)CC1] | 107 | Compound 15 |
| 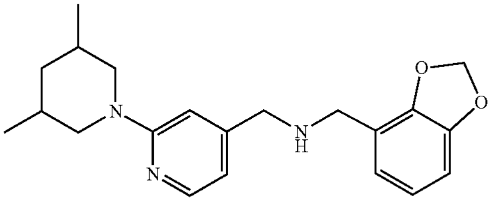 [SMILES: CC1CC(C)CN(c2cc(CNCc3cccc4c3OCO4)ccn2)C1] | 132.7 | Compound 16 |
| 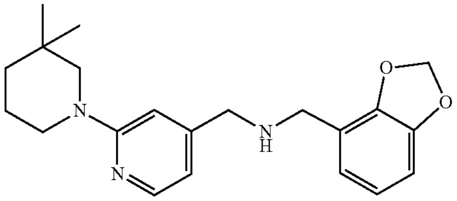 [SMILES: CC1(C)CCCN(c2cc(CNCc3cccc4c3OCO4)ccn2)C1] | 149.5 | Compound 17 |
| 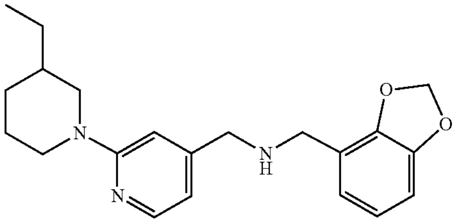 [SMILES: CCC1CCCN(c2cc(CNCc3cccc4c3OCO4)ccn2)C1] | 123.9 | Compound 18 |

TABLE 2-continued
Structures according to the invention with relative TRPM8 activation in %.
| Structure | Relative TRPM8 activation (%) | Compound |
|---|---|---|
| 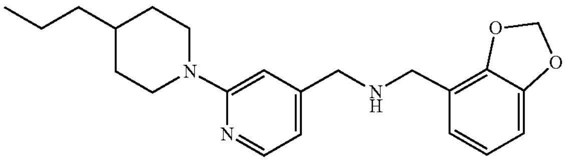 [SMILES: CCCC1CCN(c2cc(CNCc3cccc4c3OCO4)ccn2)CC1] | −0.8 | Compound 18 a |
| 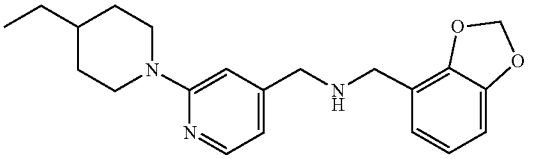 [SMILES: CCC1CCN(c2cc(CNCc3cccc4c3OCO4)ccn2)CC1] | 16 | Compound 19 |
| 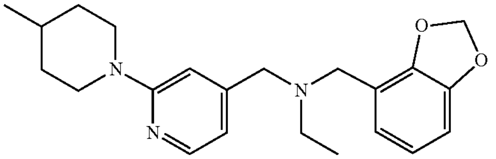 [SMILES: CCN(Cc1ccnc(N2CCC(C)CC2)c1)Cc1cccc2c1OCO2] | 3.4 | Compound 19 a |
| 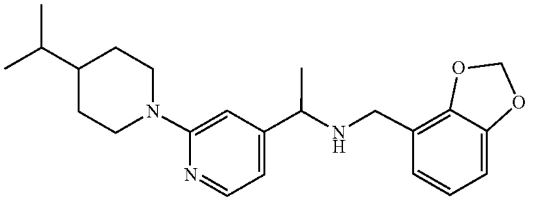 [SMILES: CC(NCc1cccc2c1OCO2)c1ccnc(N2CCC(C(C)C)CC2)c1] | 25.8 | Compound 20 |
| 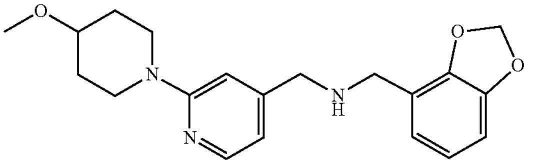 [SMILES: COC1CCN(c2cc(CNCc3cccc4c3OCO4)ccn2)CC1] | 43.1 | Compound 21 |
| 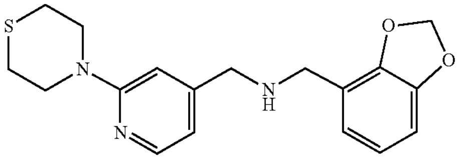 [SMILES: c1cc(CNCc2ccnc(N3CCSCC3)c2)c2c(c1)OCO2] | 155.4 | Compound 22 |
| 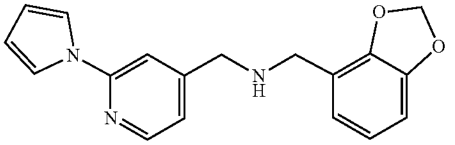 [SMILES: c1cc(CNCc2ccnc(-n3cccc3)c2)c2c(c1)OCO2] | 3 | Compound 22 a |
| 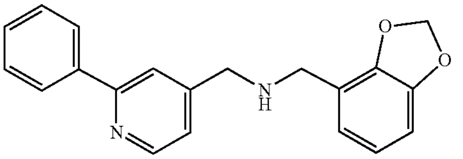 [SMILES: c1ccc(-c2cc(CNCc3cccc4c3OCO4)ccn2)cc1] | −1.9 | Compound 22 b |

TABLE 2-continued
Structures according to the invention with relative TRPM8 activation in %.
| Structure | Relative TRPM8 activation (%) | Compound |
|---|---|---|
| 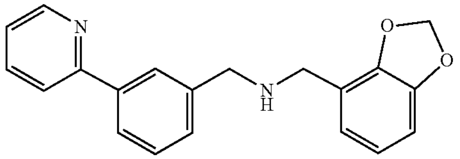 [SMILES: c1ccc(-c2cccc(CNCc3cccc4c3OCO4)c2)nc1] | 3.6 | Compound 22 c |
| 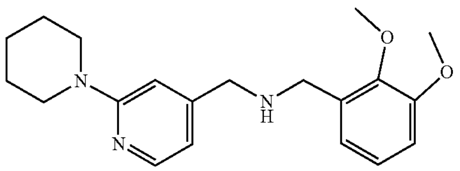 [SMILES: COc1cccc(CNCc2ccnc(N3CCCCC3)c2)c1OC] | 120.8 | Compound 23 |
| 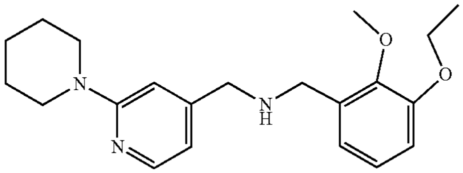 [SMILES: CCOc1cccc(CNCc2ccnc(N3CCCCC3)c2)c1OC] | 112.7 | Compound 24 |
| 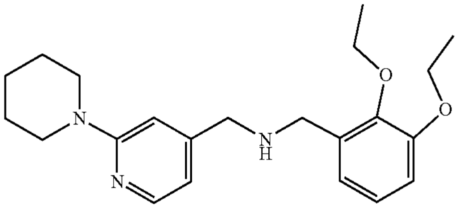 [SMILES: CCOc1cccc(CNCc2ccnc(N3CCCCC3)c2)c1OCC] | 82 | Compound 25 |
| 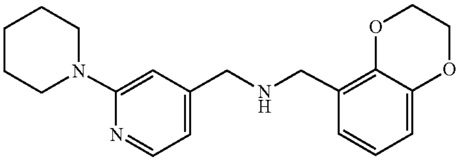 [SMILES: c1cc(CNCc2ccnc(N3CCCCC3)c2)c2c(c1)OCCO2] | 92.7 | Compound 26 |
| 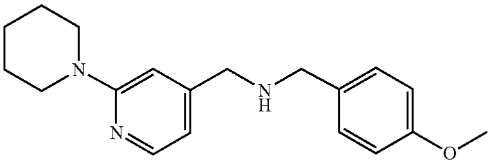 [SMILES: COc1ccc(CNCc2ccnc(N3CCCCC3)c2)cc1] | 129.7 | Compound 27 |
| 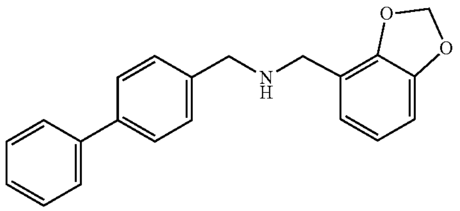 [SMILES: c1ccc(-c2ccc(CNCc3cccc4c3OCO4)cc2)cc1] | 5.4 | Compound 28 |
| 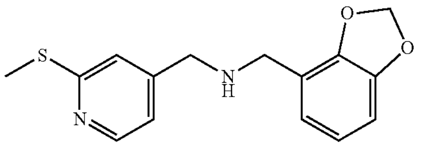 [SMILES: CSc1cc(CNCc2cccc3c2OCO3)ccn1] | 73 | Compound 29 |

TABLE 2-continued
Structures according to the invention with relative TRPM8 activation in %.
| Structure | Relative TRPM8 activation (%) | Compound |
|---|---|---|
| 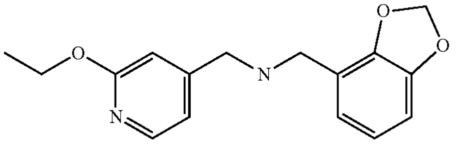 | 9 | Compound 30 |
| 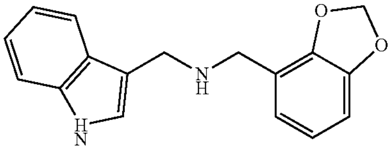 [SMILES: c1cc(CNCc2c[nH]c3ccccc23)c2c(c1)OCO2] | 0 | Compound 31 |
| 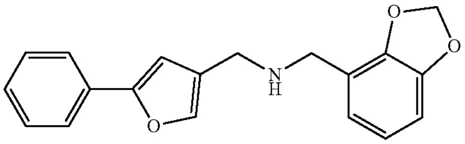 [SMILES: c1ccc(-c2cc(CNCc3cccc4c3OCO4)co2)cc1] | 0 | Compound 31 a |
| 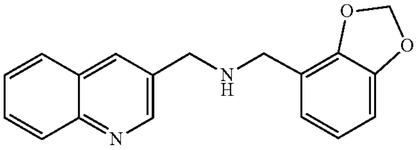 [SMILES: c1cc(CNCc2cnc3ccccc3c2)c2c(c1)OCO2] | 27.7 | Compound 32 |
| 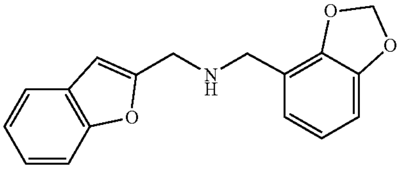 [SMILES: c1cc(CNCc2cc3ccccc3o2)c2c(c1)OCO2] | 1.3 | Compound 32 a |
| 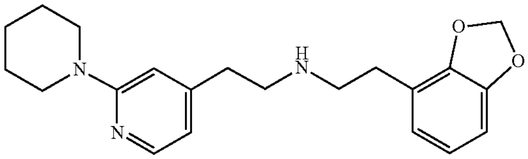 [SMILES: c1cc(CCNCCc2ccnc(N3CCCCC3)c2)c2c(c1)OCO2] | 6.49 | Compound 34 |
| 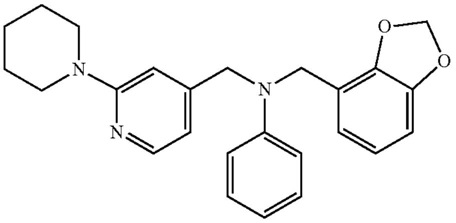 [SMILES: c1ccc(N(Cc2ccnc(N3CCCCC3)c2)Cc2cccc3c2OCO3)cc1] | 0 | Compound 35 |
| 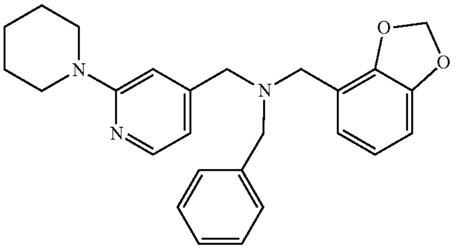 [SMILES: c1ccc(CN(Cc2ccnc(N3CCCCC3)c2)Cc2cccc3c2OCO3)cc1] | 2 | Compound 36 |

TABLE 2-continued
| Structures according to the invention with relative TRPM8 activation in %. | | |
|---|---|---|
| Structure | Relative TRPM8 activation (%) | Compound |
| 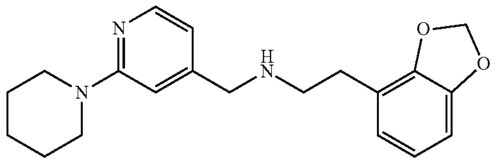 [SMILES: c1cc(CCNCc2ccnc(N3CCCCC3)c2)c2c(c1)OCO2] | 18.2 | Compound 37 |
| 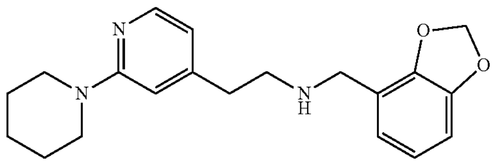 [SMILES: c1cc(CNCCc2ccnc(N3CCCCC3)c2)c2c(c1)OCO2] | 15.8 | Compound 38 |
| 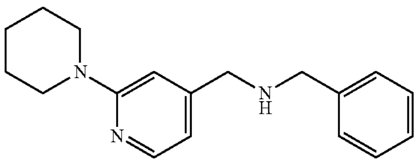 [SMILES: c1ccc(CNCc2ccnc(N3CCCCC3)c2)cc1] | 116.4 | Compound 39 |
| 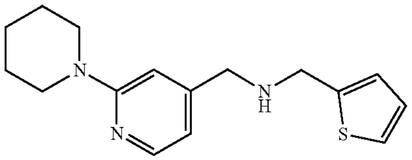 [SMILES: c1csc(CNCc2ccnc(N3CCCCC3)c2)c1] | 112.4 | Compound 40 |
| 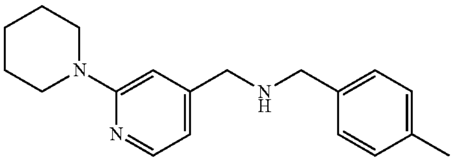 [SMILES: Cc1ccc(CNCc2ccnc(N3CCCCC3)c2)cc1] | 117.9 | Compound 41 |
| 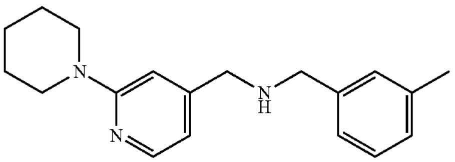 [SMILES: Cc1cccc(CNCc2ccnc(N3CCCCC3)c2)c1] | 107.3 | Compound 42 |
| 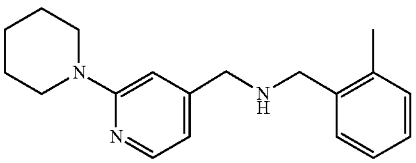 [SMILES: Cc1ccccc1CNCc1ccnc(N2CCCCC2)c1] | 100.9 | Compound 43 |
| 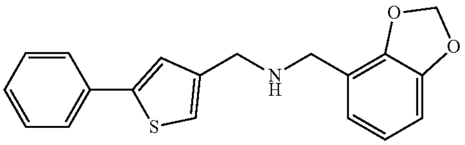 | 0 | Compound 43 a |

TABLE 2-continued
Structures according to the invention with relative TRPM8 activation in %.
| Structure | Relative TRPM8 activation (%) | Compound |
| --- | --- | --- |
| 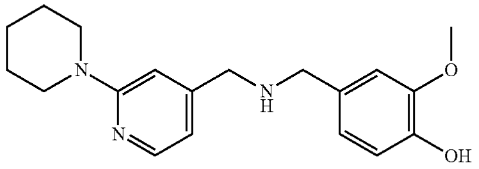 [SMILES: COc1cc(CNCc2ccnc(N3CCCCC3)c2)ccc1O] | 42 | Compound 44 |
| 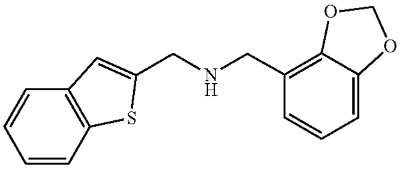 | 10.7 | Compound 45 |
| 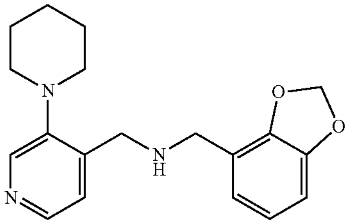 [SMILES: c1cc(CNCc2ccncc2N2CCCCC2)c2c(c1)OCO2] | 3 | Compound 46 |
| 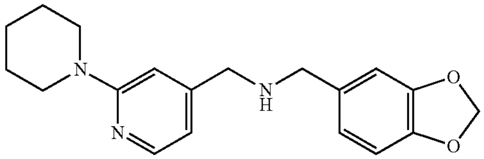 [SMILES: c1cc(CNCc2ccc3c(c2)OCO3)cc(N2CCCCC2)n1] | 102.5 | Compound 47 |
| 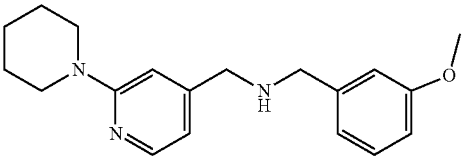 [SMILES: COc1cccc(CNCc2ccnc(N3CCCCC3)c2)c1] | 113.3 | Compound 49 |
| 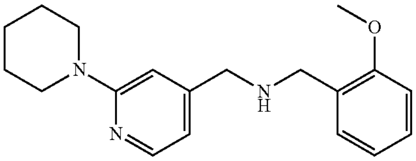 [SMILES: COc1ccccc1CNCc1ccnc(N2CCCCC2)c1] | 97.1 | Compound 50 |
| 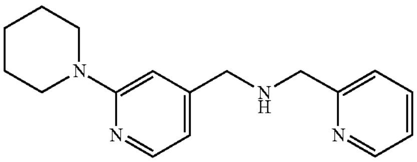 | 102.6 | Compound 51 |
| 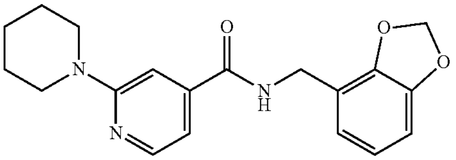 | 0 | Compound a |

TABLE 2-continued
| Structure | Relative TRPM8 activation (%) | Compound |
|---|---|---|
| 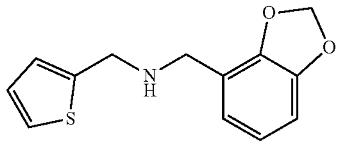 [SMILES: c1csc(CNCc2cccc3c2OCO3)c1] | 0 | Compound 52 |
| 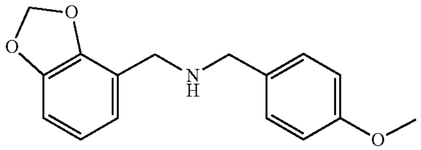 [SMILES: COc1ccc(CNCc2cccc3c2OCO3)cc1] | 2 | Compound 53 |
| 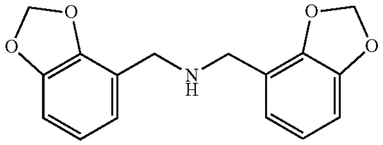 [SMILES: c1cc(CNCc2cccc3c2OCO3)c2c(c1)OCO2] | 3 | Compound 54 |
| 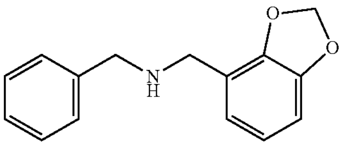 [SMILES: c1ccc(CNCc2cccc3c2OCO3)cc1] | 1 | Compound 55 |
| 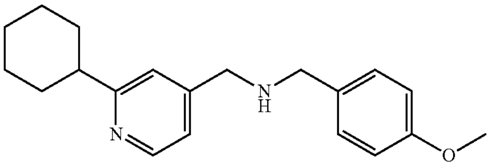 | 120 | Compound 56 |
| 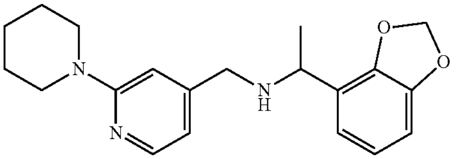 | 8 | Compound 57 |
| 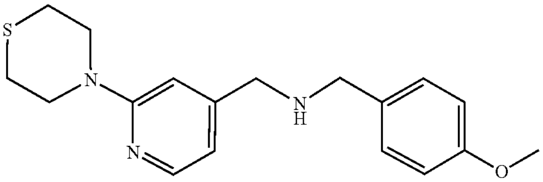 [SMILES: COc1ccc(CNCc2ccnc(N3CCSCC3)c2)cc1] | 131 | Compound 58 |
| 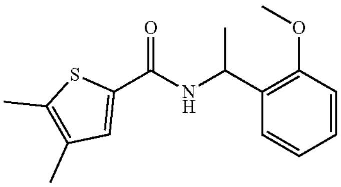 [SMILES: COc1ccccc1C(C)NC(=O)c1cc(C)c(C)s1] | −4 | Compound 59 |
| 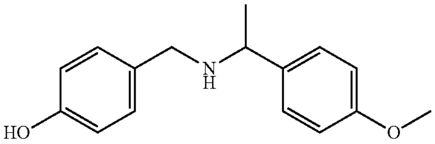 [SMILES: COc1ccc(C(C)NCc2ccc(O)cc2)cc1] | 6 | Compound 60 |
Structures according to the invention with relative TRPM8 activation in %.

TABLE 2-continued
Structures according to the invention with relative TRPM8 activation in %.
| Structure | Relative TRPM8 activation (%) | Compound |
|---|---|---|
| 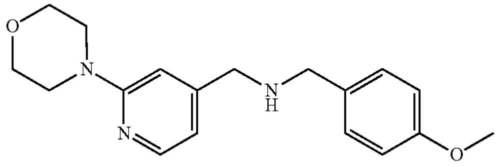 [SMILES: COc1ccc(CNCc2ccnc(N3CCOCC3)c2)cc1] | 114 | Compound 61 |
| 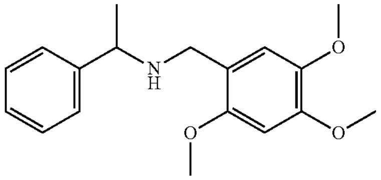 [SMILES: COc1cc(OC)c(OC)cc1CNC(C)c1ccccc1] | 14 | Compound 62 |
| 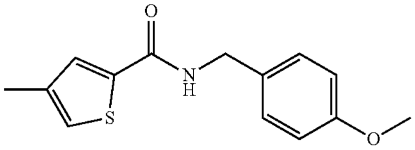 | −1 | Compound 63 |
| 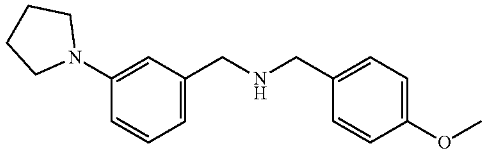 [SMILES: COc1ccc(CNCc2cccc(N3CCCC3)c2)cc1] | 108 | Compound 64 |
| 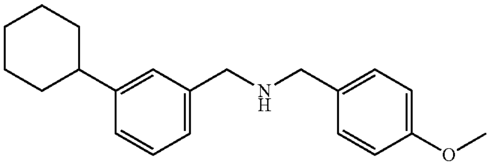 [SMILES: COc1ccc(CNCc2cccc(C3CCCCC3)c2)cc1] | 75 | Compound 65 |
| 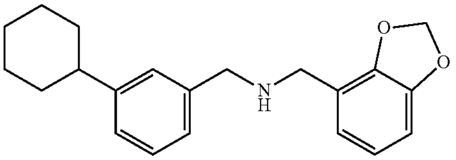 | 2 | Compound 66 |
| 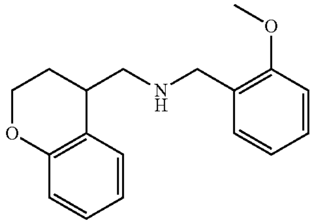 [SMILES: COc1ccccc1CNCC1CCOc2ccccc21] | −1 | Compound 67 |
| 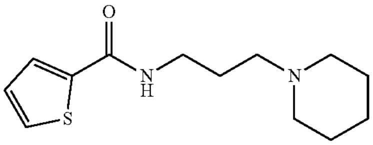 [SMILES: O=C(NCCCN1CCCCC1)c1cccs1] | 0 | Compound 68 |

TABLE 2-continued
Structures according to the invention with relative TRPM8 activation in %.
| Structure | Relative TRPM8 activation (%) | Compound |
|---|---|---|
| 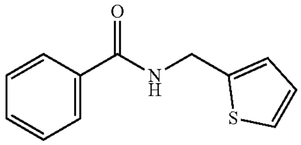 [SMILES: O=C(NCc1cccs1)c1ccccc1] | 0 | Compound 69 |
| 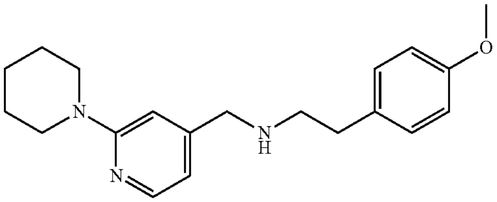 [SMILES: COc1ccc(CCNCc2ccnc(N3CCCCC3)c2)cc1] | — | Compound 70 |
| 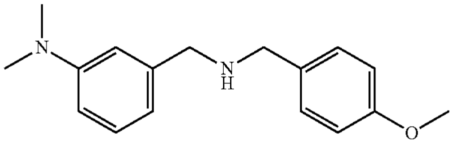 | 67 | Compound 71 |
| 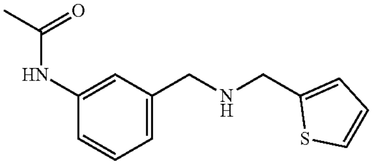 [SMILES: CC(=O)Nc1cccc(CNCc2cccs2)c1] | 2 | Compound 72 |
| 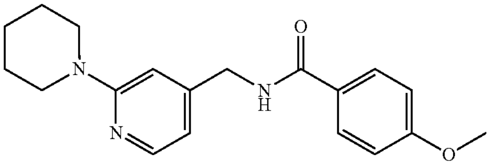 | −3 | Compound 73 |
| 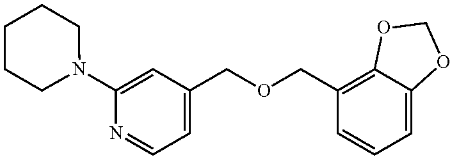 | 1 | Compound 74 |
| 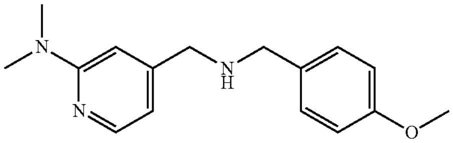 | 113 | Compound 75 |
| 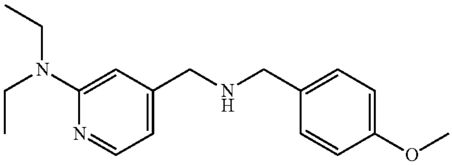 [SMILES: CCN(CC)c1cc(CNCc2ccc(OC)cc2)ccn1] | 114 | Compound 76 |

TABLE 2-continued
Structures according to the invention with relative TRPM8 activation in %.
| Structure | Relative TRPM8 activation (%) | Compound |
|---|---|---|
| 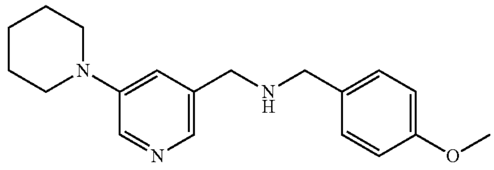 [SMILES: COc1ccc(CNCc2cncc(N3CCCCC3)c2)cc1] | — | Compound 77 |
| 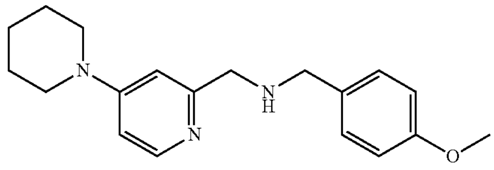 [SMILES: COc1ccc(CNCc2cc(N3CCCCC3)ccn2)cc1] | — | Compound 79 |
| 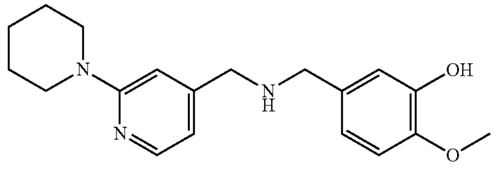 [SMILES: COc1ccc(CNCc2ccnc(N3CCCCC3)c2)cc1O] | 113 | Compound 80 |
| 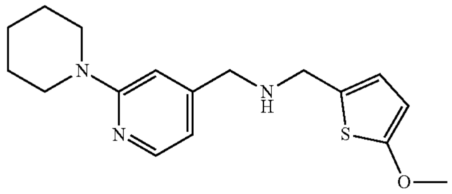 [SMILES: COc1ccc(CNCc2ccnc(N3CCCCC3)c2)s1] | — | Compound 81 |
| 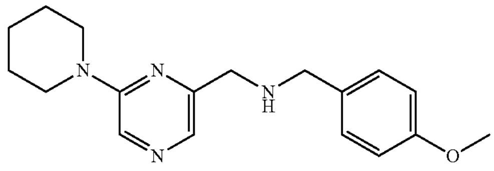 | — | Compound 82 |
| 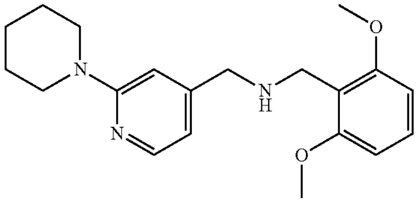 [SMILES: COc1cccc(OC)c1CNCc1ccnc(N2CCCCC2)c1] | 86 | Compound 83 |
| 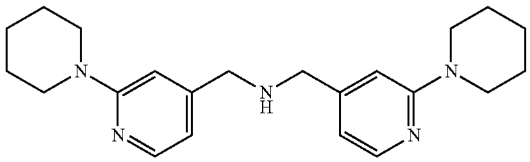 [SMILES: c1cc(CNCc2ccnc(N3CCCCC3)c2)cc(N2CCCCC2)n1] | 57 | Compound 84 |
| 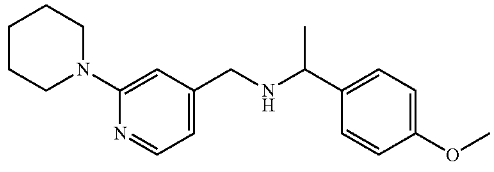 | 118 | Compound 85 |

TABLE 2-continued

Structures according to the invention with relative TRPM8 activation in %.

| Structure | Relative TRPM8 activation (%) | Compound |
|---|---|---|
| 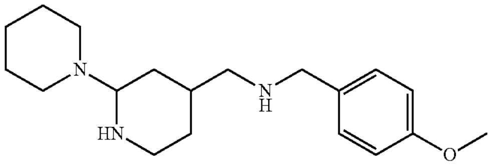 [SMILES: COc1ccc(CNCC2CCNC(N3CCCCC3)C2)cc1] | — | Compound 86 |
| 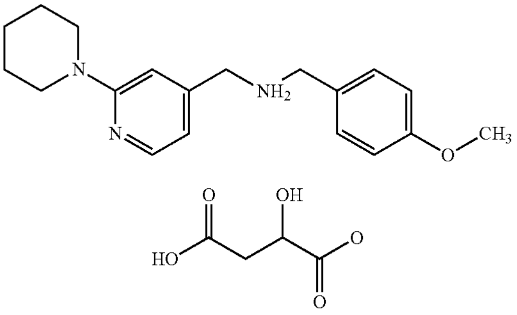 | 133 | Compound 87 |
| 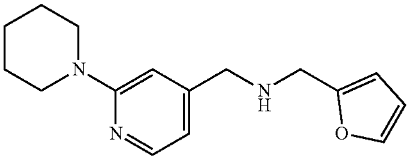 | — | Compound 88 |
| 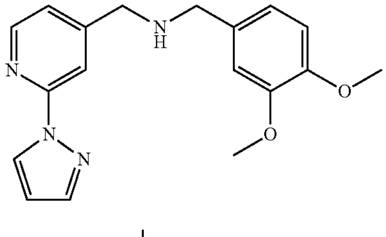 | — | Compound 89 |
| 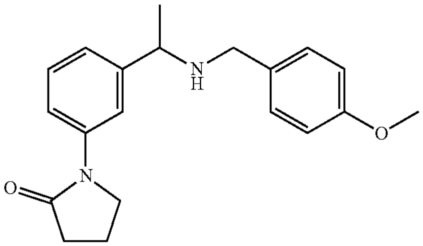 [SMILES: COc1ccc(CNC(C)c2cccc(N3CCCC3=O)c2)cc1] | — | Compound 90 |

in particular compounds 4, 8, 11, 12, 13, 14, 15, 16, 17, 18, 22, 23, 24, 25, 26, 27, 29, 39, 40, 41, 42, 43, 47, 49, 50, 51, 56, 58, 61, 64, 65, 71, 75, 76, 80, 83, 84, 85 and 87 (TRPM8 activity a 50%) and further preferably compounds 8, 11, 12, 13, 14, 15, 16, 17, 18, 22, 23, 24, 27, 39, 40, 41, 42, 43, 47, 49, 51, 56, 58, 61, 64, 75, 76, 80, 85 and 87 (TRPM8 activity a 100%) and particularly preferably compounds 8, 11, 13, 14, 16, 17, 18, 22, 23, 24, 27, 39, 40, 41, 49, 56, 58, 61, 75, 76, 80, 85 and 87 (TRPM8 activity a 110%).

The cooling agents according to the general formula (I) or (II) listed in Table 2 are either present in neutral, uncharged form or are present in the form of their salts, such as acid addition salt, with inorganic or organic, monovalent or polyvalent carboxylic acids, as described in detail above. In this respect, what has been said above also applies equally here.

Particularly preferred are those compounds in which in the general formula (I) or (II) R1 is an optionally substituted phenyl group (aryl group) and/or an optionally substituted thiophenyl group (heteroaryl group) and/or an optionally substituted pyridinyl group (heteroaryl group) and/or an optionally substituted 1,3-benzodioxolyl group and R7 represents an optionally substituted phenyl group (aryl group) and/or an optionally substituted thiophenyl group (heteroaryl group) and/or optionally substituted pyridinyl group (heteroaryl group) and/or an optionally substituted 1,3-benzodioxolyl group. For these compounds, particularly high TRPM8 activities and sensory intensive cooling effects could be determined. Even in very small application quantities, the compounds show significantly higher cooling intensities compared to compounds of the prior art.

Because of their relative TRPM8 activation, compounds 8 (TRPM8 activation of 174.6%), 27 (TRPM8 activation of 129.7%) and 39 (TRPM8 activation of 116.4) are the most preferred.

Compound 8 is characterised in that R1 represents a benzodioxol-4-yl group and R7 represents a substituted heteroaryl group (here: a substituted pyridinyl group). More precisely, the pyridinyl group is substituted with a heterocycloalkyl group (piperidinyl group).

Compound 27 is characterised in that R1 represents an anisole group, i.e. a substituted monocyclic and 6-membered aryl residue (here: a phenyl group substituted with an alkoxy group) and R7 represents a substituted heteroaryl group (here: a substituted pyridinyl group). More precisely, the pyridinyl group is substituted with a heterocycloalkyl group (piperidinyl group).

In compound 39, on the other hand, the aryl residue, i.e. the phenyl group, is not additionally substituted, for example.

It has been shown that these compounds have particularly high TRPM8 activities and consequently show intensive and at the same time efficient cooling effects, i.e. only small amounts of the substance according to the invention are necessary to produce an intensive cooling effect (low EC50 values, see experimental data in Table 5). Intensive cooling effects could also be demonstrated in the sensory evaluation, i.e. the tasting of the respective samples. Thus, the panelists assessed the cooling effect of compound 27 with a 6.84 and that of compound 39 with 7.02 (in each case at application amounts of 5 ppm). Accordingly, the sensorically evaluated cooling intensity, taking into account the amount used of both compounds, was far above that determined for the cooling substance WS-3 as a reference in a six times higher concentration (amount used: 30 ppm; cooling intensity determined by the senses: 5.4).

Compound 40, in which R1 is an optionally substituted thiophenyl group (heteroaryl group) and R7 is an optionally substituted pyridinyl group (heteroaryl group), also shows very high TRPM8 activities as well as sensory intensely perceived cooling effects (sensory cooling intensity: 7.5) and is thus suitable as a particularly efficient cooling agent.

All the compounds mentioned have in common that they have at least one aromatic structure as residue R1 and/or R2. The said substances sensorically show very high cooling intensities and are characterised by extraordinarily high TRPM8 activations.

Based on the above table, it can also be concluded that in particular the compounds of the general formula (I) or formula (II), which can be further summarised and specified under the general formulae (IIIa) or (IIIb), show particularly high TRPM8 activities and consequently also particularly efficient cooling effects with high cooling intensities:

Formula (IIIa)

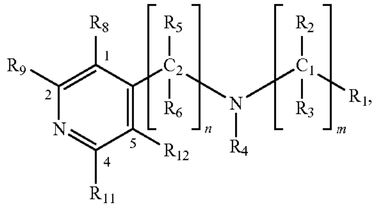

or

-continued

Formula (IIIb)

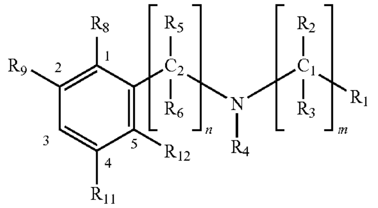

wherein the residues each have the meanings defined above according to formula (I), and wherein preferably the residues represent the following groups:

R1 preferably represents an optionally substituted aryl or heteroaryl group, more preferably an optionally substituted phenyl group or an optionally substituted thiophenyl group or an optionally substituted 1,3-benzodioxolyl group; and wherein preferably at least one of the residues R8, R9, R11 and R12 of the optionally substituted heteroaryl group does not represent a hydrogen atom, but preferably the residue R9, and wherein R9 preferably represents an optionally substituted heterocycloalkyl group, and further preferably represents an optionally substituted piperidinyl group.

In a preferred variant of formula (IIIa), R1 represents optionally substituted phenyl group, optionally substituted benzyl group, optionally substituted tolyl group, optionally substituted xylolyl group, optionally substituted phenol group, optionally substituted dihydroxybenzene group, optionally substituted pyridinyl group, optionally substituted piperidinyl group, optionally substituted tetrahydropyranyl group, optionally substituted pyrollyl group, optionally substituted imidazolyl group, optionally substituted pyrimidinyl group, optionally substituted oxazolyl group, optionally substituted indolyl group, optionally substituted benzothiophenyl group, optionally substituted furanyl group, optionally substituted benzofuranyl group, optionally substituted thiophenyl group, optionally substituted 1,3-benzodioxolyl group, optionally substituted benzodioxanyl group, optionally substituted morpholinyl group or optionally substituted quinolinyl group.

In an even more preferred variant of formula (IIIa)

R1 represents an optionally substituted benzodioxolyl group or

R1 represents an optionally substituted phenyl group or

R1 represents an optionally substituted benzodioxanyl group or

R1 represents an optionally substituted thiophenyl group or

R1 represents an optionally substituted pyridinyl group or

R1 represents an optionally substituted furanyl group.

Such compounds exhibit particularly high TRPM8 activity.

In a most preferred variant of the general formula (IIIa), there is

R1 represents an optionally substituted benzodioxolyl group or

R1 represents an optionally substituted phenyl group or

R1 represents an optionally substituted thiophenyl group or

R1 represents an optionally substituted pyridinyl group.

Such compounds have a particularly high TRPM8 activity a 100%.

Still further preferably, the R1-benzodioxolyl group of the general formula (IIIa) is unsubstituted; or the R1-phenyl group of the general formula (IIIa) is substituted with at least one OH group, or with at least one alkyl group, preferably methyl or ethyl or a mixture thereof, or with at least one alkoxy group, preferably ethoxy or methoxy or a mixture thereof, or with at least one phenyl group, or with at least one alkylthio group, preferably methylthio; or the R1-thiophenyl group is substituted with at least one alkoxy group, preferably ethoxy or methoxy or a mixture thereof.

The at least one alkyl substituent or the at least one alkoxy substituent is attached to the R1-phenyl group in the ortho, meta or para position to the $C_2$—N—$C_1$ linker, but preferably in the para position to the linker of the general formula (IIIa). Such compounds exhibit a particularly high TRPM8 activity.

The residues R2, R3, R4, R5 and R6 in the general formula (IIIa) stand independently of each other for hydrogen, a linear or branched alkyl group, preferably methyl, ethyl, propyl, butyl, a phenyl group or a benzyl group.

The residues R2, R3, R5 or R6 preferably each represent a hydrogen atom and/or an alkyl group. Even more preferred are each R2, R3, R5 and R6 methyl, ethyl or linear or branched propyl, even more preferred a methyl group. However, hydrogen radicals are particularly preferred.

Preferably, R4 on the nitrogen atom of the $C_2$—N—$C_1$ linker is hydrogen, methyl or ethyl.

The residues R8, R9, R11 and R12 on the pyridine ring in formula (IIIa) independently represent hydrogen, an optionally substituted piperidinyl group, an optionally substituted morpholinyl group, an optionally substituted thiomorpholinyl group, an optionally substituted hexamethyleneimine group, an optionally substituted imidazolyl group, an optionally substituted pyridinyl group, an optionally substituted pyrrolidinyl group, an optionally substituted pyrrolyl group, an optionally substituted phenyl group, an alkylthio group, an alkoxy group, preferably ethoxy or methoxy, or an —N-(alkyl)$_2$ group wherein the alkyl is preferably methyl or ethyl, or an optionally substituted cyclohexyl group.

In a preferred variant, in the general formula (IIIa) at least one of the residues R8, R9, R11 and R12 is a piperidinyl group or a morpholinyl group, an optionally substituted thiomorpholinyl group or a hexamethyleneimine group, or an optionally substituted imidazolyl group, or a pyridinyl group or a pyrollidinyl group or a pyrollyl group or a phenyl group or an alkylthio group or an alkoxy group, preferably ethoxy or methoxy, or an —N-(alkyl)$_2$ group wherein the alkyl is preferably methyl or ethyl, or a cyclohexyl group.

Preferably, at least one of the residues R8, R9, R11 and R12 in the general formula (IIIa) is an optionally substituted piperidinyl group. The piperidinyl group is preferably bonded to the pyridine ring of the general formula (IIIa) in the ortho, meta or para position via the nitrogen atom. Even more preferably, the piperidinyl group is bonded via the nitrogen atom in the ortho-position to the nitrogen atom of the pyridine ring in formula (IIIa).

Most preferably, the residue R9 in the general formula (IIIa) represents a piperidinyl group or a morpholinyl group or a hexamethyleneimine group or a pyridinyl group or a pyrollidinyl group or a pyrollyl group or a phenyl group or an alkylthio group or an alkyloxy group, preferably ethoxy or methoxy, or an —N-(alkyl)$_2$ group, wherein the alkyl is preferably methyl or ethyl, or a cyclohexyl group, so that the previously defined residue is bonded in ortho-position to the nitrogen atom of the pyridine ring of the general formula (III).

Even more preferably, the previously defined piperidinyl residue is in turn at least monosubstituted with an alkyl group, preferably methyl, ethyl or linear or branched propyl, or at least monosubstituted with an alkoxy group, preferably methoxy or ethoxy.

Preferably, in the general formula (IIIa), m and n are each independently 0, 1 or 2. Most preferably, m and n are each 1.

Such compounds having the previously described and defined structures as represented by general formula (IIIa) exhibit a particularly prominent TRPM8 activation a 100%, such as the particularly preferred compounds 1, 8, 11, 12, 13, 14, 15, 16, 17, 18, 22, 23, 24, 27, 39, 40, 41, 42, 43, 47, 49, 51, 56, 58, 61, 64, 75, 76, 80, 85 and 87.

However, it should be noted that the nitrogen atom in the pyridine ring in formula (IIIa) can also be arranged in another position of the heteroaromatic ring, for example in ortho or meta position to the $C_2$—N—$C_1$ chain or to the $C_2$—N—$C_1$ linker, respectively. Preferably, the nitrogen atom in the pyridine ring is arranged in para position to the $C_2$—N—$C_1$ chain.

In a further variant, the nitrogen atom in the pyridine ring in formula (IIIa) can be replaced by a C atom, so that the aromatic ring with the residues R8, R9, R11 and R12 represents a phenyl group and the compounds according to the invention are represented by the above general formula (IIIb). For example, compounds 22c, 28, 53, 55, 59, 60, 62, 63, 64, 65, 66, 67, 69, 71, 72 or 82 fall under this alternative structure of general formula (III).

For such structures, the definition of the residues or the substitutes is the same as for the general formula (IIIa).

Preferably, in such structures of general formula (IIIb)

- R1 represents an optionally substituted benzodioxolyl group or
- R1 represents an optionally substituted thiophenyl group or
- R1 represents an optionally substituted phenyl group or
- R1 represents an optionally substituted chromanyl group or
- R1 represents an optionally substituted pyrimidinyl group.

In a most preferred variant of the general formula (IIIb)

- R1 represents an optionally substituted benzodioxolyl group or
- R1 represents an optionally substituted thiophenyl group or
- R1 represents an optionally substituted phenyl group.

Still further preferably, the R1-benzodioxolyl group of general formula (IIIb) is unsubstituted; or the R1-thiophenyl group of general formula (IIIb) is either unsubstituted or substituted with at least one alkyl group, preferably methyl; or the R1-phenyl group of general formula (IIIb) is substituted with at least one OH group, or with at least one alkyl group, preferably methyl or ethyl or a mixture thereof, or with at least one alkoxy group, preferably ethoxy or methoxy or a mixture thereof.

Most preferably, in the general formula (IIIb), the residue R1 is an alkoxylated, preferably a methoxylated, phenyl group.

The residues R8, R9, R11 and R12 on the phenyl ring in the formula (IIIb) independently of one another represent hydrogen, an optionally substituted pyridinyl group, an alkoxy group, preferably ethoxy or methoxy or a mixture thereof, an optionally substituted cyclohexyl group, an —N(alkyl)$_2$ group, preferably an —N(methyl)$_2$ group, or an —NH—(C=O)—CH3 group.

In a preferred variant, in the general formula (IIIb) at least one of the residues R8, R9, R11 and R12 is a pyridinyl group, an alkoxy group, preferably ethoxy or methoxy or a mixture thereof, a cyclohexyl group, an —N(alkyl)$_2$ group, preferably an —N(methyl)$_2$ group, or an —NH—(C=O)—CH3 group.

Preferably, in the general formula (IIIb), m and n are each independently 0, 1 or 2. Most preferably, m and n are each 1.

Of the compounds of the general formulae (IIIa) or (IIIb) defined above, the compounds of the general formula (IIIa) are the most preferred. These cooling substances are characterised by a high TRPM8 activation and at the same time sensorically show very high cooling intensities. Even in low concentrations, they cause intensive cooling effects and are usually well below the EC50 reference value of 1.72 μM for the substance WS-3, as shown in the following experimental section.

Of the physiological cooling agents as defined by the general formulae (IIIa) or (IIIb), those compounds are explicitly excluded which have the following structure:

(1)

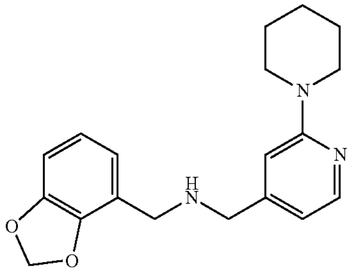

(2)

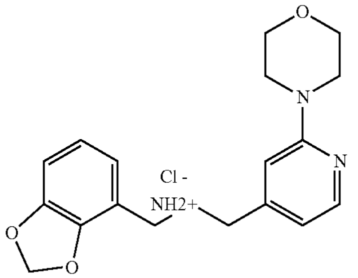

(3)

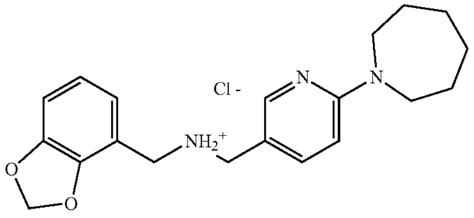

(4)

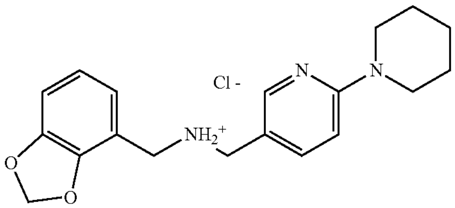

(5)

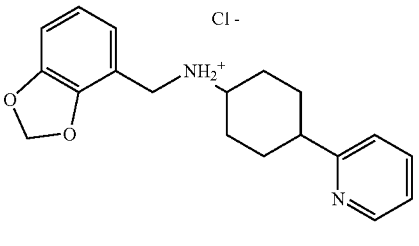

-continued (6)

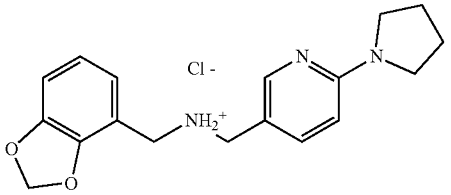

(7)

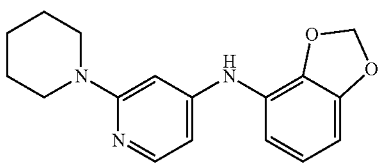

(8)

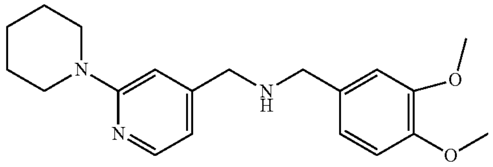

However, this disclaimer does not apply insofar as it relates to the uses of these particular compounds as described in detail below.

As can also be seen from the table, compounds according to formula (III) are also particularly preferred in which R1 represents an optionally substituted phenyl group and R9 represents an optionally substituted piperidinyl group and which can be derived from the following basic structure according to formula (IV):

Formula (IV)

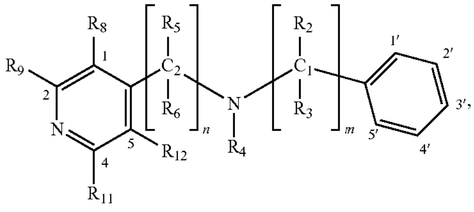

wherein at one, two, three, four or five of the positions 1, 2, 4 or 5 or 1', 2', 3', 4' or 5' of the respective aromatic moiety of the general formula (IV) a substituent/residue as indicated in formula (III) may optionally be arranged in each case, for example a piperidinyl group at position 2 of the heteroaromatic ring or for example a methoxy group at the 3' position of the phenyl group. Suitable substituents result from the above description in connection with the general formula (I) or (II) and the residues described therein.

Again, compounds seem particularly advantageous in which m and n are each 1 and/or R2 to R6 preferably each represent a hydrogen atom and/or an alkyl, such as a methyl group, although hydrogen atoms are preferred as residues.

Also preferred are compounds which can be derived from the following alternative structure according to formula (V), where n and m are preferably each 1 and the above-mentioned also applies with regard to substitution possibilities:

Formula (V)

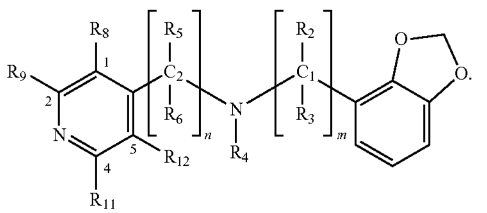

From the above description, the following preferred structures according to the general formula (VI) are thus also inherent:

Formula (VI)

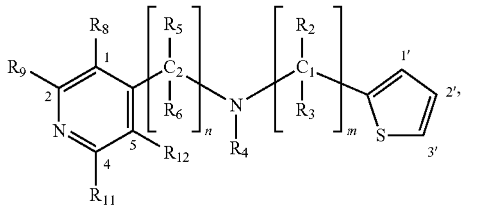

wherein at one, two, three or four of the positions 1, 2, 4 or 5 or 1', 2' or 3' of the respective aromatic moiety of the general formula (VI) a substituent/residue as indicated in formula (III) may optionally be arranged in each case, for example a piperidinyl group at position 2 of the heteroaromatic ring. Suitable substituents result from the above description in connection with the general formula (I) or (II) and the residues described therein, so that the substitution possibilities and residues according to the above definitions within the framework of formulae (I) and (II) also hold and are applicable here.

With regard to formulae (IV) to (VI), it should also be noted that the nitrogen atom can also be arranged at a different position of the heteroaromatic ring, for example in the ortho or meta position to the $C_2$—N—$C_1$ chain. Preferably, however, the nitrogen atom is arranged as shown. It has been shown that such structures are able to induce particularly high and efficient cooling effects and TRPM8 activities.

It has also been shown that an optionally substituted heterocycloalkyl group, and particularly preferably an optionally substituted piperidinyl group, is preferably arranged at position 2, so that particularly efficient cooling agents are obtained by optional substitution at positions 1", 2", 3", 4" or 5" of the piperidinyl group according to the following formula (VII):

Formula (VII)

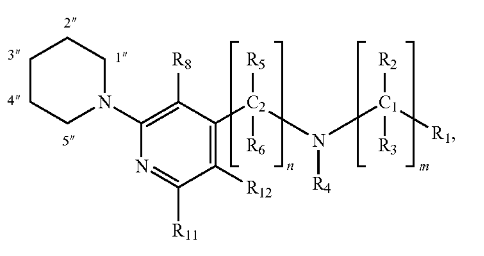

wherein the residues R2 to R6 and R8, R11 and R12 as well as the respective substituents at the positions 1", 2", 3", 4" or 5" may independently of one another be the functional groups defined above or in the context of formulae (I) and (II), and R1 preferably represents an optionally substituted aryl or heteroaryl group, even more preferably an optionally substituted phenyl group or an optionally substituted thiophenyl group or an optionally substituted 1,3-benzodioxolyl group.

Here, too, m and n are preferably 1.

These structures are characterised in particular by their efficient cooling effects and high TRPM8 activities, so that they are especially preferable.

The physiological amine cooling agents according to the invention are not yet known from the prior art but can be prepared according to generally known standard methods of preparative organic chemistry, which are shown in generalised form in the following schemes.

Method A:

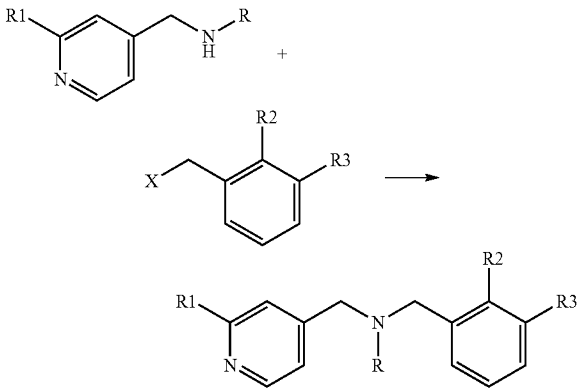

The haloalkyl derivative is dissolved in dry DCM and is reacted with a corresponding pyridine derivative and a nitrogenous base.

Method B:

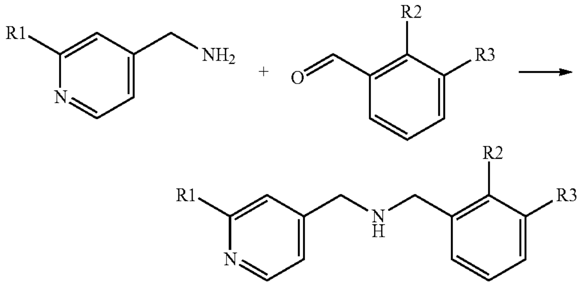

The aldehyde is dissolved in THF and reacted with the corresponding amine and subsequent addition of a reducing agent.

Method C:

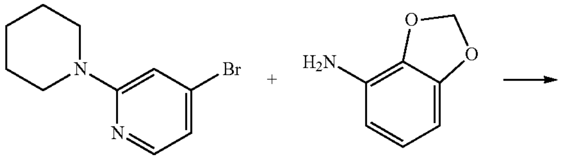

-continued

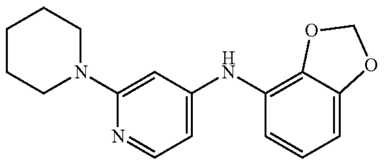

The corresponding halogen derivative and the amine are dissolved in dry toluene and reacted with the addition of tri-tert-butylphosphine and potassium phosphate. The corresponding halogen derivative (1.0 eq.) and the amine (1.1 eq.) are dissolved in dry toluene and tri-tert-butylphosphine (0.1 eq.) and potassium phosphate (3.0 eq.) are added. The reaction mixture is purged with argon for 15 minutes, $Pd_2(dba)_3$ is added and again purged with argon for 15 minutes. The reaction mixture is stirred at 100° C. overnight. Water (160 mL) and DCM (160 mL) are added for work-up. The resulting phases are separated, and the aqueous phase is extracted with DCM (3×160 mL). The combined organic phases are dried over $Na_2SO_4$, filtered and the solvent is removed in vacuo. The crude product was purified by column chromatography (reversed phase, 0 to 100% acetonitrile in water).

Method D:

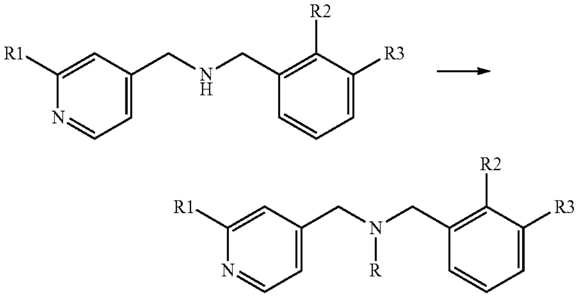

A suspension consisting of the amine and $Cs_2CO_3$ in DMF is reacted with the desired halogen substitution reagent.

Method E:

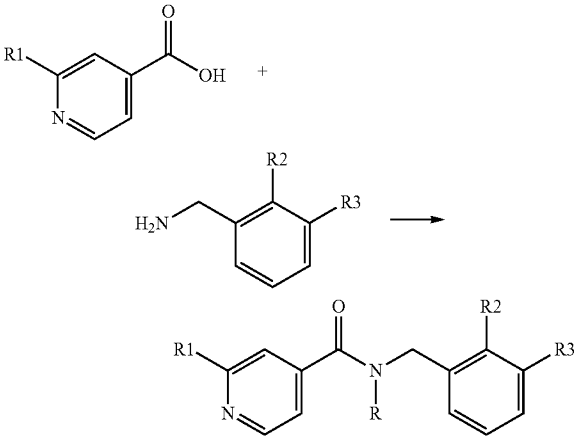

The corresponding carboxylic acid, HBTU and EDC×HCl are dissolved and then reacted with the desired amine and DIPEA.

Method F:

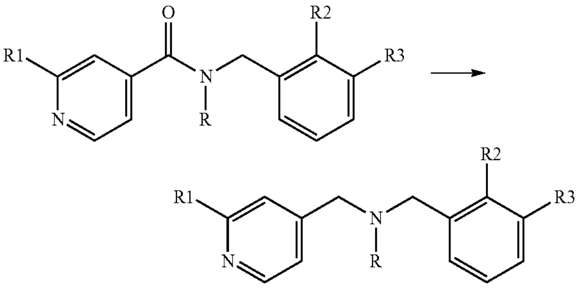

The desired amide is dissolved in dry THF under argon atmosphere and the borane dimethyl sulphide complex is slowly added at 0° C.

In principle, the present invention covers all mixtures of the individual compounds of formula (I) and formula (II) (and consequently also of formulae (III) to (VII)) and their use as cooling agents or cooling agent mixtures. Nevertheless, the present compounds are also suitable for mixing with other, already known cooling agents.

Accordingly, another object of the invention relates to a physiological cooling agent mixture comprising or consisting of:

(a) one, two, three or more cooling agent(s) of formula (I) or formula (II) or as set out in Table 1 or Table 2 and defined above; and optionally (b) at least one further physiological cooling agent; and/or optionally (c) at least one solvent.

In a preferred embodiment, the present invention relates to a cooling agent mixture comprising at least one of the compounds according to formula (I) and/or (II) or (III) to (VII) as defined above. Optionally, the cooling agent mixture also comprises a further physiological cooling agent and optionally at least one suitable solvent.

The particular advantage of such coolant mixtures is that a synergistic enhancement of the cooling effect can be observed.

Suitable cooling agents forming component (b) and different from the cooling agent(s) forming component (a) are selected from the group consisting of menthol, menthol methyl ether (FEMA GRAS 4054), monomenthyl glutamate (FEMA GRAS 4006), menthoxy-1,2-propanediol (FEMA GRAS 3784), dimenthyl glutarate (FEMA GRAS 4604), hydroxymethylcyclohexylethanone (FEMA GRAS 4742), 2-(4-ethylphenoxy)-N-(1H-pyrazol-3-yl)-N-(thiophen-2-ylmethyl)acetamide (FEMA GRAS 4880), WS-23 (2-isopropyl-N,2,3-trimethylbutyramide, FEMA GRAS 3804), N-(4-(cyanomethyl)phenyl)-2-isopropyl-5,5-dimethylcyclohexane carboxamide (FEMA GRAS 4882), N-(3-hydroxy-4-methoxyphenyl)-2-isopropyl-5,5-dimethylcyclohexane carboxamide (FEMA GRAS 4881), N-(2-hydroxy-2-phenylethyl)-2-isopropyl-5,5-dimethylcyclohexane-1-carboxamide (FEMA GRAS 4896), 3,4-methylenedioxy cinnamic acid, (E)-3-benzo[1,3]dioxol-5-yl-N,N-diphenyl-2-propenamide (FEMA GRAS 4788), menthol propylene glycol carbonate (FEMA GRAS 3806), menthyl N-ethyloxamate, monomethyl succinate (FEMA GRAS 3810), WS-3 (N-ethyl-p-menthane-3-carboxamide, FEMA GRAS 3455), menthol ethylene glycol carbonate (FEMA GRAS 3805), WS-5 (ethyl 3-(p-menthane-3-carboxamido)acetate, FEMA GRAS 4309), WS-12 (1R,2S, 5R)-N-(4-methoxyphenyl)-p-menthane carboxamide (FEMA GRAS 4681), WS-27 (N-ethyl-2,2-diisopropylbutanamide, FEMA GRAS 4557), N-cyclopropyl-5-methyl-2-isopropylcyclohexanecarboxamide (FEMA GRAS 4693), WS-116 (N-(1,1-dimethyl-2-hydroxyethyl)-2,2-diethylbutanamide, FEMA GRAS 4603), menthoxyethanol (FEMA GRAS 4154), N-(4-cyanomethylphenyl)-p-menthanecarboxamide (FEMA GRAS 4496), N-(2-(pyridin-2-yl)ethyl)-3-p-menthanecarboxamide (FEMA GRAS 4549), N-(2-hydroxyethyl)-2-isopropy-1-2,3-dimethylbutanamide (FEMA GRAS 4602), (2S,5R)-N-[4-(2-amino-2-oxoethyl)phenyl]-p-menthanecarboxamide (FEMA GRAS 4684), N-cyclopropyl-5-methyl-2-isopropylcyclohexanecarboxamide (FEMA GRAS 4693), 2-[(2-p-menthoxy)ethoxy]ethanol (FEMA GRAS 4718), (2,6-diethyl-5-isopropyl-2-methyltetrahydropyran (FEMA GRAS 4680), trans-4-tert-butylcyclohexanol (FEMA GRAS 4724), 2-(p-tolyloxy)-N-(1H-pyrazol-5-yl)-N-((thiophen-2-yl)methyl)acetamide (FEMA GRAS 4809), menthone glycerol ketal (FEMA GRAS 3807 and 3808), (−)-Menthoxypropane-1,2-diol, 3-(1-menthoxy)-2-methylpropane-1,2-diol (FEMA GRAS 3849), isopulegol, (+)-cis and (−)-trans-p-menthane-3,8-diol (62:38, FEMA GRAS 4053), 2,3-dihydroxy-p-menthane, 3,3,5-trimethylcyclohexanone glycerol ketal, menthyl pyrrolidone carboxylate, (1R,3R,4S)-3-menthyl-3,6-dioxaheptanoate, (1R,2S,5R)-3-menthyl methoxyacetate, (1R,2S,5R)-3-menthyl-3,6,9-trioxadecanoate, (1R,2S,5R)-3-menthyl-3,6,9-trioxadecanoate, (1R,2S,5R)-3-menthyl-(2-hydroxyethoxy)acetate, (1R, 2S,5R)-menthyl-11-hydroxy-3,6,9-trioxaundecanoate, cubebol (FEMA GRAS 4497), 2-isopropyl-5-methylcyclohexyl-4-(dimethylamino)-4-oxobutanoate (FEMA GRAS 4230), menthyl lactate (FEMA GRAS 3748), 6-isopropyl-3,9-dimethyl-1,4-dioxaspiro[4.5]decan-2-one (FEMA GRAS 4285), N-benzo[1,3]dioxol-5-yl-3-p-menthane carboxamide, N-(1-isopropyl-1,2-dimethylpropyl)-1,3-benzodioxole-5-carboxamide, N-(R)-2-oxotetrahydrofuran-3-yl-(1R,2S,5R)-p-menthane-3-carboxamide, mixture of 2,2,5,6,6-pentamethyl-2,3,6,6a-tetrahydropentalen-3a(1H)-ol and 5-(2-hydroxy-2-methylpropyl)-3,4,4-trimethylcyclopent-2-en-1-one; (2S,5R)-2-isopropyl-5-methyl-N-(2-(pyridin-4-yl)ethyl)cyclohexanecarboxamide; (1S,2S,5R)-N-(4-(cyanomethyl)phenyl)-2-isopropyl-5-methylcyclohexanecarboxamide, 1,7-isopropyl-4,5-methyl-bicyclo[2.2.2]oct-5-ene derivatives, 4-methoxy-N-phenyl-N-[2-(pyridin-2-yl)ethyl]benzamide, 4-methoxy-N-phenyl-N-[2-(pyridin-2-yl)ethyl]benzenesulfonamide, 4-chloro-N-phenyl-N-[2-(pyridin-2-yl)ethyl]benzenesulfonamide, 4-cyano-N-phenyl-N-[2-(pyridin-2-yl)ethyl]benzenesulfonamide, 4-((benzhydrylamino)methyl)-2-methoxyphenol, 4-((bis(4-methoxyphenyl)methylamino)methyl)-2-methoxyphenol, 4-((1,2-diphenylethylamino)methyl)-2-methoxyphenol, 4-((benzhydryloxy)methyl)-2-methoxyphenol, 4-((9H-fluoren-9-ylamino)methyl)-2-methoxyphenol, 4-((benzhydrylamino)methyl)-2-ethoxyphenol, 1-(4-methoxyphenyl)-2-(1-methyl-1H-benzo[d]imidazol-2-yl)vinyl-4-methoxybenzoate, 2-(1-isopropyl-6-methyl-1H-enzo[d]imidazol-2-yl)-1-(4-methoxyphenyl) vinyl-4-methoxybenzoate, (Z)-2-(1-isopropyl-5-methyl-1H-benzo[d]imidazol-2-yl)-1-(4-methoxyphenyl)vinyl-4-methoxybenzoate, 3-alkyl-p-methan-3-ol derivatives, derivatives of fenchyl, D-bornyl, L-bornyl, exo-norbornyl, 2-methylisobornyl, 2-ethylfenchyl, 2-methylbornyl, cis-pinan-2-yl, verbanyl and isobornyl, menthyloxamate derivatives, menthyl 3-oxocarboxylic acid esters, N-alpha-(menthancarbonyl)amino acid amides, p-menthane carboxamide and WS-23 analogues, (−)-(1R,2R,4S)-dihydroumbellulol, p-menthane alkyloxyamide, cyclohexane derivatives, butanone derivatives, mixture of 3-menthoxy-1-propanol and 1-menthoxy-2-propanol, 1-[2-ydroxyphenyl]-4-[2-nitrophenyl]-1,2,3,6-tetrahydropyrimidin-2-one, 4-methyl-3-(1-pyrrolidinyl)-2-[5H]-furanone and mixtures thereof. FEMA stands for Flavor and Extracts Manufacturers Association and GRAS is defined as Generally Regarded As Safe. A FEMA GRAS designation means that the substance so designated has been tested according to standard methods and is considered to be toxicologically safe.

In principle, all known substances with a cooling effect are suitable as component (b). For reasons of food safety, however, those compounds are preferred which have a designation according to FEMA GRAS or if the cooling mixture in question requires this.

A first important representative of the substances forming component (b) is monomenthyl succinate (FEMA GRAS 3810). Both the succinate and the analogous monomenthyl glutarate (FEMA GRAS 4006) are important representatives of monomenthyl esters based on di- and polycarboxylic acids.

The next important group of preferred menthol compounds in the sense of the invention comprises carbonate esters of menthol and polyols, such as glycols, glycerol or carbohydrates, such as menthol ethylene glycol carbonate (FEMA GRAS 3805=Frescolat® MGC), menthol propylene glycol carbonate (FEMA GRAS 3784=Frescolat® MPC), menthol 2-methyl-1,2-propanediol carbonate (FEMA GRAS 3849) or the corresponding sugar derivatives. Also preferred are N-(4-cyanomethylphenyl)-p-menthanecarboxamide (FEMA GRAS 4496), N-(2-(pyridin-2-yl)ethyl)-3-p-menthanecarboxamide (FEMA GRAS 4549) and (E)-3-benzo[1, 3]dioxol-5-yl-N,N-diphenyl-2-propenamide (FEMA GRAS 4788) as component (b).

In the sense of the invention, the menthol compounds menthyl lactate (FEMA GRAS 3748=Frescolat® ML) and in particular menthone glyceryl acetal (FEMA GRAS 3807) or menthone glyceryl ketal (FEMA GRAS 3808), which is marketed under the name Frescolat® MGA, are preferred.

This group of compounds also includes 3-(1-menthoxy)-1,2-propanediol, also known as Cooling Agent 10 (FEMA GRAS 3784), and 3-(1-menthoxy)-2-methyl-1,2-propanediol (FEMA GRAS 3849), which has an additional methyl group.

Among the above-mentioned substances, menthone glyceryl acetal/ketal and menthone lactate as well as menthol ethylene glycol carbonate and menthol propylene glycol carbonate, which the applicant markets under the names Frescolat® MGA, Frescolat® ML, Frecolat® MGC and Frescolat® MPC, have proved to be particularly advantageous.

Further preferred components result from the following table (Table 3):

TABLE 3

| Other suitable substances as components (b) | |
|---|---|
| Structure | Name |
| 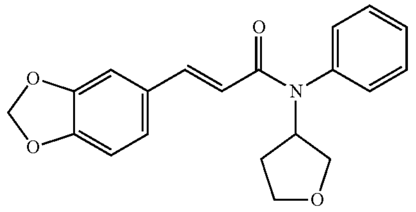 [SMILES: O=C(/C=C/c1ccc2c(c1)OCO2)N(c1ccccc1)C1CCOC1] | (E)-3-(1,3-benzodioxol-5-yl)-N-phenyl-N-tetrahydrofuran-3-yl-prop-2-enamide |
| 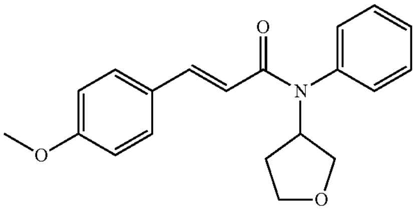 [SMILES: COc1ccc(/C=C/C(=O)N(c2ccccc2)C2CCOC2)cc1] | (E)-3-(4-methoxyphenyl)-N-phenyl-N-tetrahydrofuran-3-yl-prop-2-enamide |
| 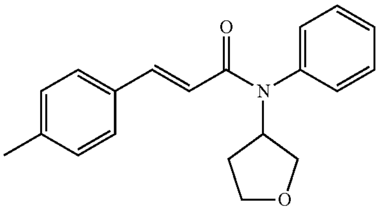 [SMILES: Cc1ccc(/C=C/C(=O)N(c2ccccc2)C2CCOC2)cc1] | (E)-N-phenyl-3-(p-tolyl)-N-tetrahydrofuran-3-yl-prop-2-enamide |
| 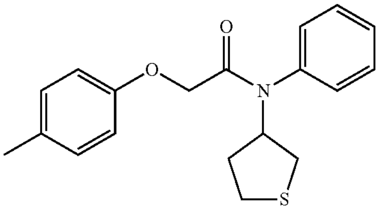 [SMILES: Cc1ccc(OCC(=O)N(c2ccccc2)C2CCSC2)cc1] | 2-(4-Methylphenoxy)-N-phenyl-N-tetrahydrothiophen-3-yl-acetamide |
| 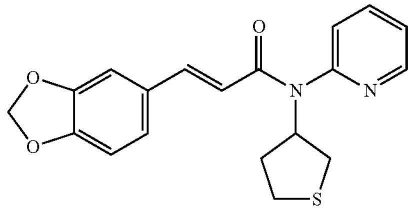 [SMILES: O=C(/C=C/c1ccc2c(c1)OCO2)N(c1ccccn1)C1CCSC1] | (E)-3-(1,3-benzodioxol-5-yl)-N-(2-pyridyl)-N-tetrahydrothiophen-3-yl-prop-2-enamide |
| 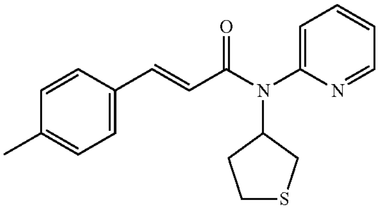 [SMILES: Cc1ccc(/C=C/C(=O)N(c2ccccn2)C2CCSC2)cc1] | (E)-3-(p-tolyl)-N-(2-pyridyl)-N-tetrahydrothiophen-3-yl-prop-2-enamide |
| 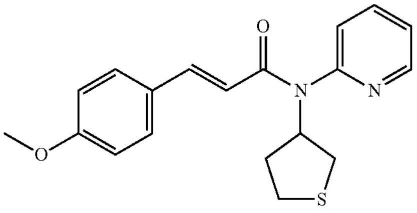 [SMILES: COc1ccc(/C=C/C(=O)N(c2ccccn2)C2CCSC2)cc1] | (E)-3-(4-methoxyphenyl)-N-(2-pyridyl)-N-tetrahydrothiophen-3-yl-prop-2-enamide |

TABLE 3-continued

| Other suitable substances as components (b) | |
|---|---|
| Structure | Name |
| 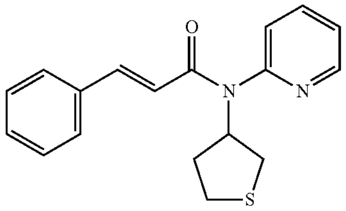 [SMILES: O=C(/C=C/c1ccccc1)N(c1ccccn1)C1CCSC1] | (E)-3-Phenyl-N-(2-pyridyl)-N-tetrahydrothiophen-3-yl-prop-2-enamide |
| 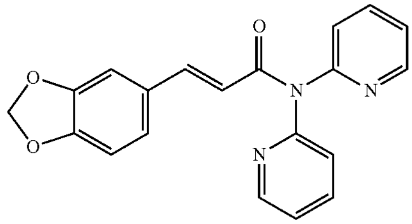 [SMILES: O=C(/C=C/c1ccc2c(c1)OCO2)N(c1ccccn1)c1ccccn1] | (E)-3-(1,3-benzodioxol-5-yl)-N,N-bis(2-pyridyl)prop-2-enamide |
| 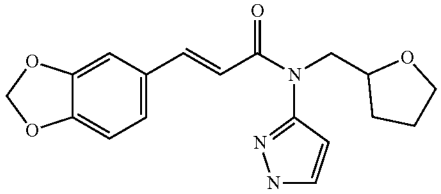 | (E)-3-(1,3-benzodioxol-5-yl)-N-(1H-pyrazol-3-yl)-N-(tetrahydrofuran-2-ylmethyl)prop-2-enamide |
| 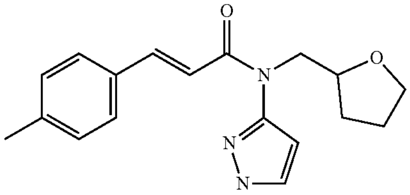 | (E)-3-(p-tolyl)-N-(1H-pyrazol-3-yl)-N-(tetrahydrofuran-2-ylmethyl)prop-2-enamide |
| 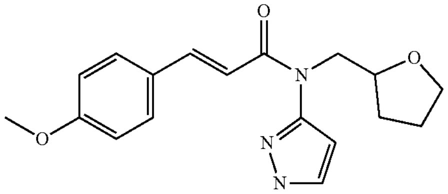 | (E)-3-(4-methoxyphenyl)-N-(1H-pyrazol-3-yl)-N-(tetrahydrofuran-2-ylmethyl)prop-2-enamide |
| 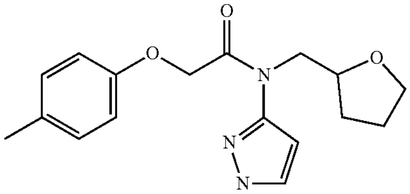 [SMILES: Cc1ccc(OCC(=O)N(CC2CCCO2)c2cc[nH]n2)cc1] | 2-(4-Methylphenoxy)-N-(1H-pyrazol-3-yl)-N-(tetrahydrofuran-2-ylmethyl)acetamide |
| 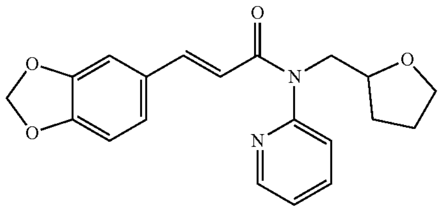 [SMILES: O=C(/C=C/c1ccc2c(c1)OCO2)N(CC1CCCO1)c1ccccn1] | (E)-3-(1,3-benzodioxol-5-yl)-N-(2-pyridyl)-N-(tetrahydrofuran-2-ylmethyl)prop-2-enamide |

TABLE 3-continued

| Other suitable substances as components (b) | |
|---|---|
| Structure | Name |
| 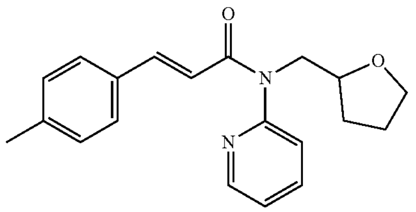 [SMILES: Cc1ccc(/C=C/C(=O)N(CC2CCCO2)c2ccccn2)cc1] | (E)-3-(p-tolyl)-N-(2-pyridyl)-N-(tetrahydrofuran-2-ylmethyl)prop-2-enamide |
| 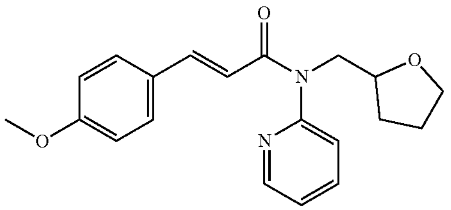 [SMILES: COc1ccc(/C=C/C(=O)N(CC2CCCO2)c2ccccn2)cc1] | (E)-3-(4-methoxyphenyl)-N-(2-pyridyl)-N-(tetrahydrofuran-2-ylmethyl)prop-2-enamide |
| 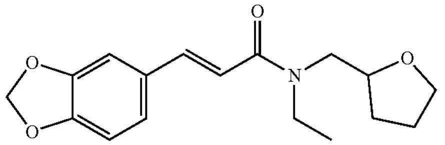 [SMILES: CCN(CC1CCCO1)C(=O)/C=C/c1ccc2c(c1)OCO2] | (E)-3-(1,3-benzodioxol-5-yl)-N-ethyl-N-(tetrahydrofuran-2-ylmethyl)prop-2-enamide |
| 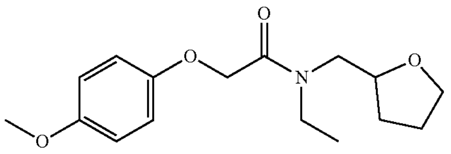 [SMILES: CCN(CC1CCCO1)C(=O)COc1ccc(OC)cc1] | N-ethyl-2-(4-methoxyphenoxy)-N-(tetrahydrofuran-2-ylmethyl)acetamide |
| 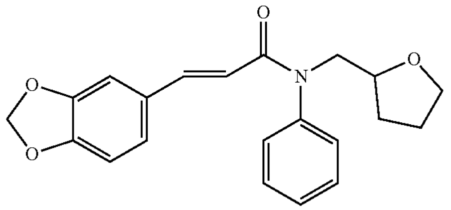 [SMILES: O=C(/C=C/c1ccc2c(c1)OCO2)N(CC1CCCO1)c1ccccc1] | (E)-3-(1,3-benzodioxol-5-yl)-N-phenyl-N-(tetrahydrofuran-2-ylmethyl)prop-2-enamide |
| 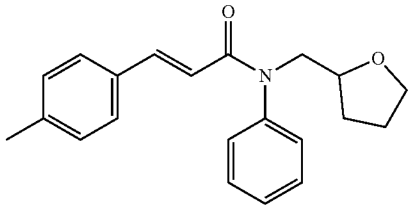 [SMILES: Cc1ccc(/C=C/C(=O)N(CC2CCCO2)c2ccccc2)cc1] | (E)-N-phenyl-3-(p-tolyl)-N-(tetrahydrofuran-2-ylmethyl)prop-2-enamide |
| 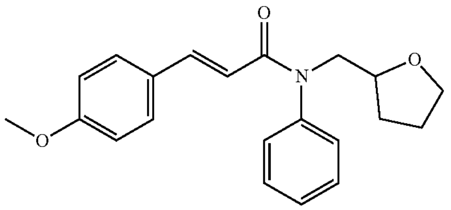 | (E)-3-(4-methoxyphenyl)-N-phenyl-N-(tetrahydrofuran-2-ylmethyl)prop-2-enamide |

TABLE 3-continued

| Other suitable substances as components (b) | |
|---|---|
| Structure | Name |
| 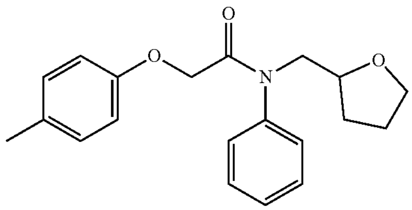 [SMILES: Cc1ccc(OCC(=O)N(CC2CCCO2)c2ccccc2)cc1] | 2-(4-Methylphenoxy)-N-phenyl-N-(tetrahydrofuran-2-ylmethyl)acetamide |
| 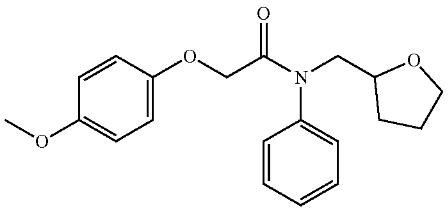 [SMILES: COc1ccc(OCC(=O)N(CC2CCCO2)c2ccccc2)cc1] | 2-(4-Methoxyphenoxy)-N-phenyl-N-(tetrahydrofuran-2-ylmethyl)acetamide |
| 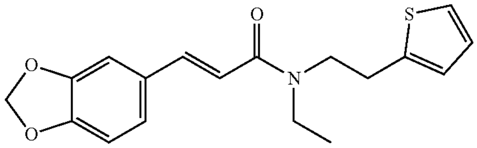 [SMILES: CCN(CCc1cccs1)C(=O)/C=C/c1ccc2c(c1)OCO2] | (E)-3-(1,3-Benzodioxol-5-yl)-N-ethyl-N-[2-(2-thienyl)ethyl]prop-2-enamid |
| 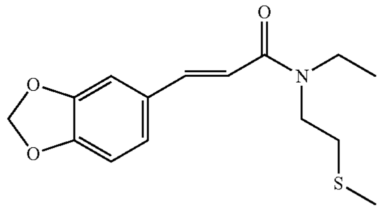 [SMILES: CCN(CCSC)C(=O)/C=C/c1ccc2c(c1)OCO2] | (E)-3-(1,3-benzodioxol-5-yl)-N-ethyl-N-(2-methylsulfanylethyl)prop-2-enamide |
| 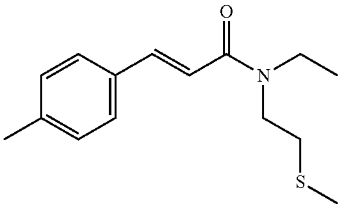 | (E)-N-ethyl-N-(2-methylsulfanylethyl)-3-(p-tolyl)prop-2-enamide |
| 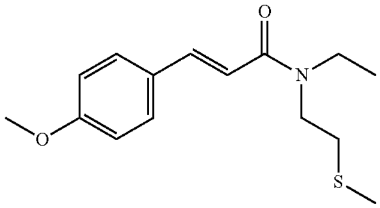 | (E)-N-ethyl-3-(4-methoxyphenyl)-N-(2-methylsulfanylethyl)prop-2-enamide |
| 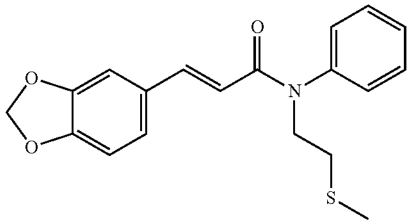 [SMILES: CSCCN(C(=O)/C=C/c1ccc2c(c1)OCO2)c1ccccc1] | (E)-3-(1,3-benzodioxol-5-yl)-N-(2-methylsulfanylethyl)-N-phenyl-prop-2-enamide |

TABLE 3-continued

| Other suitable substances as components (b) | |
|---|---|
| Structure | Name |
| 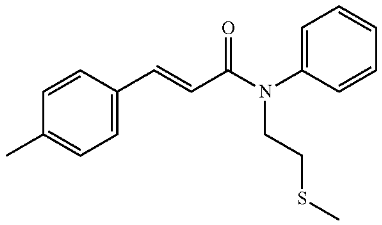 [SMILES: CSCCN(C(=O)/C=C/c1ccc(C)cc1)c1ccccc1] | (E)-N-(2-methylsulfanylethyl)-N-phenyl-3-(p-tolyl)prop-2-enamide |
| 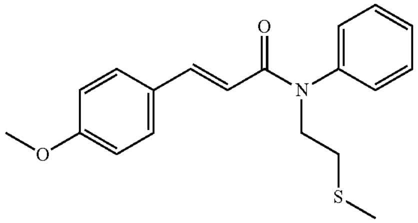 [SMILES: COc1ccc(/C=C/C(=O)N(CCSC)c2ccccc2)cc1] | (E)-3-(4-methoxyphenyl)-N-(2-methylsulfanylethyl)-N-phenyl-prop-2-enamide |
| 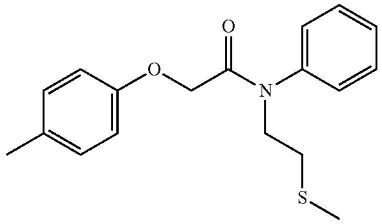 [SMILES: CSCCN(C(=O)COc1ccc(C)cc1)c1ccccc1] | 2-(4-Methylphenoxy)-N-(2-methylsulfanylethyl)-N-phenyl-acetamide |
| 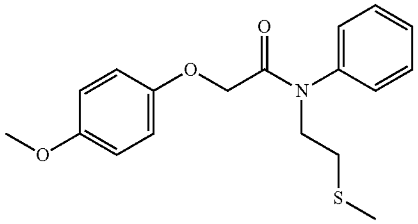 [SMILES: COc1ccc(OCC(=O)N(CCSC)c2ccccc2)cc1] | 2-(4-Methoxyphenoxy)-N-(2-methylsulfanylethyl)-N-phenyl-acetamide |
| 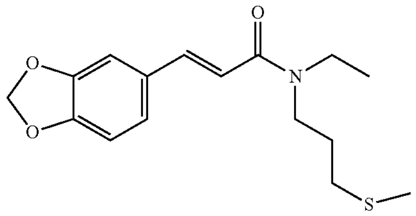 [SMILES: CCN(CCCSC)C(=O)/C=C/c1ccc2c(c1)OCO2] | (E)-3-(1,3-benzodioxol-5-yl)-N-ethyl-N-(3-methylsulfanylpropyl)prop-2-enamide |
| 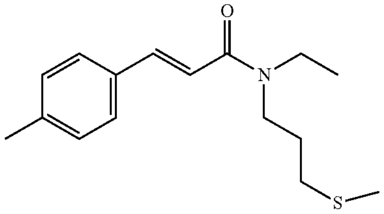 | (E)-N-ethyl-N-(3-methylsulfanylpropyl)-3-(p-tolyl)prop-2-enamide |

TABLE 3-continued

| Other suitable substances as components (b) | |
|---|---|
| Structure | Name |
| 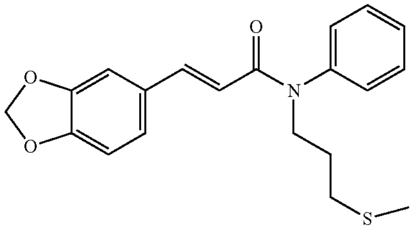 [SMILES: CSCCCN(C(=O)/C=C/c1ccc2c(c1)OCO2)c1ccccc1] | (E)-3-(1,3-benzodioxol-5-yl)-N-(3-methylsulfanylpropyl)-N-phenyl-prop-2-enamide |
| 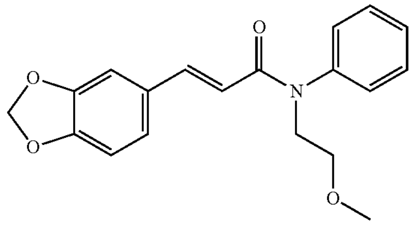 [SMILES: COCCN(C(=O)/C=C/c1ccc2c(c1)OCO2)c1ccccc1] | (E)-3-(1,3-benzodioxol-5-yl)-N-(2-methoxyethyl)-N-phenyl-prop-2-enamide |
| 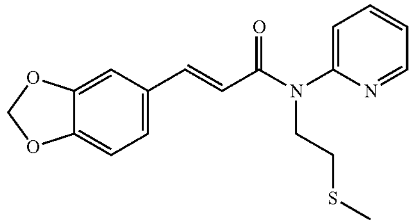 [SMILES: CSCCN(C(=O)/C=C/c1ccc2c(c1)OCO2)c1ccccn1] | (E)-3-(1,3-benzodioxol-5-yl)-N-(2-methylsulfanylethyl)-N-(2-pyridyl)prop-2-enamide |
| 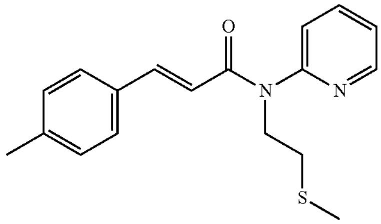 [SMILES: CSCCN(C(=O)/C=C/c1ccc(C)cc1)c1ccccn1] | (E)-N-(2-methylsulfanylethyl)-3-(p-tolyl)-N-(2-pyridyl)prop-2-enamide |
| 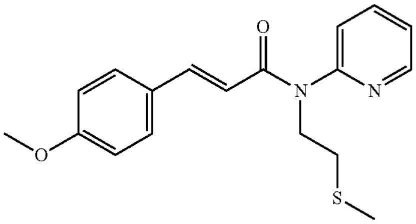 [SMILES: COc1ccc(/C=C/C(=O)N(CCSC)c2ccccn2)cc1] | (E)-3-(4-methoxyphenyl)-N-(2-methylsulfanylethyl)-N-(2-pyridyl)prop-2-enamide |
| 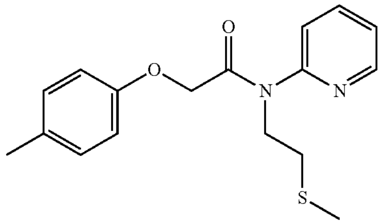 [SMILES: CSCCN(C(=O)COc1ccc(C)cc1)c1ccccn1] | 2-(4-Methylphenoxy)-N-(2-methylsulfanylethyl)-N-(2-pyridyl)acetamide |

TABLE 3-continued

| Other suitable substances as components (b) | |
|---|---|
| Structure | Name |
| 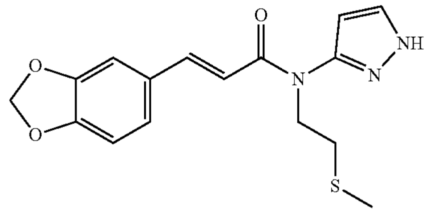 [SMILES: CSCCN(C(=O)/C=C/c1ccc2c(c1)OCO2)c1cc[nH]n1] | (E)-3-(1,3-benzodioxol-5-yl)-N-(2-methylsulfanylethyl)-N-(1H-pyrazol-3-yl)prop-2-enamide |
| 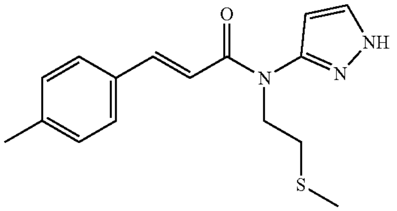 [SMILES: CSCCN(C(=O)/C=C/c1ccc(C)cc1)c1cc[nH]n1] | (E)-N-(2-methylsulfanylethyl)-3-(p-tolyl)-N-(1H-pyrazol-3-yl)prop-2-enamide |
| 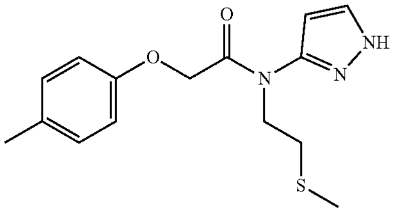 [SMILES: CSCCN(C(=O)COc1ccc(C)cc1)c1cc[nH]n1] | 2-(4-Methylphenoxy)-N-(2-methylsulfanylethyl)-N-(1H-pyrazol-3-yl)acetamide |
| 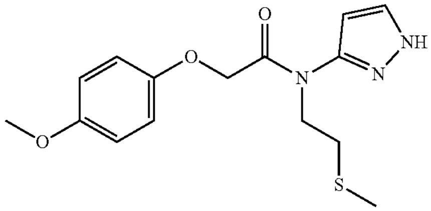 [SMILES: COc1ccc(OCC(=O)N(CCSC)c2cc[nH]n2)cc1] | 2-(4-Methoxyphenoxy)-N-(2-methylsulfanylethyl)-N-(1H-pyrazol-3-yl)acetamide |

In the 1970s, menthol compounds were developed for the first time which have a C—C bond in the 3-position and of which a number of representatives can also be used in the sense of the invention. These substances are generally referred to as WS types. The basic body is a menthol derivative in which the hydroxyl group is replaced by a carboxyl group (WS-1). All other WS types are derived from this structure, such as the species WS-3, WS-4, WS-5, WS-12, WS-14, WS-23, WS-27 and WS-30, which are also preferred in the sense of the invention, or the esters or N-substituted amides of the aforementioned compounds.

Further particularly preferred is the cooling agent 2-(p-tolyloxy)-N-(1H-pyrazol-5-yl)-N-((thiophen-2-yl)methyl) acetamide (FEMA GRAS 4809). In addition, 2-(4-ethylphenoxy)-N-(1H-pyrazol-3-yl)-N-(thiophen-2-ylmethyl) acetamide (FEMA GRAS 4880) and/or N-(3-hydroxy-4-methoxyphenyl)-2-isopropyl-5,5-dimethylcyclohexane carboxamide (FEMA GRAS 4881) and/or N-(4-(cyanomethyl)phenyl)-2-isopropyl-5,5-dimethylcyclohexane carboxamide (FEMA GRAS 4882).

The coolant mixtures according to the invention may contain components (a) and (b) in a weight ratio of about 0.1:99.9 to about 99.0:0.1, preferably from about 1:99 to about 99:1, even more preferably from about 10:90 to about 90:10, still more preferably from about 25:75 to about 75:25 and in particular from about 40:60 to about 60:40 relative to the total coolant mixture.

In order to exploit and optimise the cooling effect of the cooling agents and to ensure easier processing in flavourings and semi-finished or other end products, the cooling agents must be converted into a solution before processing. However, in some cases the solubility of the cooling agents according to the invention is not sufficient, so that this causes problems during storage, handling or further processing.

On the one hand, the aforementioned cooling agents forming component (b) of the cooling agent mixture may act as a solvent for the cooling agent(s) forming component (a) of the cooling agent mixture.

Advantageously, the coolant mixture according to the invention also comprises at least one solvent as a further component (c).

Single solvents or solvent systems have proven to be advantageous, wherein the solvent is selected from the group consisting of benzyl alcohol, 2-phenylethanol, benzyl benzoate, diethyl succinate, triethyl citrate, triacetin, ethanol, peppermint oil, anethole, optamint, propylene glycol, phenoxyethanol and mixtures thereof.

Optamint, for example, is a mixture of more than 50 different natural essential oils and natural or nature-identical flavouring substances. Optamints have variable compositions of different (partly fractionated) oils, which preferably represent a mixture of, for example, different peppermint oils and spearmint oils, as well as eucalyptus globulus oil, star anise oil, menthol, menthone, isomenthone, menthyl acetate, anethole, eucalyptol, etc. An exact reproduction of the composition of the Optamints is therefore not possible. The Optamint® product series is commercially available from Symrise AG.

For example, benzyl alcohol or 2-phenylethanol or benzyl benzoate may be used as solvents in the cooling agent mixture according to the invention.

The use of benzyl alcohol or 2-phenyethanol or benzyl benzoate can be used, for example, to bring the cooling agents of the invention into solution and also to obtain a stable solution, i.e. cooling agent mixture, for appropriate storage.

Solvent systems, i.e. solvent combinations of two or more solvents, can also be used to dissolve the cooling agents according to the invention. Especially with regard to the later field of application, the use of solvents, which can also show a cooling effect, can save a further step in the (final-) production step.

In an exemplary embodiment, the solvent in the cooling agent mixture is therefore a binary system of two solvent substances selected from the group consisting of benzyl alcohol, 2-phenylethanol, benzyl benzoate, diethyl succinate, triethyl citrate, triacetin, ethanol, peppermint oil, anethole, optamint, propylene glycol, phenoxyethanol and further cooling agents as described above as component (b).

Suitable according to the present invention are, for example, binary solvent systems of benzyl alcohol and a further substance selected from the group consisting of 2-phenylethanol, benzyl benzoate, diethyl succinate, triethyl citrate, triacetin, ethanol, peppermint oil, anethole, optamint, propylene glycol, phenoxyethanol and further cooling agents as described above as component (b).

Also suitable are binary solvent combinations or—mixtures which, for example, contain or consist of benzyl alcohol with another solvent. Thus, the binary solvent combinations or mixtures selected from benzyl alcohol and 2-phenylethanol, benzyl alcohol and benzyl benzoate, benzyl alcohol and diethyl succinate, benzyl alcohol and triethyl citrate, benzyl alcohol and triacetin, benzyl alcohol and ethanol, benzyl alcohol and peppermint oil, benzyl alcohol and anethole, benzyl alcohol and optamint, benzyl alcohol and propylene glycol, benzyl alcohol and menthol, benzyl alcohol and menthyl lactate (Frescolat® ML), benzyl alcohol and menthol propylene glycol carbonate (Frescolat® MPC), benzyl alcohol and menthol ethylene glycol carbonate (Frescolat® MGC), benzyl alcohol and menthone glyceryl acetal (Frescolat® MGA), benzyl alcohol and menthone carboxylic acid esters and amides are also suitable.

Furthermore, the following binary solvent combinations or mixtures are also suitable.—mixtures are suitable: 2-phenylethanol and menthol propylene glycol carbonate (Frescolat® MPC), diethyl succinate and 2-phenylethanol, triacetin and benzyl benzoate, triethyl citrate and triacetin, 2-phenylethanol and peppermint oil, 2-phenylethanol and optamint, anethole and triacetin, peppermint oil and menthyl lactate (Frescolat® ML), triacetin and menthone glyceryl acetal (Frescolat® MAG), optamint and menthyl lactate (Frescolat® ML), triethyl citrate and menthol ethylene glycol carbonate (Frescolat® MGC).

Suitable coolant mixtures in the sense of the present invention therefore contain as solvent (c), for example, a binary solvent combination or mixture as described above.

The binary solvent mixtures in the sense of the present invention have, for example, the following ratios: solvent (1):solvent (2) in a ratio of from 10:1 to 1:10, preferably in a ratio of from 8:2 to 2:8, still more preferably from 6:4 to 4:6 and most preferably in a ratio of 5:5.

The aforementioned suitable binary solvent mixtures can dissolve the cooling agents according to the invention and keep the cooling agents stably in solution in a wide range variably, depending on the solvent or combination of said solvents, in an amount of 2 wt.-% to 50 wt.-%, preferably 5 wt.-% to 40 wt.-% and further preferably 5 wt.-% to 20 wt.-%.

In another exemplary embodiment, the solvent or solvent system for the cooling agents according to the invention is a ternary system of three solvents selected from the group consisting of benzyl alcohol, 2-phenylethanol, benzyl benzoate, diethyl succinate, triethyl citrate, triacetin, ethanol, peppermint oil, anethole, optamint, propylene glycol, phenoxyethanol and further cooling agents as described above as component (b).

Suitable here are, for example, ternary solvent combinations or mixtures of benzyl alcohol and two further substances selected from the group consisting of 2-phenylethanol, benzyl benzoate, diethyl succinate, triethyl citrate, triacetin, ethanol, peppermint oil, anethole, optamint, propylene glycol, phenoxyethanol and further cooling agents, as also described above as component (b).

Suitable are ternary solvent combinations or mixtures which, for example, contain or consist of benzyl alcohol with two further solvents, the two further solvents being selected from the group consisting of 2-phenylethanol and benzyl benzoate, 2-phenylethanol and diethyl succinate, triethyl citrate and triacetin, triacetin and ethanol, triacetin and peppermint oil, menthol ethylene glycol carbonate (Frescolat® MGC) and anethole, 2-phenylethanol and optamint, optamint and propylene glycol, diethyl succinate and menthol, triacetin and menthyl lactate (Frescolat® ML), anethole and menthol propylene glycol carbonate (Frescolat® MPC), triacetin and menthol ethylene glycol carbonate (Frescolat® MGC), 2-phenylethanol and menthone glyceryl acetal (Frescolat® MGA), 2-phenylethanol and menthone carboxylic acid esters and amides, 2-phenylethanol and menthol propylene glycol carbonate (Frescolat® MPC), triacetin and benzyl benzoate, 2-phenylethanol and peppermint oil, anethole and triacetin, peppermint oil and menthyl lactate (Frescolat® ML), triacetin and menthol glyceryl acetal (Frescolat® MGA), optamint and menthyl lactate (Frescolat® ML), triethyl citrate and menthol ethylene glycol carbonate (Frescolat® MGC). Benzyl benzoate and menthol ethylene glycol carbonate (Frescolat® MGC), 2-phenylethanol and triethyl citrate, triethyl citrate and diethyl succinate, peppermint oil and menthyl lactate (Frescolat® ML), and ethanol and menthyl lactate (Frescolat® ML).

Moreover, the following ternary solvent combinations or mixtures are, for example, also suitable:

triethyl citrate, triacetin, menthyl lactate (Frescolat® ML),
triacetin, 2-phenylethanol and peppermint oil,
2-phenylethanol, optamint and peppermint oil,
2-phenylethanol, triacetin and optamint,
anethole, benzyl alcohol and triacetin,
2-Phenylethanol, benzyl benzoate and optamint
2-Phenylethanol, diethyl succinate and optamint
triethyl citrate, triacetin and peppermint oil,
optamint, triacetin and ethanol,
triacetin, menthol ethylene glycol carbonate (Frescolat® MGC) and anethole,
2-Phenylethanol, optamint and propylene glycol, diethyl succinate, triacetin and menthol, triacetin, benzyl benzoate and menthyl lactate (Frescolat® ML), anethole, menthol propylene glycol carbonate (Frescolat® MPC) and menthol ethylene glycol carbonate (Frescolat® MGC), triacetin, 2-phenylethanol and menthone glyceryl acetal (Frescolat® D MGA), peppermint oil, 2-phenylethanol and menthane carboxylic acid esters and amides, triacetin, 2-phenylethanol and menthol propylene glycol carbonate (Frescolat® MPC), menthyl lactate (Frescolat® ML), 2-phenylethanol and peppermint oil, anethole, triacetin and menthone glyceryl acetal (Frescolat® MGA), optamint, benzyl benzoate and menthyl lactate (Frescolat® ML), and benzyl benzoate, triethyl citrate and menthol ethylene glycol carbonate (Frescolat® MGC).

The ternary solvent mixtures in the sense of the present invention have, for example, the following ratios: solvent (1):solvent (2):solvent (3) in a ratio of from 10:1:15 to 5:1:3, or in a ratio of from 4:1:7 to 7:1:4, or in a ratio of from 2:2:4 to 4:4:2.

The aforementioned suitable ternary solvent mixtures were shown to be particularly good in their ability to dissolve the cooling agents of the invention and to keep the cooling agents stably and variably in solution in a wide range, depending on the solvent or combination of said solvents, in an amount of from 2 wt.-% to 50 wt.-%, preferably from 5 wt.-% to 40 wt.-% and further preferably from 5 wt.-% to 20 wt.-%.

This has the advantage that the cooling agent(s) according to the invention can thereby be prepared in a variable amount suitable for the final formulation, so that the range of cooling agent mixtures in which the cooling agent(s) is/are present in dissolved form is broad.

In another suitable embodiment, the solvent or solvent system for the cooling agents according to the invention is a quaternary system of four solvents selected from the group consisting of: benzyl alcohol, 2-phenylethanol, benzyl benzoate, diethyl succinate, triethyl citrate, triacetin, ethanol, peppermint oil, anethole, optamint, propylene glycol, phenoxyethanol and further cooling agents as described above as component (b).

Suitable here are, for example, quaternary solvent combinations of benzyl alcohol and three further substances selected from the group consisting of: 2-phenylethanol, benzyl benzoate, diethyl succinate, triethyl citrate, triacetin, ethanol, peppermint oil, anethole, optamint, propylene glycol, phenoxyethanol and further cooling agents as described above as component (b).

Suitable quaternary solvent combinations or mixtures are those containing or consisting of, for example, benzyl alcohol with three further solvents, wherein the three further solvents are selected from the group consisting of:

2-phenylethanol, triethyl citrate and triacetin, peppermint oil, 2-phenylethanol and triethyl citrate, triethyl citrate, menthyl lactate (Frescolat® ML) and diethyl succinate triethyl citrate, triacetin and anethole, 2-phenylethanol, triacetin, and optamint, peppermint oil, benzyl alcohol and menthyl lactate (Frescolat® ML), optamint, ethanol and menthyl lactate (Frescolat® ML), 2-phenylethanol, benzyl benzoate and diethyl succinate, triethyl citrate, triacetin and ethanol, peppermint oil, anethole and optamint, 2-phenylethanol, benzyl benzoate and propylene glycol, 2-phenylethanol, benzyl benzoate and menthol propylene glycol carbonate (Frescolat® MPC), triethyl citrate, optamint and ethanol, triacetin, benzyl benzoate and menthoxy-2-methyl-1,2-propanediol, menthone glyceryl acetal (Frescolat® MGA), triacetin and anethole.

The following quaternary solvent combinations and solvent mixtures are also suitable: anethole, triacetin, peppermint oil and menthol ethylene glycol carbonate (Frescolat® MGC), triacetin, ethanol, 2-phenylethanol and peppermint oil, 2-phenylethanol, optamint, diethyl succinate and peppermint oil, anethole, 2-phenylethanol, benzyl alcohol and triacetin.

The aforementioned suitable quaternary solvent mixtures were shown to be particularly good in their ability to dissolve the cooling agents of the invention and to keep the cooling agents stably and variably in solution in a wide range, depending on the solvent or combination of said solvents, in an amount of from 2 wt.-% to 50 wt.-%, preferably 5 wt.-% to 40 wt.-% and further preferably 5 wt.-% to 20 wt.-%.

This has the advantage that the cooling agent(s) according to the invention can thereby be prepared in a variable amount suitable for the final formulation, so that the range of cooling agent mixtures in which the cooling agent(s) is/are present in dissolved form is broad.

The coolant mixtures according to the invention preferably contain or consist of component (a) and/or component (b) in an amount of 2 wt.-% to 20 wt.-%, preferably from 2 wt.-% to 10 wt.-%, even more preferably from 5 wt.-% to 10 wt.-%, very particularly preferably from 5 wt.-% to 8 wt.-%, and/or component (c) in an amount of 80 wt.-% to 98 wt.-%, preferably 90 wt.-% to 98 wt.-%, even more preferably from 90 wt.-% to 95 wt.-%, very particularly preferably from 92 wt.-% to 95 wt.-%, based on the total coolant mixture, with the proviso that components (a) and/or (b) and/or (c) together give 100% by weight.

This composition of the coolant mixture according to the invention is particularly advantageous as it allows the amount of coolant(s) in the final formulation to be controlled.

Preferably, the final product contains the cooling agent(s) in an amount of about 0.00001 wt.-% to 50 wt.-%, preferably 0.0001 wt.-% to 10 wt.-%, more preferably 0.001 wt.-% to 5 wt.-%, and more preferably 0.005 wt.-% to 1 wt.-% or 0.1 wt.-% to 20 wt.-%, more preferably 0.5 wt.-% to 15 wt.-% or 1 wt.-% to 5 wt.-% based on the weight of the final product, particularly in the case of oral care compositions.

Suitable coolant mixtures according to the invention have, for example, the following composition or consist, for example, of:

5-10 wt.-% of cooling agent(s) in 95-90 wt.-% of benzyl alcohol, or 8-10 wt.-% of cooling agent(s) in 92-90 wt.-% of benzyl alcohol, or 1-4 wt.-% of cooling agent(s) in 99-96 wt.-% of triethyl citrate, or 1-3 wt.-% of cooling agent(s) in 99-97 wt.-% of triacetin, or 3-6 wt.-% of cooling agent(s) in 97-94 wt.-% of diethyl succinate, or 5-15 wt.-% of cooling agent(s) in 95-85 wt.-% 2-phenylethanol, or 5-10 wt.-% of cooling agent(s) in 95-90 wt.-% of benzyl benzoate, or 1-3 wt.-% cooling agent(s) in 99-97 wt.-% optamint, or
1-4 wt.-% cooling agent(s) in 99-96 wt.-% other coolants as described above as component (b), or
2-4 wt.-% cooling agent(s) in 98-96 wt.-% propylene glycol, or
0.5-2 wt.-% cooling agents(s) in 95.5-98 wt.-% ethanol, or
0.5-2 wt.-% of cooling agent(s) in 95.5-98 wt.-% of menthyl acetate, or
1-4 wt.-% of cooling agent(s) in 99-96 wt.-% of peppermint oil, or
2-5 wt.-% cooling agent(s) in 98-95 wt.-% anethole, whereby both components (cooling agent(s) and solvent) in the coolant mixture always add up to 100% by weight. For example, a suitable coolant mixture according to the invention consists of 5-10 wt.-% cooling agent(s) in 95-90 wt.-% benzyl alcohol, particularly preferably 8-10 wt-% cooling agent(s) in 92-90 wt.-% benzyl alcohol.

Another aspect of the present invention relates to a flavour preparation comprising or consisting of (d) one, two, three or more cooling agent(s) of formula (I) or formula (II) (or any of formulae (I) to (VII)) or as set out in Table 1 or Table 2 and defined above; and
(e) at least one flavouring.

The particular advantage of these mixtures or flavour preparations is that the cooling agents are able, even in small concentrations, to mask unpleasant, for example bitter or astringent, taste sensations of flavours, especially of sweeteners, while at the same time imparting an intensive and efficient cooling effect.

The preparations according to the invention may contain one or more flavouring substances (component (e)) selected from the group formed by acetophenone, allyl capronate, alpha-ionone, beta-ionone, anisaldehyde, anisyl acetate, anisyl formate, anethole, benzaldehyde, benzothiazole, benzyl acetate, benzyl alcohol, benzyl benzoate, beta-ionone, butyl butyrate, butyl capronate, butylidene phthalide, carvone, camphene, caryophyllene, cineole, cinnamyl acetate, citral, citronellol, citronellal, citronellyl acetate, cyclohexyl acetate, cymene, damascone, decalactone, dihydrocoumarin, dimethyl anthranilate, dimethyl anthranilate, dodecalactone, ethoxyethyl acetate, ethyl butyric acid, ethyl butyrate, ethyl caprinate, ethyl capronate, ethyl crotonate, ethyl furaneol, ethyl guaiacol, ethyl isobutyrate, ethyl isovalerate, ethyl lactate, ethyl methyl butyrate, ethyl propionate, eucalyptol, eugenol, ethyl heptylate, 4-(p-hydroxyphenyl)-2-butanone, gamma-decalactone, geraniol, geranyl acetate, geranyl acetate, grapefruit aldehyde, methyl dihydrojasmonate (e.g. Hedion®), heliotropin, 2-heptanone, 3-heptanone, 4-heptanone, trans-2-heptenal, cis-4-heptenal, trans-2-hexenal, cis-3-hexenol, trans-2-hexenoic acid, trans-3-hexenoic acid, cis-2-hexenyl acetate, cis-3-hexenyl acetate, cis-3-hexenyl capronate, trans-2-hexenyl capronate, cis-3-hexenyl formate, cis-2-hexyl acetate, cis-3-hexyl acetate, trans-2-hexyl acetate, cis-3-hexyl formate, para-hydroxybenzylacetone, isoamyl alcohol, isoamyl isovalerate, isobutyl butyrate, isobutyraldehyde, isoeugenol methyl ether, isopropyl methyl thiazole, lauric acid, leavulinic acid, linalool, linalool oxide, linalyl acetate, menthol, menthofuran, methyl anthranilate, methyl butanol, methyl butyric acid, 2-methyl butyl acetate, methyl capronate, methyl cinnamate, 5-methyl furfural, 3,2,2-methyl cyclopentenolone, 6,5,2-methyl heptenone, methyl dihydro jasmonate, methyl jasmonate, 2-methyl methyl butyrate, 2-methyl 2-pentenolic acid, methyl thiobutyrate, 3,1-methyl thiohexanol, 3-methyl thiohexyl acetate, nerol, nerylacetate, trans,trans-2,4-nonadienal, 2,4-nonadienol, 2,6-nonadienol, 2,4-nonadienol, nootkatone, delta octalactone, gamma octalactone, 2-octanol, 3-octanol, 1,3-octenol, 1-octyl acetate, 3-octyl acetate, palmitic acid, paraldehyde, phellandrene, pentanedione, phenyl ethyl acetate, phenyl ethyl alcohol, phenyl ethyl alcohol, phenyl ethyl isovalerate, piperonal, propionaldehyde, propyl butyrate, pulegone, pulegol, sinensal, sulfurol, terpinene, terpineol, terpinolene, 8,3-thiomenthanone, 4,4,2-thiomethylpentanone, thymol, delta-undecalactone, gamma-undecalactone, valencene, valeric acid, vanillin, acetoin, ethylvanillin, ethylvanillin isobutyrate (=3-ethoxy-4-isobutyryloxybenzaldehyde), 2,5-dimethyl-4-hydroxy-3(2H)-furanone and its derivatives (preferably homofuraneol (=2-ethyl-4-hydroxy-5-methyl-3(2H)-furanone), homofuronol (=2-ethyl-5-methyl-4-hydroxy-3(2H)-furanone and 5-ethyl-2-methyl-4-hydroxy-3(2H)-furanone), maltol and maltol derivatives (preferably ethyl maltol), coumarin and coumarin derivatives, gamma-lactones (preferably gamma-undecalactone, gamma-nonalactone, gamma-decalactone), delta-lactones (preferably 4-methyldeltadecalacton, massoilactone, deltadecalactone, tuberolactone), methyl sorbate, divanilline, 4-hydroxy-2 (or 5)-ethyl-5 (or 2)-methyl-3(2H)-furanone, 2-hydroxy-3-methyl-2-cyclopentenone, 3-hydroxy-4,5-dimethyl-2(5H)-furanone, acetic acid isoamyl ester, butyric acid ethyl ester, butyric acid n-butyl ester, butyric acid isoamyl ester, 3-methyl butyric acid ethyl ester, n-hexanoic acid ethyl ester, n-hexanoic acid allyl ester, n-hexanoic acid n-butyl ester, n-octanoic acid ethyl ester, ethyl 3-methyl-3-phenylglycidate, ethyl 2-trans-4-cis-decadienoate, 4-(p-hydroxyphenyl)-2-butanone, 1,1-dimethoxy-2,2,5-trimethyl-4-hexane, 2,6-dimethyl-5-hepten-1-al and phenylacetaldehyde, 2-methyl-3-(methylthio)furan, 2-methyl-3-furanthiol, bis(2-methyl-3-furyl)disulphide, furfuryl mercaptan, methional, 2-acetyl-2-thiazoline, 3-mercapto-2-pentanone, 2,5-dimethyl-3-furanthiol, 2,4,5-trimethylthiazole, 2-acetylthiazole, 2,4-dimethyl-5-ethylthiazole, 2-acetyl-1-pyrroline, 2-methyl-3-ethylpyrazine, 2-ethyl-3,5-dimethylpyrazine, 2-ethyl-3,6-dimethylpyrazine, 2,3-diethyl-5-methylpyrazine, 3-isopropyl-2-methoxypyrazine, 3-isobutyl-2-methoxypyrazine, 2-acetylpyrazine, 2-pentylpyridine, (E,E)-2,4-decadienal, (E,E)-2,4-nonadienal, (E)-2-octenal, (E)-2-nonenal, 2-undecenal, 12-methyltridecanal, 1-penten-3-one, 4-hydroxy-2,5-dimethyl-3(2H)-furanone, guaiacol, 3-hydroxy-4,5-dimethyl-2(5H)-furanone, 3-hydroxy-4-methyl-5-ethyl-2(5H)-furanone, cinnamaldehyde, cinnamalcohol, methyl salicylate, isopulegol as well as stereoisomers, enantiomers, positional isomers, diastereomers, cis/trans isomers or epimers (not explicitly mentioned here) of these substances.

For the purposes of the present invention, artificial and natural sweeteners and sweetener enhancers are also particularly suitable as flavouring substances of component (e). These can be selected from the group consisting of sugar alcohols (e.g. erythritol, threitol, arabitol, ribotol, xylitol, sorbitol, mannitol, dulcitol, lactitol);
proteins (e.g. miraculin, monellin, thaumatin, curculin, brazzein);
synthetic sweeteners (e.g. Magap, sodium cyclamate, acesulfame K, neohesperidin dihydrochalcone, saccharin sodium salt, aspartame, superaspartame, neotame, alitame, sucralose, stevioside, rebaudioside, lugduname, carrelame, sucrononate, sucrooctate, monatin, phenylodulcin);
sweet-tasting amino acids (e.g. glycine, D-leucine, D-threonine, D-asparagine, D-phenylalanine, D-tryptophane, L-proline);
sweet-tasting low molecular weight substances, such as hemandulcin, dihydrochalcone glycosides, glycyrrhizin, glycerrhetinic acid, their derivatives and salts, extracts of liquorice (*Glycyrrhizza glabra* ssp.), *Lippia dulcis* extracts, *Momordica* ssp. extracts and/or plant extracts, such as *Momordica grosvenori* [Luo Han Guo] and the mogrosides obtained therefrom, *Hydrangea dulcis* or *Stevia* ssp. (e.g. *Stevia rebaudiana*) extracts or steviosides obtained therefrom.

Component (e) comprises at least one of the flavouring substances mentioned above.

The flavouring preparations according to the invention may contain components (d) and (e) in a ratio by weight of about 1:99 to about 99:1, preferably about 10:90 to about 90:10, more preferably about 25:75 to about 75:25 and in particular about 40:60 to 60:40.

In a further preferred variant, the one or more cooling agent(s) or the cooling agent mixture or the aroma preparation is present in encapsulated form. This is of particular interest, for example, when the capsules loaded with the one or more cooling agent(s) are applied to textile surfaces, for example as a component of fabric softeners or laundry after-treatment agents, or a finish is obtained by using capsules loaded with the one or more cooling agent(s), by forced application, for example on pantyhose.

Capsules are spherical aggregates containing at least one solid or liquid core enclosed in at least one continuous shell. During encapsulation, the one or more cooling agent(s), or the cooling agent mixture, or the flavour preparation is encapsulated by means of a coating material/envelope material so that they are in the form of macrocapsules with diameters of about 0.1 to about 5 mm or microcapsules with diameters of about 0.0001 to about 0.1 mm.

Consequently, a further embodiment of the present invention also relates to physiological cooling agents or physiological cooling agent mixtures or flavouring preparations in encapsulated form.

Suitable coating materials are, for example, starches, including their degradation products and chemically or physically produced derivatives (in particular dextrins and maltodextrins), gelatine, gum arabic, agar-agar, ghatti gum, gellan gum, modified and non-modified celluloses, pullulan, curdlan, carrageenans, alginic acid, alginates, pectin, inulin, xanthan gum and mixtures of two or more of these substances.

Among the above-mentioned coating materials, gelatine (especially pork, beef, poultry and/or fish gelatine) is preferred, preferably having a swelling factor of greater than or equal to 20, preferably greater than or equal to 24. Furthermore, gelatine is particularly preferred as it is readily available and can be obtained with different swelling factors.

Also preferred are maltodextrins (in particular based on cereals, especially maize, wheat, tapioca or potatoes), which preferably have DE values in the range of 10 to 20. Further preferred are celluloses (e.g. cellulose ether), alginates (e.g. sodium alginate), carrageenan (e.g. beta-, jota-, lambda- and/or kappa-carrageenan), gum arabic, curdlan and/or agar agar.

Also preferred are alginate capsules such as those described in detail in the following publications: EP 0389700 A1, U.S. Pat. Nos. 4,251,195, 6,214,376, WO 2003 055587 or WO 2004 050069 A1.

In another preferred embodiment, the shell of the capsules consists of melamine-formaldehyde resins or coacervation products of cationic monomers or biopolymers (such as chitosan) and anionic monomers, such as (meth)acrylates or alginates.

The capsules are generally finely dispersed liquid or solid phases coated with film-forming polymers, during the production of which the polymers are deposited on the material to be coated after emulsification and coacervation or interfacial polymerisation. According to another process, molten waxes are taken up in a matrix ("microsponge"), which may additionally be coated with film-forming polymers as microparticles. According to a third method, particles are alternately coated with polyelectrolytes of different charge ("layer-by-layer" method). The microscopically small capsules can be dried and used like powder.

In addition to mononuclear microcapsules, multinuclear aggregates, also called microspheres, are also known, which contain two or more nuclei distributed in the continuous shell material. Mono- or multinuclear microcapsules can also be enclosed by an additional second, third, etc. shell. The shell may be made of natural, semi-synthetic or synthetic materials. Natural shell materials are, for example, gum arabic, agar-agar, agarose, maltodextrins, alginic acid or its salts, e.g. sodium or calcium alginate, fats and fatty acids, cetyl alcohol, collagen, chitosan, lecithin, gelatine, albumin, shellac, polysaccharides such as starch or dextran, polypeptides, protein hydrolysates, sucrose and waxes. Semi-synthetic enveloping materials include chemically modified celluloses, in particular cellulose esters and -ethers, e.g. cellulose acetate, ethyl cellulose, hydroxypropyl cellulose, hydroxypropyl methyl cellulose and carboxymethyl cellulose, as well as starch derivatives, in particular starch ethers and esters. Synthetic coating materials are, for example, polymers such as polyacrylates, polyamides, polyvinyl alcohol or polyvinylpyrrolidone.

Examples of coating materials/envelope materials of the prior art for the production of microcapsules are the following commercial products (the envelope material is indicated in brackets in each case): Hallcrest Microcapsules (gelatine, gum arabic), Coletica Thalaspheres (marine collagen), Lipotec Millicapseln (alginic acid, agar-agar), Induchem Unispheres (lactose, microcrystalline cellulose, hydroxypropylmethylcellulose), Unicerin C30 (lactose, microcrystalline cellulose, hydroxypropylmethylcellulose), Kobo Glycospheres (modified starch, fatty acid esters, phospholipids), Softspheres (modified agar-agar) and Kuhs Probiol Nanospheres (phospholipids) as well as Primaspheres and Primasponges (chitosan, alginates) and Primasys (phospholipids).

Chitosan microcapsules and methods for their production are sufficiently known from the prior art WO 01/01926, WO 01/01927, WO 01/01928, WO 01/01929. Microcapsules with average diameters in the range from 0.0001 mm to 5 mm, preferably from 0.001 mm to 0.5 mm and in particular from 0.005 mm to 0.1 mm, consisting of a shell membrane and a matrix containing the active substances, can be obtained, for example, by (1) preparing a matrix from gel formers, cationic polymers and active ingredients, (2) if necessary, dispersing the matrix in an oil phase, (3) treating the dispersed matrix with aqueous solutions of anionic polymers and, if necessary, removing the oil phase in the process.

The aforementioned steps (1) and (3) are interchangeable in that anionic polymers are used instead of the cationic polymers in step (1) and vice versa.

One can also create the capsules by alternately coating the active substance with layers of differently charged polyelectrolytes (layer-by-layer technology). In this context, reference is made to European Patent EP 1064088 B1 (Max Planck Society).

The two essential properties of the new cooling substances or new cooling substance mixtures are, as mentioned, on the one hand, to modulate the TRPM8 receptor as antagonists or agonists and in this way to trigger a physiological reaction, namely an intensive and efficient cooling effect on the skin or mucous membrane, and on the other hand, to reduce or mask unpleasant flavours. Primarily, however, the ability to induce intensive and efficient cooling effects, even when small quantities are applied, should be emphasised.

A further aspect of the present invention therefore relates to the use of the physiological cooling agent or physiological cooling agent mixture according to the invention as a modulator, preferably for in vivo and/or in vitro modulation, of the cold menthol receptor TRPM8, in particular as a TRPM8 receptor agonist or as a TRPM8 receptor antagonist.

In the use according to the invention, the receptor TRPM8 is brought into contact with at least one cooling agent according to the invention or a physiological cooling agent mixture according to the invention, which modulates the permeability of these cells to $Ca^{2+}$ ions in a cellular activity assay using cells recombinantly expressing the human TRPM8 receptor.

Suitable modulators can act either only as antagonists or agonists, especially only as agonists, or both as antagonists and agonists. In particular, an agonistic or antagonistic effect can occur depending on the respective modulator concentration selected.

An "agonist" is a substance that mediates an activation of the TRPM8 receptor, i.e. induces a $Ca^{2+}$ ion influx into the cold-sensitive neurons and thus conveys a feeling of cold.

An "antagonist", on the other hand, is a compound that can counteract this activation of the TRPM8 receptor.

The modulators according to the invention, i.e. the one physiological cooling agent or the cooling agent mixture, can exert their effect by binding reversibly or irreversibly, specifically or non-specifically to a TRPM8 receptor molecule. Usually, binding occurs non-covalently via ionic and/or non-ionic, such as hydrophobic, interactions with the receptor molecule. The term "specific" includes both exclusive interactions with one or more different TRPM8 receptor molecules (such as TRPM8 molecules of different origins or different isoforms). The term "non-specific", on the other hand, is an interaction of the modulator with several different receptor molecules of different function and/or sequence, but where a desired agonistic and/or antagonistic modulation (as described above) of the TRPM8 receptor can be detected as a consequence.

In a use according to the invention, preferably in a variant described above as preferred, the modulator has an agonistic or antagonistic effect on the cellular $Ca^{2+}$ ion permeability.

Particularly preferred is a variant of the use according to the invention in which the modulator is a TRPM8 receptor agonist.

Due to its physiological property of inducing a cooling effect on skin or mucous membrane, another aspect of the present invention relates to the use of the cooling agent according to the invention or the cooling agent mixture according to the invention for producing a physiological cooling effect on skin or mucous membrane in a human being or in an animal.

Alternatively, the cooling agent according to the invention or the cooling agent mixture according to the invention is used to induce a cooling effect by means of a package containing the physiological cooling agent or the physiological cooling agent mixture or a textile containing the physiological cooling agent or the physiological cooling agent mixture.

Due to its/their additional properties, namely to reduce or mask unpleasant, for example bitter or astringent, flavours, a further aspect of the present invention relates to the use of the physiological cooling agent according to the invention or the cooling agent mixture according to the invention to improve the flavour properties of flavourings. In this way, known taste disadvantages of flavourings, especially also of sweeteners such as the steviosides, can be reduced or masked. In particular, the pungent, bitter or metallic aftertaste is effectively reduced or masked even when small amounts are added.

The cooling agents according to the invention or the physiological cooling agent mixtures according to the invention or the flavouring preparations according to the invention have a broad field of application, in particular in foodstuffs, food supplements, cosmetic or pharmaceutical preparations, animal feed, textiles, packaging or tobacco products.

In particular, the physiological cooling agents or the physiological cooling agent mixtures or the flavouring preparations according to the invention are used for the production of foodstuffs, food supplements, cosmetic or pharmaceutical preparations, animal feed, textiles, packaging or tobacco products because of their cooling properties and/or flavour-enhancing properties.

A further aspect of the present invention is therefore the use of one or more cooling agents according to the invention or of the cooling agent mixture according to the invention or of the flavouring preparation according to the invention for the production of foodstuffs, food supplements, cosmetic or pharmaceutical preparations, animal feedstuffs, textiles, packaging or tobacco products.

On the basis of the advantageous properties described, the cooling agents according to the invention, as represented and defined by the general formulae (I) or (II), are suitable for the uses according to the invention, namely use as a modulator, for generating a physiological cooling effect on the skin or mucous membrane of humans or animals, or for inducing a cooling effect, for improving the taste properties of flavouring substances, in particular to reduce or mask an unpleasant taste, for the preparation of foodstuffs, food supplements, cosmetic or pharmaceutical preparations, animal feedstuffs, textiles, packaging or tobacco products, or for use as a medicament, as described in detail herein, preferably selected from the group consisting of the compounds set out in Table 4.

TABLE 4
| Preferably used structures according to the invention | |
| --- | --- |
| Structure | Compound |
| 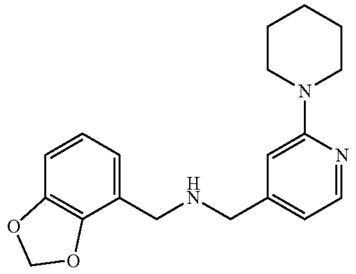 [SMILES: c1cc(CNCc2ccnc(N3CCCCC3)c2)c2c(c1)OCO2] | Compound 1 |
| 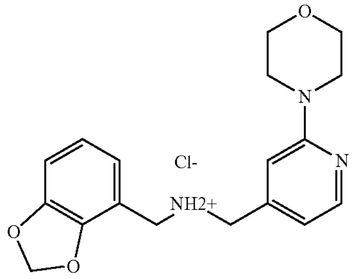 [SMILES: c1cc(C[NH2+]Cc2ccnc(N3CCOCC3)c2)c2c(c1)OCO2 ; [Cl-]] | Compound 2 |
| 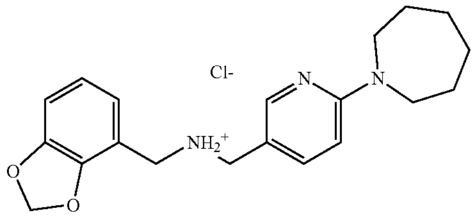 [SMILES: c1cc(C[NH2+]Cc2ccc(N3CCCCCC3)nc2)c2c(c1)OCO2 ; [Cl-]] | Compound 3 |
| 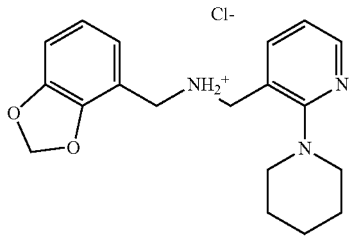 [SMILES: [Cl-] ; c1cnc(N2CCCCC2)c(C[NH2+]Cc2cccc3c2OCO3)c1] | Compound 4 |
| 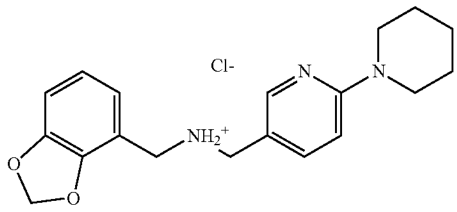 [SMILES: c1cc(C[NH2+]Cc2ccc(N3CCCCC3)nc2)c2c(c1)OCO2 ; [Cl-]] | Compound 5 |
| 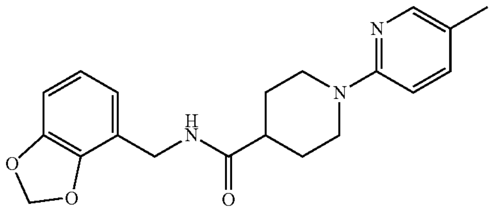 [SMILES: Cc1ccc(N2CCC(C(=O)NCc3cccc4c3OCO4)CC2)nc1] | Compound 5 a |

TABLE 4-continued
| Preferably used structures according to the invention | |
|---|---|
| Structure | Compound |
| 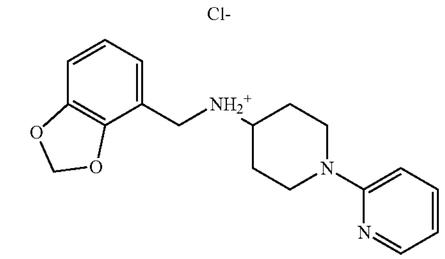 [SMILES: [Cl-] ; c1ccc(N2CCC([NH2+]Cc3cccc4c3OCO4)CC2)nc1] | Compound 6 |
| 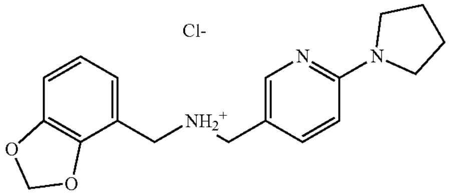 [SMILES: c1cc(C[NH2+]Cc2ccc(N3CCCC3)nc2)c2c(c1)OCO2 ; [Cl-]] | Compound 7 |
| 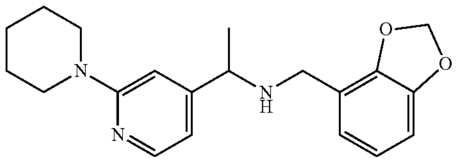 | Compound 8 |
| 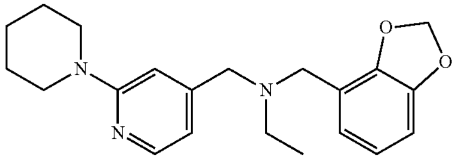 [SMILES: CCN(Cc1ccnc(N2CCCCC2)c1)Cc1cccc2c1OCO2] | Compound 9 |
| 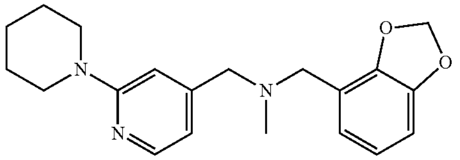 | Compound 10 |
| 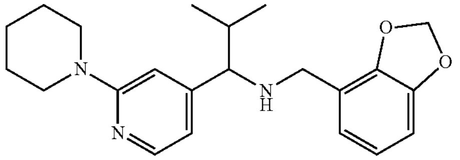 [SMILES: CC(C)C(NCc1cccc2c1OCO2)c1ccnc(N2CCCCC2)c1] | Compound 11 |
| 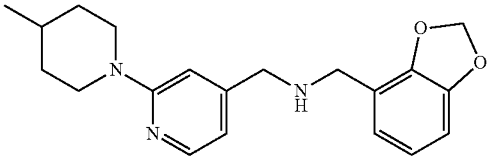 [SMILES: CC1CCN(c2cc(CNCc3cccc4c3OCO4)ccn2)CC1] | Compound 12 |
| 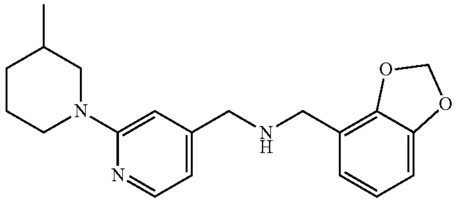 | Compound 13 |

TABLE 4-continued
| Preferably used structures according to the invention | |
|---|---|
| Structure | Compound |
| 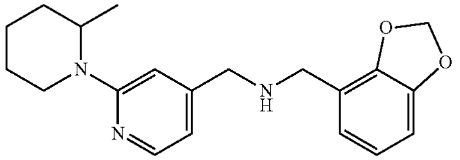 [SMILES: CC1CCCCN1c1cc(CNCc2cccc3c2OCO3)ccn1] | Compound 14 |
| 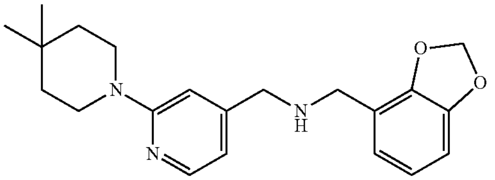 [SMILES: CC1(C)CCN(c2cc(CNCc3cccc4c3OCO4)ccn2)CC1] | Compound 15 |
| 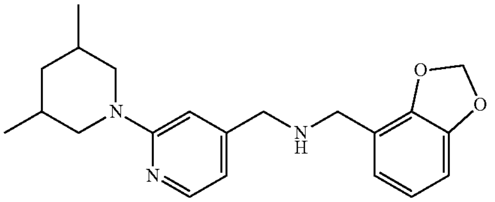 [SMILES: CC1CC(C)CN(c2cc(CNCc3cccc4c3OCO4)ccn2)C1] | Compound 16 |
| 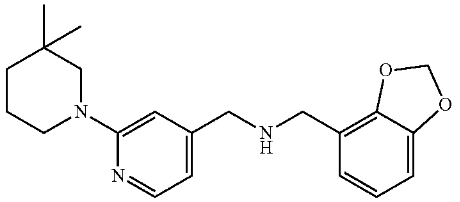 | Compound 17 |
| 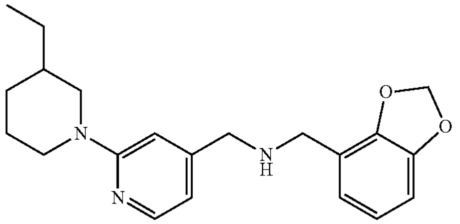 [SMILES: CCC1CCCN(c2cc(CNCc3cccc4c3OCO4)ccn2)C1] | Compound 18 |
| 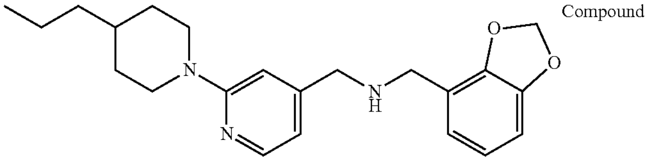 | Compound 18 a |
| 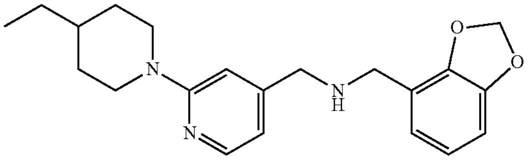 [SMILES: CCC1CCN(c2cc(CNCc3cccc4c3OCO4)ccn2)CC1] | Compound 19 |
| 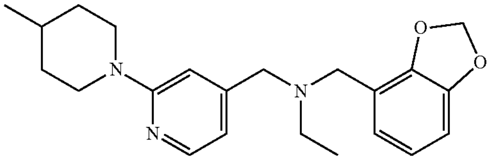 [SMILES: CCN(Cc1ccnc(N2CCC(C)CC2)c1)Cc1cccc2c1OCO2] | Compound 19 a |

TABLE 4-continued
| Preferably used structures according to the invention | |
|---|---|
| Structure | Compound |
| 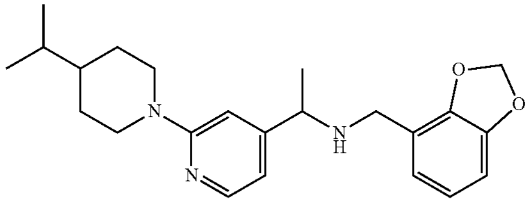 [SMILES: CC(NCc1cccc2c1OCO2)c1ccnc(N2CCC(C(C)C)CC2)c1] | Compound 20 |
| 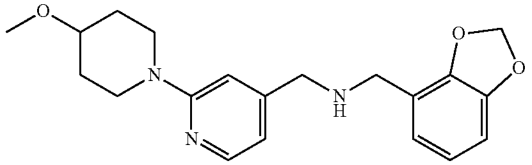 [SMILES: COC1CCN(c2cc(CNCc3cccc4c3OCO4)ccn2)CC1] | Compound 21 |
| 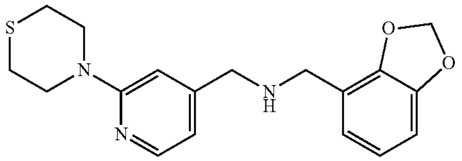 [SMILES: c1cc(CNCc2ccnc(N3CCSCC3)c2)c2c(c1)OCO2] | Compound 22 |
| 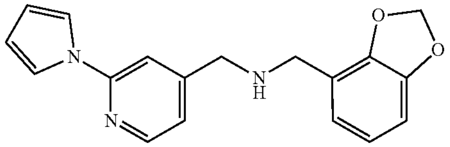 [SMILES: c1cc(CNCc2ccnc(-n3cccc3)c2)c2c(c1)OCO2] | Compound 22 a |
| 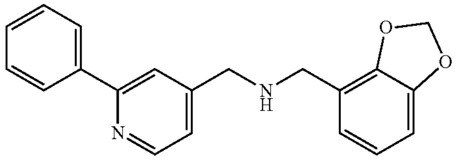 | Compound 22 b |
| 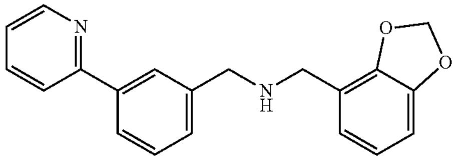 | Compound 22 c |
| 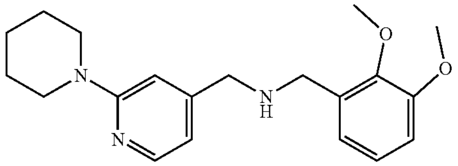 [SMILES: COc1cccc(CNCc2ccnc(N3CCCCC3)c2)c1OC] | Compound 23 |
| 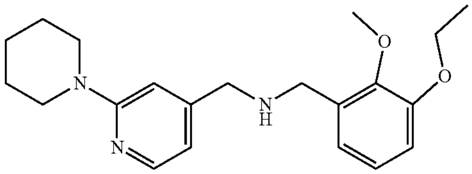 [SMILES: CCOc1cccc(CNCc2ccnc(N3CCCCC3)c2)c1OC] | Compound 24 |

TABLE 4-continued
| Preferably used structures according to the invention | |
|---|---|
| Structure | Compound |
| 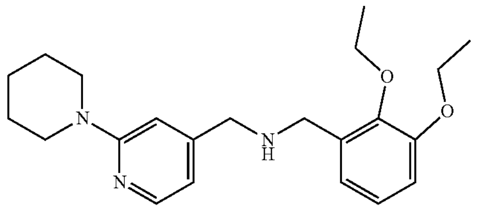 [SMILES: CCOc1cccc(CNCc2ccnc(N3CCCCC3)c2)c1OCC] | Compound 25 |
| 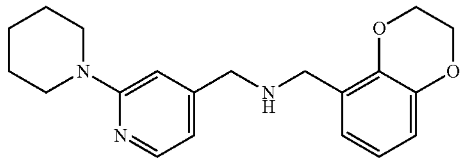 [SMILES: c1cc(CNCc2ccnc(N3CCCCC3)c2)c2c(c1)OCCO2] | Compound 26 |
| 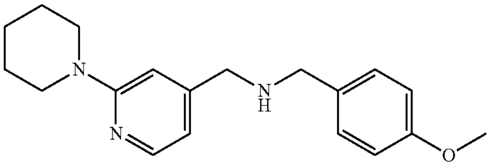 [SMILES: COc1ccc(CNCc2ccnc(N3CCCCC3)c2)cc1] | Compound 27 |
| 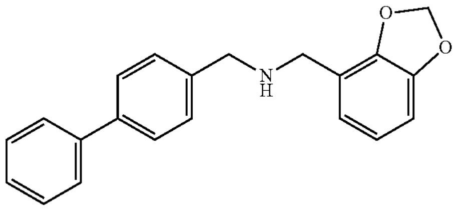 [SMILES: c1ccc(-c2ccc(CNCc3cccc4c3OCO4)cc2)cc1] | Compound 28 |
| 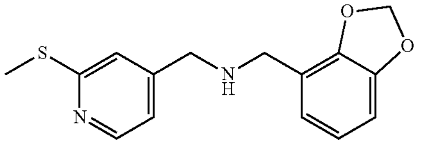 [SMILES: CSc1cc(CNCc2cccc3c2OCO3)ccn1] | Compound 29 |
| 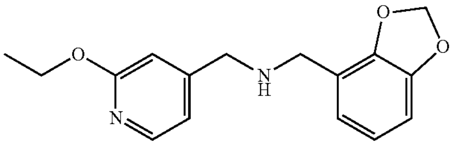 [SMILES: CCOc1cc(CNCc2cccc3c2OCO3)ccn1] | Compound 30 |
| 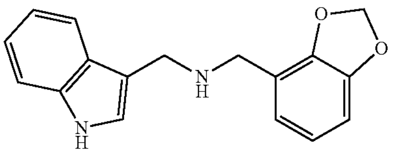 [SMILES: c1cc(CNCc2c[nH]c3ccccc23)c2c(c1)OCO2] | Compound 31 |
| 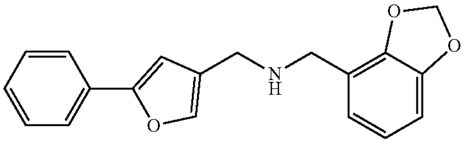 | Compound 31 a |

TABLE 4-continued
| Preferably used structures according to the invention | |
|---|---|
| Structure | Compound |
| 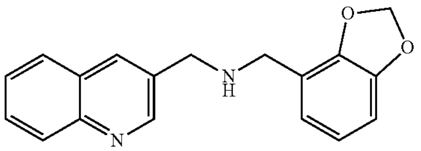 [SMILES: c1cc(CNCc2cnc3ccccc3c2)c2c(c1)OCO2] | Compound 32 |
| 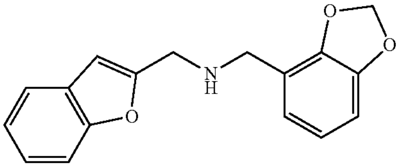 | Compound 32 a |
| 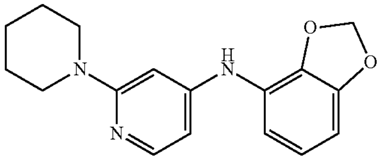 [SMILES: c1cc(Nc2ccnc(N3CCCCC3)c2)c2c(c1)OCO2] | Compound 33 |
| 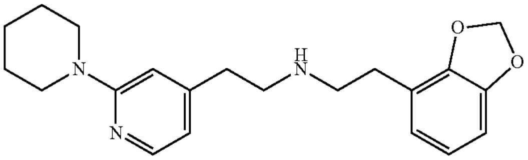 [SMILES: c1cc(CCNCCc2ccnc(N3CCCCC3)c2)c2c(c1)OCO2] | Compound 34 |
| 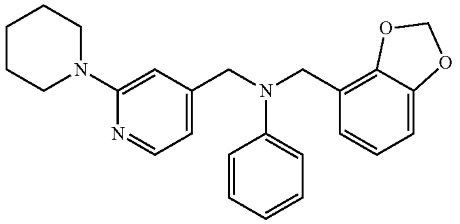 [SMILES: c1ccc(N(Cc2ccnc(N3CCCCC3)c2)Cc2cccc3c2OCO3)cc1] | Compound 35 |
| 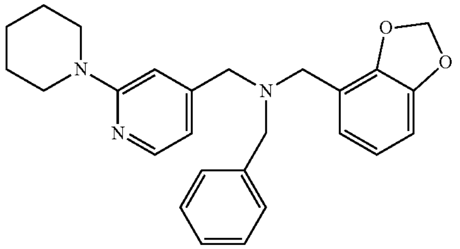 [SMILES: c1ccc(CN(Cc2ccnc(N3CCCCC3)c2)Cc2cccc3c2OCO3)cc1] | Compound 36 |
| 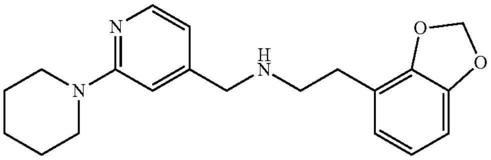 [SMILES: c1cc(CCNCc2ccnc(N3CCCCC3)c2)c2c(c1)OCO2] | Compound 37 |
| 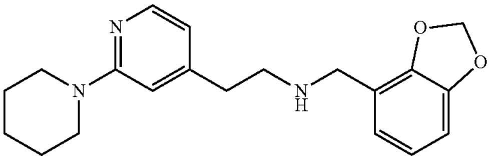 [SMILES: c1cc(CNCCc2ccnc(N3CCCCC3)c2)c2c(c1)OCO2] | Compound 38 |

TABLE 4-continued
| Preferably used structures according to the invention | |
|---|---|
| Structure | Compound |
| 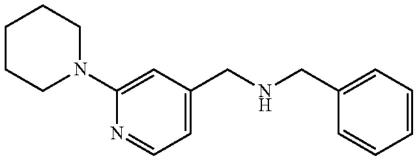 [SMILES: c1ccc(CNCc2ccnc(N3CCCCC3)c2)cc1] | Compound 39 |
| 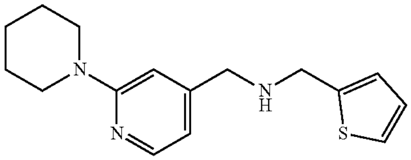 | Compound 40 |
| 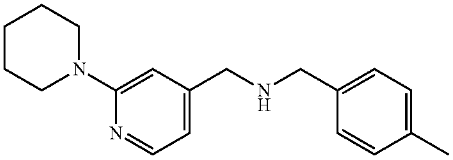 [SMILES: Cc1ccc(CNCc2ccnc(N3CCCCC3)c2)cc1] | Compound 41 |
| 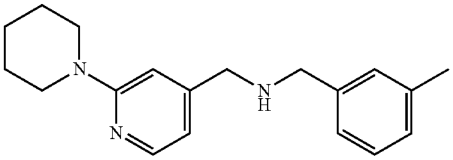 [SMILES: Cc1cccc(CNCc2ccnc(N3CCCCC3)c2)c1] | Compound 42 |
| 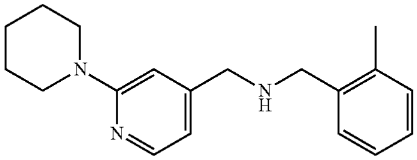 [SMILES: Cc1ccccc1CNCc1ccnc(N2CCCCC2)c1] | Compound 43 |
| 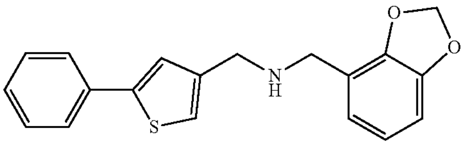 | Compound 43 a |
| 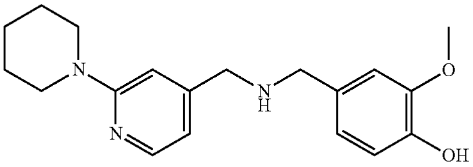 [SMILES: COc1cc(CNCc2ccnc(N3CCCCC3)c2)ccc1O] | Compound 44 |
| 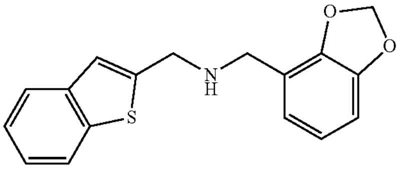 | Compound 45 |

TABLE 4-continued
| Preferably used structures according to the invention | |
|---|---|
| Structure | Compound |
| 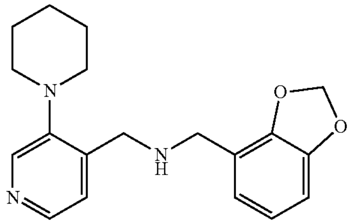 [SMILES: c1cc(CNCc2ccncc2N2CCCCC2)c2c(c1)OCO2] | Compound 46 |
| 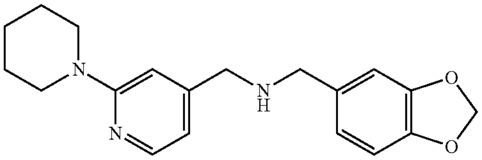 [SMILES: c1cc(CNCc2ccc3c(c2)OCO3)cc(N2CCCCC2)n1] | Compound 47 |
| 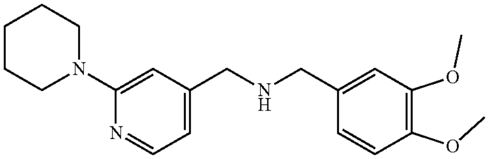 [SMILES: COc1ccc(CNCc2ccnc(N3CCCCC3)c2)cc1OC] | Compound 48 |
| 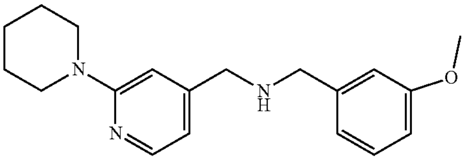 [SMILES: COc1cccc(CNCc2ccnc(N3CCCCC3)c2)c1] | Compound 49 |
| 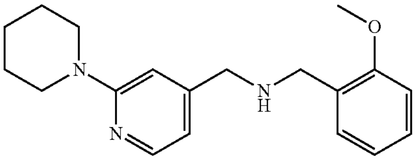 [SMILES: COc1ccccc1CNCc1ccnc(N2CCCCC2)c1] | Compound 50 |
| 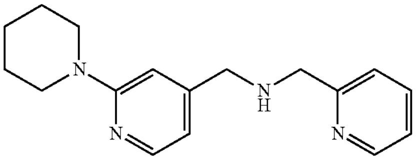 [SMILES: c1ccc(CNCc2ccnc(N3CCCCC3)c2)nc1] | Compound 51 |
| 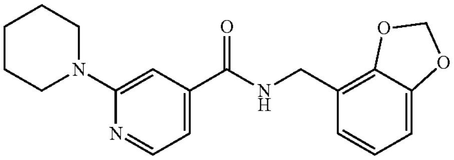 | Compound 51 a |
| 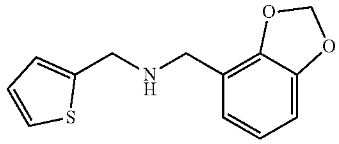 [SMILES: c1csc(CNCc2cccc3c2OCO3)c1] | Compound 52 |

TABLE 4-continued
Preferably used structures according to the invention
| Structure | Compound |
|---|---|
| 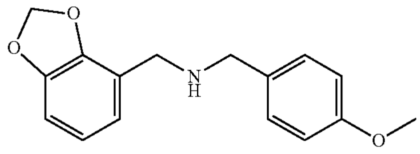 [SMILES: COc1ccc(CNCc2cccc3c2OCO3)cc1] | Compound 53 |
| 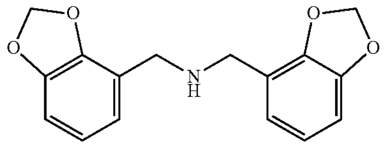 [SMILES: c1cc(CNCc2cccc3c2OCO3)c2c(c1)OCO2] | Compound 54 |
| 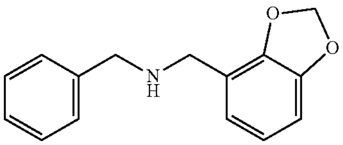 [SMILES: c1ccc(CNCc2cccc3c2OCO3)cc1] | Compound 55 |
| 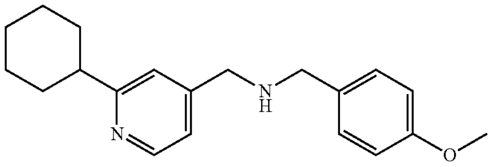 | Compound 56 |
| 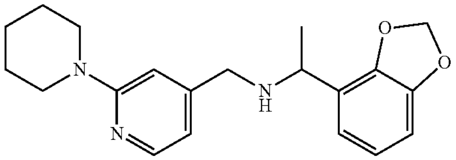 | Compound 57 |
| 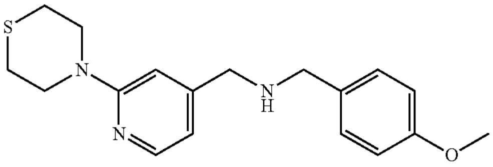 [SMILES: COc1ccc(CNCc2ccnc(N3CCSCC3)c2)cc1] | Compound 58 |
| 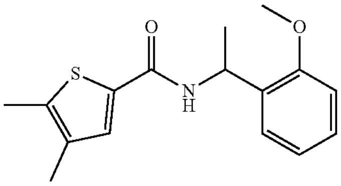 [SMILES: COc1ccccc1C(C)NC(=O)c1cc(C)c(C)s1] | Compound 59 |
| 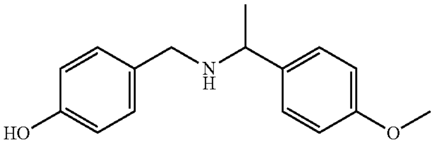 [SMILES: COc1ccc(C(C)NCc2ccc(O)cc2)cc1] | Compound 60 |
| 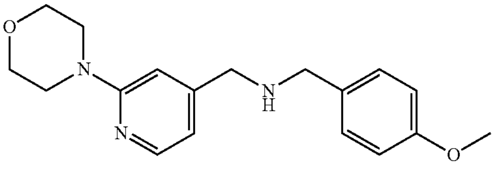 [SMILES: COc1ccc(CNCc2ccnc(N3CCOCC3)c2)cc1] | Compound 61 |

TABLE 4-continued
| Preferably used structures according to the invention | |
|---|---|
| Structure | Compound |
| 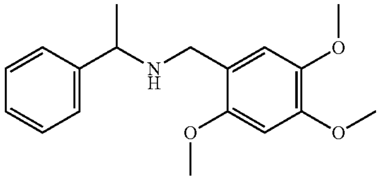 [SMILES: COc1cc(OC)c(OC)cc1CNC(C)c1ccccc1] | Compound 62 |
| 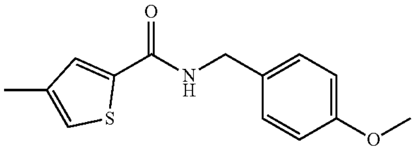 | Compound 63 |
| 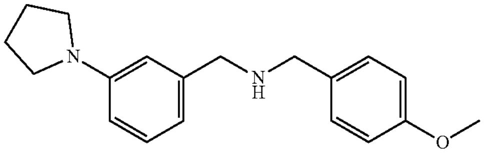 [SMILES: COc1ccc(CNCc2cccc(N3CCCC3)c2)cc1] | Compound 64 |
| 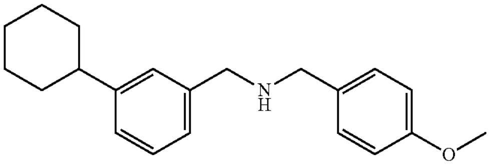 [SMILES: COc1ccc(CNCc2cccc(C3CCCCC3)c2)cc1] | Compound 65 |
| 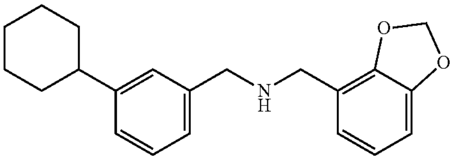 [SMILES: c1cc(CNCc2cccc3c2OCO3)cc(C2CCCCC2)c1] | Compound 66 |
| 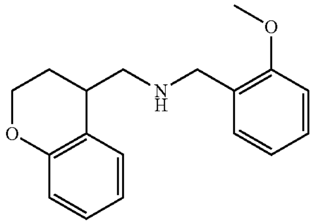 [SMILES: COc1ccccc1CNCC1CCOc2ccccc21] | Compound 67 |
| 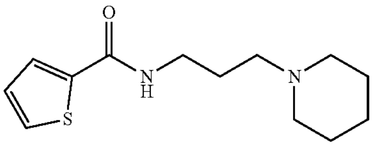 [SMILES: O=C(NCCCN1CCCCC1)c1cccs1] | Compound 68 |
| 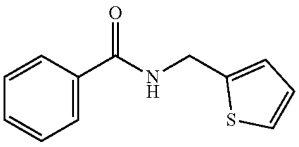 [SMILES: O=C(NCc1cccs1)c1ccccc1] | Compound 69 |

TABLE 4-continued
| Preferably used structures according to the invention | |
|---|---|
| Structure | Compound |
| 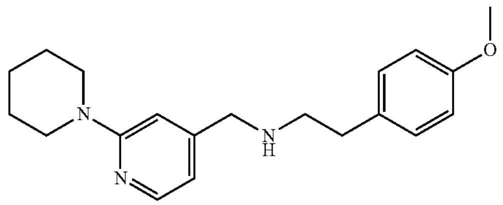 [SMILES: COc1ccc(CCNCc2ccnc(N3CCCCC3)c2)cc1] | Compound 70 |
| 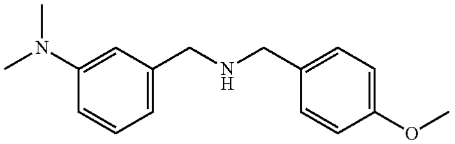 | Compound 71 |
| 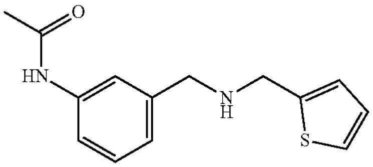 [SMILES: CC(=O)Nc1cccc(CNCc2cccs2)c1] | Compound 72 |
| 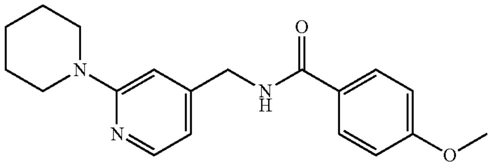 [SMILES: COc1ccc(C(=O)NCc2ccnc(N3CCCCC3)c2)cc1] | Compound 73 |
| 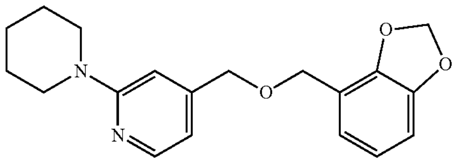 [SMILES: c1cc(COCc2ccnc(N3CCCCC3)c2)c2c(c1)OCO2] | Compound 74 |
| 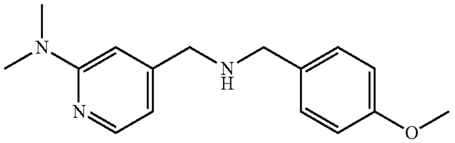 | Compound 75 |
| 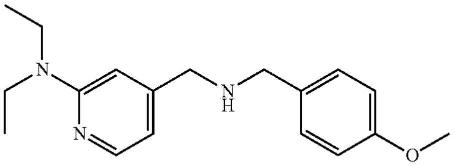 [SMILES: CCN(CC)c1cc(CNCc2ccc(OC)cc2)ccn1] | Compound 76 |
| 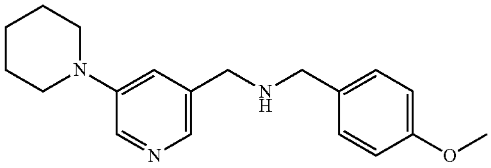 [SMILES: COc1ccc(CNCc2cncc(N3CCCCC3)c2)cc1] | Compound 77 |

TABLE 4-continued
| Preferably used structures according to the invention | |
|---|---|
| Structure | Compound |
| 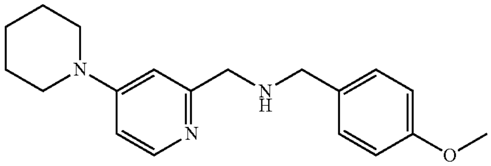 [SMILES: COc1ccc(CNCc2cc(N3CCCCC3)ccn2)cc1] | Compound 79 |
| 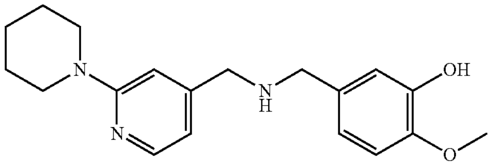 [SMILES: COc1ccc(CNCc2ccnc(N3CCCCC3)c2)cc1O] | Compound 80 |
| 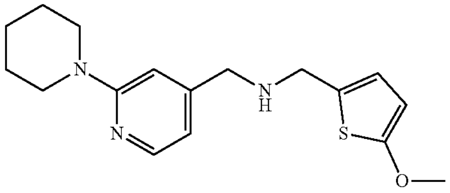 [SMILES: COc1ccc(CNCc2ccnc(N3CCCCC3)c2)s1] | Compound 81 |
| 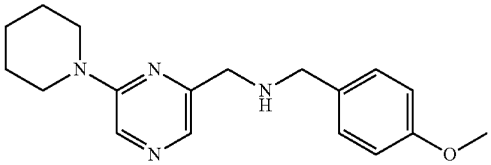 [SMILES: COc1ccc(CNCc2cncc(N3CCCCC3)n2)cc1] | Compound 82 |
| 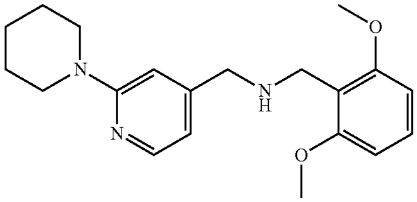 [SMILES: COc1cccc(OC)c1CNCc1ccnc(N2CCCCC2)c1] | Compound 83 |
| 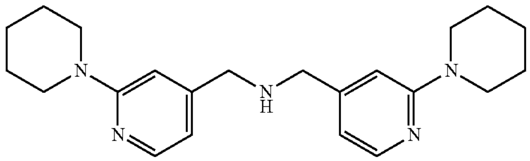 [SMILES: c1cc(CNCc2ccnc(N3CCCCC3)c2)cc(N2CCCCC2)n1] | Compound 84 |
| 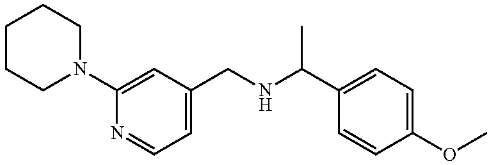 [SMILES: COc1ccc(C(C)NCc2ccnc(N3CCCCC3)c2)cc1] | Compound 85 |
| 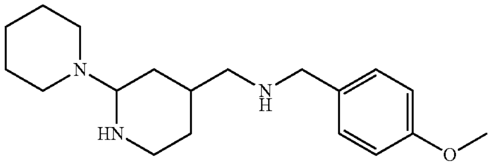 [SMILES: COc1ccc(CNCC2CCNC(N3CCCCC3)C2)cc1] | Compound 86 |

TABLE 4-continued

| Preferably used structures according to the invention | |
|---|---|
| Structure | Compound |
| 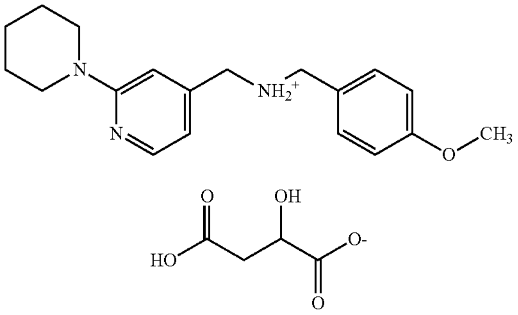 | Compound 87 |
| 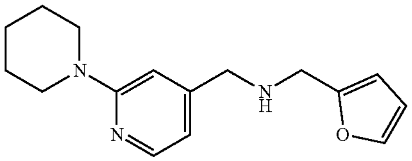 | Compound 88 |
| 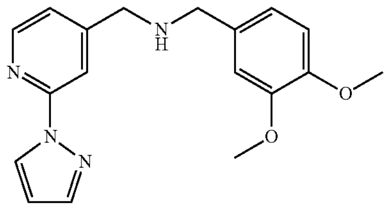 [SMILES: COc1ccc(CNCc2ccnc(-n3cccn3)c2)cc1OC] | Compound 89 |
| 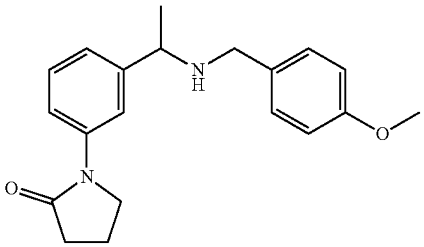 [SMILES: COc1ccc(CNC(C)c2cccc(N3CCCC3=O)c2)cc1] | Compound 90 |

Of the above compounds, the use of compounds 8, 27 and 39 is most preferred because of their pronounced TRPM8 activation, EC50 value and cooling intensity.

In a further aspect, the present invention therefore also encompasses foodstuffs, food supplements, cosmetic or pharmaceutical preparations, animal feeds, textiles, packaging or tobacco products comprising a physiological cooling agent or physiological cooling agent mixture according to the invention or a flavouring preparation according to the invention.

The content of the one or more cooling agent(s) depends on the type and use of the aforementioned products and is preferably about 0.1 ppm to 10 wt.-%, preferably 1 wt.-% to 10 wt.-%, based on the total weight of the end product. In oral care applications, for example in toothpastes or mouthwashes, the content is 0.1 ppm to 500 ppm of the one or more cooling agents.

A broad concentration range typically used to provide the desired level of sensitivity modulation may be about 0.001 ppm to 1000 ppm, or about 0.01 ppm to about 500 ppm, or about 0.05 ppm to about 300 ppm, or about 0.1 ppm to about 200 ppm, or about 0.5 ppm to about 150 ppm, or about 1 ppm to about 100 ppm.

Preferably, the foodstuffs are bakery products, for example bread, dry biscuits, cakes, other pastries, confectionery (for example chocolates, chocolate bar products, other bar products, fruit gums, hard and soft caramels, chewing gum), alcoholic or non-alcoholic beverages (e.g. coffee, tea, iced tea, wine, wine-based beverages, beer, beer-based beverages, liqueurs, spirits, brandies, (carbonated) fruit-based soft drinks, (carbonated) isotonic beverages, (carbonated) soft drinks, nectars, spritzers, fruit and vegetable juices, fruit or vegetable juice preparations, instant drinks (for example, instant cocoa drinks, instant tea drinks, instant coffee drinks, instant fruit drinks), meat products (for example, ham, fresh sausage or raw sausage preparations, seasoned or marinated fresh or cured meat products), eggs or egg products (dried egg, egg white, egg yolk), cereal products (e.g. breakfast cereals, cereal bars, pre-cooked ready-to-eat rice products), dairy products (e.g. dairy drinks, buttermilk drinks, dairy ice cream, yoghurt, kefir, cream cheese, soft cheese, hard cheese, dried milk powder, whey, whey drinks, butter, buttermilk, partially or wholly hydrolysed milk protein products), products made from soya protein or other soya bean fractions (for example, soya milk and products made from it, fruit drinks containing soya protein, preparations containing soya lecithin, fermented products such as tofu or tempeh or products derived therefrom), products derived from other vegetable protein sources, for example oat protein drinks, fruit preparations (for example jams, fruit ice creams, fruit sauces, fruit fillings, fruit fillings), vegetable preparations (for example, ketchup, sauces, dried vegetables, frozen vegetables, precooked vegetables, canned vegetables), snack foods (for example, baked or fried crisps or potato dough products, corn- or peanut-based extrudates), fat- and oil-based products or emulsions thereof (e.g. mayonnaise, tartar sauce, dressings), other ready meals and soups (e.g. dry soups, instant soups, pre-cooked soups), spices, seasoning mixtures and in particular seasonings, which are used for example in the snack sector.

The above-mentioned foodstuffs contain, in addition to conventional food ingredients, at least an effective, i.e. cooling, amount of at least one cooling agent according to the invention or of a cooling agent mixture according to the invention or of a flavouring preparation according to the invention.

The content of cooling agent or cooling agent mixture or flavouring preparation in these preparations is preferably about 0.1 wt.-% to about 10 wt.-% and in particular about 1 wt.-% to 2 wt.-%, based on the total weight of the finished preparation.

Suitable excipients may be used in the manufacture of the foodstuffs according to the invention. Suitable excipients include, but are not limited to, emulsifiers, thickeners, food acids, acidity regulators, vitamins, antioxidants, flavour enhancers, agents for masking unpleasant flavours, food colourings and the like.

Emulsifiers are characterised by the important property of being soluble in both water and fat. Emulsifiers usually consist of a fat-soluble and a water-soluble part. They are always used when water and oil are to be brought to a consistent, homogeneous mixture.

Emulsifiers: Suitable emulsifiers used in the food processing industry are selected from: ascorbyl palmitate (E 304), lecithin (E 322), phosphoric acid (E 338), sodium phosphate (E 339), potassium phosphate (E 340), calcium phosphate (E 341), magnesium orthophosphate (E 343), propylene glycol alginate (E 405), polyoxyethylene(8)stearate (E 430), polyoxyethylene stearate (E 431), ammonium phosphatides (E 442), sodium phosphate and potassium phosphate (E 450), sodium salts of fatty acids (E 470 a), mono- and diglycerides of fatty acids (E 471), acetic acid monoglycerides (E 472 a), lactic acid monoglycerides (E 472 b), citric acid monoglycerides (E 472 c), tartaric acid monoglycerides (E 472 d), diacetyl tartaric acid monoglycerides (E 472 e), sugar esters of fatty acids (E 473), sugar glycerides (E 474), polyglycerides of fatty acids (E 475), polyglycerol polyricinoleate (E 476), propylene glycol esters of fatty acids (E 477), sodium stearoyl lactylate (E 481), calcium stearoyl 2-lactylate (E 482), stearyl tartrate (E 483), sorbitan monostearate (E 491), stearic acid (E 570).

Thickening agents: Thickening agents are substances that are primarily able to bind water. The removal of unbound water leads to an increase in viscosity. Above a concentration characteristic of each thickener, network effects also occur in addition to this effect, which usually lead to a disproportionate increase in viscosity. In this case, one speaks of molecules 'communicating' with each other, i.e. becoming entangled. Most thickening agents are linear or branched macromolecules (e.g. polysaccharides or proteins) that can interact with each other through intermolecular interactions such as hydrogen bonds, hydrophobic interactions or ionic relationships. Extreme cases of thickeners are layered silicates (bentonites, hectorites) or hydrated $SiO_2$ particles, which are dispersed as particles and can bind water in their solid-like structure or interact with each other due to the described interactions. Examples are:

E 400—alginic acid
E 401—sodium alginate
E 402—potassium alginate
E 403—ammonium alginate
E 404—calcium alginate
E 405—propylene glycol alginate
E 406—agar agar
E 407—carrgeen, furcelleran
E 407—locust bean gum
E 412—Guar gum
E 413—traganth
E 414—gum arabic
E 415—xanthan gum
E 416—karaya (indian traganth)
E 417—tara gum (peruvian locust bean gum)
E 418—gellan
E 440—pectin, opekta
E 440ii—amidated pectin
E 460—microcrystalline cellulose, cellulose powder
E 461—methyl cellulose
E 462—ethyl cellulose
E 463—hydroxypropylcellulose
E 465—methyl ethyl cellulose
E 466—carboxymethyl cellulose, sodium carboxymethyl cellulose Food acids: Foodstuffs may contain carboxylic acids. Acids in the sense of the invention are preferably acids permitted in foodstuffs, in particular those mentioned herein:

E 260—acetic acid
E 270—lactic acid
E 290—carbon dioxide
E 296—malic acid
E 297—fumaric acid
E 330—citric acid
E 331—sodium citrate
E 332—potassium citrate
E 333—calcium citrate
E 334—tartaric acid
E 335—sodium tartrate
E 336—potassium tartrate
E 337—sodium potassium tartrate
E 338—phosphoric acid
E 353—metatartaric acid
E 354—calcium tartrate
E 355—adipic acid
E 363—succinic acid
E 380—triammonium citrate
E 513—sulphuric acid
E 574—gluconic acid
E 575—glucono-delta-lactone Acidity regulators: Acidity regulators are food additives that keep the acidity or basicity and thus the desired pH value of a food constant. They are mostly organic acids and their salts, carbonates, more rarely inorganic acids and their salts. The addition of an acidity regulator partly increases the stability and strength of the food, causes a desired precipitation and improves the effect of preservatives. In contrast to acidifiers, they are not used to change the taste of food. Their effect is based on the formation of a buffer system in the food in which the pH value does not change or changes only slightly on the addition of acidic or basic substances. Examples are:

E 170—calcium carbonate
E 260-263—acetic acid and acetates
E 270—lactic acid
E 296—malic acid
E 297—fumaric acid
E 325-327—lactate (lactic acid)
E 330-333—citric acid and citrates
E 334-337—tartaric acid and tartrates
E 339-341—orthophosphates
E 350-352—malates (malic acid)
E 450-452—di-, tri- and polyphosphates
E 500-504—carbonates (carbonic acid)
E 507—hydrochloric acid and chlorides
E 513-517—sulphuric acid and sulphates
E 524-528—hydroxides
E 529-530—oxides
E 355-357—adipic acid and adipates
E 574-578—gluconic acid and gluconates Vitamins: In another embodiment of the present invention, the food additives may comprise vitamins as another optional group of additives. Vitamins have a wide variety of biochemical modes of action. Some act similarly to hormones and regulate mineral metabolism (e.g. vitamin D), or act on cell and tissue growth and cell differentiation (e.g. some forms of vitamin A). Others are antioxidants (e.g. vitamin E and, under certain circumstances, vitamin C). The largest number of vitamins (e.g. the B vitamins) are precursors for enzymatic co-factors that help enzymes catalyse certain processes in metabolism. In this context, vitamins can sometimes be tightly bound to enzymes, for example as part of the prosthetic group: an example of this is biotin, which is part of the enzyme responsible for building up fatty acids. Vitamins, on the other hand, can also be less strongly bound and then act as co-catalysts, for example as groups that can be easily split off and transport chemical groups or electrons between molecules. For example, folic acid transports methyl, formyl and methylene groups into the cell. Although its support in enzyme-substrate reactions is well known, its other properties are also of great importance for the body.

In the context of the present invention, vitamins are substances selected from the group consisting of Vitamin A (retinol, retinal, beta-carotene),
Vitamin $B_1$ (thiamine),
Vitamin $B_2$ (rioflavin),
Vitamin $B_3$ (niacin, niacinamide),
Vitamin $B_5$ (panthothenic acid),
Vitamin $B_6$ (pyridoxine, pyridoxamine, paridoxal),
Vitamin $B_7$ (biotin),
Vitamin $B_9$ (folic acid, folinic acid),
Vitamin $B_{12}$ (cyanobalamin, hydroxycobalmin, methylcobalmin),
Vitamin C (ascorbic acid),
Vitamin D (cholecalciferol),
Vitamin E (tocopherols, tocotrienols) and
Vitamin K (phyllolquinone, menaquinone).

In addition to ascorbic acid, the preferred vitamins are the group of tocopherols.

Antioxidants: Both natural and artificial antioxidants are used in the food industry. Natural and artificial antioxidants differ primarily in that the former occur naturally in food and the latter are produced artificially. For example, natural antioxidants, if they are to be used as a food additive, are obtained from vegetable oils. Vitamin E—also known as tocopherol—is often made from soybean oil, for example. Synthetic antioxidants such as propyl gallate, octyl gallate and dodecyl gallate, on the other hand, are obtained by chemical synthesis. The gallates can cause allergies in sensitive individuals. Other usable antioxidants in compositions of the present invention are: sulphur dioxide (E 220), sulphites sodium sulphite (E 221), sodium hydrogen sulphite (E 222), sodium disulphite (E 223), potassium disulphite (E 224), calcium sulphite (E 226), calcium hydrogen sulphite (E 227), potassium hydrogen sulphite (E 228), lactic acid (E 270), ascorbic acid (E 300), sodium L-ascorbate (E 301), calcium L-ascorbate (E 302), ascorbic acid ester (E 304), tocopherol (E 306), alpha-tocopherol (E 307), gamma-tocopherol (E 308), delta-tocopherol (E 309), propyl gallate (E 310), octyl gallate (E 311), dodecyl gallate (E 312), isoascorbic acid (E 315), sodium isoascorbate (E 316), tertiary butyl hydroquinone (TBHQ, E 319), butyl hydroxianisole (E 320), butyl hydroxitoluene (E 321), lecithin (E 322), citric acid (E 330), salts of citric acid (E 331 & E 332) sodium citrate (E 331), potassium citrate (E 332), calcium disodium EDTA (E 385), diphosphates (E 450), disodium diphosphate (E 450a), trisodium diphosphate (E 450b), tetrasodium diphosphate (E 450c), dipotassium diphosphate (E 450d), tripotassium diphosphate (E 450e), dicalcium diphosphate (E 450f), calcium dihydrogen diphosphate (E 450g), triphosphates (E 451), pentasodium triphosphate (E 451a), pentapotassium triphosphate (E 451b), polyphosphate (E 452), sodium polyphosphate (E 452a), potassium polyphosphate (E 452b), sodium calcium polyphosphate (E 452c), calcium polyphosphate (E 452d), tin(II) chloride (E 512).

Flavour enhancers: These preparations—as well as the flavour mixtures—may further contain additional flavouring substances to enhance a salty, possibly slightly sour and/or umami flavour impression. Thus, the products or flavouring mixtures according to the invention are used in combination with at least one further substance suitable for enhancing a pleasant taste impression (salty, umami, optionally slightly sour). Preferred compounds are salty-tasting compounds and salt-enhancing compounds. Preferred compounds are disclosed in WO 2007/045566. Also preferred are umami compounds as described in WO 2008/046895 and EP 1 989 944.

Flavour corrigents: Furthermore, the flavour preparations preferred according to the invention and products thereof may also comprise flavouring substances for masking bitter and/or astringent taste sensations (flavour corrigents). The (further) flavour corrigents are selected, for example, from the following list: nucleotides (e.g. adenosine 5'-monophosphate, cytidine 5'-monophosphate) or pharmaceutically acceptable salts thereof, lactisols, sodium salts (e.g. sodium chloride, sodium lactate, sodium citrate, sodium acetate, sodium gluconoate), further hydroxyflavanones (e.g. eriodictyol, homoeriodictyol or their sodium salts), in particular according to US 2002/0188019, hydroxybenzoic acid amides according to DE 10 2004 041 496 (e.g. 2,4-dihydroxybenzoic acid vanillylamide, 2,4-dihydroxybenzoic acid N-(4-hydroxy-3-methoxybenzyl)amide, 2,4,6-trihydroxybenzoic acid N-(4-hydroxy-3-methoxybenzyl)amide, 2-hydroxybenzoic acid-N-4-(hydroxy-3-methoxybenzyl) amide, 4-hydroxybenzoic acid-N-(4-hydroxy-3-methoxybenzyl)amide, 2,4-dihydroxybenzoic acid-N-(4-hydroxy-3-methoxybenzyl)amide mono-sodium salt, 2,4-dihydroxybenzoic acid-N-2-(4-hydroxy-3-methoxyphenyl)-ethylamide, 2,4-dihydroxybenzoic acid-N-(4-hydroxy-3-ethoxybenzyl)amide, 2,4-dihydroxybenzoic acid-N-(3,4-dihydroxybenzyl)amide and 2-hydroxy-5-methoxy-N-[2-(4-hydroxy-3-methoxyphenyl)ethyl]amide (aduncamide), 4-hydroxybenzoic acid vanillylamide), bittermasking hydroxydeoxybenzoins, e.g., according to VO 2006/106023 (e.g. 2-(4-hydroxy-3-methoxyphenyl)-1-(2,4,6-tri-hydroxy-phenyl)ethanone, 1-(2,4-dihydroxyphenyl)-2-(4-hydroxy-3-methoxyphenyl)ethanone, 1-(2-hydroxy-4-methoxyphenyl)-2-(4-hydroxy-3-methoxy-phenyl)ethanone), amino acids (e.g. gamma-aminobutyric acid according to VO 2005/096841 to reduce or mask an unpleasant taste impression such as bitterness), malic acid glycosides according to VO 2006/003107, salty-tasting mixtures according to PCT/EP 2006/067120 diacetyl trimers according to WO 2006/058893, mixtures of whey proteins with lecithins and/or bitter-masking substances such as ginger diones according to VO 2007/003527.

Flavouring substances: Preferred flavouring substances are those which cause a sweet odour impression, whereby the further flavouring substance or substances which cause a sweet odour impression are preferably selected from the group consisting of: vanillin, ethyl vanillin, ethyl vanillin isobutyrate (=3 ethoxy-4-isobutyryloxybenzaldehyde), furaneol (2,5-dimethyl-4-hydroxy-3(2H)-furanone) and derivatives (e.g. homofuraneol, 2-ethyl-4-hydroxy-5-methyl-3(2H)-furanone), homofuronol (2-ethyl-5-methyl-4-hydroxy-3(2H)-furanone and 5-ethyl-2-methyl-4-hydroxy-3(2H)-furanone), maltol and derivatives (e.g. ethyl maltol), coumarin and derivatives, gamma-lactones (e.g. gamma-undecalactone, gamma-nonalactone), delta-lactones (e.g. 4-methyldeltalactone, massoilactone, deltadecalactone, tuberolactone), methyl sorbate, divanillin, 4-hydroxy-2 (or 5)-ethyl-5 (or 2)-methyl-3(2H)furanone, 2-hydroxy-3-methyl-2-cyclopentenone, 3-hydroxy-4,5-dimethyl-2(5H)-furanone, fruit esters and fruit lactones (e.g. acetic acid n-butyl ester, acetic acid isoamyl ester, propionic acid ethyl ester, butyric acid ethyl ester, butyric acid n-butyl ester, butyric acid isoamyl ester, 3-methyl butyric acid ethyl ester, n-hexanoic acid ethyl ester, n-hexanoic acid allyl ester, n-hexanoic acid n-butyl ester, n-octanoic acid ethyl ester, ethyl 3-methyl-3-phenyl glycidate, ethyl 2-trans-4-cis-decadienoate), 4-(p-hydroxyphenyl)-2-butanone, 1,1-dimethoxy-2,2,5-trimethyl-4-hexane, 2,6-dimethyl-5-hepten-1-al, 4-hydroxycinnamic acid, 4-methoxy-3-hydroxycinnamic acid, 3-methoxy-4-hydroxycinnamic acid, 2-hydroxycinnamic acid, 2,4-dihydroxybenzoic acid, 3-hydroxybenzoic acid, 3,4-dihydroxybenzoic acid, vanillic acid, homovanillic acid, vanillomandelic acid and phenylacetaldehyde.

Active substances for masking unpleasant taste sensations: Furthermore, the oral preparations may also comprise further substances which also serve to mask bitter and/or astringent taste impressions. These further taste corrigents are selected, for example, from the following list from nucleotides (e.g. adenosine 5'-monophosphate, cytidine 5'-monophosphate) or their physiologically acceptable salts, lactisols, sodium salts (e.g. sodium chloride, sodium lactate, sodium citrate, sodium acetate, sodium gluconoate), hydroxyflavanones, preferably eriodictyol, sterubin (eriodictyol-7-methyl ether), homoeriodictyol, and their sodium, potassium, calcium, magnesium or zinc salts (in particular those as described in EP 1258200 A2), hydroxybenzoic acid amides, preferably 2,4-dihydroxybenzoic acid vanillylamide, 2,4-dihydroxybenzoic acid N-(4-hydroxy-3-methoxybenzyl)amide, 2,4,6-trihydroxybenzoic acid-N-(4-hydroxy-3-methoxybenzyl)amide, 2-hydroxybenzoic acid-N-4-(hydroxy-3-methoxybenzyl)amide, 4-hydroxybenzoic acid-N-(4-hydroxy-3-methoxybenzyl)amide, 2,4-dihydroxybenzoic acid-N-(4-hydroxy-3-methoxybenzyl) amide mono-natrium salt, 2,4-dihydroxybenzoic acid-N-2-(4-hydroxy-3-methoxy-phenyl)ethylamide, 2,4-dihydroxybenzoic acid-N-(4-hydroxy-3-ethoxybenzyl) amide, 2,4-dihydroxybenzoic acid-N-(3,4-dihydroxybenzyl) amide and 2-hydroxy-5-methoxy-N-[2-(4-hydroxy-3-methoxyphenyl)ethyl]amide; 4-hydroxybenzoic acid vanillylamides (in particular those as described in WO 2006/024587); hydroxydeoxybenzoins, preferably 2-(4-hydroxy-3-methoxyphenyl)-1-(2,4,6-trihydroxyphenyl)ethanone, 1-(2,4-dihydroxyphenyl)-2-(4-hydroxy-3-methoxyphenyl)ethanone and 1-(2-hydroxy-4-methoxyphenyl)-2-(4-hydroxy-3-methoxyphenyl)ethanone) (in particular those as described in WO 2006/106023); hydroxyphenylalkanediones, such as gingerdione-[2], gingerdione-[3], gingerdione-[4], dehydrogingerdione-[2], dehydrogingerdione-[3], dehydrogingerdione-[4]) (in particular those as described in VO 2007/003527); diacetyltrimers (in particular those as described in WO 2006/058893); gamma-amino butyric acids (in particular those as described in VO 2005/096841); divanillins (in particular those as described in WO 2004/078302) and 4-hydroxydihydrochalcones (preferably as described in US 2008/0227867 A1), in particular phloretin and davidigenin; amino acids or mixtures of whey proteins with lecithins; hesperetin as disclosed in WO 2007/014879; 4-hydroxydihydrochalcones as disclosed in WO 2007/107596, or propenylphenylglycosides (chavicolglycosides) as described in EP 1955601 A1, or extracts from *Rubus suavissimus*, extracts from *Hydrangea macrophylla* as described in EP 2298084 A1, pellitorin and derived aroma compositions as described in EP 2008530 A1, umami compounds as described in WO 2008/046895 A1 and EP 1989944 A1, umami compounds as described in EP 2064959 A1 resp. EP 2135516 A1, vanillyllignans, enterodiol, as well as N-decadienoylamino acids and mixtures thereof.

Food colourings: Food colourings, or colourings for short, are food additives used to colour food. Colourings are divided into the groups of natural colourings and synthetic colourings. The nature-identical colourants are also of synthetic origin. The nature-identical colourants are synthetic replicas of naturally occurring colouring substances. Suitable colourants for use in the present composition are selected from: curcumin (E 100), riboflavin (lactoflavin, vitamin B2, E 101), tartrazine (E 102), quinoline yellow (E 104), yellow orange S (yellow orange RGL, E 110), cochineal (carminic acid, true carmine, E 120), azorubin (carmoisin, E 122), amaranth (E 123), cochineal red A (ponceau 4 R, Victoria scarlet 4 R, E 124), erythrosine (E 127), allura red AC (E 129), patent blue V (E 131), indigotine (indigo carmine, E 132), brilliant blue FCF (patent blue AE, amido blue AE, E 133), chlorophylls, chlorophyllins (E 140), copper complexes of chlorophylls, copper chlorophyllin complexes (E 141), brilliant acid green (green S, E 142), caramel colouring (sugar couleur, E 150 a), caustic sulphite caramel (E 150 b), ammonia caramel (E 150 c), sulphite ammonia caramel (E 150 d), brilliant black FCF, brilliant black PN, black PN (E 151), vegetable carbon (E 153), brown FK (E 154), brown HT (E 155), carotene (Karotin, E 160 a), annatto (bixin, norbixin, E 160 b), capsanthin (capsorubin, E 160 c), lycopene (E 160 d), beta-apo-8'-carotenal (apocarotenal, beta-apocarotenal, E 160 e), beta-apo-8'-carotenic acid ethyl ester (C30), apocarotenic ester, beta-carotenic acid ester (E 160 f), lutein (xanthophyll, E 161 b) canthaxanthin (E 161 g), betanin, betene red (E 162), anthocyanins (E 163), calcium carbonate (E 170), titanium dioxide (E 171), iron oxides, iron hydroxides (E 172), aluminium (E 173), silver (E 174), gold (E 175), litholrubin BK, ruby pigment BK (E 180).

Another aspect of the invention relates to cosmetic or pharmaceutical preparations containing either one or more of the cooling agents according to the invention or a cooling agent mixture according to the invention or a flavouring preparation according to the invention.

The compositions according to the invention may in particular be skin cosmetic, hair cosmetic, dermatological, hygienic or pharmaceutical compositions. In particular, the active ingredients according to the invention, in particular those having a cooling effect, are used for skin and/or hair cosmetics or as oral care agents.

The hair or skin care compositions or preparations according to the invention are preferably in the form of an emulsion, a dispersion, a suspension, in the form of an aqueous surfactant preparation, a milk, a lotion, a cream, a balm, an ointment, a gel, a granulate, a powder, a stick preparation, such as a lipstick, a foam, an aerosol or a spray. Such formulations are well suited for topical preparations. Suitable emulsions are oil-in-water emulsions and water-in-oil emulsions or microemulsions. As a rule, the hair or skin cosmetic preparation is used for application to the skin (topical) or hair. Topical preparations" are preparations which are suitable for applying the active substances to the skin in a fine distribution, e.g. in a form which can be absorbed by the skin. Suitable preparations for this purpose are, for example, aqueous and aqueous-alcoholic solutions, sprays, foams, foam aerosols, ointments, aqueous gels, emulsions of the O/W or W/O type, microemulsions or cosmetic stick preparations. According to one embodiment of the cosmetic composition of the invention, the cosmetic composition comprises a carrier. Preferred as a carrier is water, a gas, a water-based liquid, an oil, a gel, an emulsion or microemulsion, a dispersion or a mixture thereof. Said carriers show good skin compatibility. Particularly advantageous for topical preparations are aqueous gels, emulsions or microemulsions.

The teaching according to the invention also comprises the use of the active ingredients described herein for medicinal purposes, in particular in pharmaceutical compositions for the treatment of an individual, preferably a mammal, in particular a human, farm animal or domestic animal. For this purpose, the active ingredients are administered in the form of pharmaceutical compositions comprising a pharmaceutically acceptable excipient with at least one active ingredient according to the invention and optionally further active ingredients. These compositions may be administered, for example, by oral, rectal, transdermal, subcutaneous, intravenous, intramuscular or intranasal routes.

Examples of suitable pharmaceutical formulations or compositions include solid dosage forms such as powders, granules, tablets, pastilles, sachets, cachets, dragees, capsules, such as hard and soft gelatine capsules, suppositories or vaginal dosage forms, semi-solid dosage forms, such as ointments, creams, hydrogels, pastes or plasters, as well as liquid dosage forms, such as solutions, emulsions, in particular oil-in-water emulsions, suspensions, for example lotions, injection and infusion preparations, eye and ear drops. Implanted delivery devices can also be used to administer inhibitors according to the invention. Furthermore, liposomes, microspheres or polymer matrices may also be used. Pharmaceutical agents that may be used include, for example, cold syrups, wound ointments or wound sprays. It is also possible to incorporate the substances into plasters or tablets, especially if these contain active substances that themselves have an unpleasant taste.

A further aspect of the present invention therefore comprises the cooling agents or cooling agent mixtures according to the invention as medicaments, in particular as medicaments for use in alleviating pain and inflammatory conditions of the skin and mucous membranes. Due to their cooling properties, the cooling agents according to the invention are particularly suitable for preventing, combating or alleviating symptoms of cough, cold, inflammation, sore throat or hoarseness.

Furthermore, the substances and preparation described herein are suitable for the treatment of inflammatory conditions of the skin and mucous membrane as well as the joints due to their efficient cooling effect.

Due to their properties of modulating the receptor TRPM8, whose gene expression, i.e. that of the TRPM8 gene, is upregulated in cancers, for example in prostate carcinomas, the pharmaceutical preparations according to the invention are preferably also used in oncology, preferably in the treatment of prostate or bladder carcinomas, or for the treatment of bladder weakness. The corresponding proteins in the cell are encoded by corresponding genes in the cell nucleus. The reading of the genes in the nucleus (transcription) leads to the genesis of messenger RNA (mRNA), which is then "translated" into a protein in the cell at ribosomes (translation). The totality of both processes is often referred to as gene expression.

However, astringent, bitter and/or metallic tastes are not only found in flavourings and sweeteners as described above, but also in connection with many active pharmaceutical ingredients, which makes them difficult to take, especially in children. Typical examples of such active pharmaceutical ingredients are the following: aspirin, minoxidil, erythromycin, fenistil, betamethasone, ibuprofen, ketoprofen, dicyclofenac, metronidazole, acyclovir, imiquimod, terbafin, cyclopiroxolamine, paracetamol, and other pharmaceutical agents of the non-steroidal anti-inflammatory drug (NSAID) type and mixtures thereof.

The present invention therefore also encompasses medicaments comprising one or more cooling agents according to the invention or a cooling agent mixture according to the invention or an aroma preparation according to the invention in combination with at least one further pharmaceutical active ingredient selected from the group, consisting of aspirin, minoxidil, erythromycin, fenistil, betamethasone, ibuprofen, ketoprofen, dicyclofenac, metronidazole, acyclovir, imiquimod, terbafin, cyclopiroxolamine, paracetamol and mixtures thereof.

In studies with volunteers, it has also been shown that the cooling agents according to the invention or the cooling agent mixtures according to the invention enhance the pain-reducing properties of non-steroidal anti-inflammatory drugs (NSAIDs), in particular ibuprofen and ketoprofen, beyond the cooling effect, which was also not to be expected by the person skilled in the art. Therefore, the present invention also relates in particular to the combination with pharmaceutical agents of the non-steroidal anti-inflammatory drug (NSAID) type.

Such pharmaceutical combinations are therefore particularly beneficial for use in the treatment of inflammatory conditions of the skin and mucous membranes as well as the joints.

The medicaments may contain the cooling agents according to the invention or the cooling agent mixtures according to the invention and the pharmaceutically active substances in a weight ratio of about 1:99 to about 10:90 and in particular 2:98 to about 5:95.

The physiological cooling effect is also used in the formulation of wound and burn ointments as well as preparations against insect bites.

In the manufacture of the cosmetic or pharmaceutical preparations according to the invention, the cooling agent(s)

or cooling mixture according to the invention are usually mixed or diluted with an excipient. Excipients may be solid, semi-solid or liquid materials that serve as a vehicle, carrier or medium for the active ingredient. The active ingredient content (of one or more simultaneously contained cooling active ingredients according to the invention) can vary in a wide range and is approximately, in each case based on the total weight of the preparation, from about 0.05 ppm to 10 wt.-%, preferably 0.1 ppm to 10 wt.-%.

Suitable excipients include, for example, lactose, dextrose, sucrose, sorbitol, mannitol, starches, acacia gum, calcium phosphate, alginates, tragacanth, gelatine, calcium silicate, microcrystalline cellulose, polyvinylpyrrolidone, cellulose, water, syrup and methylcellulose. Further, the formulations may contain pharmaceutically acceptable carriers or common excipients, such as lubricants, for example tallow, magnesium stearate and mineral oil, wetting agents, emulsifying and suspending agents, preservatives, such as methyl and propyl hydroxybenzoates; antioxidants; anti-irritants; chelating agents; lubricating aids; emulsion stabilisers; film formers; gel formers; odour masking agents; taste correctors; resins; hydrocolloids; solvents; solubilizers; neutralizing agents; permeation accelerators; pigments; quaternary ammonium compounds; refatting and superfatting agents; ointment, cream or oil bases; silicone derivatives; spreading aids; stabilizers; sterilants; suppository bases; tablet excipients, such as binders, fillers, lubricants, disintegrants or coatings; propellants; drying agents; opacifiers; thickeners; waxes; plasticizers; white oils. A relevant embodiment is based on expert knowledge and is sufficiently described in the relevant technical literature.

The preparations according to the invention may additionally contain cosmetically and/or dermatologically and/or pharmacologically active ingredients in addition to conventional additives or excipients. Non-limiting examples of suitable further active substances are:

Cosmetically and/or dermatologically active ingredients: Suitable cosmetically and/or dermatologically active ingredients are e.g. colouring active ingredients, skin and hair pigmentation agents, tinting agents, tanning agents, bleaching agents, keratin-hardening substances, antimicrobial active ingredients, light-filtering active ingredients, repellent active ingredients, hyperemulsifying active ingredients, keratolytic and keratoplastic active ingredients, anti-dandruff active ingredients, antiphlogistics, keratinising active ingredients, antioxidant or free-radical scavenging active ingredients, skin moisturising or moisturising agents, refatting active substances, active substances with anti-erythmic or anti-allergic activity, branched fatty acids, such as 18-methyleicosanoic acid, and mixtures thereof. Artificially skin-tanning active ingredients suitable for tanning the skin without natural or artificial irradiation with UV rays; these are e.g. dihydroxyacetone, alloxan and walnut shell extract. Suitable keratin-curing substances are usually active ingredients such as those used in antiperspirants, e.g. potassium aluminium sulphate, aluminium hydroxychloride, aluminium lactate, etc.

Antimicrobial agents: Antimicrobial agents are used to destroy microorganisms or inhibit their growth. They thus serve both as a preservative and as a deodorising substance that reduces the development or intensity of body odour. These include, for example, common preservatives known to the skilled person, such as p-hydroxybenzoic acid esters, imidazolidinyl urea, formaldehyde, sorbic acid, benzoic acid, salicylic acid, etc. Such deodorising substances are e.g. zinc ricinoleate, triclosan, undecylenic acid alkylolamides, citric acid triethyl esters, chlorhexidine, etc.

Auxiliary substances and additives: Suitable auxiliary substances and additives for the production of hair cosmetic or skin cosmetic preparations are familiar to the skilled person and can be taken from cosmetic manuals, i.e. the corresponding technical literature. The added excipients and additives are preferably cosmetically and/or pharmaceutically acceptable excipients. Pharmaceutically acceptable excipients are those known to be usable in the field of pharmacy, food technology and related fields, in particular those listed in relevant pharmacopoeias (e.g. DAB, Ph. Eur., BP, NF) as well as other excipients whose properties do not conflict with physiological application.

Suitable excipients may be: lubricants, wetting agents, emulsifying and suspending agents, preservatives, antioxidants, anti-irritants, chelating agents, emulsion stabilisers, film formers, gel formers, odour masking agents, hydrocolloids, solvents, solubilisers, neutralising agents, permeation accelerators, pigments, quaternary ammonium compounds, refatting and superfatting agents, ointment, cream or oil bases, silicone derivatives, stabilisers, sterilants, propellants, drying agents, opacifiers, thickeners, waxes, plasticisers, white oil. A design in this respect is based on expert knowledge as found in the relevant technical literature.

Other suitable additives are selected from perfume oils, hair polymers, hair and skin conditioners, graft polymers, water-soluble or dispersible silicone-containing polymers, light stabilisers, bleaching agents, care products, colouring agents, tinting agents, tanning agents, dyes, consistency enhancers, humectants, refatting agents, collagen, protein hydrolysates, lipids, antioxidants, defoamers, antistatic agents, emollients, plasticisers, peroxide decomposers.

The preparations according to the invention may contain further typical auxiliaries and additives, such as mild surfactants, oil bodies, emulsifiers, pearlescent waxes, consistency agents, thickeners, superfatting agents, stabilisers, polymers, silicone compounds, fats, waxes, lecithins, phospholipids, UV light protection factors, humectants, biogenic agents, antioxidants, deodorants, antiperspirants, anti-dandruff agents, film formers, swelling agents, insect repellents, self-tanning agents, tyrosine inhibitors (depigmentation agents), hydrotropes, solubilisers, preservatives, perfume oils, colourants and the like.

Surfactants: Anionic, nonionic, cationic and/or amphoteric or zwitterionic surfactants may be present as surface-active agents, the proportion of which in the agents is usually about 1 wt.-% to 70 wt.-%, preferably 5 wt.-% to 50 wt.-% and in particular 10 wt.-% to 30 wt.-%.

Anionic surfactants: Typical examples of anionic surfactants are soaps, alkylbenzene sulphonates, alkane sulphonates, olefin sulphonates, alkyl ether sulphonates, glycerol ether sulphonates, α-methyl ester sulphonates, sulpho fatty acids, alkyl sulphates, alkyl ether sulphates, glycerol ether sulphates, fatty acid ether sulphates, hydroxy ether sulphates, monoglyceride (ether) sulphates, fatty acid amide (ether) sulphates, mono- and dialkyisulphosuccinates, mono- and dialkyisulphosuccinamates, sulphotriglycerides, amide soaps, ether carboxylic acids and their salts, fatty acid isethionates, fatty acid sarcosinates, fatty acid taurides, N-acyl amino acids, alkyl oligoglucoside sulphates, protein fatty acid condensates (especially wheat-based vegetable products) and alkyl(ether) phosphates. If the anionic surfactants contain polyglycol ether chains, these may have a conventional, but preferably a narrowed homologue distribution. Particularly preferred in this context are:

(a) acyl amino acid salts such as acyl glutamates, for example sodium acyl glutamate, di-TEA palmitoyl aspartate and sodium capryl/capric acid glutamate, acyl peptides, for example palmitoyl hydrolysed milk protein, sodium cocoyl hydrolysed soy protein and sodium/potassium cocoyl hydrolysed collagen and alaninates;

(b) acyl lactylate, lauroyl lactylate, caproyl lactylate (c) sulphates, such as alkyl ether sulphates such as in particular sodium, ammonium, magnesium, MIPA, TIPA laureth sulphate, sodium myreth sulphate and sodium C12-13 pareth sulphate;

alkyl sulphates, for example sodium, ammonium and TEA lauryl sulphate;

glyceride sulphates, such as sodium coco monoglyceride sulphate, amide sulphates, such as magnesium PEG-3 cocamide sulphate.

(d) sulphonates, such as alkyl sulphonates, alkylaryl sulphonates, in particular sodium C12-14 olefin sulphonate, (e) sulfosuccinates, for example dioctyl sodium sulfosuccinate, disodium laureth sulfosuccinate, disodium lauryl sulfosuccinate and disodium undecylenamido MEA sulfosuccinate;

(f) sulfoacetates, such as sodium lauryl sulfoacetate;

(g) sarcosinates, for example myristoyl sarcosine, TEA lauroyl sarcosinate, sodium lauroyl sarcosinate and sodium cocoyl sarcosinate, (l) isethionates, such as sodium/ammonium cocoyl isethionate, (h) taurates, for example sodium lauroyl taurate and sodium methyl cocoyl taurate, (i) carboxylates, for example soaps such as TEA stearate, ether carboxylates, such as sodium laureth-13-carboxylate and sodium PEG-6-cocamide carboxylate, (j) phosphates such as cetyl phosphate (mono-, di-cetyl and their mixtures), potassium cetyl phosphate, (mono-, di-cetyl and their mixtures), DEA cetyl phosphate (mono-, di-cetyl and their mixtures), DEA oleth-10-phosphate and dilaureth-4-phosphate.

Non-ionic surfactants: Typical examples of non-ionic surfactants are fatty alcohol polyglycol ethers, alkylphenol polyglycol ethers, fatty acid polyglycol esters, fatty acid amide polyglycol ethers, fatty acid amine polyglycol ethers, alkoxylated triglycerides, mixed ethers or mixed formals, optionally partially oxidised alk(en)yl oligoglycosides or glucoronic acid derivatives, fatty acid N-alkylglucamides, protein hydrolysates (in particular wheat-based vegetable products), polyol fatty acid esters, sugar esters, sorbitan esters, polysorbates and amine oxides. If the non-ionic surfactants contain polyglycol ether chains, these may have a conventional, but preferably a narrowed homologue distribution.

Cationic surfactants: Cationic surfactants contain at least one N atom that is covalently bonded to 4 alkyl or aryl groups. This leads to a positive charge regardless of the pH value. Alkylbetaine, alkylamidopropylbetaine and alkylamidopropylhydroxysulphaines are advantageous. The cationic surfactants used may further preferably be selected from the group consisting of quaternary ammonium compounds, in particular benzyltrialkylammonium chlorides or bromides, such as benzyldimethylstearylammonium chloride, and alkyltrialkylammonium salts, for example cetyltrimethylammonium chloride or bromide, alkyl dimethyl hydroxyethyl ammonium chlorides or bromides, dialkyl dimethyl ammonium chlorides or bromides, alkyl amide ethyl trimethyl ammonium ether sulphates, alkyl pyridinium salts, for example lauryl or cetyl pyridinium chloride, imidazoline derivatives and compounds having a cationic character, such as amine oxides, for example alkyl dimethyl amine oxide or alkyl amino ethyl dimethyl amine oxide. In particular, cetyltrimethylammonium salts are advantageously used. Particularly preferred are:

alkylamines, alkylimidazoles, ethoxylated amines, quaternary ammonium salts;

$RNH_2CH_2CH_2COO^-$ (at pH=7)

$RNHCH_2CH_2COO^-$ $B^+$ (at pH=12) B+=any desired cation as well as esterquats.

Amphoteric or zwitterionic surfactants: Typical examples of amphoteric or zwitterionic surfactants are alkyl betaines, alkylamidobetaines, aminopropionates, aminoglycinates, imidazolinium betaines and sulfobetaines. The surfactants mentioned are exclusively known compounds.

Typical examples of particularly suitable mild, i.e. particularly skin-compatible surfactants are fatty alcohol polyglycol ether sulphates, monoglyceride sulphates, mono- and/or dialkyl sulphosuccinates, fatty acid isethionates, fatty acid sarcosinates, fatty acid taurides, fatty acid glutamates, α-olefin sulphonates, ether carboxylic acids, alkyl oligoglucosides, fatty acid glucamides, alkylamidobetaines, amphoacetals and/or protein fatty acid condensates, the latter preferably based on wheat proteins.

Oil bodies: Examples of oil bodies are Guerbet alcohols based on fatty alcohols with 6 to 18, preferably 8 to 10 carbon atoms, esters of linear $C_6$-$C_{22}$ fatty acids with linear or branched $C_6$-$C_{22}$ fatty alcohols or esters of branched $C_6$-$C_{13}$ carboxylic acids with linear or branched $C_6$-$C_{22}$ fatty alcohols, such as e.g. myristyl myristate, myristyl palmitate, myristyl stearate, myristyl isostearate, myristyl oleate, myristyl behenate, myristyl erucate, cetyl myristate, cetyl palmitate, cetyl stearate, cetyl isostearate, cetyl oleate, cetyl behenate, cetyl erucate, stearyl myristate, stearyl palmitate, stearyl stearate, stearyl isostearate, stearyl oleate, stearyl behenate, stearyl erucate, isostearyl myristate, isostearyl palmitate, isostearyl stearate, isostearyl isostearate, isostearyl oleate, isostearyl behenate, isostearyl oleate, oleyl myristate, oleyl palmitate, oleyl stearate, oleyl isostearate, oleyl oleate, oleyl behenate, oleyl erucate, behenyl myristate, behenyl palmitate, behenyl stearate, behenyl isostearate, behenyl oleate, behenyl behenate, behenyl erucate, erucyl myristate, erucyl palmitate, erucyl stearate, erucyl isostearate, erucyl oleate, erucyl behenate and erucyl erucate. Cetearyl ethylhexanoate, cetearyl nonanoate, stearyl heptanoate and stearyl caprylate and mixtures thereof are particularly preferred.

In addition, esters of linear $C_6$-$C_{22}$ fatty acids with branched alcohols, in particular 2-ethylhexanol, esters of $C_{16}$-$C_{38}$ alkylhydroxycarboxylic acids with linear or branched $C_6$-$C_{22}$ fatty alcohols, in particular dioctylmalates, esters of linear or branched C6-C13 carboxylic acids with linear or branched C6-C13 alcohols, such as ethylhexylisononanoate, esters of linear and/or branched fatty acids with polyhydric alcohols (such as propylene glycol, dimer diol or trimer triol) and/or Guerbet alcohols, triglycerides based on $C_6$-$C_{10}$ fatty acids, liquid mono-/di-/triglyceride mixtures based on $C_6$-$C_{18}$ fatty acids, esters of $C_6$-$C_{22}$ fatty alcohols and/or Guerbet alcohols with aromatic carboxylic acids, in particular benzoic acid, esters of $C_2$-$C_{12}$ dicarboxylic acids with linear or branched alcohols with 1 to 22 carbon atoms or polyols with 2 to 10 carbon atoms and 2 to 6 hydroxyl groups, vegetable oils, branched primary alcohols, substituted cyclohexanes, linear and branched $C_6$-$C_{22}$ fatty alcohol carbonates, such as e.g. dicaprylyl carbonate (Cetiol® CC), Guerbet carbonates based on fatty alcohols with 6 to 18, preferably 8 to 10 C atoms, esters of benzoic acid with linear and/or branched $C_6$-$C_{22}$ alcohols (e.g. Finsolv® TN), linear or branched, symmetrical or asymmetrical dialkyl ethers with 6 to 22 carbon atoms per alkyl group, such as e.g. dicaprylyl ether (Cetiol® OE), ring opening products of epoxidised fatty acid esters with polyols, silicone oils (cyclomethicones, silicon methicone types, etc.) and/or aliphatic or naphthenic hydrocarbons, such as squalane, squalene or dialkylcyclohexanes are suitable.

The amount used, based on the final formulation, can be between 5 wt.-% and 80 wt.-%, preferably between 10 wt-% and 50 wt.-% and in particular between 20 wt-% and 40 wt.-%.

Emulsifiers: Suitable emulsifiers include, for example, non-ionic surfactants from at least one of the following groups:

- addition products of 2 to 30 moles of ethylene oxide and/or 0 to 5 moles of propylene oxide to linear fatty alcohols with 8 to 22 carbon atoms, to fatty acids with 12 to 22 carbon atoms, to alkylphenols with 8 to 15 carbon atoms in the alkyl group and to alkylamines with 8 to 22 carbon atoms in the alkyl group;
- alkyl and/or alkenyl oligoglycosides with 8 to 22 carbon atoms in the alk(en)yl residue and their ethoxylated analogues;
- addition products of 1 to 15 mol ethylene oxide to castor oil and/or cured castor oil;
- addition products of 15 to 60 mol ethylene oxide to castor oil and/or cured castor oil;
- partial esters of glycerol and/or sorbitan with unsaturated, linear or saturated, branched fatty acids with 12 to 22 carbon atoms and/or hydroxycarboxylic acids with 3 to 18 carbon atoms and their adducts with 1 to 30 moles of ethylene oxide;
- partial esters of polyglycerol (average degree of self-condensation 2 to 8), polyethylene glycol (molecular weight 400 to 5000), trimethylolpropane, pentaerythritol, sugar alcohols (e.g. sorbitol), alkyl glucosides (e.g. methyl glucoside, butyl glucoside, lauryl glucoside) and polyglucosides (e.g. cellulose) with saturated and/or unsaturated, linear or branched fatty acids with 12 to 22 carbon atoms and/or hydroxycarboxylic acids with 3 to 18 carbon atoms as well as their adducts with 1 to 30 mol ethylene oxide;
- mixed esters of pentaerythritol, fatty acids, citric acid and fatty alcohol and/or mixed esters of fatty acids with 6 to 22 carbon atoms, methylglucose and polyols, preferably glycerol or polyglycerol.
- wool wax alcohols;
- polysiloxane-polyalkyl-polyether copolymers or corresponding derivatives;
- block copolymers e.g. polyethylene glycol-30 dipolyhydroxystearate;
- polymer emulsifiers, e.g. Pemulen types (TR-1, TR-2) from Lubrizol or Cosmedia® SP from BASF;
- polyalkylene glycols and
- glycerol carbonate.

Particularly suitable emulsifiers are explained in more detail below:

Alkoxylates: The addition products of ethylene oxide and/or propylene oxide to fatty alcohols, fatty acids, alkyl phenols or to castor oil are known products that are commercially available. They are homologous mixtures whose average degree of alkoxylation corresponds to the ratio of the amounts of ethylene oxide and/or propylene oxide and substrate with which the addition reaction is carried out. $C_{12/18}$ a fatty acid mono- and diesters of addition products of ethylene oxide on glycerol are known as refatting agents for cosmetic preparations.

Alkyl and/or alkenyl oligoglycosides: Alkyl and/or alkenyl oligoglycosides, their preparation and their use are known from the prior art. Their preparation is carried out in particular by reacting glucose or oligosaccharides with primary alcohols having 8 to 18 carbon atoms. With regard to the glycoside residue, monoglycosides in which a cyclic sugar residue is glycosidically bonded to the fatty alcohol as well as oligomeric glycosides with a degree of oligomerisation of up to preferably about 8 are suitable. The degree of oligomerisation is a statistical mean value based on a homologue distribution which is usual for such technical products.

Partial glycerides: Typical examples of suitable partial glycerides are hydroxystearic acid monoglyceride, hydroxystearic acid diglyceride, isostearic acid monoglyceride, isostearic acid diglyceride, oleic acid monoglyceride, oleic acid diglyceride, ricinoleic acid monoglyceride, ricinoleic acid diglyceride, linoleic acid monoglyceride, linoleic acid diglyceride, linolenic acid monoglyceride, linoleic acid diglyceride, erucic acid monoglyceride, erucic acid diglyceride, tartaric acid monoglyceride, tartaric acid diglyceride, citric acid monoglyceride, citric acid diglyceride, malic acid monoglyceride, malic acid diglyceride as well as their technical mixtures, which may still contain small amounts of triglyceride from the manufacturing process. Also suitable are addition products of 1 to 30, preferably 5 to 10 moles of ethylene oxide to the partial glycerides mentioned.

Sorbitan esters: Sorbitan esters include sorbitan monoisostearate, sorbitan sesquiisostearate, sorbitan diisostearate, sorbitan triisostearate, sorbitan monooleate, sorbitan sesquioleate, sorbitan dioleate, sorbitan trioleate, sorbitan monoerucate, sorbitan sesquierucate, sorbitan dierucate, sorbitan trierucate, sorbitan monoricinoleate, sorbitan sesquiricinoleate, sorbitan diricinoleate, sorbitan triricinoleate, sorbitan monohydroxystearate, sorbitan sesquihydroxystearate, sorbitan dihydroxystearate, sorbitan trihydroxystearate, sorbitan monotartrate, sorbitan sesquitartrate, sorbitan ditartrate, sorbitan tritartrate, sorbitan monocitrate, sorbitan sesquicitrate, sorbitan dicitrate, sorbitan tricitrate, sorbitan monomaleate, sorbitan sesquimaleate, sorbitan dimaleate, sorbitan trimaleate and their technical mixtures. Also suitable are addition products of 1 to 30, preferably 5 to 10 mol ethylene oxide to the sorbitan esters mentioned.

Polyglycerol esters: Typical examples of suitable polyglycerol esters are polyglyceryl-2 dipolyhydroxystearate (Dehymuls® PGPH), polyglycerol-3 diisostearate (Lameform® TGI), polyglyceryl-4 isostearate (Isolan® GI 34), polyglyceryl-3 oleate, diisostearoyl polyglyceryl-3 diisostearate (Isolan® PDI), polyglyceryl-3 methylglucose distearate (Tego Care® 450), polyglyceryl-3 beeswax (Cera Bellina®), polyglyceryl-4 caprate (Polyglycerol Caprate T2010/90), polyglyceryl-3 cetyl ether (Chimexane® NL), polyglyceryl-3 distearate (Cremophor® GS 32) and polyglyceryl polyricinoleate (Admul® WOL 1403) polyglyceryl dimerate isostearate and mixtures thereof. Examples of further suitable polyol esters are the mono-, di- and tri-esters of trimethylolpropane or pentaerythritol with lauric acid, coconut fatty acid, tallow fatty acid, palmitic acid, stearic acid, oleic acid, behenic acid and the like, optionally reacted with 1 to 30 mol ethylene oxide.

Anionic emulsifiers: Typical anionic emulsifiers are aliphatic fatty acids with 12 to 22 carbon atoms, such as palmitic acid, stearic acid or behenic acid, and dicarboxylic acids with 12 to 22 carbon atoms, such as azelaic acid or sebacic acid.

Also suitable are mono-, di- and trialkyl phosphates as well as mono-, di- and/or tri-PEG-alkyl phosphates and their salts, such as cetyl phosphate potassium salt as well as the citrate esters, in particular glyceryl oleate citrate and glyceryl stearyl citrate.

Amphoteric and cationic emulsifiers: Furthermore, zwitterionic surfactants can be used as emulsifiers. Surface-active compounds which have at least one quaternary ammonium group and at least one carboxylate and one sulphonate group in the molecule are referred to as zwitterionic surfactants. Particularly suitable zwitterionic surfactants are the so-called betaines such as the N-alkyl-N,N-dimethylammonium glycinates, for example the coconut alkyl dimethylammonium glycinate, N-acylaminopropyl-N,N-dimethylammonium glycinates, for example the coconut acylaminopropyl dimethyl ammonium glycinate, and 2-alkyl-3-carboxylmethyl-3-hydroxyethyl imidazolines each having 8 to 18 C atoms in the alkyl or acyl group, as well as the coconut acylaminoethyl hydroxyethyl carboxymethyl glycinate. The fatty acid amide derivative known under the CTFA designation cocamidopropyl betaine is particularly preferred. Further suitable emulsifiers are ampholytic surfactants. Ampholytic surfactants are surface-active compounds which, in addition to a $C_{8/18}$ alkyl or acyl group in the molecule, contain at least one free amino group and at least one —COOH or —$SO_3H$ group and are capable of forming internal salts. Examples of suitable ampholytic surfactants are N-alkylglycines, N-alkylpropionic acids, N-alkylaminobutyric acids, N-alkyliminodipropionic acids, N-hydroxyethyl-N-alkylamidopropylglycines, N-alkyltaurines, N-alkylsarcosines, 2-alkylaminopropionic acids and alkylaminoacetic acids each having about 8 to 18 carbon atoms in the alkyl group. Particularly preferred ampholytic surfactants are N-coconutalkylaminopropionate, coconutacylaminoethylaminopropionate and $C_{12/18}$-acylsarcosine. Finally, cationic surfactants can also be considered as emulsifiers, whereby those of the esterquat type, preferably methyl-quaternised difatty acid triethanolamine ester salts, are particularly preferred.

The amount of emulsifiers used is typically in the range of about 0.5 wt.-% to about 10 wt.-% and preferably about 1 wt.-% to about 5 wt.-%.

Fats and waxes: Typical examples of fats are glycerides, i.e. solid or liquid vegetable or animal products that essentially consist of mixed glycerol esters of higher fatty acids, waxes include, among others, natural or synthetic waxes, such as for example candelilla wax, camauba wax, Japan wax, esparto grass wax, cork wax, guaruma wax, rice germ oil wax, sugar cane wax, ouricury wax, montan wax, beeswax, shellac wax, spermaceti, lanolin (wool wax), brushing fat, ceresin, ozokerite (earth wax), petrolatum, paraffin waxes, microwaxes; chemically modified waxes (hard waxes), such as montan ester waxes, sasol waxes, hydrogenated jojoba waxes and synthetic waxes such as polyalkylene waxes and polyethylene glycol waxes. In addition to fats, fat-like substances such as lecithins and phospholipids can also be used as additives. By the term lecithins, the skilled person understands those glycero-phospholipids which are formed from fatty acids, glycerol, phosphoric acid and choline by esterification. Lecithins are therefore also often referred to in the art as phosphatidylcholines (PC). Examples of natural lecithins are the kephalins, which are also called phosphatidic acids and are derivatives of 1,2-diacyl-sn-glycerol-3-phosphoric acids. In contrast, phospholipids are usually mono- and preferably diesters of phosphoric acid with glycerol (glycerol phosphates), which are generally classified as fats. In addition, sphingosines or sphingolipids are also considered.

Pearlescent waxes: Suitable pearlescent waxes are, for example: alkylene glycol esters, especially ethylene glycol distearate; fatty acid alkanolamides, especially coconut fatty acid diethanolamide; partial glycerides, especially stearic acid monoglyceride; esters of polyvalent, optionally hydroxy-substituted carboxylic acids with fatty alcohols having 6 to 22 carbon atoms, especially long-chain esters of tartaric acid; fatty substances such as, for example, fatty alcohols, fatty ketones, fatty aldehydes, fatty ethers and fatty carbonates which in total have at least 24 carbon atoms, especially laurone and distearyl ether; fatty acids such as stearic acid, hydroxystearic acid or behenic acid, ring-opening products of olefinic epoxides having 12 to 22 carbon atoms with fatty alcohols having 12 to 22 carbon atoms and/or polyols having 2 to 15 carbon atoms and 2 to 10 hydroxyl groups, and mixtures thereof.

Consistency enhancers and thickeners: Fatty alcohols or hydroxy fatty alcohols with 12 to 22 and preferably 16 to 18 carbon atoms and, in addition, partial glycerides, fatty acids or hydroxy fatty acids can be considered as consistency enhancers. A combination of these substances with alkyl oligoglucosides and/or fatty acid N-methylglucamides of the same chain length and/or polyglycerol poly-12-hydroxystearates is preferred. Suitable thickening agents are, for example, aerosil types (hydrophilic silicas), polysaccharides, in particular xanthan gum, guar-guar, agar-agar, alginates and tyloses, carboxymethyl cellulose and hydroxyethyl and hydroxypropyl cellulose, furthermore higher molecular weight polyethylene glycol mono- and diesters of fatty acids, polyacrylates, (e.g. Carbopole® and Pemulen types from Lubrizol; Synthalene® from Sigma; Keltrol types from Kelco; Sepigel types from Seppic; Salcare types from BASF), polyacrylamides, polymers, polyvinyl alcohol and polyvinylpyrrolidone. Bentonites, such as Bentone® Gel VS-5PC (Elementis), which is a mixture of cyclopentasiloxane, disteardimonium hectorite and propylene carbonate, have also proven to be particularly effective. Other possible surfactants include ethoxylated fatty acid glycerides, esters of fatty acids with polyols such as pentaerythritol or trimethylolpropane, fatty alcohol ethoxylates with a narrowed homologue distribution or alkyl oligoglucosides as well as electrolytes such as common salt and ammonium chloride.

Superfatting agents and stabilisers: Substances such as lanolin and lecithin as well as polyethoxylated or acylated lanolin and lecithin derivatives, polyol fatty acid esters, monoglycerides and fatty acid alkanolamides can be used as superfatting agents, the latter also serving as foam stabilisers. Metal salts of fatty acids, such as magnesium stearate, aluminium stearate and/or zinc stearate or ricinoleate, can be used as stabilisers.

Polymers: Suitable cationic polymers are, for example, cationic cellulose derivatives, such as a quaternised hydroxyethyl cellulose available under the name polymer JR 400® from Dow, cationic starch, copolymers of diallylammonium salts and acrylamides, quaternised vinylpyrrolidone/vinylimidazole polymers, such as Luviquat® (BASF), condensation products of polyglycols and amines, quaternised collagen polypeptides, such as lauryldimonium hydroxypropyl hydrolyzed collagen (Lamequat® L, BASF), quaternised wheat polypeptides, polyethylenimine, cationic silicone polymers, e.g. amodimethicone, copolymers of adipic acid and dimethylaminohydroxypropyldiethylenetriamine (Cartaretine®, Sandoz), copolymers of acrylic acid with dimethyl-diallylammonium chloride (Merquat® 550, Lubrizol), polyaminopolyamides and their cross-linked water-soluble polymers, cationic chitin derivatives such as quaternised chitosan, optionally distributed in microcrystalline form, condensation products of dihaloalkylene, such as dibromobutane with bisdialkylamines, such as bis-dimethylamino-1,3-propane, cationic guar gum, such as Jaguar® CBS, Jaguar® C-17, Jaguar® C-16 (Solvay), quaternised ammonium salt polymers, such as Mirapol® A-15, Mirapol® AD-1, Mirapol® AZ-1 (Solvay).

Examples of anionic, zwitterionic, amphoteric and non-ionic polymers are vinyl acetate/crotonic acid copolymers, vinyl pyrrolidone/vinyl acrylate copolymers, vinyl acetate/butyl maleate/isobornyl acrylate copolymers, methyl vinyl ether/maleic anhydride copolymers and their esters, non-crosslinked and polyol-crosslinked polyacrylic acids, acrylamidopropyl trimethyl ammonium chloride/acrylate copolymers, octylacrylamide/methyl methacrylate/tert-butylaminoethyl methacrylate/2-hydroxypropyl methacrylate copolymers, poly-vinylpyrrolidone, vinylpyrrolidone/vinyl acetate copolymers, vinylpyrrolidone/dimethylaminoethyl methacrylate/vinylcaprolactam terpolymersand optionally derivatised cellulose ethers and silicones.

Silicone compounds: Suitable silicone compounds include, for example, dimethylpolysiloxanes, methylphenylpolysiloxanes, cyclic silicones and amino-, fatty acid-, alcohol-, polyether-, epoxy-, fluorine-, glycoside- and/or alkyl-modified silicone compounds, which may be present in liquid or resin form at room temperature. Simethicones, which are mixtures of dimethicones with an average chain length of 200 to 300 dimethylsiloxane units and hydrogenated silicates, are also suitable.

UV light protection filters: It was found that the diesters according to the invention are in particular capable of overcoming the stickiness typical of many UV filters. Another aspect of the present invention therefore relates to preparations which, in addition to the diesters, further comprise at least one UV filter. In particular, such preparations are preferred which contain (a) 1,3-propanediol dicaprylate/caprate; and
(b) at least one UV light filter
   with the proviso that component (a) has been produced entirely on a vegetable basis. Also typical are preparations containing
(a) from about 0.1 wt.-% to about 30 wt.-% of 1,3-propanediol dicaprylate/caprate; and
(b) from about 1 wt.-% to about 50 wt.-% of UV light filter
   with the proviso that the quantities with solvents and other cosmetic auxiliaries and additives add up to 100% by weight.

UV light protection filters (synonymously also often referred to as light protection factors) are, for example, organic substances which are liquid or crystalline at room temperature and which are capable of absorbing ultraviolet radiation and releasing the absorbed energy in the form of long-wave radiation, e.g. heat. Usually, the UV light protection filters are present in quantities of 0.1 wt.-% to 50 wt.-% and preferably 1 wt.-% to 45 wt.-%.

Typical UV-A filters are derivatives of benzoylmethane, such as 1-(4'-tert-butylphenyl)-3-(4'-methoxyphenyl)propane-1,3-dione, 4-tert-butyl-4'-methoxydibenzoylmethane (Parsol® 1789), 2-(4-diethylamino-2-hydroxybenzoyl)-benzoic acid hexylester (Uvinul® A Plus), 1-phenyl-3-(4'-isopropylphenyl)propane-1,3-dione as well as enamine compounds. Particularly preferred are:

terephthalylidenedibornanesulphonic acid and its salts (Mexoryl® SX);
hexyl 2-(4-diethylamino-2-hydroxybenzoyl)benzoate (Uvinul® A Plus);
2,2'-(1,4-phenylene)bis-[1H-benzimidazole-4,5-disulfonic acid], disodium salt (Neo Heliopan® AP);
menthyl anthranilate (Neo Heliopan® MA);
avobenzone (Neo Heliopan® 357)

and mixtures thereof.

UVB filters can be oil-soluble or water-soluble. Oil-soluble substances include, for example:

octocylenes;
homosalates;
octisalates;
p-aminobenzoic acid;
ethyl p-aminobenzoate+25EO;
2-ethylhexyl p-dimethylaminobenzoate;
triethanolamine salicylate (Neo Heliopan® TS);
menthyl anthranilate (Neo Heliopan® MA);
2-ethylhexyl p-methoxycinnamate (Neo Heliopan® AV);
isoamyl p-methoxycinnamate (Neo Heliopan® E 1000);
2-phenylbenzimidazolesulfonic acid (Neo Heliopan® Hydro) and its salts;
3-(4'-trimethylammonium)benzylidenboman-2-one methyl sulphate;
3-(4'-sulpho)benzylideneboman-2-one and its salts;
3-(4'-methylbenzylidene)-d,1-camphor (Neo Heliopan® MBC);
N-[(2,4)-[2-(oxoborn-3-ylidene)methyl]benzyl]acrylamide polymer;
4,4'-[(6-[4-(1,1-dimethyl)aminocarbonyl)phenylamino]-1,3,5-triazine-2,4-diyl)diimino]bis(benzoic acid-2-ethylhexyl ester) (Uvasorb® HEB);
benzylidene malonate polysiloxane (Parsol® SLX);
tris(2-ethylhexyl)-4,4',4"-(1,3,5-triazine-2,4,6-triyl-triimino)tribenzoate (Uvinul® T150);
methoxy propylamino cyclohexenylidene ethoxyethyl cyanoacetate and mixtures thereof.

Suitable broadband filters include, for example:

2-hydroxy-4-methoxybenzophenone-5-sulfonic acid (Sulisobenzone, Benzophenone-4) and their salts;
2-hydroxy-4-methoxybenzophenone (Neo Heliopan® BB);
disodium-2,2'-dihydroxy-4,4'-dimethoxy-5,5'-disulphobenzophenone;
phenol-(2H-benzotriazol-2-yl-4-methyl-6-(2-methyl-3-(1,3,3,3-tetramethyl-1-(trimethylsilyl)oxy)disiloxyanyl)propyl), (Mexoryl® XL);
2,2'-methylenebis(6-(2H-benztriazol-2-yl)-4-1,1,3,3-tetramethylbutyl)-phenol (Tinosorb® M);
tris-biphenyl triazine (Tinosorb® A2B);
bemotrizinol (Neo Heliopan® BMT);
2,4-bis[[(4-(3-sulphonato)-2-hydroxypropyloxy)-2-hydroxy]phenyl]-6-(4-methoxyphenyl)-1,3,5-triazine sodium salt;
2,4-bis[[(3-(2-propyloxy)-2-hydroxypropyloxy)-2-hydroxy]phenyl]-6-(4-methoxyphenyl)-1,3,5-triazine;
2,4-bis[[4-(2-ethylhexyloxy)-2-hydroxy]phenyl]-6-[4-(2-methoxyethylcarbonyl)phenylamino]-1,3,5-triazine;
2,4-bis[[4-(3-(2-propyloxy)-2-hydroxypropyloxy)-2-hydroxy]phenyl]-6-[4-(2-ethyl carboxyl)phenylamino]-1,3,5-triazine;
2,4-bis[[4-(2-ethylhexyloxy)-2-hydroxy]phenyl]-6-(1-methylpyrrol-2-yl)-1,3,5-triazine;

2,4-bis[[4-tris(trimethylsiloxysilylpropyloxy)-2-hydroxy]phenyl]-6-(4-methoxy phenyl)-1,3,5-triazine;

2,4-bis[[4-(2"-methylpropenyloxy)-2-hydroxy]phenyl]-6-(4-methoxyphenyl)-1,3,5-triazine;

2,4-bis[[4-(1',1',3',5,5',5'-heptamethylsiloxy-2"-methylpropyloxy)-2 hydroxy]phenyl]-6-(4-methoxyphenyl)-1,3,5-triazine;

(5,6,5',6'-tetraphenyl-3,3'-(1,4-phenylene)bis(1,2,4-triazine)

and mixtures thereof.

The UV-A and UV-B filters can of course also be used in mixtures. Particularly favourable combinations consist of the derivatives of benzoylmethane, e.g. 4-tert-butyl-4'-methoxydibenzoylmethane (Parsol® 1789) and 2-cyano-3,3-phenylcinnamic acid-2-ethylhexyl ester (Octocrylene) in combination with esters of cinnamic acid, preferably 4-methoxycinnamic acid-2-ethylhexyl ester and/or 4-methoxycinnamic acid propyl ester and/or 4-methoxycinnamic acid isoamyl ester. Advantageously, such combinations are combined with water-soluble filters, such as 2-phenylbenzimidazole-5-sulfonic acid and its alkali metal, alkaline earth metal, ammonium, alkylammonium, alkanolammonium and glucammonium salts.

Pigments, especially light protection pigments: In addition to the soluble substances mentioned, insoluble light protection pigments, namely finely dispersed metal oxides or salts, can also be used for this purpose. Examples of suitable metal oxides are in particular zinc oxide and titanium dioxide and also oxides of iron, zirconium, silicon, manganese, aluminium and cerium as well as mixtures thereof. Silicates (talc), barium sulphate or zinc stearate can be used as salts. The oxides and salts are used in the form of pigments for skin-care and skin-protecting emulsions and decorative cosmetics. The particles should have an average diameter of less than 100 nm, preferably between 5 and 50 nm and in particular between 15 and 30 nm. They may have a spherical shape, but particles may also be used which have an ellipsoidal shape or a shape which otherwise deviates from the spherical shape. The pigments may also be surface-treated, i.e. hydrophilised or hydrophobised. Typical examples are coated titanium dioxides, such as titanium dioxide T 805 (Degussa) or Eusolex® T2000, Eusolex® T, Eusolex® T-ECO, Eusolex® T-S, Eusolex® T-Aqua, Eusolex® T-45D (all Merck), Uvinul $TiO_2$ (BASF). Silicones and especially trialkoxyoctylsilanes or simethicones are used as hydrophobic coating agents. So-called micro- or nanopigments are preferably used in sunscreens. Micronised zinc oxide, such as Z-COTE® or Z-COTE HP1®, is preferably used.

Humectants: Humectants serve to further optimise the sensory properties of the composition as well as to regulate the moisture of the skin. At the same time, the cold stability of the preparations according to the invention is increased, especially in the case of emulsions. The humectants are usually present in an amount of from 0.1 wt.-% to 15 wt.-%, preferably from 1 wt.-% to 10 wt.-%, and more preferably from 5 wt-% to 10 wt-%.

Suitable substances according to the invention include amino acids, pyrrolidone carboxylic acid, lactic acid and salts thereof, lactitol, urea and urea derivatives, uric acid, glucosamine, creatinine, cleavage products of collagen, chitosan or chitosan salts/derivatives, and in particular polyols and polyol derivatives (e.g. glycerol, diglycerol, triglycerol, ethylene glycol, propylene glycol, butylene glycol, erythritol, 1,2,6-hexanetriol, polyethylene glycols such as PEG-4, PEG-6, PEG-7, PEG-8, PEG-9, PEG-10, PEG-12, PEG-14, PEG-16, PEG-18, PEG-20), sugars and sugar derivatives (including fructose, glucose, maltose, maltitol, mannitol, inositol, sorbitol, sorbitylsilanediol, sucrose, trehalose, xylose, xylitol, glucuronic acid and salts thereof), ethoxylated sorbitol (sorbeth-6, sorbeth-20, sorbeth-30, sorbeth-40), honey and hydrogenated honey, hydrogenated starch hydrolysates and mixtures of hydrogenated wheat protein and PEG-20 acetate copolymer. Preferred humectants according to the invention are glycerol, diglycerol, triglycerol and butylene glycol.

Biogenic active ingredients and antioxidants: Biogenic active ingredients are, for example, tocopherol, tocopherol acetate, tocopherol palmitate, ascorbic acid, (deoxy)ribonucleic acid and its fragmentation products, s-glucans, retinol, bisabolol, allantoin, phytantriol, panthenol, AHA acids, amino acids, ceramides, pseudoceramides, essential oils, plant extracts such as prunus extract, bambaranus extract and vitamin complexes.

Antioxidants interrupt the photochemical reaction chain that is triggered when UV radiation penetrates the skin. Typical examples are amino acids (e.g. glycine, histidine, tyrosine, tryptophan) and their derivatives, imidazoles (e.g. urocanic acid) and their derivatives, peptides such as D,L-camosine, D-camosine, L-camosine and their derivatives (e.g. anserine), carotenoids, carotenes (e.g. α-carotene, β-carotene, lycopene) and their derivatives, chlorogenic acid and its derivatives, lipoic acid and its derivatives (e.g. dihydrolipoic acid), aurothioglucose, propylthiouracil and other thiols (e.g. thioredoxin, glutathione, cysteine, cystine, cystamine and their glycosyl, N-acetyl, methyl, ethyl, propyl, amyl, butyl and lauryl, palmitoyl, oleyl, γ-linoleyl, cholesteryl and glyceryl esters) and their salts, dilaurylthiodipropionate, distearylthiodipropionate, thiodipropionic acid and their derivatives (esters, ethers, peptides, lipids, nucleotides, nucleosides and salts) as well as sulphoximine compounds (e.g. buthionine sulphoximines, homocysteine sulphoximine, butionine sulphones, penta-, hexa-, heptathionine sulphoximine) in very low tolerated dosages (e.g. pmol to μmol/kg), furthermore (metal) chelators (e.g. α-hydroxy fatty acids, palmitic acid, phytic acid, lactoferrin), α-hydroxy acids (e.g. citric acid, lactic acid, malic acid), humic acid, bile acid, bile extracts, bilirubin, biliverdin, EDTA, EGTA and derivatives thereof, unsaturated fatty acids and derivatives thereof (e.g. γ-linolenic acid, linoleic acid, oleic acid), folic acid and derivatives thereof, ubiquinone and ubiquinol and derivatives thereof, vitamin C and derivatives (e.g. ascorbyl palmitate, Mg-ascorbyl phosphate, ascorbyl acetate), tocopherols and derivatives (e.g. vitamin E acetate), vitamin A and derivatives (vitamin A palmitate) as well as coniferyl benzoate of benzoic resin, rutinic acid and its derivatives, α-glycosylrutin, ferulic acid, furfurylidene glucitol, camosine, butylhydroxytoluene, butylhydroxyanisole, nordihydroguaiak resin acid, nordihydroguaiaretic acid, trihydroxybutyrophenone, uric acid and derivatives thereof, mannose and derivatives thereof, superoxide dismutase, zinc and derivatives thereof (e.g. ZnO, $ZnSO_4$) selenium and its derivatives (e.g. selenomethionine), stilbenes and their derivatives (e.g. stilbene oxide, trans-stilbene oxide) and the derivatives (salts, esters, ethers, sugars, nucleotides, nucleosides, peptides and lipids) of these active substances suitable according to the invention.

Deodorants and germicides: Cosmetic deodorants (deodorants) counteract, mask or eliminate body odours. Body odours are caused by the action of skin bacteria on apocrine sweat, whereby unpleasant-smelling degradation products are formed. Accordingly, deodorants contain active ingredients that act as germ-inhibiting agents, enzyme inhibitors, odour absorbers or odour maskers.

Germicidal agents: In principle, all substances effective against gram-positive bacteria are suitable as germicidal agents, e.g. 2-methyl-5-cyclohexylpentanol, 1,2-decylene glycol, 4-hydroxybenzoic acid and its salts and esters, N-(4-chlorophenyl)-N'-(3,4-dichlorophenyl)urea, 2,4,4'-trichloro-2'-hydroxy-diphenyl ether (triclosan), 4-chloro-3,5-dimethyl-phenol, 2,2'-methylene-bis(6-bromo-4-chlorophenol), 3-methyl-4-(1-methylethyl)-phenol, 2-benzyl-4-chlorophenol, 3-(4-chlorophenoxy)-1,2-propanediol, 3-iodo-2-propynyl butylcarbamate, chlorhexidine, 3,4,4'-trichlorocarbanilide (TTC), antibacterial fragrances, thymol, thyme oil, eugenol, clove oil, menthol, mint oil, famesol, phenoxyethanol, glycerol monocaprinate, glycerol monocaprylate, glycerol monolaurate (GML), diglycerol monocaprinate (DMC), salicylic acid-N-alkylamides such as salicylic acid-n-octylamide or salicylic acid-n-decylamide.

Enzyme inhibitors: Suitable enzyme inhibitors are, for example, esterase inhibitors. These are preferably trialkyl citrates such as trimethyl citrate, tripropyl citrate, triisopropyl citrate, tributyl citrate and especially triethyl citrate (Hydagene CAT). These substances inhibit enzyme activity and thus reduce odour formation. Other substances that can be considered as esterase inhibitors are sterol sulphates or phosphates, such as lanosterol, cholesterol, campesterol, stigmasterol and sitosterol sulphate or phosphate, dicarboxylic acids and their esters, such as glutaric acid, glutaric acid monoethyl ester, glutaric acid diethyl ester, adipic acid, adipic acid monoethyl ester, adipic acid diethyl ester, malonic acid and malonic acid diethyl ester, hydroxycarboxylic acids and their esters, such as citric acid, malic acid, tartaric acid or tartaric acid diethyl ester, and zinc glycinate.

Odour absorbers: Suitable odour absorbers are substances that can absorb and largely retain odour-forming compounds. They lower the partial pressure of the individual components and thus also reduce their speed of dispersion. It is important that perfumes remain unaffected in the process. Odour absorbers are not effective against bacteria. They contain, for example, a complex zinc salt of ricinoleic acid as their main component or special, largely odour-neutral fragrances known to the skilled person as "fixatives", such as extracts of labdanum or styrax or certain abietic acid derivatives. Fragrances or perfume oils act as odour masking agents which, in addition to their function as odour masking agents, lend the deodorants their respective fragrance note. Perfume oils are, for example, mixtures of natural and synthetic fragrances. Natural fragrances are extracts of flowers, stems and leaves, fruits, fruit peels, roots, woods, herbs and grasses, needles and twigs as well as resins and balsams. Animal raw materials are also used, such as civet and castoreum. Typical synthetic fragrance compounds are products of the ester, ether, aldehyde, ketone, alcohol and hydrocarbon type. Ester-type fragrance compounds include benzyl acetate, p-tert-butyl cyclohexyl acetate, linalyl acetate, phenyl ethyl acetate, linalyl benzoate, benzyl formate, allyl cyclohexyl propionate, styrallyl propionate and benzyl salicylate. The ethers include, for example, benzyl ethyl ether, the aldehydes include, for example, the linear alkanals with 8 to 18 carbon atoms, citral, citronellal, citronellyloxyacetaldehyde, cyclamenaldehyde, hydroxycitronellal, lilial and bourgeonal, the ketones include, for example, the ionones and methyl cedryl ketone, the alcohols include anethole, citronellol, eugenol, isoeugenol, geraniol, linalool, phenylethyl alcohol and terpineol, and the hydrocarbons mainly include terpenes and balsams. However, mixtures of different fragrances that together create an appealing scent are preferred. Essential oils of lower volatility, which are mostly used as aroma components, are also suitable as perfume oils, e.g. sage oil, camomile oil, clove oil, melissa oil, mint oil, cinnamon leaf oil, lime blossom oil, juniper berry oil, vetiver oil, olibanum oil, galbanum oil, labdanum oil and lavandin oil. Preferably, bergamot oil, dihydromyrcenol, lilial, lyral, citronellol, phenylethyl alcohol, α-hexyl cinnamaldehyde, geraniol, benzylacetone, cyclamenaldehyde, linalool, boisambrene forte, ambroxan, indole, hedione, sandelice, lemon oil, mandarin oil, orange oil, allylamyl glycolate, cyclovertal, lavandin oil, muscatel sage oil, β-damascone, geranium oil bourbon, cyclohexyl salicylate, vertofix coeur, iso-E-super, fixolide NP, evemyl, iraldein gamma, phenylacetic acid, geranyl acetate, benzyl acetate, rose oxide, romilate, irotyl and floramate are used alone or in mixtures.

Antiperspirants: Antiperspirants reduce perspiration by influencing the activity of the eccrine sweat glands, thus counteracting underarm wetness and body odour. Aqueous or water-free formulations of antiperspirants typically contain the following ingredients:

astringent active ingredients,
oil components,
non-ionic emulsifiers,
coemulsifiers,
consistency giver,
excipients such as thickeners or complexing agents and/or
non-aqueous solvents such as ethanol, propylene glycol and/or glycerine.

Salts of aluminium, zirconium or zinc are particularly suitable as astringent antiperspirant agents. Such suitable antihydrotic active ingredients are e.g. aluminium chloride, aluminium chlorohydrate, aluminium dichlorohydrate, aluminium sesquichlorohydrate and their complex compounds e.g. with propylene glycol-1,2, aluminium hydroxyallantoinate, aluminium chloride tartrate, aluminium zirconium trichlorohydrate, aluminium zirconium tetrachlorohydrate, aluminium zirconium pentachlorohydrate and their complex compounds e.g. with amino acids such as glycine. In addition, antiperspirants may contain common oil-soluble and water-soluble excipients in smaller amounts. Such oil-soluble excipients may be, for example:

anti-inflammatory, skin-protecting or fragrant essential oils,
synthetic skin-protecting active substances and/or
oil-soluble perfume oils.

Common water-soluble additives are e.g. preservatives, water-soluble fragrances, pH adjusters, e.g. buffer mixtures, water-soluble thickeners, e.g. water-soluble natural or synthetic polymers, such as xanthan gum, hydroxyethyl cellulose, polyvinyl pyrrolidone or high molecular weight polyethylene oxides.

Film formers: Common film formers are, for example, chitosan, microcrystalline chitosan, quaternised chitosan, polyvinylpyrrolidone, vinylpyrrolidone-vinyl acetate copolymers, polymers of the acrylic acid series, quaternary cellulose derivatives, hydrolysed jojoba esters, collagen, hyaluronic acid or its salts and similar compounds.

Anti-dandruff agents: Anti-dandruff agents include piroctone olamine (1-hydroxy-4-methyl-6-(2,4,4-trimethylpentyl)-2-(1H)-pyridinone monoethanolamine salt), Crinipan® AD (Climbazole), Ketoconazol®, (4-acetyl-1-{-4-[2-(2.4-dichlorophenyl) r-2-(1H-imidazol-1-ylmethyl)-1,3-dioxylan-c-4-ylmethoxyphenyl}piperazine, ketoconazole, elubiol, selenium disulphide, sulphur colloidal, sulphur polyethylene glycol sorbitan monooleate, sulphur rizinol polyethoxylate, sulphur tar distillates, salicylic acid (or in combination with hexachlorophene), undecylenic acid monoethanolamide sulphosuccinate Na salt, Lamepon® UD (protein undecylenic acid condensate), zinc pyrithione, aluminium pyrithione and magnesium pyrithione/dipyrithione magnesium sulphate.

Swelling agents: montmorillonite, clay minerals, pemulene and alkyl-modified carbopol types (Lubrizol) can serve as swelling agents for aqueous phases. Other suitable polymers or swelling agents are known to the skilled person from the relevant technical literature.

Insect repellents: N,N-diethyl-m-toluamide, 1,2-pentanediol or ethyl butylacetylaminopropionate are suitable insect repellents. Dihydroxyacetone is suitable as a self-tanning agent. Tyrosine inhibitors that prevent the formation of melanin and are used in depigmentation agents include arbutin, ferulic acid, kojic acid, coumaric acid and ascorbic acid (vitamin C).

Hydrotropes: Hydrotropes such as ethanol, isopropyl alcohol or polyols can also be used to improve the flow behaviour; these substances largely correspond to the carriers described at the beginning. Polyols which are considered here preferably have 2 to 15 carbon atoms and at least two hydroxyl groups. The polyols may contain further functional groups, in particular amino groups, or be modified with nitrogen. Typical examples are:

- glycerol;
- alkylene glycols, such as ethylene glycol, diethylene glycol, propylene glycol, butylene glycol, pentylene glycol, caprylyl glycol as well as polyethylene glycols with an average molecular weight of 100 to 1000 Dalton;
- technical oligoglycerol mixtures with an intrinsic degree of condensation of 1.5 to 10, such as technical diglycerol mixtures with a diglycerol content of 40 to 50 wt.-%;
- methyol compounds, such as in particular trimethylolethane, trimethylolpropane, trimethylolbutane, pentaerythritol and dipentaerythritol;
- lower alkyl glucosides, especially those with 1 to 8 carbons in the alkyl residue, such as methyl and butyl glucoside;
- sugar alcohols with 5 to 12 carbon atoms, such as sorbitol or mannitol;
- sugar with 5 to 12 carbon atoms, such as glucose or sucrose;
- amino sugars, such as glucamine;
- dialcoholamines, such as diethanolamine or 2-amino-1,3-propanediol.

Preservatives: Suitable preservatives are, for example, phenoxyethanol, formaldehyde solution, parabens, o-cymen-5-ol, 4-hydroxyacetophenone, tropolone or sorbic acid as well as the silver complexes known under the name Surfacine® and the other classes of substances that can be found in the relevant literature and are therefore also known to the skilled person.

Perfume oils and aromas: As perfume oils, mixtures of natural and synthetic fragrances shall be mentioned. Natural fragrances are extracts of flowers (lily, lavender, roses, jasmine, neroli, ylang-ylang), stems and leaves (geranium, patchouli, petitgrain), fruits (anise, coriander, cumin, juniper), fruit peels (bergamot, lemon, oranges), roots (mace, angelica, celery, cardamom, costus, irs, calmus), woods (pine, sandalwood, guaiac, cedar, rosewood), herbs and grasses (tarragon, lemongrass, sage, thyme), needles and twigs (spruce, fir, pine, mountain pine), resins and balsams (galbanum, elemi, benzoin, myrrh, olibanum, opoponax). Animal raw materials are also used, such as civet and castoreum. Typical synthetic fragrance compounds are products of the ester, ether, aldehyde, ketone, alcohol and hydrocarbon type. Ester-type fragrance compounds include benzyl acetate, phenoxyethyl isobutyrate, p-tert-butyl cyclohexyl acetate, linalyl acetate, dimethyl benzyl carbinyl acetate, phenyl ethyl acetate, linalyl benzoate, benzyl formate, ethyl methyl phenyl glycinate, allyl cyclohexyl propionate, styrallyl propionate and benzyl salicylate. The ethers include, for example, benzyl ethyl ether, the aldehydes include, for example, the linear alkanals with 8 to 18 carbon atoms, citral, citronellal, citronellyloxyacetaldehyde, cyclamenaldehyde, hydroxycitronellal, lilial and bourgeonal, and the ketones include, for example, the jonones, α-isomethyl ionone and methylcedryl ketone, the alcohols include anethole, citronellol, eugenol, isoeugenol, geraniol, linalool, phenylethyl alcohol and terpineol, and the hydrocarbons mainly include the terpenes and balsams. Preferably, however, mixtures of different fragrances are used, which together create an appealing scent. Essential oils of lower volatility, which are mostly used as aroma components, are also suitable as perfume oils, e.g. sage oil, camomile oil, clove oil, melissa oil, mint oil, cinnamon leaf oil, lime blossom oil, juniper berry oil, vetiver oil, olibanum oil, galbanum oil, labolanum oil and lavandin oil. Preferably, bergamot oil, dihydromyrcenol, lilial, lyral, citronellol, phenylethyl alcohol, α-hexyl cinnamaldehyde, geraniol, benzylacetone, cyclamenaldehyde, linalool, boisambrene forte, ambroxan, indole, hedione, sandelice, lemon oil, mandarin oil, orange oil, allylamyl glycolate, cyclovertal are preferred, lavandin oil, muscatel sage oil, β-damascone, geranium oil bourbon, cyclohexyl salicylate, vertofix coeur, iso-E-super, fixolide NP, evemyl, iraldein gamma, phenylacetic acid, geranyl acetate, benzyl acetate, rose oxide, romillate, irotyl and floramate are used alone or in mixtures.

Suitable aromas include peppermint oil, spearmint oil, anise oil, star anise oil, caraway oil, eucalyptus oil, fennel oil, lemon oil, wintergreen oil, clove oil, menthol and the like.

Colouring matter: The colouring matter may be substances suitable and authorised for cosmetic or pharmaceutical use, as listed in the technical literature, such as cochineal red A (C.I. 16255), patent blue V (C.I.42051), indigotine (C.I.73015), chlorophyllin (C.I.75810), quinoline yellow (C.I.47005), titanium dioxide (C.I.77891), indanthrene blue RS (C.I. 69800) and madder lake (C.I.58000). Luminol may also be included as a luminescent dye. These dyes are usually used in concentrations of 0.001 to 0.1 wt.-%, based on the total mixture.

Preferred preparations according to the invention are selected from the group of products for the treatment, protection, care and cleansing of the skin and/or hair or as a make-up product, either as leave-on or rinse-off products.

Formulations include, for example, dispersions, suspensions, creams, lotions or milks, depending on the manufacturing method and ingredients, gels (including hydrogels, e.g. hydrodispersion gels, oleogels), sprays (e.g. pump sprays or sprays with propellant) foams or impregnating solutions for wipes, soaps, washing liquids, shower and bath preparations, bath products (capsules, oil, tablets, salts, bath salts, soaps, etc.), effervescent preparations, skin care products, such as emulsions, ointments, pastes, gels (as described above), oils, balms, serums, powders (e.g. face powders, body powders), masks, sticks, roll-on sticks, aerosols (foaming, non-foaming or post-foaming), deodorants and/or antiperspirants, mouthwashes and mouth rinses, insect repellents, sunscreens, after-sun preparations, shaving products, aftershave balms, pre- and aftershave lotions, depilatories, hair care products such as shampoos (including 2-in-1 shampoos, anti-dandruff shampoos, baby shampoos, shampoos for dry scalps, concentrated shampoos), conditioners, hair tonics, hair tonics, hair conditioners, styling creams, pomades, perming and setting lotions, hair sprays, e.g. styling aids (e.g. gel or wax), hair straighteners (detanglers, relaxers), hair dyes such as temporary hair dyes, semi-permanent hair dyes, permanent hair dyes, hair conditioners, hair mousses, eye care products, make-ups, make-up removers or baby products.

Particularly preferably, the formulations according to the invention are in the form of an emulsion, in particular in the form of a W/O, O/W, W/0/W, O/W/O emulsion, PIT emulsion, e.g. a Pickering emulsion, an emulsion with a low oil content, a micro- or nanoemulsion, a gel (including hydrogel, hydrodispersion gel, oleogel) or a solution.

The total proportion of excipients and additives may be from 1 wt.-% to 50 wt.-%, preferably from 5 wt.-% to 40 wt.-%, based on the final preparation. The preparation of the agents may be carried out by conventional cold or hot processes; preferably the phase inversion temperature method is used.

The present invention also includes oral care compositions containing one or more cooling agents according to the invention or a cooling agent mixture according to the invention or a flavouring preparation according to the invention.

Oral care compositions according to the invention may be formulated in a manner known per se, e.g. as toothpaste, tooth gel, or aqueous or aqueous-alcoholic oral care compositions (mouthwash).

Toothpastes or dentifrices are generally understood to be gel-like or paste-like preparations of water, thickening agents, humectants, abrasive or cleaning agents, surfactants, sweeteners, flavouring agents, deodorising agents and agents against oral and dental diseases. All conventional cleaning agents, such as chalk, dicalcium phosphate, insoluble sodium metaphosphate, aluminium silicates, calcium pyrophosphate, finely divided synthetic resins, silicic acids, aluminium oxide and aluminium oxide trihydrate can be used in the toothpastes according to the invention.

Preferably suitable cleaning agents for the toothpastes according to the invention are, above all, finely divided xerogel silicas, hydrogel silicas, precipitated silicas, alumina trihydrate and finely divided alpha-alumina or mixtures of these cleaning agents in amounts of 15 to 40 wt-% of the toothpaste. Suitable humectants are predominantly low molecular weight polyethylene glycols, glycerol, sorbitol or mixtures of these products in amounts up to 50 wt.-%. Among the known thickening agents the thickening, fine-particle gel silicas and hydrocolloids, such as carboxymethyl cellulose, hydroxyethyl cellulose, hydroxypropyl guar, hydroxyethyl starch, polyvinyl pyrrolidone, high molecular weight polyethylene glycol, plant gums such as traganth, agar agar, carragheen moss, gum arabic, xantham gum and carboxyvinyl polymers (e.g. Carbopol® types) are suitable. In addition to the mixtures of menthofuran and menthol compounds, the oral and dental care agents may in particular contain surface-active substances, preferably anionic and non-ionic high foaming surfactants, such as the substances already mentioned above, but in particular alkyl ether sulphate salts, alkyl polyglucosides and mixtures thereof.

Other common toothpaste additives are:

- preservatives and antimicrobials such as methyl, ethyl or propyl p-hydroxybenzoate, sodium sorbate, sodium benzoate, bromochlorophene, phenyl salicylic acid esters, thymol and the like;
- anticalculus agents, e.g. organophosphates such as 1-hydroxyethane-1,1-diphosphonic acid, 1-phosphonpropane-1,2,3-tricarboxylic acid and others known e.g. from U.S. Pat. No. 3,488,419, DE 2224430 A1 and DE 2343196 A1;
- other caries-inhibiting substances such as sodium fluoride, sodium monofluorophosphate, stannous fluoride;
- sweeteners, such as saccharin sodium, sodium cyclamate, sucrose, lactose, maltose, fructose or Apartam®, (L-aspartyl-L-phenylalanine methyl ester), stivia extracts or their sweetening components, especially ribeaudiosides;
- additional aromas such as eucalyptus oil, anise oil, fennel oil, caraway oil, methyl acetate, cinnamaldehyde, anethole, vanillin, thymol and mixtures of these and other natural and synthetic aromas;
- pigments such as titanium dioxide;
- dyes;
- buffer substances such as primary, secondary or tertiary alkali phosphates or citric acid/sodium citrate;
- wound-healing and anti-inflammatory substances such as allantoin, urea, azulene, camomile active ingredients and acetylsalicylic acid derivatives.

Hydrotropes, such as ethanol, isopropyl alcohol, or polyols can also be used to improve the flow behaviour; these substances largely correspond to the carriers described at the beginning. Polyols which are considered here preferably have 2 to 15 carbon atoms and at least two hydroxyl groups. The polyols may contain further functional groups, in particular amino groups, or be modified with nitrogen. Typical examples are:

- glycerol;
- alkylene glycols, such as ethylene glycol, diethylene glycol, propylene glycol, butylene glycol, hexylene glycol as well as polyethylene glycols with an average molecular weight of 100 to 1000 Dalton;
- technical oligoglycerol mixtures with an intrinsic degree of condensation of 1.5 to 10, such as technical diglycerol mixtures with a diglycerol content of 40 to 50 wt.-%;
- methyol compounds, such as in particular trimethylolethane, trimethylolpropane, trimethylolbutane, pentaerythritol and dipentaerythritol;
- lower alkyl glucosides, especially those with 1 to 8 carbons in the alkyl residue, such as methyl and butyl glucoside;
- sugar alcohols with 5 to 12 carbon atoms, such as sorbitol or mannitol,
- sugar with 5 to 12 carbon atoms, such as glucose or sucrose;
- amino sugars, such as glucamine;
- dialcoholamines, such as diethanolamine or 2-amino-1,3-propanediol.

Suitable preservatives include, for example, phenoxyethanol, formaldehyde solution, parabens, pentanediol or sorbic acid as well as the silver complexes known under the name Surfacine® and other classes of substances known to the skilled person and suitable for this purpose.

Perfume oils are those already defined above. In particular, peppermint oil, spearmint oil, anise oil, star anise oil, caraway oil, eucalyptus oil, fennel oil, citron oil, wintergreen oil, clove oil, menthol and the like may be used as aromas.

A preferred embodiment of the cosmetic preparations are toothpastes in the form of an aqueous, pasty dispersion containing polishing agents, humectants, viscosity regulators and optionally other usual components, as well as containing the mixture of menthofuran and menthol compounds in amounts of 0.5 to 2 wt.-%.

In mouthwashes, a combination with aqueous-alcoholic solutions of various degrees of essential oils, emulsifiers, astringent and tonic drug extracts, anti-tartar, antibacterial additives and flavour correctors is readily possible. Another preferred embodiment of the invention is a mouthwash in the form of an aqueous or aqueous-alcoholic solution containing the mixture of menthofuran and menthol compounds in amounts of 0.5 to 2 wt.-%. In mouthwashes which are diluted before use, sufficient effects can be achieved with higher concentrations, according to the intended dilution ratio.

Oral care preparations according to the invention contain, based on the total weight of the composition, preferably 0.1 ppm to 10 wt.-%, preferably 1 ppm to 10 wt.-%, of at least one active ingredient according to the invention, i.e. a cooling agent, or an active ingredient mixture, i.e. cooling agent mixture or flavouring preparation.

The present invention also comprises chewing gum containing one or more cooling agents according to the invention or a cooling agent mixture according to the invention or a flavouring preparation according to the invention.

Chewing gum compositions typically contain a water-insoluble and a water-soluble component. The water-insoluble base, also referred to as the “gum base”, typically comprises natural or synthetic elastomers, resins, fats and oils, plasticisers, fillers, colourants and optionally waxes. The proportion of the base in the total composition usually constitutes 5 to 95 wt.-%, preferably 10 to 50 wt.-% and in particular 20 to 35 wt.-%. In a typical embodiment of the invention, the base is composed of 20 to 60 wt.-% of synthetic elastomers, 0 to 30 wt.-% of natural elastomers, 5 to 55 wt.-% of plasticisers, 4 to 35 wt.-% of fillers and, in minor amounts, additives such as dyes, antioxidants and the like, with the proviso that they are water-soluble at most in minor amounts.

Suitable synthetic elastomers are, for example, polyisobutylenes with average molecular weights (according to GPC) of 10 000 to 100 000 and preferably 50 000 to 80 000, isobutylene-isoprene copolymers (butyl elastomers), styrene-butadiene copolymers (styrene:butadiene ratio e.g. 1:3 to 3:1), polyvinyl acetates with average molecular weights (according to GPC) of 2 000 to 90 000 and preferably 10 000 to 65 000, polyisoprenes, polyethylene, vinyl acetate-vinyl laurate copolymers and mixtures thereof. Examples of suitable natural elastomers include rubbers such as smoked or liquid latex or guayule, and natural rubbers such as jelutong, lechi caspi, perillo, sorva, massaranduba balata, massaranduba chocolate, nispero, rosindinba, chicle, gutta hang 1kang and mixtures thereof. The choice of synthetic and natural elastomers and their mixing ratios is essentially determined by whether or not the chewing gums are intended to produce bubbles (“bubble gums”). Elastomer mixtures containing jelutong, chicle, sorva and massaranduba are preferably used.

In most cases, the elastomers prove to be too hard or too little deformable during processing, so that it has proved advantageous to use special plasticisers as well, which must of course also meet all the requirements for approval as food additives in particular. In this respect, esters of resin acids are particularly suitable, for example esters of lower aliphatic alcohols or polyols with wholly or partially cured, monomeric or oligomeric resin acids. In particular, the methyl, glycerol or pentareythritol esters and mixtures thereof are used for this purpose. Alternatively, terpene resins can also be considered, which can be derived from alpha-pinene, beta-pinene, delta-limonene or mixtures thereof.

Suitable fillers or texturising agents include magnesium or calcium carbonate, ground pumice, silicates, especially magnesium or aluminium silicates, days, aluminium oxides, talc, titanium dioxide, mono-, di- and tricalcium phosphate and cellulose polymers.

Suitable emulsifiers are tallow, hardened tallow, hardened or partially hardened vegetable oils, cocoa butter, partial glycerides, lecithin, triacetin and saturated or unsaturated fatty acids with 6 to 22 and preferably 12 to 18 carbon atoms and mixtures thereof.

Suitable colourants and whitening agents are, for example, the FD and C types approved for the colouring of foods, plant and fruit extracts and titanium dioxide.

The base compounds may contain waxes or be wax-free; examples of wax-free compositions can be found, among others, in patent specification U.S. Pat. No. 5,286,500.

In addition to the water-insoluble gum base, chewing gum preparations regularly contain a water-soluble portion formed, for example, by softeners, sweeteners, fillers, flavourings, flavour enhancers, emulsifiers, colourings, acidifiers, antioxidants and the like, with the proviso that the constituents have at least sufficient water solubility. Depending on the water solubility of the specific representatives, individual components can therefore belong to both the water-insoluble and the water-soluble phase. However, it is also possible to use combinations of, for example, a water-soluble and a water-insoluble emulsifier, in which case the individual representatives are in different phases. Usually, the water-insoluble portion constitutes 5 to 95 wt.-% and preferably 20 to 80 wt.-% of the preparation.

Water-soluble softeners or plasticisers are added to chewing gum compositions to improve chewability and chewing feel and are typically present in the mixtures in amounts of 0.5 wt.-% to 15 wt.-%. Typical examples are glycerol, lecithin and aqueous solutions of sorbitol, hydrogenated starch hydrolysates or corn syrup.

Both sugar-containing and sugar-free compounds are suitable sweeteners, which are used in amounts of 5 to 95 wt.-%, preferably 20 to 80 wt.-% and in particular 30 to 60 wt.-%, based on the chewing gum composition. Typical saccharide sweeteners are sucrose, dextrose, maltose, dextrin, dried invert sugar, fructose, levulose, galactose, corn syrup and mixtures thereof. Sugar substitutes include sorbitol, mannitol, xylitol, hydrogenated starch hydrolysates, maltitol and mixtures thereof. Furthermore, so-called HIAS (“High Intensity Artificial Sweeteners”) can also be considered as additives, such as sucralose, aspartame, acesulfame salts, alitame, saccharin and saccharin salts, cyclamic acid and its salts, glycyrrhizines, dihydrochalcones, thaumatin, monellin and the like alone or in mixtures. Particularly effective are also the hydrophobic HIAS, which are the subject of the international patent application WO 2002 091849 A1 (Wrigleys), as well as stevia extracts and their active ingredients, in particular ribeaudioside A. The amount used of these substances depends primarily on their performance capacity and is typically in the range of 0.02 to 8 wt.-%.

Fillers such as polydextrose, raftilose, rafitilin, fructooligosaccharides (NutraFlora), palatinose oligosaaccharides, guar gum hydrolysate (Sun Fiber) and dextrins are particularly suitable for the production of low-calorie chewing gums.

The choice of other flavourings is virtually unlimited and not critical to the essence of the invention. Typically, the total percentage of all flavourings is 0.1 to 15 wt.-%, and preferably 0.2 to 5 wt.-%, based on the chewing gum composition. Suitable further flavourings are, for example, essential oils, synthetic flavourings and the like, such as anise oil, star anise oil, caraway oil, eucalyptus oil, fennel oil, citron oil, wintergreen oil, clove oil, and the like, such as are also used, for example, in oral and dental care compositions.

The chewing gums can also contain excipients and additives that are suitable for dental care, especially for combating plaque and gingivitis, such as chlorhexidine, CPC or trichlosan. Furthermore, pH regulators (e.g. buffers or urea), active ingredients against caries (e.g. phosphates or fluorides), biogenic active ingredients (antibodies, enzymes, caffeine, plant extracts) can be contained, as long as these substances are approved for food and do not interact with each other in an undesirable way.

The present invention also includes cooling plasters. Plasters according to the invention can be constructed in any way, for example according to the matrix system, the membrane system or the non-woven system.

The plasters according to the invention are manufactured in the usual way.

In its simplest form, the matrix system consists of 3 parts: the flexible support film, the adhesive matrix containing the active ingredient and a release film. If a non-adhesive matrix is used, an edge zone of the support film must be provided with adhesive for adhesion to the skin.

A membrane system, on the other hand, has at least 5 parts: a flexible support film, a reservoir with dissolved or suspended active ingredient, a membrane for controlling the release of active ingredient, an adhesive layer applied to the membrane and a release film.

In the nonwoven system, the layer containing the active ingredient consists of an absorbent nonwoven or porous polymer impregnated with an active ingredient solution or—suspension. This layer, which is firmly attached to the support film, is covered by a peel-off film. The edge of the support film is provided with adhesive for application to the skin.

In principle, all active ingredients according to the invention can be formulated in this way. The excipients to be used are those customary for the production of plasters. In addition to the adhesive agent, usually a polymer with a glass transition temperature between −70 and −10° C., in particular −55 and −25° C., as well as a carrier film coated with this adhesive agent, and the active ingredient, emulsifiers, thickening agents and substances intended to influence the release of the active ingredient, and other auxiliaries are frequently added.

The sticky polymers with the above mentioned low glass temperatures are known. The self-adhesive tapes and films are intended to adhere to the human skin on mere contact, but the cohesion of the adhesive layer and its adhesion to the carrier film are intended to be greater than the adhesion to the skin, so that they can be removed again largely without residue. These are usually copolymers based on acrylic and methacrylic acid esters of alcohols with 2 to 12, in particular 4 to 8 carbon atoms, which may contain numerous other comonomers as copolymerised units, for example (meth) acrylic acid, (meth)acrylonitrile, (meth)acrylamide, N-tert-butyl (meth)acrylamide, vinyl esters such as vinyl acetate, vinyl propionate or vinyl butyrate, other vinyl compounds such as styrene, and also butadiene. Particularly emphasised are butyl acrylate and 2-ethylhexyl acrylate. The polymers may be crosslinked by addition of small amounts of comonomers having 2 or more copolymerisable double bonds, i.e. for example diacrylates, such as butanediol diacrylate, or divinyl compounds, such as divinylbenzene, or by addition of other crosslinking agents, e.g. melamine-formaldehyde resins. Furthermore, polyisobutylenes and polyvinyl ethers of different molecular weights can be used as sticky polymers.

The particle size of the dispersions should be between 50 and 500 nm, in particular between 50 and 200 nm. The particle size and the degree of cross-linking can be adjusted in a known manner depending on the polymerisation conditions and the comonomers. Smaller particle sizes and an increased degree of cross-linking can cause an increase in the release of the active substance.

Matrix patches can be prepared in the usual way by dissolving or finely dispersing the active ingredient in a suitable polymer solution and then drawing out this self-adhesive mass containing the active ingredient to form a film by means of a roller or doctor blade application process. In some cases, it is useful to dissolve or finely disperse the active ingredient in an organic solvent, e.g. ethanol or acetone, before adding it to the polymer solution. In this way, a better distribution of the active ingredient in the polymer can be achieved.

The patches can also be prepared by incorporating the active ingredient in fine powder form (particle size below 200 μm, in particular below 50 μm) into the aqueous latex dispersion, or by dispersing or dissolving it in an aqueous emulsifier solution and mixing this mixture with the aqueous latex dispersion at a temperature of 10 to 80, in particular 30 to 70° C. In addition, the salt of an active substance in aqueous solution can also be mixed with the polymer dispersion at a pH at which the active substance is predominantly present in the water-soluble ionised form. The active ingredient is then brought into the uncharged water-insoluble form by pH shift and simultaneously emulsified into the dispersion.

It is useful to prepare the active substance, add the emulsifier and water and then mix with the polymer dispersion. The dispersion containing the active ingredient obtained in this way is optionally provided with further excipients and, as mentioned above, is drawn out to form a film on a support film and dried in a manner known per se. The drying temperature can be between room temperature and 100° C., whereby an optimum between the desired rapid drying and the formation of bubbles in the film to be avoided as well as thermal stress on the active ingredient is generally 35 to 45° C. This process has the great advantage of avoiding organic solvents. However, in principle, all other common manufacturing processes for matrix patches can also be considered.

The resulting films have thicknesses of 10 to 800 μm, preferably 50 to 300 μm. The film production can be continuous or discontinuous. The application process can be repeated several times until the film has reached the desired thickness. The sticky polymer layer contains the active ingredient in a concentration ranging from 1 to 40 wt.-%, in particular from 5 to 25 wt.-%. The same concentration also applies to the reservoir liquid in the membrane system and to the active ingredient solution or dispersion with which the nonwoven or porous polymer is impregnated in the nonwoven system.

As emulsifiers for both the active ingredients according to the invention, i.e. the cooling agent or the cooling agent mixture according to the invention or the flavouring preparation according to the invention as well as the polymers, the surfactants customary for this purpose are used, such as the sodium salt of longer-chain fatty acids and the sulphuric acid half-ester of a (possibly oxethylated) fatty alcohol as examples of anionic surfactants as well as polyoxethylated alkylphenols and longer-chain fatty alcohols (e.g. hexadecan-(I)-ol) and glycerol fatty acid partial esters as examples of non-ionic surfactants and co-emulsifiers.

The desired viscosity of the ready-to-extract mass can be adjusted e.g. with polyacrylic acids or cellulose derivatives. Melamine-formaldehyde resins, for example, can be used as additional cross-linking agents that improve the cohesion and thus the adhesive properties of the films.

Swelling agents such as polyvinylpyrrolidone, cellulose derivatives or polyacrylates have the effect of improving the release of active ingredients, as the film can absorb more water and the diffusion resistance is reduced as a result. The release of the active ingredients can also be improved by the addition of hydrophilic plasticisers such as glycerol, 1,2-propanediol of polyethylene glycols and lipophilic plasticisers such as triacetin, dibutyl phthalate or isopropyl myristate.

Matrix patches usually result in a 1st order release of active ingredient. The use of fillers that adsorb the active ingredient, such as aerosil, microcrystalline cellulose or lactose, results in approximately a 0th order release.

The support film onto which the self-adhesive composition containing the active ingredient is dried is practically impermeable to both the active ingredient and water vapour. It can, for example, consist of an aluminium-plastic composite film, a metallised plastic film, a plastic film which is provided with a barrier layer of e.g. polyvinylidene chloride towards the active substance side, or of a simple plastic film, e.g. polyester film.

The plasters according to the invention, which are constructed according to the membrane system, are also produced in the usual manner. The plasters constructed according to the nonwoven system are produced by impregnating nonwovens or porous polymers attached to the support film with a solution or dispersion of the active substance in a hydrophilic or lipophilic solvent or solvent mixture. The impermeable peel-off film is then applied.

In principle, the active ingredient content can vary over a wide range, such as 0.1 ppm to 10 wt.-%, preferably 1 ppm to 10 wt.-%.

Furthermore, the present invention relates to textile products equipped with a cooling agent or cooling agent mixture according to the invention.

The finishing of textiles with cooling substances is used in particular where garments can come into direct contact with the skin so that the active substance can develop its effects, e.g. locally or systemically, through transdermal transfer. Recently, textiles have been reported that are equipped with so-called wellness additives, i.e. substances that promote well-being.

An insecticidal finish, on the other hand, is of interest with regard to material protection, e.g. finishing the textile against moth damage etc., but also in particular to ward off parasitic insects such as mosquitoes.

The basic problem in finishing textiles with active substances is the binding of the active substance to the textile carrier, which on the one hand must guarantee the permanence of the finish and on the other hand must be selected in such a way that the active substance does not lose its effect. Various approaches have been proposed in the state of the art.

For example, cyclodextrins have been proposed for binding active ingredients to textiles. Cyclodextrins are cyclic oligosaccharides formed by enzymatic degradation of starch. The most common cyclodextrins are α-, ß- and γ-cyclodextrins, which consist of six, seven and eight α-1,4-linked glucose units, respectively. A characteristic property of cyclodextrin molecules is their ring structure with largely unchanging dimensions. The inner diameter of the rings is about 570 pm for α-cyclodextrin, about 780 pm for ß-cyclodextrin and about 950 pm for γ-cyclodextrin. Due to their structure, cyclodextrins are able to entrap guest molecules, especially hydrophobic guest molecules, in varying amounts until saturation.

The state of the art describes the finishing of textiles with fragrances and other low-molecular organic active ingredients that are bound to the textile via an amylose-containing substance with an amylose content of at least 30%. The amylose content of the amylose-containing substance binds the active ingredient to the textile and releases it in a controlled manner so that the effect is maintained over a long period of time. It is assumed that, similar to cyclodextrins, the active substance is reversibly bound in the cavities formed by the helical conformation of the amylose in the sense of an inclusion compound, whereby on the one hand a fixation of the active substance on the surface of the textile carrier is achieved and on the other hand a controlled release is possible.

In addition to amylose, all substances, in particular amylose-containing starches, i.e. native starches, modified starches and starch derivatives, whose amylose content is at least 30 wt.-% and in particular at least 40 wt.-% are suitable for finishing textiles according to the invention. The starch may be native, e.g. maize starch, wheat starch, potato starch, sorghum starch, rice starch or maranta starch, obtained by partial digestion of native starch or chemically modified. Also suitable is pure amylose as such, e.g. enzymatically obtained amylose, e.g. amylose obtained from sucrose. Mixtures of amylose and starch are also suitable, provided that the total content of amylose is at least 30 wt.-%, based on the total weight of the mixture. It is understood that here and in the following all indications in wt.-% which refer to amylose or amylose-containing substances are always referred to the total weight of amylose+starch in the case of mixtures of amylose and starch, unless expressly stated otherwise. Particularly suitable according to the invention are amylose-containing substances, in particular amylose and amylose-containing starches as well as amylose/starch mixtures, the amylose content of which is at least 40 wt.-% and in particular at least 45 wt.-%, based on the total weight of the substance. As a rule, the amylose content will not exceed 90 wt.-% and in particular 80 wt.-%. Such substances are known and commercially available. For example, amylose-containing starches are sold by the companies Cerestar under the trade name Amylogel® and National Starch under the trade names HYLON® V and VII.

In order to achieve the binding of the active substance(s) to the textile, the textile may be provided with the amylose-containing substance usually in an amount of at least 0.5 wt.-%, preferably at least 1 wt.-% and in particular at least 2 wt.-%, each based on the weight of the textile. As a rule, the amylose-containing substance is used in an amount of not more than 25 wt-%, frequently not more than 20 wt.-% and in particular not more than 15 wt.-%, based on the weight of the textile, so as not to adversely affect the tactile properties of the textile. First, the textile material is finished with the amylose-containing substance as such and then the textile thus finished is treated with a suitable preparation of the active substance. In this way, the amylose-containing substance present on the textile material is loaded with the active substance. However, it is also possible to use the amylose-containing substance together with an active substance to finish the textile. In this case, the active ingredient and the amylose-containing substance can be used both as a mixture of separate components and in the already prefabricated form of the amylose-active ingredient complex. As a rule, the active ingredient is used in a quantity that is sufficient for the desired effect. The upper limit is determined by the maximum absorption capacity of the amylose units of the amylose-containing substance used and will usually not exceed 20 wt.-% and often 10 wt.-%, based on the amylose content of the substance. If desired, the active substance is generally used in an amount of 0.00001 to 15 wt.-%, 0.0001 to 10 wt.-%, 0.001 to 5 wt.-%, 0.005 to 1 wt.-% or 0.1 to 10 wt.-% or 0.5 to 5 wt.-%, based on the amylose portion of the amylose-containing substance.

Combinations of active substances according to the invention with other active substances known per se and suitable for textile finishing can also be used for textile finishing.

In principle, all organic compounds and mixtures of organic compounds which are known to be active substances and which induce a physiological effect in living organisms such as humans and animals, including microorganisms, are suitable as further active substances. Active substances which are known to be able to form inclusion compounds with cyclodextrins should be mentioned. Particularly suitable are active substances which have hydrocarbon groups and, in particular, aliphatic, cycloaliphatic and/or aromatic structures. The molecular weight of the active ingredients is typically below 1000 Daltons and often in the range of 100 to 600 Daltons. Also suitable are inorganic compounds such as hydrogen peroxide, which are known to be able to be bound in cyclodextrins.

Other active ingredients include, in particular, pharmaceutical active ingredients and active ingredients that promote the well-being of living beings, especially humans, and are commonly referred to as "wellness additives". Unlike pharmaceutical active ingredients, wellness additives do not necessarily have to have a therapeutic effect. Rather, the effect promoting well-being can be based on a variety of factors such as caring, stimulating, cosmetic or other effects. Equally suitable are organic active substances that act against parasitic organisms. These include, for example, active substances which act against fungi and/or microorganisms, e.g. fungicides and bactericides, or which act against animal pests such as snails, worms, mites, insects and/or rodents, e.g. nematicides, molluscicides, insecticides, acaricides, rodenticides and repellents, as well as active substances against weeds, i.e. herbicides, or fragrances.

Preferred active pharmaceutical ingredients are those known to be absorbable through the skin. These include, for example, ibuprofen, flurbiprofen, acetylsalicylic acid, acetamidophen, apomorphine, butylated hydroxytoluene, chamzulene, gujazulene, chlorthalidone, cholecalciferol, dicumarol, digoxin, diphenylhydantoin, furosemide, hydroflumethiazide, indomethacin, iproniazid phosphate, nitroglycerin, nicotine, nicotinamide, oubain, oxprenolol, papaverine alkaloids such as papaverine, laudanosine, ethaverine and narcotine as well as berberine, furthermore retionol, trans-retinoic acid, pretinol, spironolactone, sulpiride, theophylline, theobromine, corticosteroids and derivatives such as testosterone, 17-methyltestosterone, cortisone, corticosterone, dexamethasone, triamcinolone, methylprednisolone, fludrocortisone, fluocortolone, prednisone, prednisolone, progesterone, including estrogens and gestagens such as estradiol, estriol, ethinylestradiol-3-methylether, norethisterone and ethisterone, as well as phenethylamine and derivatives such as tyramine, adrenaline, noradrenaline and dopamine. Examples of active ingredients suitable according to the invention with activity against parasitic organisms are, for example, nematicides, bactericides, fungicides, insecticides, insect repellents, acaricides and molluscicides. Examples of bactericidal and fungicidal substances include: antibiotics, e.g. cycloheximide, griseofulvin, kasugamycin, natamycin, polyoxin, streptomycin, penicillin or gentamycin; organic compounds and complexes of biocidal metals, e.g. complexes of silver, copper, tin and/or zinc such as bis(tributyltin) oxide, copper, zinc and tin naphthenates, oxine copper such as Cu-8, tris-N-(cyclohexyldiazeniumdioxy)aluminium, N-(cyclohexyldiazeniumdioxy)tributyltin, bis-N-(cyclohexyldiazeniumdioxy)copper; quaternary ammonium salts, e.g. benzyl-Cs- to cis-alkyldimethylammonium halides, especially chlorides (benzalkonium chlorides); aliphatic nitrogen fungicides and bactericides such as cymoxanil, dodine, dodicin, guazidine, iminoctadine, dodemorph, fenpropimorph, fenpropidin, tridemorph; substances with peroxide groups such as hydrogen peroxide, and organic peroxides such as dibenzoyl peroxide; organic chlorine compounds such as chlorhexidine; triazole fungicides such as azaconazole, cyproconazole, diclobutrazole, difenoconazole, diniconazole, epoxiconazole, fenbuconazole, fluquinconazole, flusilazole, flutriafol, hexaconazole, metconazole, propiconazole, tetraconazole, tebuconazole and triticonazole; strobilurins such as dimoxystrobin, fluoxastrobin, kresoxim-methyl, metominostrobin, orysastrobin, picoxystrobin, pyraclostrobin and trifloxystrobin; sulphonamides such as tolylfluanid and diclofluanid; iodine compounds such as diiodomethyl-p-tolyl sulfone, napcocide 3-lod-2-propynyl alcohol, 4-chlorophenyl-3-iodopropargyl formal, 3-bromo-2,3-diiodo-3-propenylethyl carbonate, 2,3,3-triiodoallyl alcohol, 3-iodo-2-propynyl n-hexyl carbamate, 3-bromo-2,3-diiodo-2-propenyl alcohol, 3-iodo-2-propynyl phenyl carbamate, 3-iodo-2-propynyl n-butyl carbamate, 0-1-(6-iodo-3-oxohex-5-inyl)phenyl carbamate, 0-1-(6-iodo-3-oxohex-5-inyl)butyl carbamate; isothiazolinones such as N-methylisothiazolin-3-one, 5-chloro-N-methylisothiazolin-3-one, 4,5-dichloro-N-octylisothiazolin-3-on, 1,2-benzisothiazol-3(2H)on, 4,5-trimethylisothiazol-3-one and N-octyl-isothiazolin-3-one.

Examples of insecticides and acaricides are: organophosphates such as acephate, azamethiphos, azinphos-methyl, chlorpyrifos, chlorpyriphos-methyl, chlorfenvinphos, diazinon, dichlorvos, dicrotophos, dimethoate, disulfoton, ethion, fenitrothion, fenthion, isoxathion, malathion, methamidophos, methidathion, methyl parathion, mevinphos, monocrotophos, oxydemeton-methyl, paraoxon, parathion, phenthoate, phosalone, phosmet, phosphamidon, phorate, phoxim, pirimiphos-methyl, profenofos, prothiofos, sulprophos, triazophos, trichlorfon; in particular pyrethroids such as acrinatrin, allethrin, bioallethrin, barthrin, bifenthrin, bioethanomethrin, cyclethrin, cycloprothrin, cyfluthrin, beta-cyfluthrin, cyhalothrin, gamma-cyhalothrin, lambda-cyhalothrin, cypermethrin, α-cypermethrin, ß-cypermethrin, λ-cypermethrn, zeta-cypermethrin, cyphenothrin, deltamethrin, dimefluthrin, dimethrin, empenthrin, fenfluthrin, fenprithrin, fenpropathrin, fenvalerate, esfenvalerate, flucythrinate, fluvinate, tau-fluvinate, furethrin, permethrin, biopermethrin, trans-permethrin, phenothrin, prallethrin, profluthrin, pyresmethrin, resmethrin, bioresmethrin, cismethrin, tefluthrin, terallethrin, tetramethrin, tralomethrin, transfluthrin, etofenprox, flufenprox, halfenprox, protrifenbute and silafulfen; pyrrole and pyrazole insecticides such as acetoprole, ethiprole, fipronil, tebufenpyrad, tolfenpyrad, chlorfenapyr and vaniliprole.

Examples of repellent active ingredients are in particular anthraquinone, acridine bases, copper naphthenate, butopyronoxyl, dibutyl phthalate, dimethyl phthalate, dimethyl carbate, ethohexadiol, hexamides, metho-quin-butyl, N-methylneodecanamide, camphor, bergamot oil, pyrethrum, clove oil, geranium oil, thyme oil and in particular diethyl-m-toluamide and 1-piperidinecarboxylic acid 2-(2-hydroxyethyl)-1-methylpropyl ester (Picardin). Examples of wellness additives are in particular the substances and substance mixtures listed below, e.g. fats, preferably of vegetable origin, e.g. lecithins, vegetable oils such as jojoba oil, tea tree oil, clove oil, evening primrose oil, almond oil, coconut oil, avocado oil, soybean oil and the like, fatty acids, e.g. ω-6-fatty acids, linolenic acid, linoleic acid, waxes of animal or vegetable origin such as beeswax, candelilla wax, shea butter, shorea butter, mango seed butter, Japan wax and the like, vitamins, in particular fat-soluble vitamins, e.g. tocopherols, vitamin E, vitamin A and the like, corticosteroids such as cortisone, corticosterone, dexamethasone, triamcinolone, methylprednisolone, fludrocortisone, fluocortolone, prednisone, prednisolone, progesterone, amino acids, e.g. arginine, methionine; plant extracts such as algae extract, horse chestnut extract, mango extract and the like.

To improve the wash permanence of the finish according to the invention, it has proved useful to fix the amylose-containing substance to the textile with a binder. Suitable binders include film-forming, water-insoluble polymers and low-molecular reactive substances that polymerise when heated. As a rule, the binder is used in a quantity such that the weight ratio of amylose-containing substance to water-insoluble polymer is in the range from 1:1 to 100:1, preferably in the range from 1.5:1 to 50:1 and in particular in the range from 2:1 to 20:1.

As a rule, the film-forming polymers are used in the form of an aqueous dispersion of finely divided polymer particles. The particle size is of secondary importance for the success according to the invention. However, it is generally below 5 μm (weight average) and is usually 50 nm to 2 μm.

In particular, the film-forming polymer may have a glass transition temperature TG in the range of −40 to 100° C., preferably −30 to +60° C., especially −20 to +40° C. If the polymeric binder comprises several polymer components, at least the main component should have a glass transition temperature in this range. In particular, the glass transition temperature of the main constituent is in the range from −30° C. to +60° C., and more preferably in the range from −20° C. to +40° C. Preferably, all polymeric components have a glass transition temperature in these ranges. The stated glass transition temperatures refer to the "midpoint temperature" determined by DSC according to ASTM-D 3418-82. In the case of cross-linkable binders, the glass transition temperature refers to the non-cross-linked state.

Examples of suitable film-forming polymers are based on the following classes of polymers:

(1) polyurethane resins;
(2) acrylic resins (pure acrylates: copolymers of alkyl acrylates and alkyl methacrylates);
(3) styrene acrylates (copolymers of styrene and alkyl acrylates);
(4) styrene/butadiene copolymers;
(5) polyvinyl esters, in particular polyvinyl acetates and copolymers of vinyl acetate with vinyl propionate;
(6) vinyl ester olefin copolymers, e.g. vinyl acetate/ethylene copolymers;
(7) vinyl ester acrylate copolymers, e.g. vinyl acetate/alkyl acrylate copolymers and vinyl acetate/alkyl acrylate ethylene terpolymers.

Such polymers are known and commercially available, e.g. polymers of classes (2) to (7) in the form of aqueous dispersions under the names ACRONAL, STYROFAN, BUTOFAN (BASF-AG), MOWILITH, MOWIPLUS, APPRETAN (Clariant), VINNAPAS, VINNOL (WACKER). Aqueous polyurethane dispersions (1) suitable for the process according to the invention are in particular those used for coating textiles. Suitable substances are sufficiently known to the skilled person. Aqueous polyurethane dispersions are, for example, commercially available, e.g. under the trade names Alberdingk® of the company Alberdingk, Impranil® of the company BAYER AG, Permutex® of the company Stahl, Waalwijk, Netherlands, of the company BASF SE, or can be produced according to known processes, such as those described in the relevant technical literature. The film-forming polymers may be self-crosslinking, i.e. the polymers have functional groups (crosslinkable groups) which react with each other, with the functional groups of the amylose or with a low-molecular crosslinking agent to form a bond when the composition dries, optionally when heated. Examples of crosslinkable functional groups include aliphatically bonded OH groups, $NH—CH_2—OH$ groups, carboxylate groups, anhydride groups, capped isocyanate groups and amino groups. Often one will use a polymer that still has free OH groups as reactive groups. As a rule, the proportion of reactive functional groups is 0.1 to 3 mol/kg polymer. Cross-linking can be effected within the polymer by reaction of complementary reactive functional groups. Preferably, crosslinking of the polymer is effected by addition of a crosslinker having reactive groups which are complementary in reactivity to the functional groups of the crosslinker. Suitable pairs of functional groups having complementary reactivity are known to the skilled person. Examples of such pairs are OH/COOH, OH/NCO, $NH_2$/COOH, $NH_2$/NCO and $M^{2+}$/COOH, where $M^{2+}$ is a divalent metal ion such as $Zn^{2+}$, $Ca^{2+}$, or $Mg^{2+}$. Examples of suitable crosslinking agents are the diols or polyols mentioned below for polyurethanes; primary or secondary diamines, preferably primary diamines, e.g. alkylenediamines such as hexamethylenediamine, diethylenetriamine, triethylenetetramine, tetraethylenepentamine, N,N-bis[(aminopropyl)amino]-ethane, 3,6-dioxaoctanediamine, 3,7-dioxanonanediamine, 3,6,9-trioxaundecandiamine or jeffamines, (4,4-diaminodicyclohexyl)methane, (4,4'-diamino-3,3-dimethyldicycohexyl)methane; amino alcohols such as ethanolamine, hydroxypropylamine; ethoxylated di- and oligoamines; dihydrazides of aliphatic or aromatic dicarboxylic acids such as adipic acid dihydrazide; dialdehydes such as glyoxal; partially or completely O-methylated melamines, as well as compounds or oligomers which contain on average two or more, preferably three or more isocyanate groups or reversibly e.g. hydrogen sulphite blocked isocyanate groups. In this case, the weight ratio of crosslinker to polymeric binder is such that the molar ratio of the reactive groups in the polymeric binder (total amount of reactive groups in the polymers) to the reactive groups in the crosslinker is usually in the range of 1:10 to 10:1 and preferably in the range of 3:1 to 1:3. Usually, the weight ratio of polymeric binder (calculated as solid) to crosslinker is in the range of 100:1 to 1:1 and in particular in the range of 50:1 to 5:1.

As an alternative to fixing the amylose-containing substance with water-insoluble polymers, the amylose or the amylose-containing substance can also be fixed to the textile material with reactive compounds which have at least one group that is reactive towards the OH groups of the amylose and at least one further functional group that is reactive towards the functional groups on the fibres of the textile material, e.g. OH groups, $NH_2$ groups or COOH groups. The reactive compounds include the crosslinkers mentioned above as well as the substances proposed in DE 40 35 378 A for the fixation of cyclodextrins, e.g. N-hydroxymethyl and N-alkoxymethyl derivatives of urea or urea-like compounds such as dimethylolurea (bis(hydroxymethyl)urea), di(methoxymethyl)urea, dimethylolalkanediol diurethanes such as N,N-dimethylolethyleneurea (N,N-bis(hydroxymethyl)imidazolin-2-one), N,N-dimethylol-dihydroxyethyleneurea (N,N-bis(hydroxymethyl)-4,5-dihydroxyimidazolin-2-one), dimethylolpropyleneurea and the like. Such materials are commercially available in the form of aqueous formulations for the finishing of textiles, e.g. under the trade names Fixapret® and Fixapret®-eco of BASF SE. Reactive materials that can be used to fix the amylose-containing substance to the textile material include, in particular, compounds with 2, 3, 4 or more (possibly reversibly blocked) isocyanate groups, especially those with bisulphite or CH-acidic compounds or oximenes, e.g. butanone oxime reversibly blocked polyisocyanate prepolymers based on polyether and polyester urethanes described in DE 2837851, DE 19919816 and the earlier patent application EP 03015121. Such products are also commercially available, for example under the trade names PROTOLAN®367 and PROTOLAN®357 from Rotta GmbH, Mannheim.

For the fixation of the amylose-containing substance, the procedure known for the fixation of cyclodextrins can also be used in an analogous manner, in which the cyclodextrin or, in the present case, the amylose-containing substance is provided with reactive anchors, for example by treating it with dicarboxylic acids or dicarboxylic anhydrides such as maleic acid, fumaric acid, maleic anhydride, succinic acid, succinic anhydride or adipic acid, with diisocyanates, e.g. toluene diisocyanate, isophorone diisocyanate, tetramethylene diisocyanate or hexamethylene diisocyanate. for example toluene diisocyanate, isophorone diisocyanate, tetramethylene diisocyanate or hexamethylene diisocyanate, or with aminocarboxylic acids in a manner known per se such that only one of the functionalities present in these compounds reacts with the OH groups of the amylose-containing substance and the other is retained for binding to the reactive groups of the fibre material. Reactive anchors can also be produced on the amylose-containing substance by reaction with 1,3,5-trichlorotriazine, 2,3-dichloroquinoxaline-5,6-carboxylic acid chloride as well as with chlorodifluoropyrimidine. Furthermore, alkoxysilanes such as diethoxydimethylsilane, dimethoxydimethylsilane, triethoxyphenylsilane, tetraethoxysilane as well as dimeric, trimeric and higher condensation products of these compounds can be used to fix the amylose.

In principle, all textile materials can be finished in this way, i.e. non-manufactured goods as well as manufactured goods. Textile materials here and in the following comprise woven, knitted, warp-knitted and non-woven fabrics. The textile materials can be composed of natural fibre yarns, synthetic fibre yarns and/or blended yarns. In principle, all fibre materials commonly used for the production of textiles can be considered as fibre materials. These include cotton, wool, hemp fibre, sisal fibres, flax, ramie, polyacrylonitrile fibres, polyester fibres, polyamide fibres, viscose fibres, silk, acetate fibres, triacetate fibres, aramid fibres and the like, as well as mixtures of these fibre materials.

The textile materials can be finished or treated with the amylose-containing substance in a manner known per se, e.g. by means of processes described for the finishing of textiles with cyclodextrins.

For example, processes in which the amylose-containing substance, optionally as a complex with the active ingredient, is already spun into the fibre, filament and/or yarn from which the fabric is made, have to be mentioned.

However, the textile material is often treated with the amylose-containing substance or a complex of amylose-containing substance and active ingredient before or after finishing. As a rule, the textile is treated with an aqueous liquor containing a sufficient quantity of the amylose-containing substance and, if necessary, the active ingredient. Depending on the type of application and the desired amount in which the amylose-containing substance is to be applied, the concentration of amylose-containing substance in the liquor is in the range from 1 to 40 wt.-%, in particular in the range from 2 to 20 wt-% and especially in the range from 4 to 15 wt.-%.

The type of treatment is of secondary importance and can, for example, be applied as a minimum application, e.g. by spray application, as a normal application in the padder or as a high-moisture application. In this case, the textile material is soaked with the aqueous liquor. If necessary, excess liquor can be removed afterwards, e.g. by squeezing to a liquor absorption of about 30 to 120%. Another possibility for treating the textile with amylose-containing substance or complex of amylose-containing substance and active ingredient is to prepare a liquor with water containing the desired amount of amylose-containing substance and possibly active ingredient, e.g. 0.5 to 20 wt.-% (based on the mass of the textile to be finished). The textile material is soaked for a certain period of time, e.g. 10 to 60 minutes, with the treatment liquor in finishing units suitable for this purpose (e.g. reel skid; roller skid; paddle; etc.) and then squeezed off and/or spun off as indicated above. The liquor ratio here is usually in the range of 1:2 to 1:50 and in particular in the range of 1:3 to 1:20.

Such procedures are known to the skilled person from the relevant technical literature.

As a rule, the treatment with the liquor is followed by a drying process. The temperatures are usually in the range of 100 to 200° C. and preferably in the range of 120 to 180° C. Drying can be carried out in the usual devices for this purpose, for example, in the case of ready-made products by tumble drying at the temperatures specified above. In the case of non-manufactured goods, the textile material is usually passed over one or more stenter frames after application.

If the amylose-containing substance is used together with a film-forming polymer, drying leads to a fixation of the amylose-containing substance on the textile fibres. As a rule, the drying temperature will then not fall below 100° C. and is preferably in the range from 120 to 200° C. and in particular in the range from 140 to 180° C. Generally, drying takes place for a period of 1 to 10 minutes, in particular 1 to 2 minutes, although longer drying times are also suitable. For treatment with an aqueous liquor, it has been shown to be advantageous if the aqueous liquor contains, in addition to the amylose-containing substance and optionally the active substance, at least one surface-active substance (or surfactant) which is suitable for dispersing the amylose-containing substance and the active substance in the aqueous liquor. Preferably, the surfactant is an oligomeric or polymeric dispersant. The term oligomeric or polymeric dispersant, in contrast to low molecular weight surfactants, comprises dispersants whose number average molecular weight is usually at least 2000 daltons, e.g. 2000 to about 100000 daltons and in particular in the range of about 3000 to 70000 daltons. As a rule, the aqueous liquor contains the polymeric or oligomeric dispersant in an amount of 0.5 to 20 wt.-%, preferably 1 to 18 wt.-% and in particular 5 to 15 wt.-%, based on the amylose-containing substance.

Suitable oligomeric or polymeric dispersants are soluble in water and comprise neutral and amphoteric water-soluble polymers as well as cationic and anionic polymers, the latter being preferred. Examples of neutral polymeric dispersants include polyethylene oxide, ethylene oxide/propylene oxide copolymers, preferably block copolymers, polyvinylpyrrolidone, and copolymers of vinyl acetate with vinylpyrrolidone.

The preferred anionic oligomeric or polymeric dispersants are characterised by the fact that they have carboxyl groups and/or sulphonic acid groups and are usually used as salts, e.g. as alkali metal salts or ammonium salts. Preferred anionic dispersants are, for example, carboxylated derivatives of cellulose such as carboxymethyl cellulose, homopolymers of ethylenically unsaturated C3- to C8-mono- and C4- to C8-dicarboxylic acids, e.g. of acrylic acid, methacrylic acid, maleic acid, itaconic acid, copolymers of at least two different ethylenically unsaturated C3- to C8-mono- and C4- to C8-dicarboxylic acids as mentioned above, and copolymers of at least one of the abovementioned ethylenically unsaturated C3- to C8-mono- or C4- to C8-dicarboxylic acids with at least one neutral comonomer. Examples of neutral comonomers are N-vinyllactams such as N-vinylpyrrolidone, vinyl esters of aliphatic C2- to C16-carboxylic acids such as vinyl acetate, vinyl propionate, amides of the aforementioned ethylenically unsaturated carboxylic acids, such as acrylamide, methacrylamide and the like, hydroxy-C1 to C4 alkyl (meth)acrylates such as hydroxyethyl acrylate and methacrylate, esters of ethylenically unsaturated C3- to C8-mono- or C4- to C8-dicarboxylic acids with polyethers, e.g. esters of acrylic acid or methacrylic acid with polyethylene oxides or ethylene oxide/propylene oxide block copolymers, vinyl aromatics such as styrene and C2- to C16-olefins such as ethylene, propene, 1-hexene, 1-octene, 1-decene, 1-dodecene and the like. Further preferred are homopolymers of ethylenically unsaturated sulfonic acids such as styrenesulfonic acid and acrylamidopropanesulfonic acid and their copolymers with the aforementioned comonomers. In the copolymers, the proportion of ethylenically unsaturated acid will generally be at least 20 wt.-% and will not exceed a value of 90 wt.-% and in particular 80 wt.-%, in each case based on the total weight of all the monomers constituting the polymer. Copolymers of at least one of the above-mentioned acids and at least one comonomer are known for this purpose and commercially available, for example the copolymers of acrylic acid and maleic acid as Sokalan trademarks of BASF SE.

Also preferred anionic dispersants are phenolsulfonic acid-formaldehyde condensates and naphthalenesulfonic acid-formaldehyde condensates (e.g. BASF's Tamol and Setamol brands) and lignosulfonates.

Suitable dispersants are also low molecular weight anionic, non-ionic, cationic, ampholytic and zwitterionic surfactants. Suitable surfactants are e.g. the alkali metal, ammonium or amine salts of C8 to C18 alkyl sulphates, such as sodium lauryl sulphate; C8 to C18 alkyl sulphonates, such as dodecyl sulphonate; C8 to C18 alkyl ether sulphates; as well as C8 to C18 alkyl ethoxylates; polyoxyethylene sorbitan esters; C8 to C18 alkyl glycinates; C8 to C18 alkyl dimethylamine oxides; betaines, etc. Preferred are the alkyl sulphates and alkyl sulphonates.

If the amylose-containing substance is not used together with a film-forming, water-insoluble polymer, the textile can be treated with the polymer in a separate step. In particular, the treatment is carried out together with the amylose-containing substance. Accordingly, a particular embodiment relates to a process in which the aqueous liquor additionally comprises a dispersed, film-forming, water-insoluble polymer of the type described above. The amount of film-forming polymer is chosen such that the weight ratio of amylose-containing substance to water-insoluble polymer is in the range from 1:1 to 100:1, preferably in the range from 1.5:1 to 50:1 and in particular in the range from 2:1 to 20:1.

The finishing of the textile with the cooling substance according to the invention or the cooling substance mixture according to the invention can be carried out in a separate operation or in one operation together with the finishing with the amylose-containing substance.

If the textile is treated with the active ingredient in a separate process, the textile is also treated with an aqueous liquor of the active ingredient. For this purpose, the active ingredient, which is usually insoluble in water, is usually emulsified or dispersed in water, if necessary using suitable surface-active substances. Suitable surface-active substances are in particular the low-molecular-weight surfactants mentioned above and among them preferably the non-ionic surfactants, in particular polyoxyethylene sorbitan esters, esters of mono- or oligosaccharides with C6- to C18-fatty acids and especially preferably C8- to C18-alkyl ethoxylates, in particular those with a degree of ethoxylation in the range from 6 to 50.

As a rule, the aqueous liquor contains the active substance in an amount of 0.1 to 10 wt-% and in particular in an amount of 0.2 to 5 wt.-%. The amount of surface-active substance is usually in the range of 0.5 to 50 wt.-% and in particular in the range of 3 to 30 wt.-%, based on the active substance. The application of the active substance from aqueous liquor can be carried out by the methods customary for this purpose, e.g. by means of a padder. However, it is also possible to finish the active substance and the amylose-containing substance in one step. In this case, one can basically proceed as described for the finishing with the amylose-containing substance, whereby the aqueous liquor of the amylose-containing substance now additionally contains the at least one active substance. The active substance can be added separately to the liquor or in the form of an inclusion compound, i.e. in the form of a host-guest complex with the amylose-containing substance.

The present invention can be used to finish any textile, i.e. non-manufactured goods as well as manufactured goods. Textile materials comprise here and hereinafter woven fabrics, knitted fabrics, warp knitted fabrics and non-woven fabrics. The textile materials can be composed of natural fibre yarns, synthetic fibre yarns and/or blended yarns. In principle, all fibre materials normally used for the production of textiles can be considered as fibre materials. These include cotton, wool, hemp fibre, sisal fibres, flax, ramie, polyacrylonitrile fibres, polyester fibres, polyamide fibres, viscose fibres, silk, acetate fibres, triacetate fibres, aramid fibres and the like, as well as mixtures of these fibre materials. Also suitable are glass fibres as well as blends of the aforementioned fibre materials with glass fibres, e.g. glass fibre/kevlar blends. The type of textile material depends primarily on the desired application. The textiles to be finished may be ready-made products such as clothing, including underwear and outerwear, e.g. shirts, trousers, jackets, outdoor, trekking and military equipment, roofs, tents, nets, e.g. insect nets and curtains, hand and bath towels, bed linen and the like. Similarly, the finishing can be done on the raw fabric in bale or roll form.

With an amylose-based active ingredient finish, the active ingredients remain in the textiles finished with it even after several washes. In addition, the textiles finished in this way are characterised by a pleasant feel, which is particularly advantageous for the wearing comfort of clothing made from these textiles.

The textiles equipped with active substances against parasitic organisms such as insects and acarids are, in addition to protecting humans, also particularly suitable in animal protection for protection against ticks, mites, fleas and the like.

The present invention further relates to cooling tobacco products.

The active ingredients according to the invention, i.e. the cooling active ingredient according to the invention or the cooling agent mixture according to the invention or the flavouring preparation according to the invention, can also advantageously be used for the manufacture of tobacco products. Examples of such tobacco products include, cigars, cigarettes, pipe tobacco, chewing tobacco, and snuff. The production of tobacco products supplemented with cooling additives is known per se.

In principle, the active ingredient content, i.e. the content of the cooling agent according to the invention or of the cooling agent mixture according to the invention can vary over a wide range, such as, for example, 0.05 ppm to 10 wt.-%, preferably 0.1 ppm to 10 wt.-%.

The active ingredients according to the invention are also advantageously suitable for the production of packaging materials.

The production is also carried out in a manner known per se. The active ingredients can be incorporated into the packaging material, in free or e.g. encapsulated form, or applied to the packaging material, in free or encapsulated form. In this way, suitably finished plastic packaging materials can be produced in accordance with the information in the literature on the production of polymer films. The production of suitably coated papers is also known to the skilled person.

Finally, the present invention relates to methods for modulating, in particular in vitro and/or in vivo modulating, the cold menthol receptor TRPM8, comprising the following steps:

(i) providing at least one physiological cooling agent or physiological cooling agent mixture according to the invention or providing a cosmetic or pharmaceutical preparation according to the invention; and (ii) contacting the cooling agent or the cooling agent mixture or the cosmetic or pharmaceutical preparation of step (i) with the receptor; or for producing a physiological cooling effect on skin or mucous membrane, comprising the following steps:

(iii) providing at least one physiological cooling agent or physiological cooling agent mixture according to the invention or providing a cosmetic or pharmaceutical preparation according to the invention; and (iv) of the cooling agent or the cooling agent mixture or the cosmetic or pharmaceutical preparation from step (iii) with human skin or mucous membrane; or for improving the flavour properties of flavouring substances comprising the following steps:

(v) providing at least one physiological cooling agent according to the invention or a physiological cooling agent mixture according to the invention or providing a cosmetic or pharmaceutical preparation according to the invention and at least one flavouring agent;

(vi) mixing the two components; and if necessary (vii) incorporation of the mixture into an oral preparation.

Further aspects of the present invention will be apparent from the following examples and the appended patent claims.

EXAMPLES

The following examples serve to illustrate the invention without limiting it Unless otherwise indicated, all data refer to weight.

Production of active substances: The active substances used according to the invention can be produced by a person skilled in the art in the field of organic synthesis following known synthesis methods, as described in more detail below.

Cloning of Human TRPM8

The starting point for cloning the human TRPM8 receptor is an LnCaP cDNA bank. This is commercially available (e.g. BioChain, Hayward, USA) or can be produced from the androgene-sensitive human prostate adenocarcinoma cell line LnCaP (e.g. ATCC, CRL1740 or ECACC, 891 1021 1) using standard kits.

The coding TRPM8 sequence (see e.g. http://www.ncbi.nlm.nih.gov/entrez/viewer.fcgi?db=nuccore&id=109689694) can be PCR amplified and cloned using standard methods. The human TRPM8 gene isolated in this way was used to produce the plasmid plnd_M8. Alternatively, the TRPM8 gene can also be produced synthetically.

Generation of the HEK293 Test Cells

As a test cell system, a stably transfected HEK293 cell line was produced with human TRPM8 DNA. Preference is given to HEK293, which offers the possibility of inducing TRPM8 expression with tetracycline via the introduced plasmid.

Methods for the production of suitable test cell systems are known to the skilled person and can be found in the relevant technical literature.

Assay on TRPM8 Modulators

A test similar to the one already described in the literature by Behrendt H. J. et al., *Br. J. Pharmacol.* 141, 2004, 737-745, is performed. The agonisation or antagonisation of the receptor can be quantified by means of a Cab-sensitive dye (e.g. FURA, Fluo-4 etc.). Agonists alone cause an increase in the $Ca^{2+}$ signal; antagonists cause a reduction in the $Ca^{2+}$ signal in the presence of e.g. menthol (in each case detected via the dye Fluo-4, which has different fluorescence properties due to $Ca^{2+}$ ions).

First, a fresh culture of transformed HEK cells is prepared in cell culture flasks in a manner known per se. The HEK293-TRPM8 test cells are detached from the cell culture flasks using trypsin and 40,000 cells/well are seeded with 100 μl medium in 96-hole plates (Greiner #655948 poly-D-lysine-coated). Tetracycline is added to the growth medium to induce receptor TRPM8 (DMEM/HG, 10% FCS tetracycline-free, 4 mM L-glutamine, 15 μg/ml blasticidin, 100 μg/ml hygromycin B, 1 μg/ml tetracycline).

The following day, the cells are loaded with Fluo-4AM dye and the test is performed. The procedure is as follows: Addition of 100 μl/well staining solution Ca-4 Kit (RB 141, Molecular Devices) to each 100 μl medium (DMEM/HG, 10% FCS tetracycline-free, 4 mM L-glutamine, 15 μg/ml blasticidin, 100 μg/ml hygromycin B, 1 μg/ml tetracycline).

Incubation in incubator, 30 minutes/37° C./5% $CO_2$, 30 minutes/RT.

Preparation of the test substances (different concentrations in 200 μl HBSS buffer), as well as positive controls (different concentrations of menthol, icilin or lonomycin in 200 μl HBSS buffer) and negative controls (only 200 μl HBSS buffer) addition of the test substances in amounts of 50 μl/well and measurement of the fluorescence change (e.g. in the assay device FLIPR, Molecular Devices or NovoStar, BMG) at 485 nm excitation, 520 nm emission, and evaluation of the potency of the different substances/concentrations and determination of the EC50 values.

The test substances are used in triplicates in concentrations of 0.1-200 μM in the assay. Normally, the compounds are kept ready in DMSO solutions and diluted down to a maximum DMSO concentration of 2% for the assay. Surprisingly, our own evaluations during the performance of the described assay showed that the compounds to be used according to the invention (as described herein) are particularly suitable as agonists of TRPM8.

With the aid of the assay described, the activity of the active substances is determined in relation to activation of the TRPM8 channel. This is done in a concentration-dependent manner. As a standard, 6 to 10 concentrations are measured for each active substance. From the determined activity values, the EC50 value can be determined as the inflection point of the sigmoidal curve using a mathematical method (4-parameter or 5-parameter logistic curve fitting). These are standard methods of biochemistry that are quite familiar to the skilled person.

The EC50 values determined for selected modulators according to the invention are shown in the following Table 5. An EC50 value of 1.72 μM was determined for the substance WS-3, which serves as a reference.

TABLE 5

EC50 values of modulators according to the invention

| Structure | Activity in vitro assay (EC50) (μM) | Compound |
|---|---|---|
| 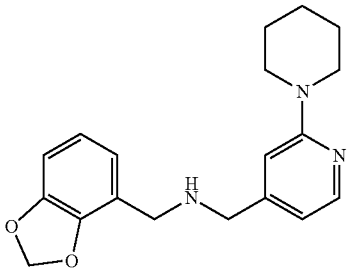 [SMILES: c1cc(CNCc2ccnc(N3CCCCC3)c2)c2c(c1)OCO2] | 0.115 | Compound 1 |
| 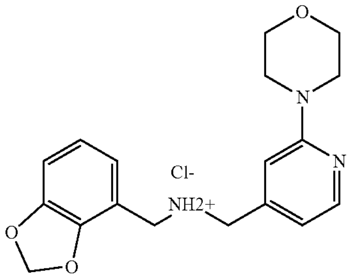 [SMILES: c1cc(C[NH2+]Cc2ccnc(N3CCOCC3)c2)c2c(c1)OCO2 ; [Cl-]] | 13.04 | Compound 2 |
| 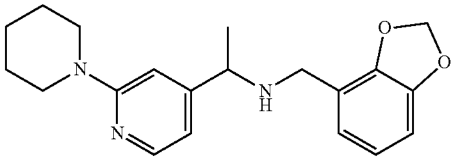 [SMILES: CC(NCc1cccc2c1OCO2)c1ccnc(N2CCCCC2)c1] | 0.15 | Compound 8 |
| 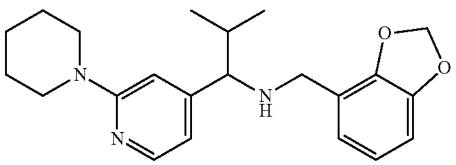 [SMILES: CC(C)C(NCc1cccc2c1OCO2)c1ccnc(N2CCCCC2)c1] | 8.35 | Compound 11 |
| 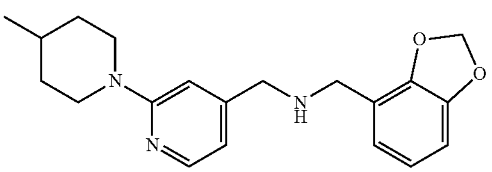 [SMILES: CC1CCN(c2cc(CNCc3cccc4c3OCO4)ccn2)CC1] | 2.01 | Compound 12 |

TABLE 5-continued
| EC50 values of modulators according to the invention | | |
|---|---|---|
| Structure | Activity in vitro assay (EC50) (μM) | Compound |
| 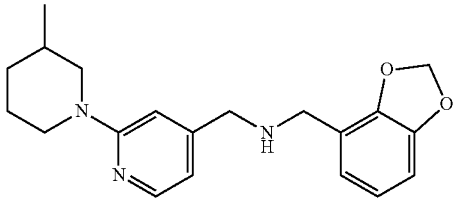 [SMILES: CC1CCCN(c2cc(CNCc3cccc4c3OCO4)ccn2)C1] | 0.60 | Compound 13 |
| 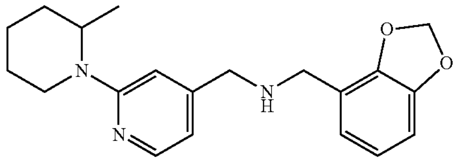 [SMILES: CC1CCCCN1c1cc(CNCc2cccc3c2OCO3)ccn1] | 0.33 | Compound 14 |
| 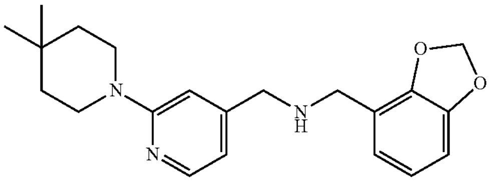 [SMILES: CC1(C)CCN(c2cc(CNCc3cccc4c3OCO4)ccn2)CC1] | 2.63 | Compound 15 |
| 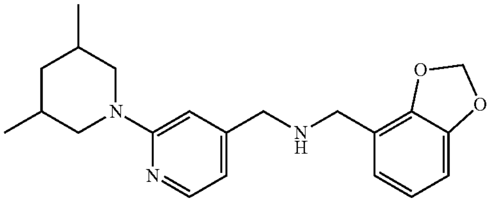 [SMILES: CC1CC(C)CN(c2cc(CNCc3cccc4c3OCO4)ccn2)C1] | 2.53 | Compound 16 |
| 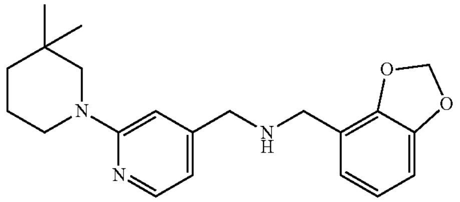 [SMILES: CC1(C)CCCN(c2cc(CNCc3cccc4c3OCO4)ccn2)C1] | 0.72 | Compound 17 |
| 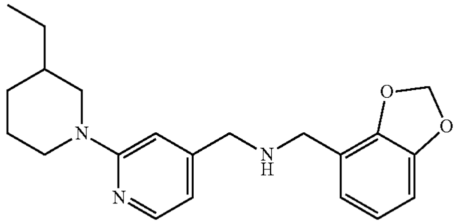 [SMILES: CCC1CCCN(c2cc(CNCc3cccc4c3OCO4)ccn2)C1] | 2.01 | Compound 18 |
| 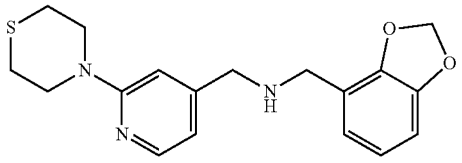 [SMILES: c1cc(CNCc2ccnc(N3CCSCC3)c2)c2c(c1)OCO2] | 1.19 | Compound 22 |

TABLE 5-continued
EC50 values of modulators according to the invention
| Structure | Activity in vitro assay (EC50) (µM) | Compound |
|---|---|---|
| 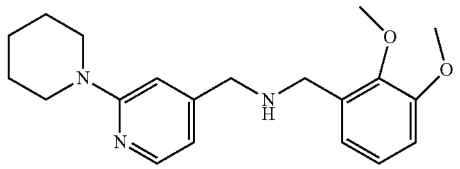 [SMILES: COc1cccc(CNCc2ccnc(N3CCCCC3)c2)c1OC] | 0.76 | Compound 23 |
| 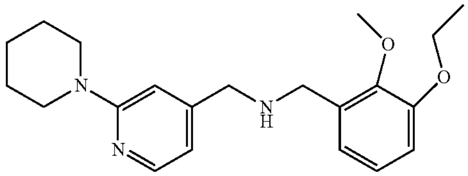 [SMILES: CCOc1cccc(CNCc2ccnc(N3CCCCC3)c2)c1OC] | 1.11 | Compound 24 |
| 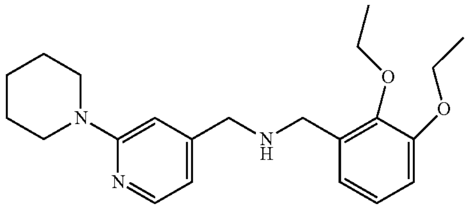 [SMILES: CCOc1cccc(CNCc2ccnc(N3CCCCC3)c2)c1OCC] | 5.86 | Compound 25 |
| 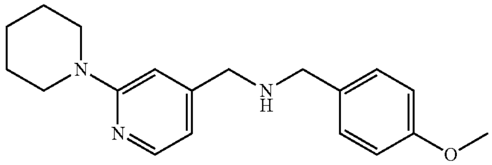 [SMILES: COc1ccc(CNCc2ccnc(N3CCCCC3)c2)cc1] | 0.1 | Compound 27 |
| 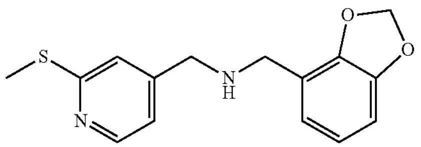 [SMILES: CSc1cc(CNCc2cccc3c2OCO3)ccn1] | 6.5 | Compound 29 |
| 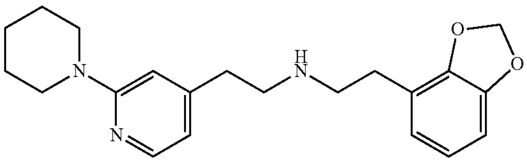 [SMILES: c1cc(CCNCCc2ccnc(N3CCCCC3)c2)c2c(c1)OCO2] | 0.8 | Compound 34 |
| 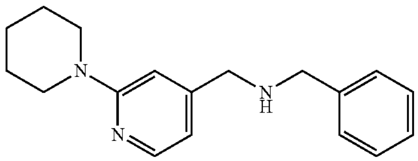 [SMILES: c1ccc(CNCc2ccnc(N3CCCCC3)c2)cc1] | 0.06 | Compound 39 |
| 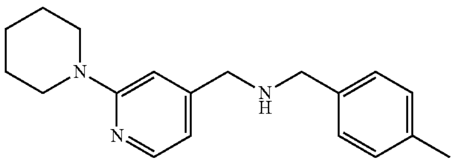 [SMILES: Cc1ccc(CNCc2ccnc(N3CCCCC3)c2)cc1] | 0.15 | Compound 41 |

TABLE 5-continued

EC50 values of modulators according to the invention

| Structure | Activity in vitro assay (EC50) (μM) | Compound |
|---|---|---|
| 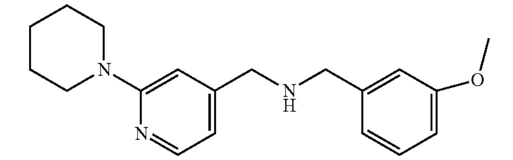 [SMILES: COc1cccc(CNCc2ccnc(N3CCCCC3)c2)c1] | 0.6 | Compound 49 |
| 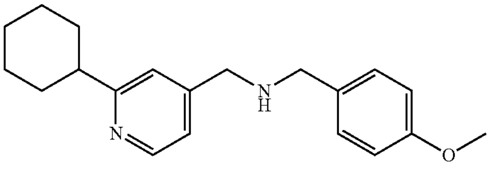 [SMILES: COc1ccc(CNCc2ccnc(C3CCCCC3)c2)cc1] | 0.1 | Compound 56 |
| 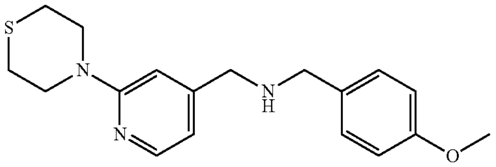 [SMILES: COc1ccc(CNCc2ccnc(N3CCSCC3)c2)cc1] | 15.8 | Compound 58 |
| 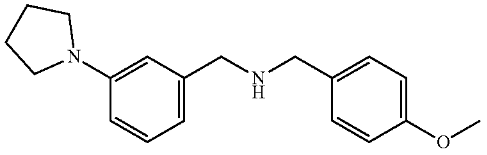 [SMILES: COc1ccc(CNCc2cccc(N3CCCC3)c2)cc1] | 1.77 | Compound 64 |
| 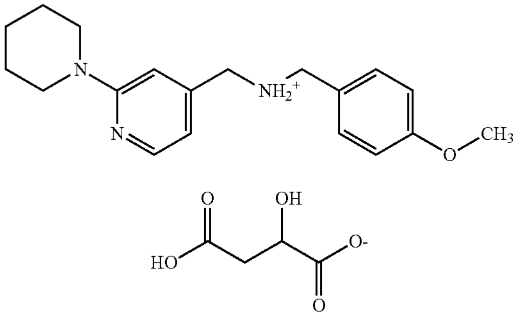 | 0.00695 | Compound 87 |

The EC50 value describes the concentration of cooling substance necessary for half-maximum effect and is thus a measure of the potency of an agonistic pharmaceutical (potency of a pharmaceutical as a function of dose or concentration), where potency corresponds to the reciprocal value of the EC50. Consequently, a low EC50 value corresponds to a high potency of the active substance.

Thus, it can be seen from Table 5 above that the compounds of the invention described herein have excellent cooling properties and can produce intense cooling effects even at low concentrations and are generally well below the EC50 reference value of 1.72 μM for substance WS-3.

As the above table shows, those structures of the general formula (I) have proved to be particularly advantageous in which R1 represents an optionally substituted phenyl group or an optionally substituted 1,3-benzodioxolyl group and R7 represents an optionally substituted pyridinyl group. The latter is preferably substituted with a piperidinyl group. Corresponding particularly suitable structures can also be found in formulae (III) to (VII).

Furthermore, it was observed that in said structures m and n are mostly 1. Consequently, the structures according to the general formulae (I) to (VII) in which m and/or n is/are 1 are preferred.

Accordingly, compounds 1, 8, 13, 17, 14, 17, 22, 23, 24, 27, 34, 39, 41, 49 and 56 (EC50 value ≤1.0 μM) are particularly preferred with regard to the EC50 values. The lowest EC50 value, i.e. a high active substance potency, is shown by the acid addition salt of compound 87 with a value of 0.00695 μM. The counterpart, namely the neutral, uncharged compound 27, has an EC value at 0.1 μM. Consequently, the salt compound shows more intense TRPM8 activation than its uncharged equivalent at the same concentration.

Particularly efficient cooling effects in terms of TRPM8 activity as well as EC50 values can be observed for compounds 1, 8, 13, 17, 14, 17, 22, 23, 24, 27, 39, 41, 49 and 56. A particularly efficient cooling effect with regard to TRPM8 activation as well as the EC50 value is exhibited by the acid addition salt of compound 87.

In addition to the TRPM8 activity and active ingredient potency (EC50 value) described above, the compounds according to the invention also exhibit an intensive cooling effect.

In order to quantify the cooling effect, comparative tests are carried out using menthan-3-carboxylic acid-N-ethylamide as a reference. For these comparative tests, the skilled person replaces the compound or compounds to be used according to the invention with menthan-3-carboxylic acid-N-ethylamide (also referred to as WS-3). Then the intensities of the cooling effects of the respective compounds or active substances are sensory evaluated by trained panellists (n=10 to 11) as described below and compared with each other.

The investigation of the cooling intensity was carried out as follows: Test solutions containing 5 ppm of the compounds of the invention were each tasted in a 5% sugar solution as well as a corresponding solution containing 30 ppm of the reference substance WS-3. This concentration for WS-3 was chosen because WS-3 has been shown to exhibit good cooling effects at such concentrations. The corresponding test solutions were tasted by the panellists for a time of exactly 40 seconds, rinsing the entire oral cavity with the corresponding test solution and then spitting out the sample or reference solution. Following the tasting, the test persons rated the respective cooling intensity after one minute according to a scale from 1 (very weak) to 9 (very strong).

The results of the sensory tasting of exemplarily selected compounds according to the invention are shown in the following Table 6.

TABLE 6

Results of the sensory tasting

| Structure | Cooling intensity | Compound |
|---|---|---|
| 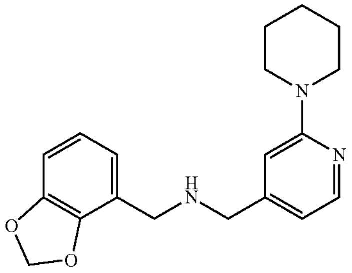 [SMILES: c1cc(CNCc2ccnc(N3CCCCC3)c2)c2c(c1)OCO2] | 5.8 | Compound 1 |
| 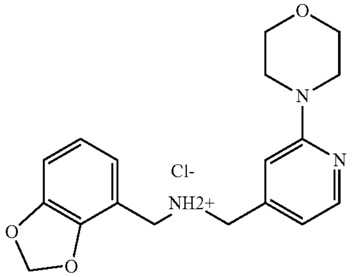 [SMILES: c1cc(C[NH2+]Cc2ccnc(N3CCOCC3)c2)c2c(c1)OCO2 ; [Cl-]] | 0.46 | Compound 2 |
| 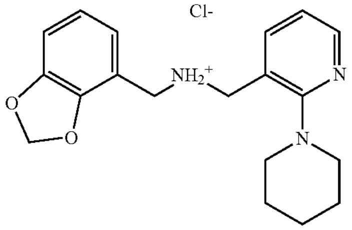 [SMILES: c1cnc(N2CCCCC2)c(C[NH2+]Cc2cccc3c2OCO3)c1 ; [Cl-]] | 0.82 | Compound 4 |
| 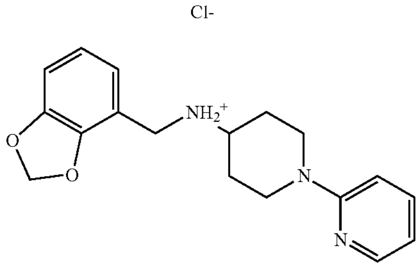 [SMILES: [Cl-] ; c1ccc(N2CCC([NH2+]Cc3cccc4c3OCO4)CC2)nc1] | 0.6 | Compound 6 |

TABLE 6-continued
| Results of the sensory tasting | | |
|---|---|---|
| Structure | Cooling intensity | Compound |
| 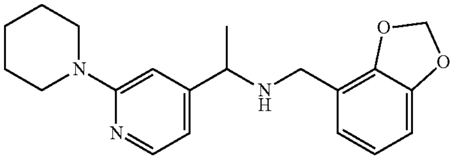 [SMILES: CC(NCc1cccc2c1OCO2)c1ccnc(N2CCCCC2)c1] | 7 | Compound 8 |
| 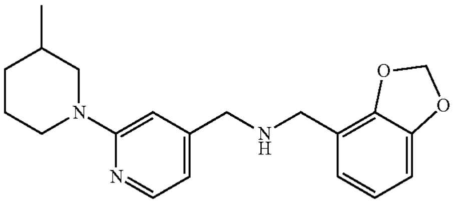 [SMILES: CC1CCCN(c2cc(CNCc3cccc4c3OCO4)ccn2)C1] | 5.95 | Compound 13 |
| 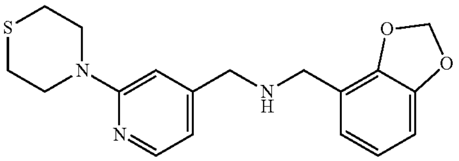 [SMILES: c1cc(CNCc2ccnc(N3CCSCC3)c2)c2c(c1)OCO2] | 3.1 | Compound 22 |
| 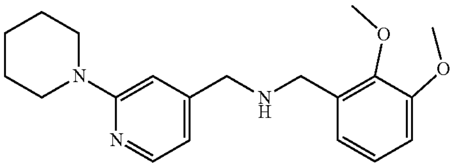 [SMILES: COc1cccc(CNCc2ccnc(N3CCCCC3)c2)c1OC] | 3.3 | Compound 23 |
| 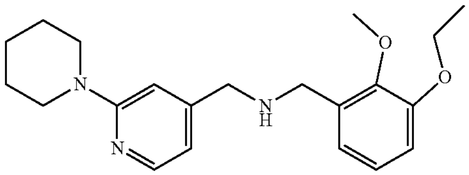 [SMILES: CCOc1cccc(CNCc2ccnc(N3CCCCC3)c2)c1OC] | 3.7 | Compound 24 |
| 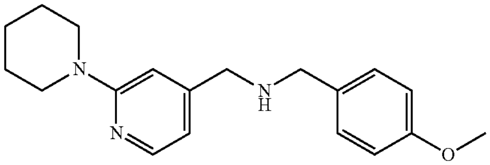 | 6.84 | Compound 27 |
| 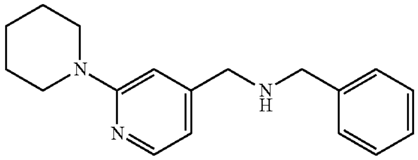 | 7.02 | Compound 39 |
| 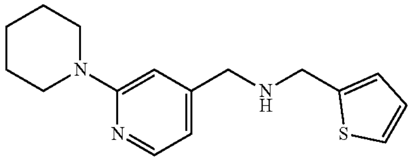 | 7.5 | Compound 40 |

TABLE 6-continued

Results of the sensory tasting

| Structure | Cooling intensity | Compound |
|---|---|---|
| 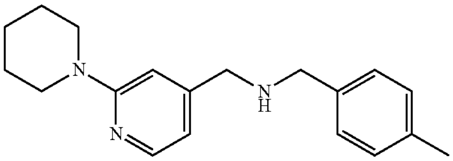 [SMILES: Cc1ccc(CNCc2ccnc(N3CCCCC3)c2)cc1] | 7.2 | Compound 41 |
| 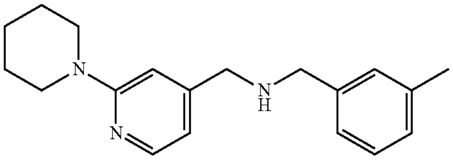 [SMILES: Cc1cccc(CNCc2ccnc(N3CCCCC3)c2)c1] | 5.91 | Compound 42 |
| 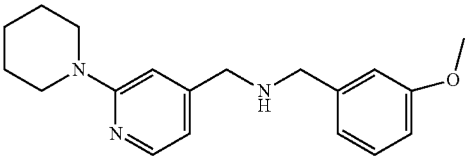 [SMILES: COc1cccc(CNCc2ccnc(N3CCCCC3)c2)c1] | 3.85 | Compound 49 |
| 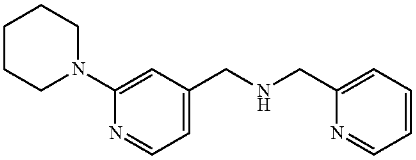 | 5.5 | Compound 51 |
| 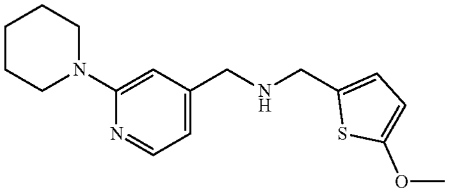 [SMILES: COc1ccc(CNCc2ccnc(N3CCCCC3)c2)s1] | 7 | Compound 81 |
| 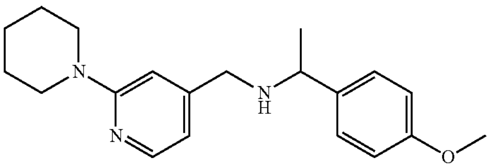 [SMILES: COc1ccc(C(C)NCc2ccnc(N3CCCCC3)c2)cc1] | 2.1 | Compound 85 |

Surprisingly, it has been shown that the compounds described herein produce a noticeably more intense cooling effect compared to the WS-3 reference sample. In particular, it has been shown that the WS-3 containing reference sample showed a cooling intensity of about 5.4 in the sensory evaluation, while the cooling intensity of the compounds according to the invention, such as compound 51 was surprisingly evaluated as 5.5 and the compound N-(1,3-benzodioxol-4-ylmethyl)-1-[2-(1-piperdyl)-4-pyridyl] ethanamine (compound 1) was evaluated as about 5.8, while compound 13 was evaluated as 5.95; 1-(4-methoxyphenyl)-N-[[2-(1-piperidyl)-4-pyridyl]methyl]methanamine (compound 27) was surprisingly rated high at 6.84, compound 8 at 7, 1-phenyl-N-[[2-(1-piperidyl)-4-pyridyl]methyl]methanamine (compound 39) with 7.02 and 1-[2-(1-piperidyl)-4-pyridyl]-N-(2-thienylmethyl)methanamine (compound 40) even with 7.5. Compounds 39, 40, 41 and 42 gave a rating of 7.02, 7.5, 7.2 and 5.91, respectively. Compound 81 also gave a high rating of 7.

It should also be noted that WS-3 is capable of producing noticeably lower cooling intensities despite a six-fold higher concentration. Conversely, significantly lower concentrations of the compounds according to the invention are necessary to produce significantly more intensive cooling effects compared to common cooling substances (such as WS-3). This shows that the compounds according to the invention already produce an intensive and thus highly effective cooling effect when used in low concentrations and that only very small amounts need to be used in corresponding final formulations, such as product formulations containing these cooling substances, in order to produce cooling effects that are perceived as intensive.

A particularly pronounced combination of TRPM8 activation, EC50 value and cooling intensity among the tested cooling substances is shown by compounds 1, 8, 13, 23, 27, 39 and 41, which is why these compounds are the most preferred.

In this context, it is preferred that in the corresponding comparisons the cooling effect of the samples with the compound(s) to be used according to the invention is preferably prolonged by at least 10 minutes, preferably by at least 15 minutes, further preferably at least 20 minutes and particularly preferably at least 30 minutes compared to the reference samples.

Synthesis Examples

In the following examples, the decimal point is represented by a dot.

Preparation of Amines According to the Invention

Method A:

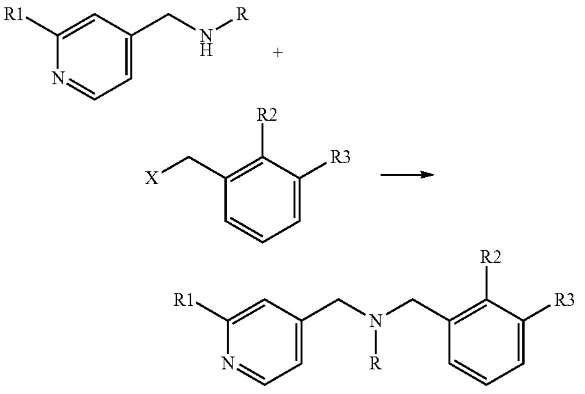

The haloalkyl derivative (1.0 eq.) was dissolved in dry DCM and the corresponding pyridine derivative (1.1 eq.) and a nitrogenous base (2.0 eq.) were added. The reaction mixture was stirred overnight at room temperature. Water and DCM were added to the reaction solution and the two phases were separated. The organic phase was dried over $Na_2SO_4$, filtered and the solvent was removed in vacuo. The crude material was purified by column chromatography and the desired product was obtained as oil or solid.

Method B:

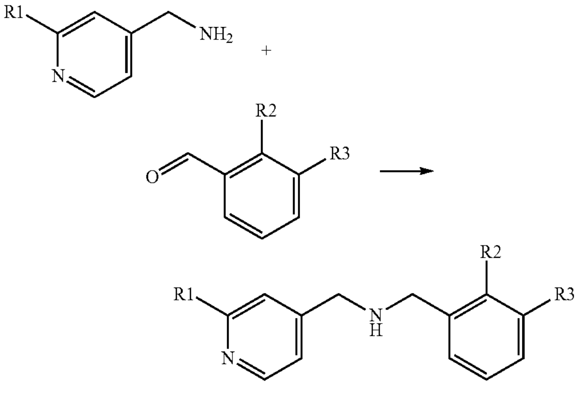

The aldehyde (1.0 eq.) was dissolved in THF and the corresponding amine (1.0 eq.) was added at room temperature. This was followed by the addition of acetic acid (3.0 eq.). The reaction mixture was stirred for 5 minutes, then STAB (1.5 eq.) was added as reducing agent. The reaction mixture was stirred overnight at room temperature under argon atmosphere. The precipitated crystals were filtered off and washed with THF. The filtrate was concentrated in vacuo and the crude material was purified by column chromatography (DCM:MeOH, 95:5). The desired product was obtained as a colourless oil.

Method C:

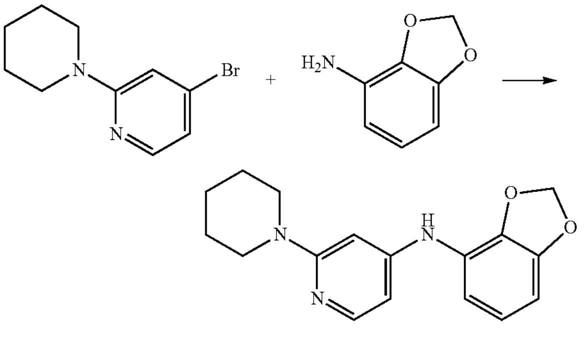

The corresponding halogen derivative (1.0 eq.) and the amine (1.1 eq.) were dissolved in dry toluene and tri-tert-butylphosphine (0.1 eq.) and potassium phosphate (3.0 eq.) were added. The reaction mixture was purged with argon for 15 minutes, then $Pd_2$ $(dba)_3$ was added and again purged with argon for 15 minutes. The reaction mixture was stirred at 100° C. overnight. Water (160 mL) and DCM (160 mL) were added for work-up. The resulting phases were separated and the aqueous phase was extracted with DCM (3×160 mL). The combined organic phases were dried over $Na_2SO_4$, filtered and the solvent was removed in vacuo. The crude product was purified by column chromatography (reversed phase, 0-100% acetonitrile in water).

Method D:

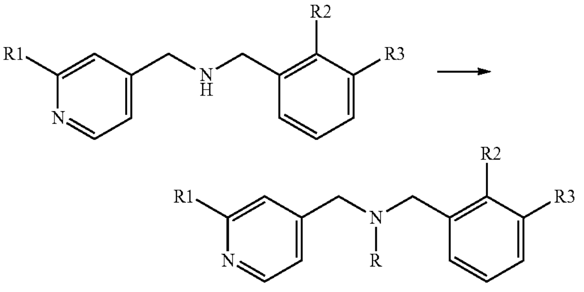

To a suspension consisting of the amine (1.0 eq.), $Cs_2CO_3$ (3.0 eq.) in DMF was added the desired halogen substitution reagent (1.7 eq.) at 0° C. The reaction was heated to 40° C. and stirred for 48 hours. Water and dichloromethane (ratio 1:4) were then added to the reaction solution. The two phases were separated and the aqueous phase was washed three times with dichloromethane. The combined organic phases were dried over $Na_2SO_4$, filtered and the solvent was removed in vacuo. The crude material was purified by preparative thin layer chromatography and the desired product was obtained as oil or solid.

Method E:

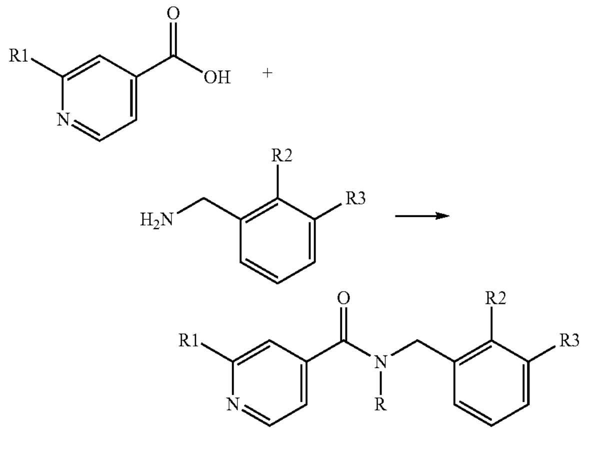

The corresponding carboxylic acid (1.0 eq.), HBTU (1.15 eq.), EDC×HCl (1.3 eq.) were dissolved in DMF and stirred at room temperature for 3 hours. Then the desired amine (1.1 eq.) and base DIPEA (3.5 eq.) were added to the reaction mixture and the reaction solution was stirred overnight at room temperature. Water was then added to the reaction and the product was extracted twice with a mixture of hexane/ethyl acetate (1:3). The organic phase was dried over $Na_2SO_4$, filtered and the solvent was removed in vacuo. The crude material was purified by preparative thin layer chromatography and the desired product was obtained as oil or solid.

Method F:

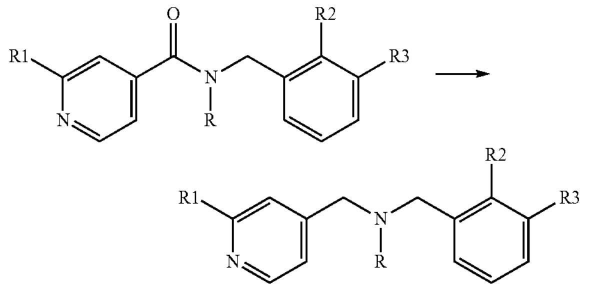

The desired amide was dissolved in dry THF under argon atmosphere. The reaction mixture was cooled to 0° C. and the borane dimethyl sulphide complex was slowly added. The reaction was stirred at room temperature for 16 hours, after which water and 2M NaOH were carefully added. DCM was then added and the phases were separated. The aqueous phase was extracted with DCM. The combined organic phases were dried over $MgSO_4$, filtered and concentrated in vacuo. The crude product was purified by column chromatography (reversed phase) and the product was isolated as BH3 complex. This complex was taken up in MeOH, water and 35% HCl and the reaction mixture was heated to 40° C. The solvents were then removed in vacuo and the product treated with 2M NaOH. The product was then extracted with DCM, the solvent was again removed in vacuo and the desired product was obtained as oil.

With regard to the following synthesis examples, it should be noted that the numbering of the examples does not necessarily correspond to the naming of the compounds according to Table 1.

In the following $^1H$ NMR data, the decimal point is replaced by a dot.

Example 1: Preparation of N-(1,3-benzodioxol-4-ylmethyl)-1-[2-(1-piperidyl)-4-pyridyl]ethanamine

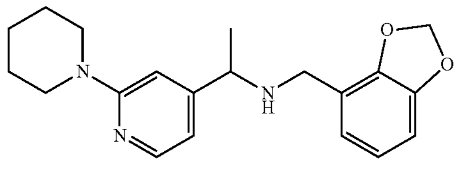 [SMILES: CC(NCc1cccc2c1OCO2)c1ccnc(N2CCCCC2)c1]

Analogue method B: 9% yield $^1H$ NMR (300 MHz, chloroform-d) δ 8.05 (d, J=5.1 Hz, 1H), 6.79-6.56 (m, 4H), 6.49 (dd, J=5.2, 1.3 Hz, 1H), 5.88 (dd, J=8.2, 1.5 Hz, 2H), 3.61 (q, J=6.7 Hz, 2H), 3.54 (s, 1H), 3.52-3.40 (m, 4H), 1.58 (t, J=3.1 Hz, 6H), 1.26 (d, J=6.6 Hz, 3H).

Example 2: Preparation of N-(1,3-benzodioxol-4-ylmethyl)-N-[[2-(1-piperidyl)-4-pyridyl]methyl]ethanamine

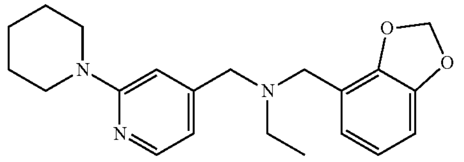 [SMILES: CCN(Cc1ccnc(N2CCCCC2)c1)Cc1cccc2c1OCO2]

Method D: 36% yield $^1H$ NMR (400 MHz, chloroform-d) δ 8.10 (d, J=5.1 Hz, 1H), 6.94 (dd, J=7.8, 1.3 Hz, 1H), 6.82 (t, J=7.7 Hz, 1H), 6.75 (dd, J=7.7, 1.3 Hz, 2H), 6.62 (dd, J=5.2, 1.2 Hz, 1H), 5.95 (s, 2H), 3.61 (s, 2H), 3.53 (d, J=5.5 Hz, 6H), 2.55 (q, J=7.1 Hz, 2H), 1.66 (d, J=3.1 Hz, 6H), 1.10 (t, J=7.1 Hz, 3H).

Example 3: Preparation of N-(1,3-benzodioxol-4-ylmethyl)-N-methyl-1-[2-(1-piperidyl)-4-pyridyl]methanamine

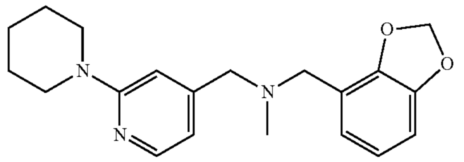 [SMILES: CN(Cc1ccnc(N2CCCCC2)c1)Cc1cccc2c1OCO2]

Method A: 23% yield $^1H$ NMR (300 MHz, chloroform-d): δ 8.10 (dd, J=5.1, 0.7 Hz, 1H), 6.89-6.69 (m, 4H), 6.58 (dd, J=5.1, 1.3 Hz, 1H), 5.95 (s, 2H), 3.53 (s, 6H), 3.45 (s, 2H), 2.23 (s, 3H), 1.64 (d, J=2.8 Hz, 6H).

Example 4: Preparation of N-(1,3-benzodioxol-4-ylmethyl)-2-methyl-1-[2-(1-piperidyl)-4-pyridyl]propan-1-amine

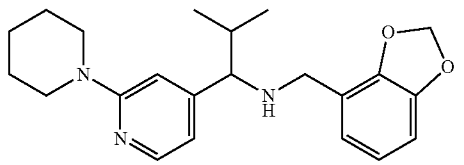 [SMILES: CC(C)C(NCc1cccc2c1OCO2)c1ccnc(N2CCCCC2)c1]

Method B: 5% yield

$^1$H NMR (300 MHz, chloroform-d) δ 8.04 (d, J=5.1 Hz, 1H), 6.77-6.57 (m, 3H), 6.54 (s, 1H), 6.45 (dd, J=5.2, 1.3 Hz, 1H), 5.86 (q, J=1.5 Hz, 2H), 3.61 (d, J=13.6 Hz, 1H), 3.48-3.36 (m, 5H), 3.13 (d, J=6.8 Hz, 1H), 1.85-1.70 (m, 1H), 1.59 (q, J=3.0 Hz, 6H), 0.88 (d, J=6.7 Hz, 3H), 0.70 (d, J=6.8 Hz, 3H).

Example 5: Preparation of N-(1,3-benzodioxol-4-ylmethyl)-1-[2-(4-methyl-1-piperidyl)-4-pyridyl]methanamine

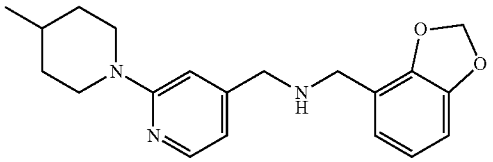 [SMILES: CC1CCN(c2cc(CNCc3cccc4c3OCO4)ccn2)CC1]

Method A: 21% yield

$^1$H NMR (400 MHz, DMSO) δ: 7.99 (d, J=5.1 Hz, 1H), 6.91 (dd, J=5.5, 3.6 Hz, 1H), 6.84-6.76 (m, 3H), 6.56 (d, J=5.1 Hz, 1H), 5.98 (s, 2H), 4.26 (d, J=12.9 Hz, 2H), 3.62 (s, 2H), 3.60 (s, 2H), 2.74 (td, J=12.6, 2.5 Hz, 2H), 2.60 (br, 1H), 1.69-1.52 (m, 3H), 1.13-1.01 (m, 2H), 0.92 (d, J=6.4 Hz, 3H).

Example 6: Preparation of N-(1,3-benzodioxol-4-ylmethyl)-1-[2-(3-methyl-1-piperidyl)-4-pyridyl]methanamine

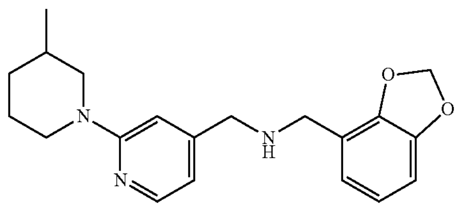 [SMILES: CC1CCCN(c2cc(CNCc3cccc4c3OCO4)ccn2)C1]

Method A: 41% yield

$^1$H NMR (300 MHz, DMSO) δ: 7.98 (d, J=5.1 Hz, 1H), 6.94-6.86 (m, 1H), 6.83-6.73 (m, 3H), 6.55 (dd, J=5.1, 1.2 Hz, 1H), 5.97 (s, 2H), 4.23-4.12 (m, 2H), 3.61 (s, 2H), 3.59 (s, 2H), 2.71 (td, J=12.4, 2.9 Hz, 1H), 2.60 (s, 1H), 2.39 (dd, J=12.8, 10.6 Hz, 1H), 1.82-1.72 (m, 1H), 1.69-1.34 (m, 3H), 1.10 (qd, J=12.2, 3.8 Hz, 1H), 0.89 (d, J=6.6 Hz, 3H).

Example 7: Preparation of N-(1,3-benzodioxol-4-ylmethyl)-1-[2-(2-methyl-1-piperidyl)-4-pyridyl]methanamine

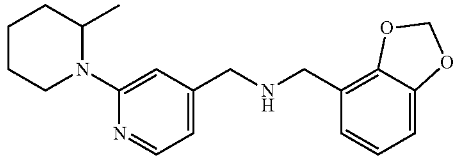 [SMILES: CC1CCCCN1c1cc(CNCc2cccc3c2OCO3)ccn1]

Method A: 32% yield

$^1$H NMR (300 MHz, DMSO) δ: 7.98 (d, J=5.1 Hz, 1H), 6.90 (dd, J=5.2, 4.0 Hz, 1H), 6.85-6.77 (m, 2H), 6.72 (s, 1H), 6.53 (dd, J=5.0, 1.2 Hz, 1H), 5.97 (s, 2H), 4.63 (d, J=7.1 Hz, 1H), 4.09 (d, J=13.2 Hz, 1H), 3.60 (s, 4H), 2.88-2.76 (m, 1H), 2.59 (s, 1H), 1.74-1.53 (m, 5H), 1.38 (dd, J=8.6, 4.3 Hz, 1H), 1.05 (d, J=6.8 Hz, 3H).

Example 8: Preparation of N-(1,3-benzodioxol-4-ylmethyl)-1-[2-(4,4-dimethyl-1-piperidyl)-4-pyridyl]methanamine

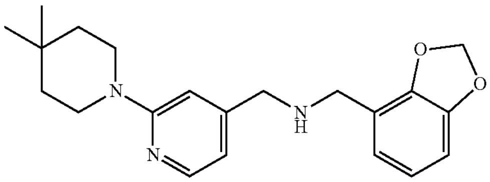 [SMILES: CC1(C)CCN(c2cc(CNCc3cccc4c3OCO4)ccn2)CC1]

Method A: 20% yield

$^1$H NMR (300 MHz, DMSO) δ: 7.99 (d, J=5.1 Hz, 1H), 6.91 (dd, J=5.5, 3.6 Hz, 1H), 6.84-6.77 (m, 3H), 6.57 (dd, J=5.1, 1.1 Hz, 1H), 5.98 (s, 2H), 3.62 (s, 2H), 3.61 (s, 2H), 3.53-3.47 (m, 4H), 1.38-1.32 (m, 4H), 0.96 (s, 6H).

Example 9: Preparation of N-(1,3-benzodioxol-4-ylmethyl)-1-[2-(3,5-dimethyl-1-piperidyl)-4-pyridyl]methanamine

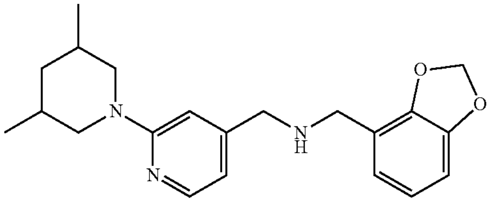 [SMILES: CC1CC(C)CN(c2cc(CNCc3cccc4c3OCO4)ccn2)C1]

Method A: 6% yield

$^1$H NMR (300 MHz, DMSO) δ: 7.98 (d, J=5.1 Hz, 1H), 6.91 (dd, J=5.2, 4.0 Hz, 1H), 6.84-6.76 (m, 3H), 6.56 (dd, J=5.1, 1.1 Hz, 1H), 5.97 (s, 2H), 4.27 (dd, J=12.8, 3.8 Hz, 2H), 3.62 (s, 2H), 3.60 (s, 2H), 2.68 (s, 1H), 2.21 (dd, J=12.8, 11.3 Hz, 2H), 1.76 (d, J=12.9 Hz, 1H), 1.62-1.45 (m, 2H), 0.89 (d, J=6.6 Hz, 6H), 0.82-0.69 (m, 1H).

Example 10: Preparation of N-(1,3-benzodioxol-4-ylmethyl)-1-[2-(3,3-dimethyl-1-piperidyl)-4-pyridyl]methanamine

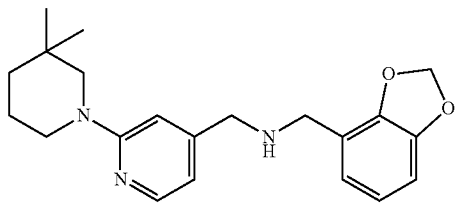 [SMILES: CC1(C)CCCN(c2cc(CNCc3cccc4c3OCO4)ccn2)C1]

Method A: 26% yield $^1$H NMR (300 MHz, DMSO) δ: 7.95 (d, J=5.1 Hz, 1H), 6.90 (dd, J=5.2, 4.0 Hz, 1H), 6.84-6.78 (m, 2H), 6.76 (s, 1H), 6.55-6.50 (m, 1H), 5.97 (s, 2H), 3.61 (s, 2H), 3.59 (s, 2H), 3.45 (t, J=5.6 Hz, 2H), 3.23 (s, 2H), 1.61-1.52 (m, 2H), 1.42-1.34 (m, 2H), 0.90 (s, 6H).

Example 11: Preparation of N-(1,3-benzodioxol-4-ylmethyl)-1-[2-(3-ethyl-1-piperidyl)-4-pyridyl]methanamine

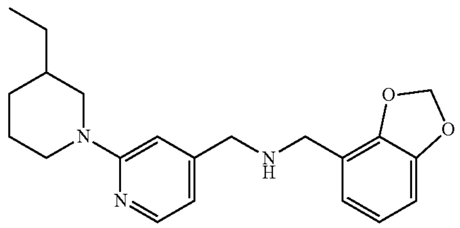 [SMILES: CCC1CCCN(c2cc(CNCc3cccc4c3OCO4)ccn2)C1]

Method A: 31% yield $^1$H NMR (300 MHz, DMSO) δ: 7.98 (d, J=5.1 Hz, 1H), 6.94-6.86 (m, 1H), 6.84-6.70 (m, 3H), 6.55 (d, J=5.1 Hz, 1H), 5.97 (s, 2H), 4.18 (dd, J=20.1, 13.8 Hz, 2H), 3.61 (s, 2H), 3.60 (s, 2H), 2.82-2.58 (m, 2H), 2.46-2.39 (m, 1H), 1.83 (d, J=12.9 Hz, 1H), 1.66 (d, J=12.8 Hz, 1H), 1.48-1.00 (m, 5H), 0.90 (t, J=7.1 Hz, 3H).

Example 12: Preparation of N-(1,3-benzodioxol-4-ylmethyl)-1-[2-(4-propyl-1-piperidyl)-4-pyridyl]methanamine

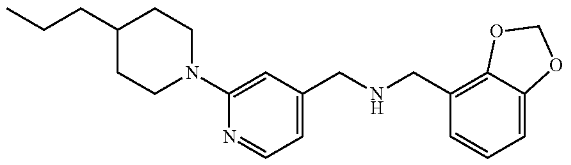 [SMILES: CCCC1CCN(c2cc(CNCc3cccc4c3OCO4)ccn2)CC1]

Method A: 34% yield $^1$H NMR (300 MHz, DMSO) δ: 7.98 (d, J=5.0 Hz, 1H), 6.90 (dd, J=5.2, 4.0 Hz, 1H), 6.84-6.75 (m, 3H), 6.56 (dd, J=5.1, 1.2 Hz, 1H), 5.97 (s, 2H), 4.27 (dt, J=13.3, 3.2 Hz, 2H), 3.62 (s, 2H), 3.60 (s, 2H), 2.79-2.60 (m, 3H), 1.74-1.64 (m, 2H), 1.58-0.94 (m, 8H), 0.87 (t, J=7.2 Hz, 3H).

Example 13: Preparation of N-(1,3-benzodioxol-4-ylmethyl)-1-[2-(4-ethyl-1-piperidyl)-4-pyridyl]methanamine

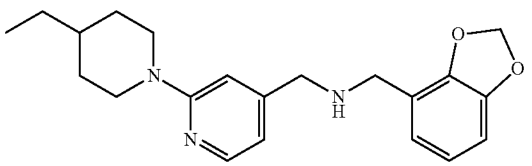 [SMILES: CCC1CCN(c2cc(CNCc3cccc4c3OCO4)ccn2)CC1]

Method A: 16% yield $^1$H NMR (300 MHz, DMSO) δ: 8.06 (d, J=5.0 Hz, 1H), 6.98 (dd, J=5.5, 3.6 Hz, 1H), 6.91-6.84 (m, 3H), 6.64 (dd, J=5.1, 1.1 Hz, 1H), 6.05 (s, 2H), 4.35 (d, J=13.0 Hz, 2H), 3.69 (s, 2H), 3.68 (s, 2H), 2.80 (td, J=12.7, 2.6 Hz, 2H), 1.83-1.74 (m, 2H), 1.49-1.39 (m, 1H), 1.32 (p, J=7.3 Hz, 2H), 1.19-1.08 (m, 2H), 0.96 (t, J=7.4 Hz, 3H).

Example 14: Preparation of N-(1,3-benzodioxol-4-ylmethyl)-N-[[2-(4-methyl-1-piperidyl)-4-pyridyl]methyl]ethanamine

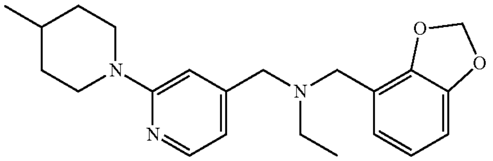 [SMILES: CCN(Cc1ccnc(N2CCC(C)CC2)c1)Cc1cccc2c1OCO2]

Method D: 37% yield $^1$H NMR (400 MHz, DMSO) δ: 7.98 (d, J=5.1 Hz, 1H), 6.90-6.75 (m, 4H), 6.57 (dd, J=5.1, 1.1 Hz, 1H), 5.98 (s, 2H), 4.22 (dt, J=13.0, 2.9 Hz, 2H), 3.52 (s, 2H), 3.47 (s, 2H), 2.74 (td, J=12.7, 2.6 Hz, 2H), 2.43 (q, J=7.1 Hz, 2H), 1.68-1.52 (m, 3H), 1.08 (td, J=12.1, 4.1 Hz, 2H), 1.01 (t, J=7.1 Hz, 3H), 0.91 (d, J=6.4 Hz, 3H).

Example 15: Preparation of N-(1,3-benzodioxol-4-ylmethyl)-1-[2-(4-isopropyl-1-piperidyl)-4-pyridyl]ethanamine

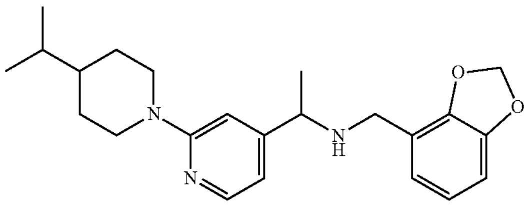 [SMILES: CC(NCc1cccc2c1OCO2)c1ccnc(N2CCC(C(C)C)CC2)c1]

Method B: 13% yield $^1$H NMR (300 MHz, chloroform-d) δ 8.05 (d, J=5.1 Hz, 1H), 6.76-6.59 (m, 4H), 6.49 (dd, J=5.2, 1.3 Hz, 1H), 5.91-5.81 (m, 2H), 4.28 (d, J=12.7 Hz, 2H), 3.67-3.46 (m, 3H), 2.68 (t, J=11.7 Hz, 2H), 1.70 (d, J=10.4 Hz, 2H), 1.39 (p, J=6.5 Hz, 1H), 1.26 (d, J=6.6 Hz, 3H), 1.20 (d, J=6.3 Hz, 3H), 0.84 (d, J=6.7 Hz, 6H).

Example 16: Preparation of N-(1,3-benzodioxol-4-ylmethyl)-2-(1-piperidyl)pyridine-4-carboxamide

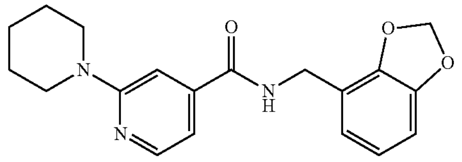 [SMILES: O=C(NCc1cccc2c1OCO2)c1ccnc(N2CCCCC2)c1]

Method E: 47% yield $^1$H NMR (300 MHz, DMSO) δ: 9.08 (t, J=5.8 Hz, 1H), 8.18 (d, J=5.1 Hz, 1H), 7.18 (d, J=1.4 Hz, 1H), 7.02-6.92 (m, 1H), 6.82 (qt, J=6.9, 3.6 Hz, 3H), 6.02 (s, 2H), 4.43 (d, J=5.7 Hz, 2H), 3.56 (t, J=5.2 Hz, 4H), 1.66-1.48 (m, 6H)

Example 17: Preparation of N-(1,3-benzodioxol-4-ylmethyl)-1-[2-(4-methoxy-1-piperidyl)-4-pyridyl]methanamine

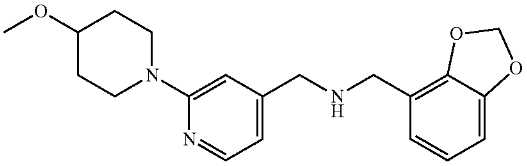 [SMILES: COC1CCN(c2cc(CNCc3cccc4c3OCO4)ccn2)CC1]

Method A: 36% yield $^1$H NMR (300 MHz, DMSO) δ: 7.99 (d, J=5.1 Hz, 1H), 6.93-6.86 (m, 1H), 6.85-6.75 (m, 3H), 6.58 (d, J=5.1 Hz, 1H), 5.97 (s, 2H), 3.93 (dd, J=12.2, 5.7 Hz, 2H), 3.61 (s, 4H), 3.35-3.44 (m, 1H), 3.16-3.04 (m, 2H), 2.65 (s, 1H), 1.93-1.82 (m, 2H), 1.45-1.30 (m, 2H).

Example 18: Preparation of N-(1,3-benzodioxol-4-ylmethyl)-1-(2-thiomorpholino-4-pyridyl)methanamine

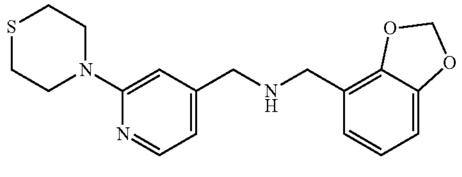 [SMILES: c1cc(CNCc2ccnc(N3CCSCC3)c2)c2c(c1)OCO2]

Method A: 30% yield $^1$H NMR (300 MHz, chloroform-d) δ 8.10 (d, J=5.1 Hz, 1H), 6.82-6.73 (m, 3H), 6.65 (s, 1H), 6.57 (dd, J=5.1, 1.3 Hz, 1H), 5.96 (s, 2H), 3.99-3.91 (m, 4H), 3.79 (s, 2H), 3.73 (s, 2H), 2.71-2.61 (m, 4H), 1.69 (s, 1H).

Example 19: Preparation of N-(1,3-benzodioxol-4-ylmethyl)-1-(2-pyrrol-1-yl-4-pyridyl)methanamine

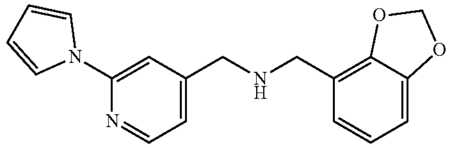 [SMILES: c1cc(CNCc2ccnc(-n3cccc3)c2)c2c(c1)OCO2]

Method A: 5% yield $^1$H NMR (300 MHz, chloroform-d) δ 8.36 (d, J=5.1 Hz, 1H), 7.55 (t, J=2.3 Hz, 2H), 7.40 (s, 1H), 7.13-7.07 (m, 1H), 6.91-6.74 (m, 3H), 6.37 (t, J=2.3 Hz, 2H), 5.99 (s, 2H), 3.88 (s, 2H), 3.83 (s, 2H), 1.82 (s, 1H).

Example 20: Preparation of N-(1,3-benzodioxol-4-ylmethyl)-1-(2-phenyl-4-pyridyl)methanamine

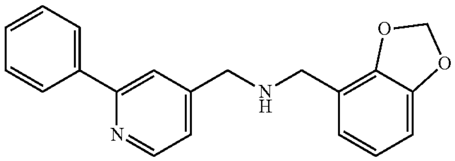 [SMILES: c1ccc(-c2cc(CNCc3cccc4c3OCO4)ccn2)cc1]

Method A: 25% yield $^1$H NMR (300 MHz, DMSO) δ: 8.57 (d, J=5.2 Hz, 1H), 8.16-8.02 (m, 2H), 7.94 (s, 1H), 7.56-7.38 (m, 3H), 7.33 (dd, J=5.0, 1.4 Hz, 1H), 6.94 (dd, J=5.8, 3.4 Hz, 1H), 6.87-6.75 (m, 2H), 5.97 (s, 2H), 3.80 (s, 2H), 3.67 (s, 2H), 2.84 (s, 1H)

Example 21: Preparation of N-(1,3-benzodioxol-4-ylmethyl)-1-[3-(2-pyridyl)phenyl]methane-amine

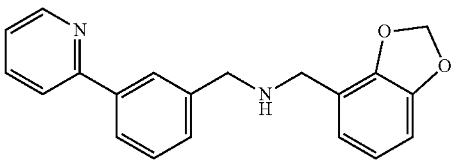 [SMILES: c1ccc(-c2cccc(CNCc3cccc4c3OCO4)c2)nc1]

Analogue method A: 32% yield $^1$H NMR (300 MHz, chloroform-d) δ 8.69 (dt, J=4.8, 1.5 Hz, 1H), 7.98 (d, J=1.9 Hz, 1H), 7.87 (dt, J=6.8, 2.1 Hz, 1H), 7.77-7.72 (m, 2H), 7.48-7.38 (m, 2H), 7.25-7.18 (m, 1H), 6.84-6.71 (m, 3H), 5.95 (s, 2H), 3.90 (s, 2H), 3.84 (s, 2H), 1.84 (s, 1H).

Example 22: Preparation of N-[(2,3-dimethoxyphenyl)methyl]-1-[2-(1-piperidyl)-4-pyridyl]methanamine

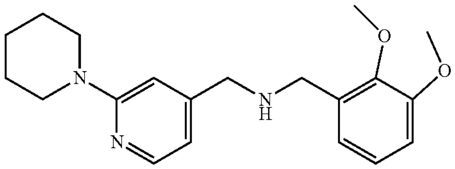 [SMILES: COc1cccc(CNCc2ccnc(N3CCCCC3)c2)c1OC]

Method B: 40% yield $^1$H NMR (300 MHz, CDCl3) δ 8.03 (d, J=5.1 Hz, 1H), 6.96 (t, J=7.9 Hz, 1H), 6.80 (td, J=7.8, 1.6 Hz, 2H), 6.60 (s, 1H), 6.48 (dd, J=5.2, 1.3 Hz, 1H), 3.80 (s, 3H), 3.76 (s, 3H), 3.73 (s, 2H), 3.62 (s, 2H), 3.45 (d, J=4.7 Hz, 4H), 1.70 (s, 1H), 1.58 (s, 6H).

Example 23: Preparation of N-[(3-ethoxy-2-methoxy-phenyl)methyl]-1-[2-(1-piperidyl)-4-pyridyl]methanamine

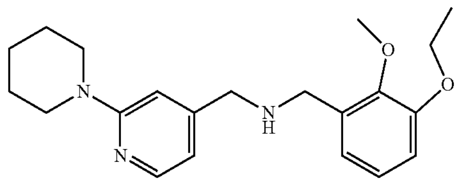 [SMILES: CCOc1cccc(CNCc2ccnc(N3CCCCC3)c2)c1OC]

Method B: 30% yield $^1$H NMR (300 MHz, CDCl3) δ 8.09 (d, J=5.3 Hz, 1H), 7.00 (t, J=7.8 Hz, 1H), 6.85 (dq, J=7.8, 1.6 Hz, 2H), 6.67 (s, 1H), 6.54 (dd, J=5.1, 1.3 Hz, 1H), 4.08 (q, J=7.0 Hz, 2H), 3.85 (s, 3H), 3.79 (s, 2H), 3.68 (s, 2H), 3.52 (d, J=4.7 Hz, 4H), 1.77 (s, 1H), 1.64 (d, J=6.5 Hz, 6H), 1.46 (t, J=7.0 Hz, 3H).

Example 24: Preparation of N-[(2,3-diethoxyphenyl)methyl]-1-[2-(1-piperidyl)-4-pyridyl]methanamine

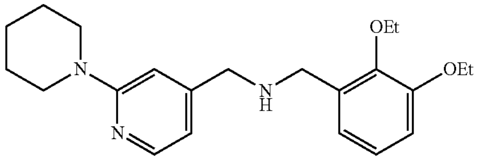 [SMILES: CCOc1cccc(CNCc2ccnc(N3CCCCC3)c2)c1OCC]

Method B: 30% yield

1H NMR (400 MHz, DMSO) δ: 7.99 (d, J=5.1 Hz, 1H), 7.01-6.94 (m, 2H), 6.89 (dd, J=6.8, 2.9 Hz, 1H), 6.76 (s, 1H), 6.57 (dd, J=5.1, 1.1 Hz, 1H), 4.01 (q, J=7.0 Hz, 2H), 3.92 (q, J=7.0 Hz, 2H), 3.65 (s, 2H), 3.60 (s, 2H), 3.48 (t, J=5.4 Hz, 4H), 1.61-1.49 (m, 6H), 1.33 (t, J=7.0 Hz, 3H), 1.20 (t, J=7.0 Hz, 3H).

Example 25: Preparation of N-(2,3-dihydro-1,4-benzodioxin-5-ylmethyl)-1-[2-(1-piperidyl)-4-pyridyl]methanamine

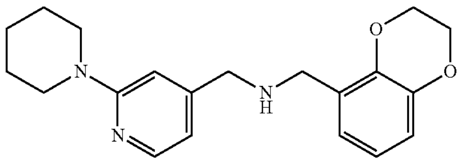 [SMILES: c1cc(CNCc2ccnc(N3CCCCC3)c2)c2c(c1)OCCO2]

Method B: 29% yield $^1$H NMR (300 MHz, CDCl3) δ 8.10 (d, J=5.1 Hz, 1H), 6.80 (s, 3H), 6.68 (s, 1H), 6.54 (dd, J=5.1, 1.3 Hz, 1H), 4.34-4.19 (m, 4H), 3.77 (s, 2H), 3.70 (s, 2H), 3.53 (t, J=4.6 Hz, 4H), 1.81 (s, 1H), 1.70-1.56 (m, 6H).

Example 26: Preparation of 1-(4-methoxyphenyl)-N-[[2-(1-piperidyl)-4-pyridyl]methyl]methanamine

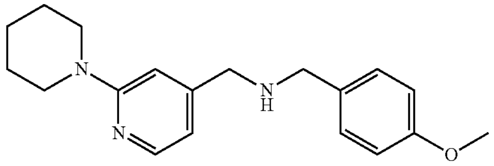

Method B: 24% yield $^1$H NMR (300 MHz, chloroform-d) δ 8.11 (d, J=5.1 Hz, 1H), 7.24 (d, J=2.1 Hz, 2H), 6.91-6.84 (m, 2H), 6.64 (s, 1H), 6.54 (dd, J=5.1, 1.3 Hz, 1H), 3.80 (s, 3H), 3.73 (s, 2H), 3.70 (s, 2H), 3.54 (d, J=4.9 Hz, 4H), 1.64 (s, 6H), 1.58 (s, 1H).

Example 27: Preparation of N-(1,3-benzodioxol-4-ylmethyl)-1-(4-phenylphenyl)methanamine

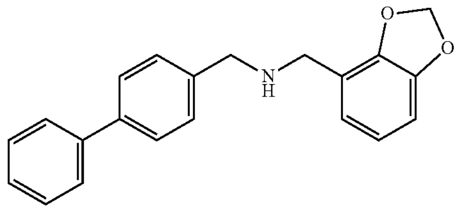 [SMILES: c1ccc(-c2ccc(CNCc3cccc4c3OCO4)cc2)cc1]

Analogue method A: 32% yield $^1$H NMR (300 MHz, CDCl3) δ 7.48 (dd, J=9.3, 7.3 Hz, 4H), 7.39-7.29 (m, 4H), 7.24 (t, J=7.3 Hz, 1H), 6.75-6.62 (m, 3H), 5.87 (s, 2H), 3.75 (d, J=3.5 Hz, 4H), 1.64 (s, 1H).

Example 28: Preparation of N-(1,3-benzodioxol-4-ylmethyl)-1-(2-methylsulfanyl-4-pyridyl)methanamine

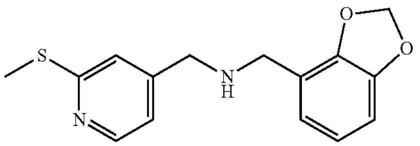 [SMILES: CSc1cc(CNCc2cccc3c2OCO3)ccn1]

Method A: 58% yield $^1$H NMR (400 MHz, chloroform-d) δ 8.39 (dd, J=5.1, 0.8 Hz, 1H), 7.23 (dd, J=1.5, 0.8 Hz, 1H), 6.99 (dd, J=5.2, 1.4 Hz, 1H), 6.88-6.74 (m, 3H), 5.99 (s, 2H), 3.81 (s, 2H), 3.78 (s, 2H), 2.59 (s, 3H).

Example 29: Preparation of N-(1,3-benzodioxol-4-ylmethyl)-1-(2-ethoxy-4-pyridyl)methanamine

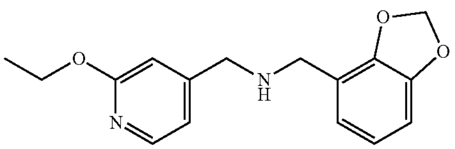

Method A: 11% yield $^1H$ NMR (300 MHz, DMSO) δ: 8.04 (d, J=5.2 Hz, 1H), 6.95-6.86 (m, 2H), 6.84-6.78 (m, 2H), 6.75 (s, 1H), 5.97 (s, 2H), 4.27 (q, J=7.1 Hz, 2H), 3.66 (s, 2H), 3.62 (s, 2H), 1.30 (t, J=7.0 Hz, 3H).

Example 30: Preparation of 1-(1,3-benzodioxol-4-yl)-N-(1H-Indol-2-ylmethyl)methanamine

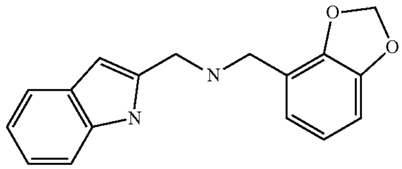 [SMILES: c1cc(CNCc2cc3ccccc3[nH]2)c2c(c1)OCO2]

Analogue method A: 13% yield $^1H$ NMR (300 MHz, DMSO-$d_6$) δ 10.84 (s, 1H), 7.57 (d, J=7.7 Hz, 1H), 7.35-7.30 (m, 1H), 7.22 (d, J=2.4 Hz, 1H), 7.06 (ddd, J=8.1, 6.9, 1.3 Hz, 1H), 6.99-6.91 (m, 2H), 6.84-6.76 (m, 2H), 5.97 (s, 2H), 3.84 (s, 2H), 3.70 (s, 2H).

Example 31: Preparation of 1-(1,3-benzodioxol-4-yl)-N-[(5-phenyl-3-furyl)methyl]methanamine

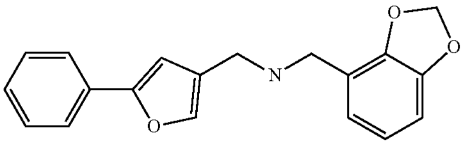 [SMILES: c1ccc(-c2cc(CNCc3cccc4c3OCO4)co2)cc1]

Analogue method B: 12% yield $^1H$ NMR (300 MHz, chloroform-d) δ 7.75-7.62 (m, 2H), 7.48-7.35 (m, 3H), 7.28-7.23 (m, 1H), 6.90-6.75 (m, 3H), 6.70 (d, J=0.8 Hz, 1H), 5.99 (s, 2H), 3.86 (s, 2H), 3.71 (d, J=0.9 Hz, 2H).

Example 32: Preparation of 1-(1,3-benzodioxol-4-yl)-N-(3-quinolylmethyl)methanamine

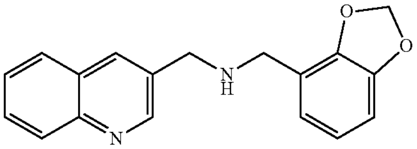 [SMILES: c1cc(CNCc2cnc3ccccc3c2)c2c(c1)OCO2]

Analogue method A: 26% yield $^1H$ NMR (300 MHz, chloroform-d) δ 8.83 (d, J=2.2 Hz, 1H), 8.03 (d, J=7.9 Hz, 2H), 7.73 (dd, J=8.1, 1.5 Hz, 1H), 7.62 (ddd, J=8.4, 6.9, 1.5 Hz, 1H), 7.47 (ddd, J=8.1, 6.9, 1.2 Hz, 1H), 6.79-6.61 (m, 3H), 5.89 (s, 2H), 3.93 (s, 2H), 3.79 (s, 2H), 1.75 (s, 1H).

Example 33: Preparation of 1-(1,3-benzodioxol-4-yl)-N-(benzofuran-2-ylmethyl)methanamine

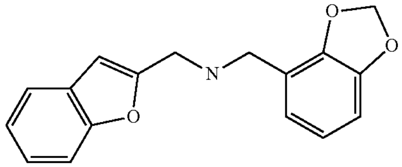 [SMILES: c1cc(CNCc2cc3ccccc3o2)c2c(c1)OCO2]

Analogue method A: 22% yield $^1H$ NMR (300 MHz, $CDCl_3$) δ 7.65-7.55 (m, 2H), 7.51-7.45 (m, 1H), 7.34-7.21 (m, 2H), 6.85-6.73 (m, 3H), 5.96 (s, 2H), 3.93 (d, J=1.1 Hz, 2H), 3.87 (s, 2H), 1.69 (s, 1H).

Example 34: Preparation of N-(1,3-benzodioxol-4-yl)-2-(1-piperidyl)pyridin-4-amine

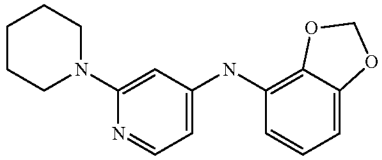 [SMILES: c1cc(Nc2ccnc(N3CCCCC3)c2)c2c(c1)OCO2]

Method C: 17% yield $^1H$ NMR (300 MHz, DMSO-$d_6$) δ 8.27 (s, 1H), 7.75 (d, J=5.6 Hz, 1H), 6.86-6.78 (m, 1H), 6.70 (ddd, J=11.2, 8.0, 1.3 Hz, 2H), 6.11 (dd, J=5.7, 1.8 Hz, 1H), 6.04 (d, J=1.9 Hz, 1H), 6.00 (s, 2H), 3.38 (t, J=5.2 Hz, 4H), 1.59-1.45 (m, 6H).

Example 35: Preparation of N-[2-(1,3-benzodioxol-4-yl)ethyl]-2-[2-(1-piperidyl)-4-pyridyl]ethanamine

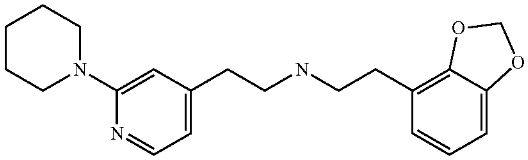 [SMILES: c1cc(CCNCCc2ccnc(N3CCCCC3)c2)c2c(c1)OCO2]

Analogue method E: 40% yield; then analogue method F: 23% yield

1H NMR (300 MHz, chloroform-d) δ 8.07 (d, J=5.1 Hz, 1H), 6.83-6.59 (m, 3H), 6.48 (s, 1H), 6.42 (dd, J=5.1, 1.3 Hz, 1H), 5.92 (s, 2H), 3.53 (d, J=4.8 Hz, 4H), 3.01-2.85 (m, 4H), 2.84-2.57 (m, 4H), 1.66 (d, J=3.1 Hz, 6H).

Example 36: Preparation of N-(1,3-benzodioxol-4-ylmethyl)-N-[[2-(1-piperidyl)-4-pyridyl]methy]aniline

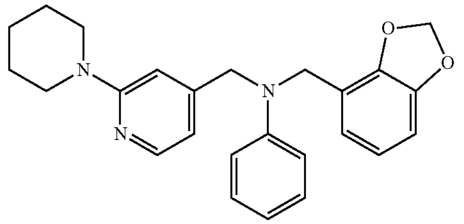 [SMILES: c1ccc(N(Cc2ccnc(N3CCCCC3)c2)Cc2cccc3c2OCO3)cc1]

Method A: 29% yield $^1$H NMR (300 MHz, DMSO-$d_6$) δ 7.98 (d, J=5.1 Hz, 1H), 6.90 (dd, J=5.3, 3.9 Hz, 1H), 6.84-6.76 (m, 3H), 6.56 (dd, J=5.1, 1.2 Hz, 1H), 5.97 (s, 2H), 3.60 (d, J=4.6 Hz, 4H), 3.48 (t, J=5.2 Hz, 4H), 2.59 (s, 1H), 1.56 (d, J=18.8 Hz, 6H).

Then benzylation according to method D: 44% yield $^1$H NMR (300 MHz, chloroform-d) δ 8.09 (d, J=5.2 Hz, 1H), 7.18 (dd, J=8.7, 7.2 Hz, 2H), 6.77-6.69 (m, 6H), 6.55-6.45 (m, 2H), 5.95 (s, 2H), 4.58 (s, 2H), 4.53 (s, 2H), 3.49 (d, J=5.6 Hz, 4H), 1.62 (d, J=2.9 Hz, 6H).

Example 37: Preparation of N-(1,3-benzodioxol-4-ylmethyl)-1-phenyl-N-[[2-(1-piperidyl)-4-pyridyl]methyl]methanamine

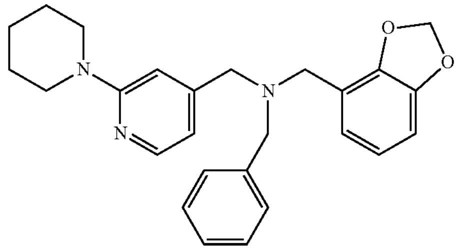 [SMILES: c1ccc(CN(Cc2ccnc(N3CCCCC3)c2)Cc2cccc3c2OCO3)cc1]

Method D: 36% yield $^1$H NMR (400 MHz, chloroform-d) δ 8.12 (d, J=5.1 Hz, 1H), 7.44-7.39 (m, 2H), 7.37-7.31 (m, 2H), 7.28-7.21 (m, 1H), 6.98 (dd, J=7.9, 1.2 Hz, 1H), 6.83 (t, J=7.8 Hz, 1H), 6.79-6.72 (m, 2H), 6.67 (dd, J=5.1, 1.2 Hz, 1H), 5.96 (s, 2H), 3.61 (s, 4H), 3.55 (d, J=4.8 Hz, 4H), 3.51 (s, 2H), 1.66 (d, J=3.3 Hz, 6H).

Example 38: Preparation of 2-(1,3-benzodioxol-4-yl)-N-[[2-(1-piperidyl)-4-pyridyl]methyl]ethanamine

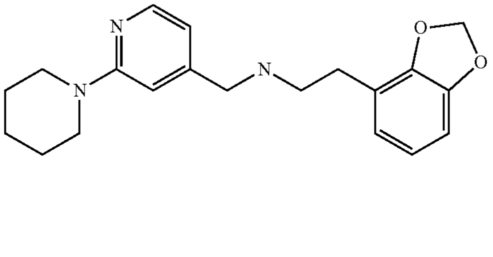 [SMILES: c1cc(CCNCc2ccnc(N3CCCCC3)c2)c2c(c1)OCO2]

Analogue method E: 36% yield, then analogue method F: 36% yield $^1$H NMR (300 MHz, chloroform-d) δ 8.10 (dd, J=5.1, 0.7 Hz, 1H), 6.86-6.64 (m, 3H), 6.60 (s, 1H), 6.50 (dd, J=5.1, 1.3 Hz, 1H), 5.93 (s, 2H), 3.74 (s, 2H), 3.53 (d, J=5.0 Hz, 4H), 2.92 (td, J=6.5, 1.5 Hz, 2H), 2.82 (td, J=6.5, 1.5 Hz, 2H), 1.65 (q, J=3.2, 2.6 Hz, 7H).

Example 39: Preparation of N-(1,3-benzodioxol-4-ylmethyl)-2-[2-(1-piperidyl)-4-pyridyl]ethanamine

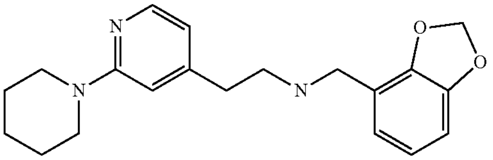 [SMILES: c1cc(CNCCc2ccnc(N3CCCCC3)c2)c2c(c1)OCO2]

Method A: 13% yield $^1$H NMR (300 MHz, chloroform-d) δ 8.06-7.91 (m, 1H), 6.78-6.59 (m, 3H), 6.45-6.26 (m, 2H), 5.84 (s, 2H), 3.72 (s, 2H), 3.44 (d, J=4.8 Hz, 4H), 2.87-2.75 (m, 2H), 2.65 (t, J=6.9 Hz, 2H), 1.57 (q, J=2.4 Hz, 6H).

Example 40: Preparation of 1-phenyl-N-[[2-(1-piperidyl)-4-pyridyl]methyl]methanamine

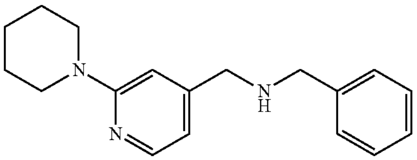 [SMILES: c1ccc(CNCc2ccnc(N3CCCCC3)c2)cc1]

Analogue method A: 15% yield $^1$H NMR (300 MHz, $CDCl_3$) δ 8.04 (d, J=5.1 Hz, 1H), 7.29-7.17 (m, 5H), 6.58 (s, 1H), 6.48 (dd, J=5.1, 1.3 Hz, 1H), 3.73 (s, 2H), 3.65 (s, 2H), 3.45 (d, J=4.8 Hz, 4H), 1.57 (d, J=6.0 Hz, 7H).

Example 41: Preparation of 1-[2-(1-piperidyl)-4-pyridyl]-N-(2-thienylmethyl)methanamine

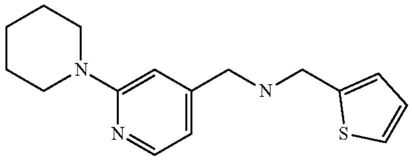 [SMILES: c1csc(CNCc2ccnc(N3CCCCC3)c2)c1]

Analogue method A: 28% yield $^1$H NMR (300 MHz, $CDCl_3$) δ 8.04 (d, J=5.1 Hz, 1H), 7.20-7.13 (m, 1H), 6.93-6.81 (m, 2H), 6.59 (s, 1H), 6.47 (dd, J=5.1, 1.3 Hz, 1H), 3.92 (d, J=0.9 Hz, 2H), 3.68 (s, 2H), 3.47 (t, J=4.6 Hz, 4H), 1.64 (s, 1H), 1.58-1.51 (m, 6H).

Example 42: Preparation of N-[[2-(1-piperidyl)-4-pyridyl]methyl]-1-(p-tolyl)methanamine

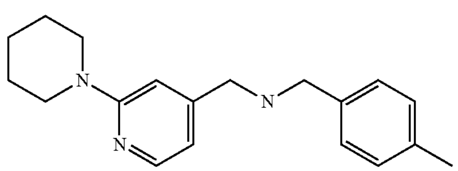 [SMILES: Cc1ccc(CNCc2ccnc(N3CCCCC3)c2)cc1]

Analogue method A: 32% yield $^1$H NMR (300 MHz, chloroform-d) δ 8.11 (d, J=5.1 Hz, 1H), 7.22 (d, J=8.0 Hz, 2H), 7.15 (d, J=7.8 Hz, 2H), 6.65 (s, 1H), 6.54 (dd, J=5.1, 1.3 Hz, 1H), 3.76 (s, 2H), 3.71 (s, 2H), 3.53 (t, J=4.6 Hz, 4H), 2.34 (s, 3H), 1.62 (s, 7H).

Example 43: Preparation of 1-(m-tolyl)-N-[[2-(1-piperidyl)-4-pyridyl]methyl]methanamine

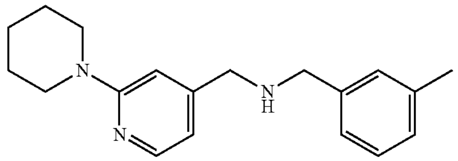 [SMILES: Cc1cccc(CNCc2ccnc(N3CCCCC3)c2)c1]

Analogue method A: 33% yield $^1$H NMR (300 MHz, DMSO-$d_6$) δ 7.99 (d, J=5.1 Hz, 1H), 7.23-7.08 (m, 3H), 7.03 (d, J=7.4 Hz, 1H), 6.76 (s, 1H), 6.57 (dd, J=5.1, 1.2 Hz, 1H), 3.61 (s, 2H), 3.57 (s, 2H), 3.51-3.46 (m, 4H), 2.65 (s, 1H), 2.28 (s, 3H), 1.61-1.48 (m, 6H).

Example 44: Preparation of N-(o-tolylmethyl)-1-[2-(1-piperidyl)-4-pyridyl]methanamine

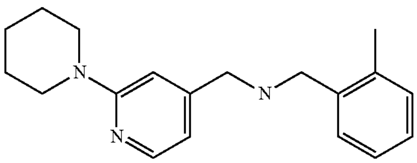 [SMILES: Cc1ccccc1CNCc1ccnc(N2CCCCC2)c1]

Method A: 26% yield $^1$H NMR (300 MHz, CDCl3) δ 8.12 (d, J=5.1 Hz, 1H), 7.31 (tt, J=4.6, 2.5 Hz, 1H), 7.22-7.12 (m, 3H), 6.68 (s, 1H), 6.57 (dd, J=5.2, 1.3 Hz, 1H), 3.77 (d, J=2.1 Hz, 4H), 3.53 (d, J=4.6 Hz, 4H), 2.34 (s, 3H), 1.64 (q, J=2.4, 1.9 Hz, 6H), 1.58 (s, 1H).

Example 45: Preparation of 1-(1,3-benzodioxol-4-yl)-N-[(5-phenyl-3-thienyl)methyl]methanamine

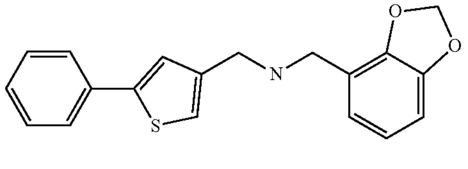

Method E: 64% yield, $^1$H NMR (300 MHz, chloroform-d) δ 7.70 (d, J=1.5 Hz, 1H), 7.59-7.44 (m, 3H), 7.40-7.21 (m, 3H), 6.85-6.65 (m, 3H), 6.33 (s, 1H), 5.91 (s, 2H), 4.55 (d, J=5.7 Hz, 2H).

then method F: 41% yield $^1$H NMR (300 MHz, chloroform-d) δ 7.56-7.48 (m, 2H), 7.34-7.25 (m, 2H), 7.23-7.16 (m, 2H), 7.01 (q, J=1.0 Hz, 1H), 6.78-6.63 (m, 3H), 5.90 (s, 2H), 4.06-3.29 (m, 4H).

Example 46: Preparation of 2-methoxy-4-[[[2-(1-piperidyl)-4-pyridyl]methylamino]-methyl]phenol

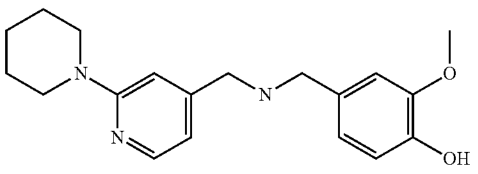 [SMILES: COc1cc(CNCc2ccnc(N3CCCCC3)c2)ccc1O]

Method B: 13% yield $^1$H NMR (300 MHz, chloroform-d) δ 8.11 (d, J=5.1 Hz, 1H), 6.89-6.84 (m, 2H), 6.79 (dd, J=8.0, 1.8 Hz, 1H), 6.64 (s, 1H), 6.54 (dd, J=5.1, 1.3 Hz, 1H), 5.30 (s, 1H), 3.88 (s, 3H), 3.71 (d, J=3.1 Hz, 4H), 3.53 (d, J=5.0 Hz, 4H), 1.63 (d, J=3.3 Hz, 6H).

Example 47: Preparation of 1-(1,3-benzodioxol-4-yl)-N-(benzothiophen-2-ylmethyl)methanamine

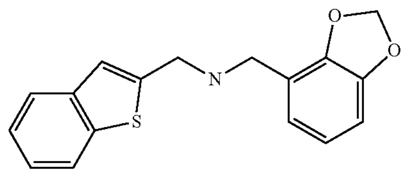

Analogue method A: 29% yield $^1$H NMR (300 MHz, CDCl3) δ 7.85-7.76 (m, 1H), 7.70 (dd, J=7.0, 1.9 Hz, 1H), 7.32 (qd, J=7.0, 1.6 Hz, 2H), 7.16 (s, 1H), 6.85-6.73 (m, 3H), 5.97 (s, 2H), 4.08 (d, J=1.1 Hz, 2H), 3.87 (s, 2H), 1.82 (s, 1H).

Example 48: Preparation of 1-(1,3-benzodioxol-4-yl)-N-[[3-(1-piperidyl)-4-pyridyl]methyl]methanamine

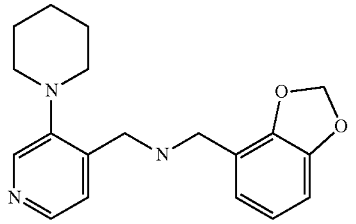

Method A: 10% yield $^1$H NMR (400 MHz, chloroform-d) δ 8.34 (s, 1H), 8.30 (d, J=4.8 Hz, 1H), 7.34 (d, J=4.8 Hz, 1H), 6.86-6.74 (m, 3H), 5.98 (s, 2H), 3.86 (s, 2H), 3.79 (s, 2H), 2.96-2.86 (m, 4H), 1.68 (p, J=5.5 Hz, 4H), 1.59 (d, J=5.5 Hz, 2H).

Example 49: Preparation of 1-(1,3-benzodioxol-5-yl)-N-[[2-(1-piperidyl)-4-pyridyl]methyl]methanamine

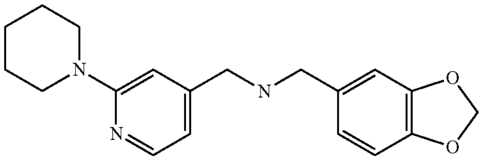 [SMILES: c1cc(CNCc2ccc3c(c2)OCO3)cc(N2CCCCC2)n1]

Method A: 19% yield $^1$H NMR (300 MHz, DMSO-d6) δ 7.98 (d, J=5.1 Hz, 1H), 6.90 (dd, J=5.3, 3.9 Hz, 1H), 6.84-6.76 (m, 3H), 6.56 (dd, J=5.1, 1.2 Hz, 1H), 5.97 (s, 2H), 3.60 (d, J=4.6 Hz, 4H), 3.48 (t, J=5.2 Hz, 4H), 2.59 (s, 1H), 1.56 (d, J=18.8 Hz, 6H).

Example 50: Preparation of 1-(3,4-dimethoxyphenyl)-N-[[2-(1-piperidyl)-4-pyridyl]methyl]methanamine

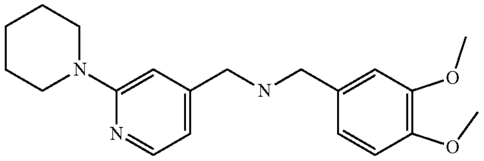 [SMILES: COc1ccc(CNCc2ccnc(N3CCCCC3)c2)cc1OC]

Method B: 53% yield $^1$H NMR (300 MHz, DMSO-d6) δ 7.98 (d, J=5.1 Hz, 1H), 6.94 (d, J=1.8 Hz, 1H), 6.89-6.74 (m, 3H), 6.56 (dd, J=5.0, 1.2 Hz, 1H), 3.72 (d, J=4.0 Hz, 6H), 3.57 (d, J=6.6 Hz, 4H), 3.48 (t, J=5.2 Hz, 4H), 2.64 (s, 1H), 1.63-1.46 (m, 6H).

Example 51: Preparation of 1-(3-methoxyphenyl)-N-[[2-(1-piperidyl)-4-pyridyl]methyl]methanamine

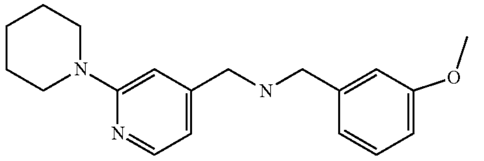 [SMILES: COc1cccc(CNCc2ccnc(N3CCCCC3)c2)c1]

Method A: 20% yield $^1$H NMR (300 MHz, DMSO-d6) δ 7.99 (d, J=5.1 Hz, 1H), 7.21 (t, J=7.8 Hz, 1H), 6.94-6.87 (m, 2H), 6.81-6.75 (m, 2H), 6.57 (dd, J=5.1, 1.2 Hz, 1H), 3.73 (s, 3H), 3.63 (s, 2H), 3.57 (s, 2H), 3.48 (t, J=5.1 Hz, 4H), 2.74-2.69 (m, 1H), 1.54 (td, J=10.7, 9.1, 5.3 Hz, 6H).

Example 52: Preparation of N-[(2-methoxyphenyl)methyl]-1-[2-(1-piperidyl)-4-pyridyl]methanamine

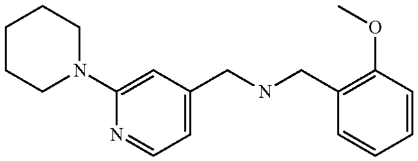 [SMILES: COc1ccccc1CNCc1ccnc(N2CCCCC2)c1]

Method A: 15% yield $^1$H NMR (300 MHz, DMSO-d6) δ 7.99 (d, J=5.1 Hz, 1H), 7.34 (dd, J=7.4, 1.8 Hz, 1H), 7.22 (ddd, J=9.1, 7.4, 1.8 Hz, 1H), 6.92 (qd, J=7.8, 1.1 Hz, 2H), 6.77 (s, 1H), 6.57 (dd, J=5.1, 1.2 Hz, 1H), 3.76 (s, 3H), 3.62 (d, J=3.7 Hz, 4H), 3.48 (t, J=5.2 Hz, 4H), 1.61-1.48 (m, 6H).

Example 53: Preparation of N-[(2-methoxyphenyl)methy]-1-[2-(1-piperidyl)-4-pyridyl]methanamine

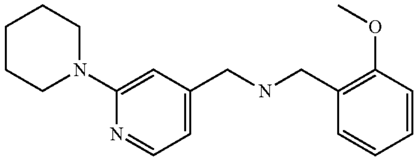 [SMILES: COc1ccccc1CNCc1ccnc(N2CCCCC2)c1]

Method A: 15% yield $^1$H NMR (300 MHz, DMSO-d6) δ 8.48 (ddd, J=4.9, 1.9, 0.9 Hz, 1H), 7.99 (d, J=5.1 Hz, 1H), 7.75 (td, J=7.7, 1.9 Hz, 1H), 7.46 (d, J=7.8 Hz, 1H), 7.24 (ddd, J=7.6, 4.8, 1.2 Hz, 1H), 6.77 (s, 1H), 6.57 (dd, J=5.1, 1.2 Hz, 1H), 3.76 (s, 2H), 3.63 (s, 2H), 3.48 (t, J=5.3 Hz, 4H), 2.84 (s, 1H), 1.66-1.45 (m, 6H).

Example 54: Preparation of 1-(1,3-benzodioxol-4-yl)-N-(2-thienylmethyl)methanamine

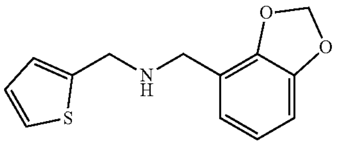 [SMILES: c1csc(CNCc2cccc3c2OCO3)c1]

Analogue method B: 35% yield $^1$H NMR (300 MHz, DMSO) δ: 7.40-7.34 (m, 1H), 6.95 (d, J=3.4 Hz, 2H), 6.90 (dd, J=5.6, 3.6 Hz, 1H), 6.84-6.77 (m, 2H), 5.97 (s, 2H), 3.86 (s, 2H), 3.66 (s, 2H), 2.78-2.55 (br, 1H).

Example 55: Preparation of N-(1,3-benzodioxol-4-ylmethyl)-1-(4-methoxyphenyl)-methanamine

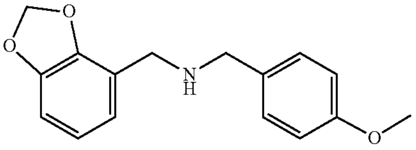 [SMILES: COc1ccc(CNCc2cccc3c2OCO3)cc1]

Method A: 35% yield $^1$H NMR (300 MHz, DMSO-d6) δ 3.79 (s, 3H), 3.67 (s, 4H), 7.30 (d, J=8.6 Hz, 2H), 6.98-6.85 (m, 5H), 6.03 (s, 2H).

Example 56: Preparation of 1-(1,3-benzodioxol-4-yl)-N-(1,3-benzodioxol-4-ylmethyl)methanamine

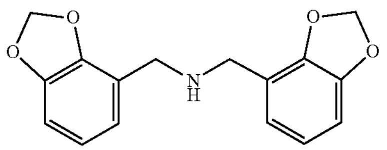 [SMILES: c1cc(CNCc2cccc3c2OCO3)c2c(c1)OCO2]

Method A: 20% yield $^1$H NMR (300 MHz, DMSO-d6) δ 6.98-6.85 (m, 2H), 6.82-6.74 (m, 4H), 5.97 (s, 4H), 3.65 (s, 4H).

Example 57: Preparation of N-(1,3-benzodioxol-4-ylmethyl)-1-phenyl-methanamine

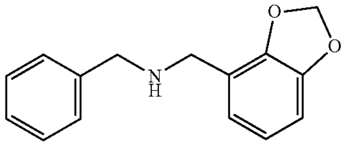 [SMILES: c1ccc(CNCc2cccc3c2OCO3)cc1]

Method A: 47% yield $^1$H NMR (300 MHz, DMSO-d6) δ 7.40-7.10 (m, 5H), 6.99-6.69 (m, 3H), 5.97 (s, 2H), 3.66 (d, J=15.1 Hz, 4H).

Example 58: Preparation of N-[(2-cyclohexyl-4-pyridyl)methyl]-1-(4-methoxyphenyl)methanamine

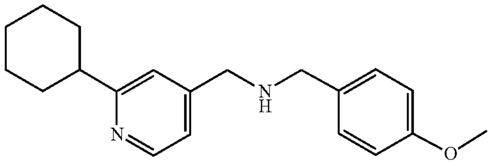

Method A: 22% yield $^1$H NMR (300 MHz, DMSO-d6) δ 8.40-8.31 (m, 1H), 7.30-7.10 (m, 4H), 6.93-6.82 (m, 2H), 3.73 (s, 3H), 3.62 (d, J=12.3 Hz, 4H), 2.62 (tt, J=11.7, 3.3 Hz, 1H), 1.93-1.64 (m, 5H), 1.58-1.04 (m, 5H).

Example 59: Preparation of 1-(1,3-benzodioxol-4-yl)-N-[[2-(1-piperidyl)-4-pyridyl]-methyl]ethanamine

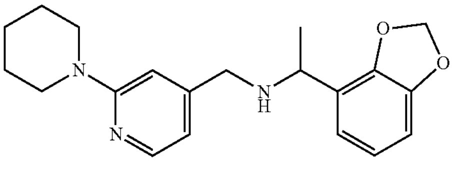

Method B: 11% yield $^1$H NMR (300 MHz, DMSO-d6) δ 7.96 (d, J=5.1 Hz, 1H), 6.94 (dd, J=7.6, 1.7 Hz, 1H), 6.90-6.75 (m, 2H), 6.69 (s, 1H), 6.52 (dd, J=5.1, 1.2 Hz, 1H), 5.96 (dd, J=9.6, 1.0 Hz, 2H), 3.82 (q, J=6.7 Hz, 1H), 3.58-3.37 (m, 6H), 2.55 (d, J=8.6 Hz, 1H), 1.55 (d, J=19.5 Hz, 6H), 1.27 (d, J=6.6 Hz, 3H).

Example 60: Preparation of 1-(4-methoxyphenyl)-N-[(2-thiomorpholino-4-pyridyl)methyl]methanamine

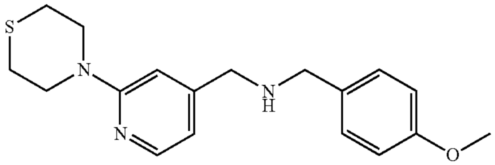 [SMILES: COc1ccc(CNCc2ccnc(N3CCSCC3)c2)cc1]

Method B: 47% yield $^1$H NMR (300 MHz, DMSO) δ: 8.01 (d, J=5.1 Hz, 1H), 7.28-7.19 (m, 2H), 6.91-6.83 (m, 2H), 6.78 (s, 1H), 6.60 (d, J=5.2 Hz, 1H), 3.93-3.83 (m, 4H), 3.73 (s, 3H), 3.58 (d, J=5.9 Hz, 4H), 2.61-2.55 (m, 4H).

Example 61: Preparation of N-[1-(2-methoxyphenyl)ethyl]-4,5-dimethyl-thiophene-2-carboxamide

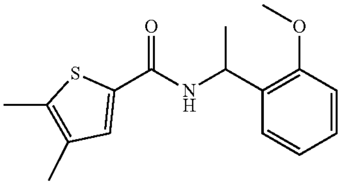 [SMILES: COc1ccccc1C(C)NC(=O)c1cc(C)c(C)s1]

Method E: 70% yield $^1$H NMR (300 MHz, DMSO-d6) δ 8.52 (d, J=8.3 Hz, 1H), 7.65 (s, 1H), 7.31 (dd, J=7.5, 1.7 Hz, 1H), 7.20 (ddd, J=9.0, 7.4, 1.7 Hz, 1H), 7.01-6.80 (m, 2H), 5.36 (p, J=7.1 Hz, 1H), 3.82 (s, 3H), 2.31 (s, 3H), 2.12 (s, 3H), 1.35 (d, J=6.9 Hz, 3H).

Example 62: Preparation of N-[1-(2-methoxyphenyl)ethyl]-4,5-dimethyl-thiophene-2-carboxamide

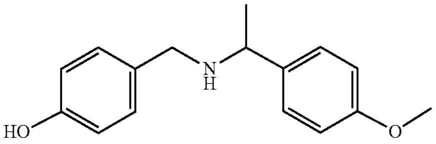 [SMILES: COc1ccc(C(C)NCc2ccc(O)cc2)cc1]

Method B: 19% yield $^1$H NMR (300 MHz, DMSO) δ: 9.16 (s, 1H), 7.28-7.21 (m, 2H), 7.09-7.00 (m, 2H), 6.91-6.84 (m, 2H), 6.71-6.62 (m, 2H), 3.73 (s, 3H), 3.61 (q, J=6.5 Hz, 1H), 3.42-3.33 (m, 2H), 2.31-2.11 (BR, 1H), 1.21 (d, J=6.6 Hz, 3H).

Example 63: Preparation of 1-(4-methoxyphenyl)-N-[(2-morpholino-4-pyridyl)methyl]methanamine

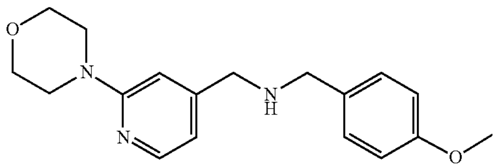 [SMILES: COc1ccc(CNCc2ccnc(N3CCOCC3)c2)cc1]

Method B: 30% yield $^1$H NMR (300 MHz, DMSO) δ: 8.03 (d, J=5.0 Hz, 1H), 7.29-7.19 (m, 2H), 6.90-6.82 (m, 2H), 6.78 (s, 1H), 6.67 (d, J=5.2 Hz, 1H), 3.73 (s, 3H), 3.71-3.64 (m, 4H), 3.59 (s, 4H), 3.46-3.37 (m, 4H), 2.76-2.56 (br, 1H).

Example 64: Preparation of 1-phenyl-N-[(2,4,5-trimethoxyphenyl)methyl]ethanamine

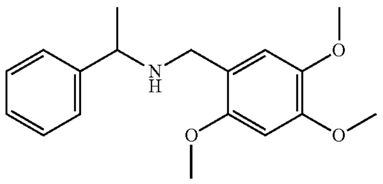 [SMILES: COc1cc(OC)c(OC)cc1CNC(C)c1ccccc1]

Method B: 88% yield $^1$H NMR (300 MHz, DMSO-d6) δ 7.41-7.15 (m, 5H), 6.90 (s, 1H), 6.63 (s, 1H), 3.76 (s, 3H), 3.69 (d, J=3.1 Hz, 6H), 3.43-3.35 (m, 2H), 1.24 (d, J=6.5 Hz, 3H).

Example 65: Preparation of N-[(4-methoxyphenyl)methyl]-4-methyl-thiophene-2-carboxamide

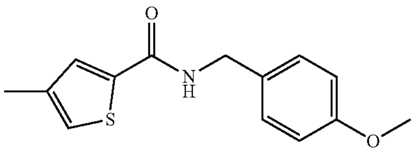

Method E: 48% yield $^1$H NMR (300 MHz, DMSO) δ: 8.88 (t, J=6.0 Hz, 1H), 7.59 (d, J=1.4 Hz, 1H), 7.36-7.30 (m, 1H), 7.26-7.18 (m, 2H), 6.92-6.84 (m, 2H), 4.35 (d, J=6.0 Hz, 2H), 3.72 (s, 3H), 2.21 (d, J=1.0 Hz, 3H).

Example 66: Preparation of 1-(4-methoxyphenyl)-N-[(3-pyrrolidin-1-ylphenyl)methyl]methanamine

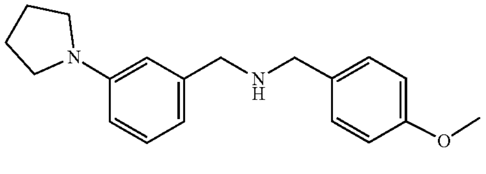 [SMILES: COc1ccc(CNCc2cccc(N3CCCC3)c2)cc1]

Method B: 49% yield $^1$H NMR (300 MHz, DMSO-d6) δ 7.27-7.20 (m, 2H), 7.08 (t, J=7.7 Hz, 1H), 6.91-6.81 (m, 2H), 6.58-6.50 (m, 2H), 6.45-6.30 (m, 1H), 3.73 (s, 3H), 3.57 (s, 4H), 3.20 (q, J=3.6 Hz, 4H), 1.97-1.89 (m, 4H).

Example 67: Preparation of N-[(3-cyclohexylphenyl)methyl]-1-(4-methoxyphenyl)methanamine

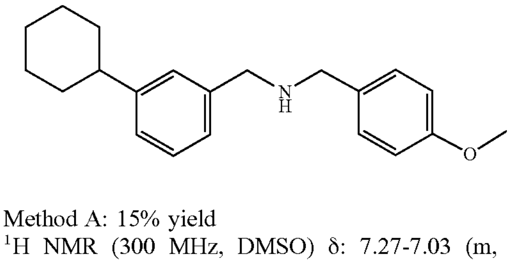

Method A: 15% yield $^1$H NMR (300 MHz, DMSO) δ: 7.27-7.03 (m, 6H), 6.91-6.82 (m, 2H), 3.73 (s, 3H), 3.60 (d, J=5.5 Hz, 4H), 2.46-2.41 (br, 1H), 1.82-1.65 (m, 5H), 1.46-1.15 (m, 6H).

Example 68: Preparation of N-(1,3-benzodioxol-4-ylmethyl)-1-(3-cyclohexylphenyl-)-methanamine

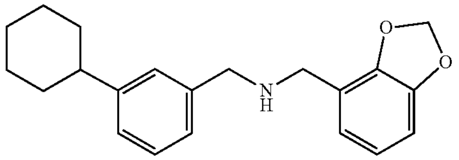 [SMILES: c1cc(CNCc2cccc3c2OCO3)cc(C2CCCCC2)c1]

Method A: 29% yield $^1$H NMR (300 MHz, DMSO) δ: 7.19 (d, J=7.4 Hz, 2H), 7.12 (dt, J=7.4, 1.6 Hz, 1H), 7.06 (dt, J=7.2, 1.6 Hz, 1H), 6.91 (dd, J=5.7, 3.5 Hz, 1H), 6.84-6.77 (m, 2H), 5.97 (s, 2H), 3.65 (s, 2H), 3.63 (s, 2H), 2.45 (s, 1H), 1.85-1.64 (m, 5H), 1.45-1.18 (m, 5H).

Example 69: Preparation of N-(chroman-4-ylmethyl)-1-(2-methoxyphenyl)methanamine

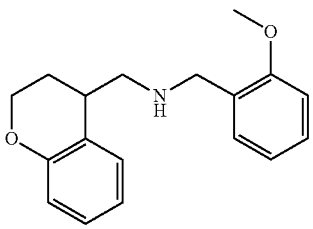 [SMILES: COc1ccccc1CNCC1CCOc2ccccc21]

Method B: 94% yield $^1$H NMR (300 MHz, DMSO-d6) δ 7.32 (dd, J=7.4, 1.8 Hz, 1H), 7.21 (dd, J=7.8, 1.8 Hz, 1H), 7.14 (dd, J=7.7, 1.7 Hz, 1H), 7.08-7.00 (m, 1H), 6.99-6.87 (m, 2H), 6.80 (td, J=7.4, 1.3 Hz, 1H), 6.71 (dd, J=8.1, 1.3 Hz, 1H), 4.17-4.00 (m, 2H), 3.77 (s, 3H), 3.72 (d, J=3.7 Hz, 2H), 2.89 (dd, J=9.7, 4.8 Hz, 1H), 2.79 (dd, J=11.8, 4.6 Hz, 1H), 2.64 (dd, J=11.8, 9.3 Hz, 1H), 1.99 (dddd, J=14.4, 13.2, 7.1, 4.1 Hz, 2H).

Example 70: Preparation of N-[3-(1-piperidyl)propyl]thiophene-2-carboxamide

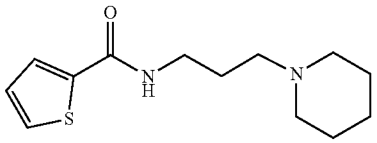 [SMILES: O=C(NCCCN1CCCCC1)c1cccs1]

Method E: 27% yield $^1$H NMR (300 MHz, DMSO-d6) δ 8.48 (t, J=5.7 Hz, 1H), 7.72 (td, J=4.7, 4.1, 1.2 Hz, 2H), 7.13 (dd, J=5.0, 3.7 Hz, 1H), 3.24 (td, J=7.1, 5.7 Hz, 2H), 2.36-2.22 (m, 6H), 1.78-1.54 (m, 2H), 1.48 (q, J=5.4 Hz, 4H), 1.37 (t, J=4.7 Hz, 2H).

Example 71: Preparation of N-(2-thienylmethyl)benzamide

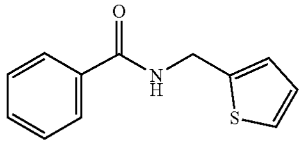 [SMILES: O=C(NCc1cccs1)c1ccccc1]

Method E: 8% yield $^1$H NMR (300 MHz, DMSO) δ: 9.13 (t, J=5.9 Hz, 1H), 7.87 (dt, J=6.8, 1.6 Hz, 2H), 7.59-7.42 (m, 3H), 7.38 (dd, J=5.0, 1.3 Hz, 1H), 7.06-6.99 (m, 1H), 6.96 (dd, J=5.0, 3.5 Hz, 1H), 4.63 (d, J=5.9 Hz, 2H).

Example 72: Preparation of 3-[[(4-methoxyphenyl) methylamino]methy]-N,N-dimethyl-aniline

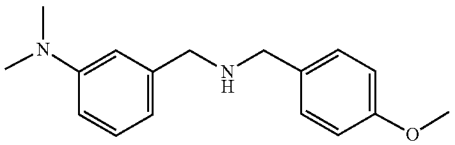

Method B: 10% yield $^1$H NMR (300 MHz, DMSO-d6) δ 7.98 (d, J=5.1 Hz, 1H), 7.25 (d, J=8.5 Hz, 2H), 6.92-6.82 (m, 2H), 6.61-6.48 (m, 2H), 3.73 (s, 3H), 3.58 (d, J=6.6 Hz, 4H), 3.00 (s, 6H).

Example 73: Preparation of N-[3-[(2-thienylmethyl-amino)methyl]phenyl]acetamide

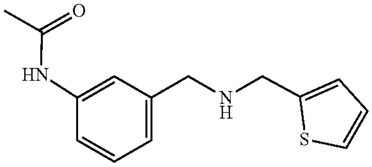 [SMILES: CC(=O)Nc1cccc(CNCc2cccs2)c1]

Method A: 9% yield $^1$H NMR (300 MHz, DMSO-d6) δ 9.89 (s, 1H), 7.58-7.39 (m, 2H), 7.41-7.29 (m, 1H), 7.22 (t, J=7.8 Hz, 1H), 7.05-6.85 (m, 3H), 3.85 (s, 2H), 3.65 (s, 2H), 2.03 (s, 3H).

Example 74: Preparation of 4-methoxy-N-[[2-(1-piperidyl)-4-pyridyl]methyl]benzamide

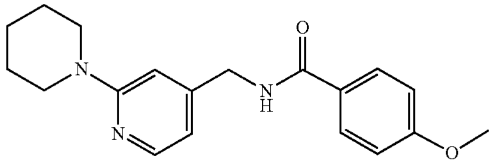 [SMILES: COc1ccc(C(=O)NCc2ccnc(N3CCCCC3)c2)cc1]

Method E: 16% yield $^1$H NMR (300 MHz, DMSO) δ: 8.86 (s, 1H), 7.99 (d, J=4.9 Hz, 1H), 7.87 (d, J=8.2 Hz, 2H), 7.01 (d, J=8.3 Hz, 2H), 6.70 (s, 1H), 6.50 (d, J=5.0 Hz, 1H), 4.36 (d, J=5.9 Hz, 2H), 3.81 (s, 3H), 3.47 (s, 4H), 1.52 (s, 6H).

Example 75: Preparation of 4-[[(4-methoxyphenyl) methylamino]methyl]-N,N-dimethyl-pyridin-2-amine

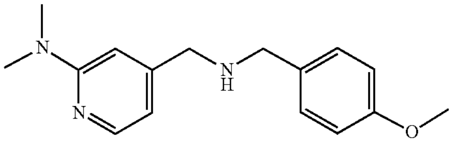

Method B: 33% yield $^1$H NMR (300 MHz, DMSO-d6) δ 7.32-7.19 (m, 2H), 7.10 (t, J=7.8 Hz, 1H), 6.89-6.84 (m, 2H), 6.71 (t, J=2.0 Hz, 1H), 6.63-6.53 (m, 2H), 3.73 (s, 3H), 3.59 (d, J=2.2 Hz, 4H), 2.88 (s, 6H).

Example 76: Preparation of N,N-diethyl-4-[[(4-methoxyphenyl)methylamino]methyl]pyridin-2-amine

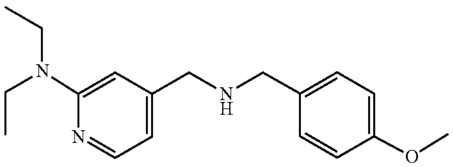 [SMILES: CCN(CC)c1cc(CNCc2ccc(OC)cc2)ccn1]

Method B: 16% yield $^1$H NMR (300 MHz, DMSO) δ: 7.94 (d, J=5.1 Hz, 1H), 7.28-7.20 (m, 2H), 6.90-6.84 (m, 2H), 6.53 (s, 1H), 6.46 (dd, J=5.1, 1.2 Hz, 1H), 3.73 (s, 3H), 3.59 (s, 2H), 3.55 (s, 2H), 3.46 (q, J=7.0 Hz, 4H), 2.65-2.54 (br, 1H), 1.08 (t, J=6.9 Hz, 6H).

Example 77: Preparation of 1-(3,4-dimethoxyphenyl)-N-[[2-(1-piperidyl)-4-pyridyl]methyl]methanamine

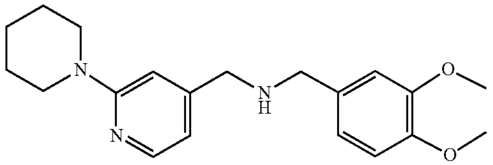 [SMILES: COc1ccc(CNCc2ccnc(N3CCCCC3)c2)cc1OC]

Method B: 13% yield

$^1$H NMR (300 MHz, DMSO) δ: 7.98 (d, J=5.0 Hz, 1H), 6.94 (d, J=1.8 Hz, 1H), 6.89-6.79 (m, 2H), 6.76 (s, 1H), 6.58-6.54 (m, 1H), 3.73 (s, 3H), 3.72 (s, 3H), 3.57 (d, J=6.6 Hz, 4H), 3.48 (t, J=5.3 Hz, 4H), 2.71-2.58 (br, 1H), 1.61-1.47 (m, 6H).

Example 78: Preparation of 2-methoxy-5-[[[2-(1-piperidyl)-4-pyridyl]methylamino]-methyl]phenol

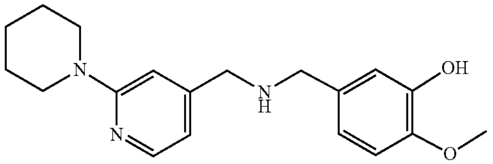 [SMILES: COc1ccc(CNCc2ccnc(N3CCCCC3)c2)cc1O]

Method B: 22% yield

$^1$H NMR (300 MHz, DMSO-d6) δ 8.82 (s, 1H), 7.98 (d, J=5.0 Hz, 1H), 6.86-6.69 (m, 5H), 6.59-6.52 (m, 1H), 3.73 (s, 3H), 3.55 (s, 4H), 3.48 (t, J=5.3 Hz, 4H), 1.56 (d, J=15.1 Hz, 6H).

Example 79: Preparation of N-[(5-methoxy-2-thienyl)methyl]-1-[2-(1-piperidyl)-4-pyridyl]methanamine

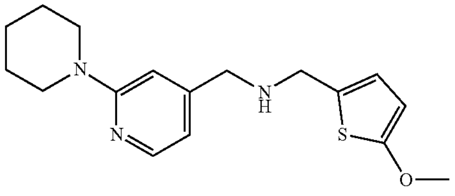 [SMILES: COc1ccc(CNCc2ccnc(N3CCCCC3)c2)s1]

Method B: 44% yield

$^1$H NMR (300 MHz, DMSO-d6) δ 7.99 (d, J=5.1 Hz, 1H), 6.75 (s, 1H), 6.55-6.50 (m, 2H), 6.08 (d, J=3.8 Hz, 1H), 3.80 (s, 3H), 3.67 (s, 2H), 3.58 (s, 2H), 3.49 (t, J=5.2 Hz, 4H), 1.60-1.48 (m, 6H).

Example 80: Preparation of N-[(2,6-dimethoxyphenyl)methyl]-1-[2-(1-piperidyl)-4-pyridyl]methanamine

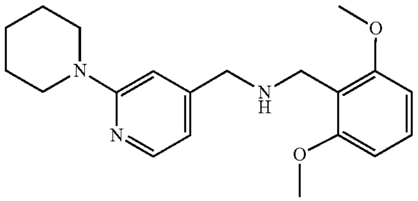 [SMILES: COc1cccc(OC)c1CNCc1ccnc(N2CCCCC2)c1]

Method B: 26% yield

$^1$H NMR (300 MHz, DMSO-d6) δ 7.98 (d, J=5.0 Hz, 1H), 7.20 (t, J=8.3 Hz, 1H), 6.74 (s, 1H), 6.64 (d, J=8.3 Hz, 2H), 6.53 (d, J=5.1 Hz, 1H), 3.75 (s, 6H), 3.65 (s, 2H), 3.55 (s, 2H), 3.47 (d, J=4.4 Hz, 4H), 1.54 (s, 6H).

Example 81: Preparation of 1-[2-(1-piperidyl)-4-pyridyl]-N-[[2-(1-piperidyl)-4-pyridyl]methyl]methanamine

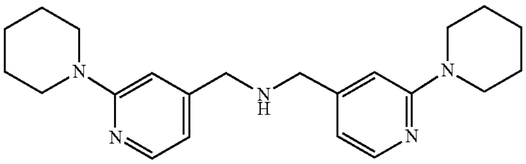 [SMILES: c1cc(CNCc2ccnc(N3CCCCC3)c2)cc(N2CCCCC2)n1]

Method A: 11% yield

$^1$H NMR (300 MHz, DMSO) δ: 7.99 (d, J=5.1 Hz, 2H), 6.75 (s, 2H), 6.56 (d, J=5.1 Hz, 2H), 3.57 (s, 4H), 3.48 (t, J=5.2 Hz, 8H), 1.62-1.47 (m, 12H).

Example 82: Preparation of 1-(4-methoxyphenyl)-N-[[2-(1-piperidyl)-4-pyridyl]-methyl]ethanamine

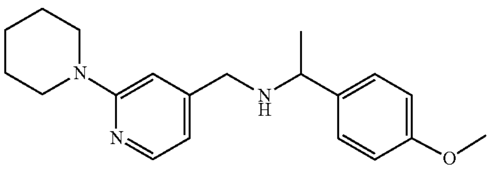 [SMILES: COc1ccc(C(C)NCc2ccnc(N3CCCCC3)c2)cc1]

Method B: 48% yield

$^1$H NMR (300 MHz, DMSO-d6) δ 7.96 (d, J=5.1 Hz, 1H), 7.30-7.17 (m, 2H), 6.94-6.78 (m, 2H), 6.68 (s, 1H), 6.56-6.45 (m, 1H), 3.73 (s, 3H), 3.60 (d, J=6.8 Hz, 1H), 3.47 (s, 4H), 3.40 (s, 1H), 1.55 (d, J=14.9 Hz, 6H), 1.23 (d, J=6.5 Hz, 3H).

FORMULATION EXAMPLES

Formulation Examples for Cosmetic Preparations

In the following tables, the decimal point is represented as a dot.

The following formulation examples F1 to F54 show a wide variety of formulations for cosmetic and pharmaceutical preparations. Cooling agent 0 means the cooling agent according to the invention according to compound 1, cooling agent 2 means compound 8, cooling agent 3 means compound 14, cooling agent 4 means compound 27, cooling agent 5 means compound 39, cooling agent 6 means compound 40, cooling agent 7 means compound 41, cooling agent 8 means compound 42, cooling agent 9 means compound 51.

TABLE F1

Transparent liquid soap (quantities in wt.-%)

| Components | INCI | Quantity |
|---|---|---|
| Tagat O 2 | PEG-20 Glyceryl Oleate | 2.5 |
| Coconut oil diethanolamine condensate | Cocamide DEA | 5.0 |
| Abil B 8842 | Cyclomethicone | 0.5 |
| Sodium laurylethersulfate, 28% | Sodium Laureth Sulfate | 35.0 |
| Tego-Betaine L7 | Cocamidopropyl Betaine | 5.0 |
| Soap, 25% | Coconut acid, Potassium salt, Potassium oleate | 20.0 |
| Hydrolite ® 5 | 1,2-Propanediol | 0.4 |
| Cooling agent 1 | | 1.0 |
| Water | Water | Ad 100 |

TABLE F2

Liquid syndet soap (quantities in wt.-%)

| Components | INCI | Quantity |
|---|---|---|
| Elfan OS 46 | Sodium Olefin C14-C16 Sulfonate | 35.5 |
| Armoteric LB | Lauryl Betaine | 8.0 |
| Elfan SG | | 10.0 |
| Elfacos GT 282 L | Talloweth-60 Myristyl Glycol | 3.0 |
| PCL Liquid 100 | Cetearyl Ethylhexanoate | 4.0 |
| Hydrolite ® 5 Green | Hydrolite ® 5 Green | 0.4 |
| Preservative | Methylchloroisothiazolinone | 0.1 |
| Cooling agent 2 | | 1.5 |
| Water | Water | Ad 100 |

TABLE F3

Body care lotion (quantities in wt.-%)

| Components | INCI | Quantity |
|---|---|---|
| Lumerol K 28 | Disodium Laureth Sulfosuccinate, Cocamidopropyl Betaine, Magnesium Lauryl Sulfate | 33.0 |
| Amphoteric surfactant B 4 | Cocamidopropyl Betaine | 10.0 |
| Pearlescent GM 4055 | MIPA-Pareth-25 Sulfate, Glycol Stearate | 4.0 |
| Sodium Chloride | Sodium Chloride | 2.0 |
| Avocado oil | Persea Gratissima (Avocado) Oil | 3.0 |
| Water | Water | Ad 100 |
| Hydrolite ® 5 | Hydrolite ® 5 Green | 0.5 |
| Euxyl ® K727 | Phenoxyethanol, Methyldibromo Glutaronitrile, Isothiazolinones | 0.3 |
| Cooling agent 3 | | 1.0 |

TABLE F4

Body care lotion with triclosan (quantities in wt.-%)

| Components | INCI | Quantity |
|---|---|---|
| Texapon N 25 | Sodium Laureth Sulfate | 37.5 |
| Lamepon S | Potassium Cocoyl Hydrolyzed Collagen | 28.0 |
| Lamesoft LMG | Hydrogenated Tallow Glycerides, TEA-Cocoyl Hydrolyzed Collagen | 5.0 |
| Lamesoft 156 | Glyceryl Laurate, TEA-Cocoyl Hydrolyzed Collagen | 5.0 |
| Sodium Chloride | Sodium Chloride | 1.7 |
| Irgasan DP 300 | Triclosan | 0.5 |
| Water | Water | Ad 100 |
| Hydrolite ® 5 | Hydrolite ® 5 Green | 0.3 |
| Euxyl ® K703 | Phenoxyethanol, Benzoic Acid, Dehydroacetic Acid | 0.4 |
| Cooling agent 4 | | 1.0 |

TABLE F5

Intimate wash (quantities in wt.-%)

| Components | INCI | Quantity |
|---|---|---|
| Tegobetaine HS | Cocamidopropyl Betaine, Glyceryl Laurate | 15.0 |
| Tagat L 2 | PEG-20 Glyceryl Laurate | 2.0 |
| Arlacide G | Chlorhexidine Digluconate | 0.1 |
| Rewoquat B 50 | Benzalkonium Chloride | 0.1 |
| Lactic acid, 80% | Lactic Acid | 0.1 |
| Water | Water | Ad 100 |
| Hydrolite ® 5 | Hydrolite ® 5 Green | 0.2 |
| Euxyl ® K700 | Potassium Sorbate, Benzyl Alcohol, Phenoxyethanol | 0.3 |
| Cooling agent 5 | | 1.3 |

TABLE F6

Liquid soap (quantities in wt.-%)

| Components | INCI | Quantity |
|---|---|---|
| Deionised water | Water | 2.0 |
| Soap bases mix | Sodium tallowates/palmitates | 95.8 |
| Titanium dioxide | Titanium dioxide | 1.0 |
| Hydrolite ® 5 | Hydrolite ® 5 Green | 1.2 |
| PreservativePreservative | Phenoxyethanol | 0.5 |
| Cooling agent 6 | | 1.0 |

TABLE F7

Shampoo (quantities in wt.-%)

| Ingredients (INCI) | Quantity |
|---|---|
| Sodium lauryl ether sulphate (e.g. Texapon NSO) | 12 |
| Cocamidopropyl betaine (e.g. Dehyton K) | 2 |
| Sodium chloride | 1.4 |
| Citric acid | 1.3 |
| 1,2-Pentanediol (Hydrolite ® 5) | 0.3 |
| Phenoxyethanol, methyl-, ethyl-, butyl- and propylparaben | 0.5 |
| Cooling agent 7 | 1.0 |
| Water | Ad 100 |

TABLE F8

2-in-1 Shampoo (quantities in wt.-%)

| Components | INCI | Quantity |
|---|---|---|
| Deionised water | Water | Ad 100 |
| Plantacare PS 10 | Sodium Laureth Sulfate, Lauryl Glucoside | 20.0 |

TABLE F8-continued

| 2-in-1 Shampoo (quantities in wt.-%) | | |
|---|---|---|
| Components | INCI | Quantity |
| Euperlan PK 771 | Glycol Distearate, Sodium Lauryl Sulfate, Cocamide MEA, Laureth-10 | 6.0 |
| Sodium chloride | Sodium Chloride | 1.4 |
| Citric acid monohydrate crystalline | Citric acid | 0.1 |
| Hydrolite ® 5 | Hydrolite ® 5 Green | 0.5 |
| Dragocid Liquid | Phenoxyethanol, Parabens | 0.5 |
| Cooling agent 8 | | 1.0 |

TABLE F9

| Anti-dandruff shampoo (quantities in wt.-%) | |
|---|---|
| Ingredients (INCI) | Quantity |
| Climbazole | 0.50 |
| Sodium Laureth Sulfate | 37.00 |
| Cocamidopropyl Betaine | 8.00 |
| PEG-6 Caprylic/Capric Glycerides | 2.50 |
| Laureth-2 | 2.00 |
| Water (Aqua), Glycerol, *Thymus Vulgaris* (Thyme), Flower/Leaf Extract | 0.50 |
| *Rosmarinus Officinalis* (Rosemary) Leaf Water, Water (Aqua), Butylene Glycol, Pentylene Glycol | 0.50 |
| Bisabolol | 0.10 |
| Panthenol | 0.50 |
| Polyquaternium-10 | 0.40 |
| 1,2-Pentanediol (Hydrolite ® 5) | 0.50 |
| Phenoxyethanol, methylparaben, ethylparaben, butylparaben, propylparaben, isobutylparaben | 0.70 |
| Cooling agent 9 | 1.50 |
| Water (Aqua) | Ad 100 |

TABLE F10

| Hair conditioner with Crinipan, rinse-off (quantities in wt.-%) | | |
|---|---|---|
| Components | INCI | Quantity |
| Lanette ® O | Cetearyl Alcohol | 4.00 |
| Dragoxat 89 | Ethylhexyl Isononanoate | 2.00 |
| Genamin ® KDM-P | Behentrimonium Chloride | 1.00 |
| SF 1550 | Phenyl trimethicone | 0.10 |
| Neo Heliopan ® BB | Benzophenone-3 | 0.10 |
| Crinipan ® AD | Climbazole | 0.80 |
| Glycerol 99.5 P. | Glycerol | 6.00 |
| Water | Water (Aqua) | Ad 100 |
| Actipone ® Alpha Pulp | Water (Aqua), Butylene Glycol, Malic Acid, *Actinidia Chinensis* (Kiwi) Fruit Juice, Citrus, *Aurantium Dulcis* (Orange), Juice, Citrus Paradisi (Grapefruit) Juice, *Pyrus Malus* (Apple) Juice, Trideceth-9, *Prunus Amygdalus Dulcis* (Sweet Almond) Seed Extract | 0.50 |
| Extrapone ® Bamboo P | Propylene Glycol, Water (Aqua), Butylene Glycol, *Bambusa Vulgaris* Shoot Extract | 0.50 |
| Sodium Hydroxide 10% solution | Sodium Hydroxide | 0.40 |
| Colour I | Colour | 0.60 |
| Colour II | Colour | 0.30 |

TABLE F10-continued

| Hair conditioner with Crinipan, rinse-off (quantities in wt.-%) | | |
|---|---|---|
| Components | INCI | Quantity |
| Hydrolite ® 5 | Hydrolite ® 5 Green | 0.40 |
| PreservativePreservative | Methylparaben | 0.20 |
| Cooling agent 1 | | 1.2 |

TABLE F11

| Sprayable hair conditioner with zinc pyrithrione-leave-on (quantities in wt.-%) | | |
|---|---|---|
| Components | INCI | Quantity |
| Monomuls 60-35 C | Hydrogenated Palm Glycerides | 1.70 |
| Cetiol OE | Dicaprylyl ether | 7.20 |
| Abil 100 | Dimethicone | 3.60 |
| Dehyquart F 75 | Distearoylethyl Hydroxyethylmonium. Methosulfate, Cetearyl Alcohol | 4.00 |
| Eumulgin B1 | Ceteareth-12 | 3.50 |
| Cetiol S | Diethylhexylcyclohexane | 7.20 |
| D-Panthenol | Panthenol | 0.10 |
| Glycerol 99.5 P. | Glycerol | 1.50 |
| Water | Water (Aqua) | Ad 100 |
| Actipone ® Rosemary | Water (Aqua), Propylene, Glycol, *Rosmarinus Officinalis*, (Rosemary) Leaf Extract | 0.10 |
| Frescolat ® ML Cryst. | Menthyl Lactate | 0.50 |
| Dragosantol 100 | Bisabolol | 0.10 |
| Zinc Omadine | Zinc pyrithione | 0.10 |
| Hydrolite ® 5 | Hydrolite ® 5 | 0.40 |
| Phenonip ® | Phenoxyethanol, methylparaben, ethylparaben, butylparaben, propylparaben, isobutylparaben | 0.30 |
| Cooling agent 1 | | 1.50 |

TABLE F12

| Hair conditioner with UV protection (quantities in wt.-%) | | |
|---|---|---|
| Components | INCI | Quantity |
| Renex PEG 6000 | PEG-150 | 2.50 |
| Hair Conditioner Base | Cetyl alcohol, Behentrimonium chloride, *Triticum Vulgare* (Wheat) bran extract, Linoleic acid | 3.00 |
| PCL-Solid | Stearyl heptanoate, Stearyl caprylate | 0.50 |
| Dow Corning 5200 | Laurylmethicone copolyol | 0.50 |
| Natrosol 250 HR | Hydroxyethylcellulose | 0.50 |
| Benzophenone-4 | Benzophenone-4 | 1.00 |
| Neo Heliopan AP | Disodium phenyldibenz-imidazole tetrasulphonate | 1.00 |
| Amino methyl propanol | Amino methyl propanol | 2.00 |
| Dow Corning 949 cationic emulsion | Amodimethicone, Cetrimonium chloride, Trideceth-12 | 2.00 |
| Hydrolite ® 5 | Hydrolite ® 5 | 0.80 |
| 1,2-hexanediol | 1,2-hexanediol | 0.50 |
| Cooling agent 2 | | 1.50 |
| Water | Water (Aqua) | Ad 100 |

TABLE F13

| Shower gel (quantities in wt.-%) | | |
|---|---|---|
| Components | INCI | Quantity |
| Deionised water | Water | Ad 100 |
| Plantacare PS 10 | Sodium Laureth Sulfate, Lauryl Glucoside | 20.0 |

TABLE F13-continued

| Shower gel (quantities in wt.-%) | | |
|---|---|---|
| Components | INCI | Quantity |
| Sodium chloride | Sodium Chloride | 1.4 |
| Citric acid monohydrate crystalline | Citric Acid | 1.3 |
| Hydrolite ® 5 | Hydrolite ® 5 | 0.6 |
| Sym Diol ® 68 | 1,2-hexanediol, caprylyl glycol | 0.4 |
| Cooling agent 3 | | 0.9 |

TABLE F14

| Shaving foam (quantities in wt.-%) | |
|---|---|
| Ingredients (INCI) | Quantity |
| Dem. Water | 77.2 |
| Triethanolamine | 4.0 |
| Edenor L2 SM (Stearinic acid, Palmitinic acid) (Cognis) | 5.3 |
| Laureth-23 | 3.0 |
| Stearylalcohol | 0.5 |
| Sodium lauryl sulphate | 3.0 |
| Extrapone Seaweed (Water, Propylene glycol, Potassium iodide, *Fucus Vesiculosus* Extract) | 1.0 |
| Dragosantol (bisabolol, farnesol) | 0.1 |
| 1,2-Pentanediol (Hydrolite ® 5) | 1.0 |
| Euxyl ® K220 (Methylisothiazolinone, Ethylhexylglyerol) | 0.6 |
| Cooling agent 4 | 0.6 |
| Propane, Butane 4.2 Bar | 4.0 |

TABLE F15

| Depilatory cream (quantities in wt.-%) | |
|---|---|
| Ingredients (INCI) | Quantity |
| Cetearyl alcohol | 10.0 |
| Ceteareth-12 | 2.0 |
| PCL Liquid (Cetearylethylhexanoate, Isopropylmyristate) | 3.0 |
| Dragosantol (bisabolol, farnesol) | 0.1 |
| Edenor L2 SM (Stearinic acid, Palmitinic acid) | 1.0 |
| Dem. Water | 52.2 |
| Urea | 5.0 |
| Dem. Water | 10.0 |
| Calcium thioglycolate | 6.0 |
| Sodium hydroxide solution, 10% | 10.0 |
| 1,2-Pentanediol (Hydrolite ® 5) | 0.5 |
| Neo Dragocid Powder (Methyl parabene, Sorbinic acid, Dehydro acetic acid, Propyl parabene) | 0.2 |
| Cooling agent 5 | 2.0 |

TABLE F16

| After Shave Tonic (quantities in wt.-%) | | |
|---|---|---|
| Components | INCI | Quantity |
| SymSol ® PF-3 | Water (Aqua), Pentylene Glycol, Sodium Lauryl Sulfoacetate, SodiumOleoyl Sarcosinate, Sodium Chloride, Disodium Sulfoacetate, SodiumOleate, Sodium Sulfate | 3.00 |
| SymSitive ® 1609 | Pentylene glycol, 4-t-butylcyclohexanol | 1.00 |
| Frescolat ® ML | Menthyl Lactate | 0.30 |
| Glycerol 99.5 P. | Glycerol | 5.00 |
| Water | Water (Aqua) | Ad 100 |
| Extrapone ® Glacier Water GW | Glycerol, water (aqua) | 1.00 |
| SymCalmin ® | Butylene Glycol, Pentylene Glycol, Hydroxyphenyl Propamidobenzoic Acid | 0.50 |

TABLE F16-continued

| After Shave Tonic (quantities in wt.-%) | | |
|---|---|---|
| Components | INCI | Quantity |
| Dragosine ® | Carnosine | 0.10 |
| Hydrolite ® 5 | Pentylene glycol | 5.00 |
| Ethanol 96% | Alcohol Denat. | 5.00 |
| Colour Pigment | Colour Pigment | 0.05 |
| Hydrolite ® 5 | 1,2-Pentanediol | 0.15 |
| Cooling agent 6 | | 1.00 |

TABLE F17

| Deodorant formulation as roll-on gel (quantities in wt.-%) | |
|---|---|
| Ingredients (INCI) | Quantity |
| 1,3-Butylene glycol | 2.00 |
| PEG-40-hydrogenated castor oil | 2.00 |
| Hydroxyethylcellulose | 0.50 |
| 1,2-Pentanediol (Hydrolite ® 5) | 0.30 |
| 1,3-Propanediol | 0.50 |
| 3-Phenylpropanol | 0.40 |
| Ethylhexyl glycerin | 0.10 |
| Cooling agent 7 | 0.50 |
| Water | Ad 100.00 |

TABLE F18

| Clear roll-on deodorant (quantities in wt.-%) | | |
|---|---|---|
| Components | INCI | Quantity |
| Methocel E4M Premium | Hydroxypropyl Methylcellulose | 0.50 |
| Water | Water (Aqua) | Ad 100 |
| Neo-PCL Water Soluble N | Trideceth-9, PEG-5 Ethylhexanoate, Water (Aqua) | 1.00 |
| Solubilizer | PEG-40 Hydrogenated Castor Oil, Trideceth-9, Propylene Glycol, Water (Aqua) | 3.00 |
| Deolite | Dimethyl Phenylpropanol, Pentylene Glycol | 0.50 |
| Locron LW | Aluminium chlorohydrate | 25.00 |
| Aloe Vera Gel Concentrate 10/1 | Aloe *Barbadensis* Leaf Juice | 1.00 |
| Propylene Glycol-1.2 99 P GC | Propylene glycol | 4.00 |
| Ethanol 96% | Alcohol Denat. | 30.00 |
| Hydrolite ® 5 | 1,2-Pentanediol | 1.00 |
| Cooling agent 8 | | 1.25 |

TABLE F19

| Deodorant stick (quantities in wt.-%) | |
|---|---|
| Ingredients (INCI) | Quantity |
| Sodium stearate | 8.00 |
| PPG-3 Myristyl ether | 70.00 |
| 1,2-Propylene glycol | 10.00 |
| 1,1-Dimethyl-3-phenylpropanol | 0.20 |
| 2-Butyloctanoic acid | 0.20 |
| 1,2-Pentanediol (Hydrolite ® 5) | 0.60 |
| Heptoxy-1,2-propanediol | 0.20 |
| Phenoxyethanol | 0.30 |
| Cooling agent 9 | 1.50 |
| Water | Ad 100 |

TABLE F20

| Antiperspirant stick (quantities in wt.-%) | | |
|---|---|---|
| Components | INCI | Quantity |
| PCL Liquid 100 | Cetearyl ethylhexanonate | to 100 |
| Silicone Fluid 345 | Cyclomethicone | 10.00 |
| CRODACOL C90 | Cetyl Alcohol | 8.00 |
| SYNCROWAX HGLC | C18-36 triglycerides | 8.00 |
| CRODAMOL PTC | Pentaerythritol Tetracaprylate/Caprate | 5.00 |
| SYNCROWAX HRC | Tribehenin | 4.00 |
| VOLPO N5 | Oleth-5 | 1.00 |
| Titanium Dioxide | | 1.00 |
| Rezal 36GP | Aluminium Tetrachlorohydrex GLY | 20.00 |
| Dry Flo C | Aluminium Starch Octenyl Succinate | 22.50 |
| Hydrolite ® 5 | 1,2-Pentanediol | 0.60 |
| Preservative | Phenoxyethanol | 0.40 |
| Hexoxy-1,2-propanediol | | 0.10 |
| Cooling agent 1 | | 1.40 |

TABLE F21

| Pump spray (quantities in wt.-%) | | |
|---|---|---|
| Components | INCI | Quantity |
| SymClariol ® | Decylene glycol | 0.50 |
| Solubilizer | PEG-40 Hydrogenated Castor Oil, Trideceth-9, Propylene Glycol, Water (Aqua) | 4.00 |
| Neo-PCL Water Soluble N | Trideceth-9, PEG-5 Ethylhexanoate, Aqua | 1.50 |
| SymRelief ® | Bisabolol. *Zingiber Officinale* (Ginger) Root Extract | 0.10 |
| Water | Water (Aqua) | Ad 100 |
| 1,2-Propylene Glycol | Propylene glycol | 6.00 |
| Hydrolite ® 5 | 1,2-Pentanediol | 0.40 |
| Sym Diol ® 68 | 1,2-hexanediol, caprylyl glycol | 0.20 |
| Cooling agent 1 | | 1.40 |

TABLE F22

| Antiperspirant (quantities in wt.-%) | |
|---|---|
| Ingredients (INCI) | Quantities |
| Reach AZP-908 SUF | 24.00 |
| Cyclomethicone (Pentamer) | Ad 100 |
| Polydecene (Silkflo 364 NF) | 17.50 |
| Neo Heliopan OS (ethylhexyl salicylate) | 2.50 |
| L-Menthyl lactate (Frescolate ML) | 0.25 |
| Polyethylene | 3.00 |
| Hydrogenated castor oil | 2.00 |
| Promyristyl PM-3 | 7.00 |
| PEG-8 Distearate | 3.00 |
| Silicon dioxide (Cab-O-Sil M-5) | 1.00 |
| Stearyl alcohol | 15.00 |
| Octyldodecanol | 0.10 |
| 1,2-Pentanediol (Hydrolite ® 5) | 0.80 |
| 3-Phenylpropanol | 0.40 |
| Cooling agent 2 | 1.60 |

TABLE F23

| Spray deodorant with triclosan (quantities in wt.-%) | |
|---|---|
| Ingredients (INCI) | Quantity |
| PEG-40-hydrogenated castor oil | 3.00 |
| Ethylhexylglycerol (Octoxyglycerol) | 0.80 |
| Ethanol | 40.00 |
| Citrate buffer | 0.50 |

TABLE F23-continued

| Spray deodorant with triclosan (quantities in wt.-%) | |
|---|---|
| Ingredients (INCI) | Quantity |
| Triclosan ® (5-chloro-2-(2,4-dichlorophenoxy)phenol) | 0.25 |
| 1,2-Pentanediol (Hydrolite ® 5) | 0.75 |
| Phenoxyethanol | 0.40 |
| Cooling agent 3 | 1.40 |
| Water | Ad 100 |

TABLE F24

| O/W Lotion (quantities in wt.-%) | |
|---|---|
| Ingredients (INCI) | Quantity |
| Paraffin oil | 5.00 |
| Isopropyl palmitate | 5.00 |
| Cetyl alcohol | 2.00 |
| Beeswax | 2.00 |
| Ceteareth-20 | 2.00 |
| PEG-20-glyceryl stearate | 1.50 |
| Glycerol | 3.00 |
| 1,2-Pentanediol (Hydrolite ® 5) | 0.30 |
| Methylparaben | 0.30 |
| Cooling agent 4 | 1.00 |
| Water | Ad 100.00 |

TABLE F25

| Body lotion (quantities in wt.-%) | |
|---|---|
| Ingredients (INCI) | Quantity |
| Cetearyl Alcohol | 2.00 |
| Ethylhexyl Isononanoate | 5.00 |
| Cetearyl Ethylhexanoate, Isopropyl Myristate | 3.00 |
| Glyceryl Oleate Citrate, Caprylic/Capric Triglyceride | 4.00 |
| Water (Aqua) | 79.50 |
| Carbomer | 0.30 |
| Sodium Benzoate | 0.100 |
| Propylene glycol | 5.00 |
| Sodium Hydroxide 30% solution | 0.30 |
| 1,2-Pentanediol (Hydrolite ® 5) | 0.30 |
| Triethylene Glycol, Imidazolidinyl Urea, Methylparaben, Propylparaben, Dehydroacetic Acid | 0.30 |
| Cooling agent 5 | 1.30 |

TABLE F26

| Cream (quantities in wt.-%) | |
|---|---|
| Ingredients (INCI) | Quantity |
| Paraffin oil | 10.00 |
| Ozokerite | 4.00 |
| Vaseline | 4.00 |
| Vegetable oil | 10.00 |
| Wool wax alcohol | 2.00 |
| Aluminum stearate | 0.40 |
| 1,2-Pentanediol (Hydrolite ® 5) | 2.00 |
| Phenoxyethanol | 0.50 |
| Cooling agent 6 | 1.50 |
| Water | Ad 100.00 |

TABLE F27

| Cream (quantities in wt.-%) | | |
|---|---|---|
| Components | INCI | Quantity |
| Dracorin ® CE | Glyceryl Stearate Citrate | 1.00 |
| Lanette ® O | Cetearyl Alcohol | 2.00 |
| Cutina ® GMS-V | Glyceryl Stearate | 1.00 |
| Tegosoft ® MM | Myristyl Myristate | 1.00 |
| Xiameter ® PMX-0246. cyclosiloxane | Cyclohexasiloxane (and) Cyclopentasiloxane | 0.50 |
| Dragoxat ® 89 | Ethylhexyl Isononanoate | 2.00 |
| PCL Liquid 100 | Cetearyl Ethylhexanoate | 4.00 |
| Neutral Oil | Caprylic/Capric Triglyceride | 4.00 |
| Carbopol ® Ultrez 21 | Acrylates/C10-30 Alkyl Acrylate Crosspolymer | 0.20 |
| Keltrol ® CG-T | Xanthan gum | 0.10 |
| Water | Water (Aqua) | Ad 100 |
| Glycerol 99.5 P. | Glycerol | 3.00 |
| Propylene Glycol-1.2 99 P GC | Propylene glycol | 2.00 |
| Sodium Benzoate | Sodium Benzoate | 0.10 |
| Sodium Hydroxide 10% solution | Sodium Hydroxide | 0.50 |
| Hydrolite ® 5 | 1,2-Pentanediol | 0.30 |
| Euxyl ® K702 | Dehydroacetic Acid, Benzoic Acid, Phenoxyethanol, Polyaminopropyl Biguanide, Ethylhexylglycerin | 0.30 |
| Cooling agent 7 | | 2.00 |

TABLE F28

| Hand and body cream (quantities in wt.-%) | | |
|---|---|---|
| Components | INCI | Quantity |
| Dracorin ® GOC | Glyceryl Oleate Citrate, Caprylic/ Capric Triglyceride | 2.00 |
| PCL-Solid | Stearyl Heptanoate, Stearyl Caprylate | 2.50 |
| Lanette ® O | Cetearyl Alcohol | 1.50 |
| Cutina ® GMS-V | Glyceryl Stearate | 1.00 |
| Dragoxat ® 89 | Ethylhexyl Isononanoate | 3.00 |
| PCL Liquid 100 | Cetearyl Ethylhexanoate | 7.00 |
| Isodragol ® | Triisononanoin | 4.00 |
| Xiameter ® PMX-0345 Cyclosiloxane | Cyclopentasiloxane (and) Cyclohexasiloxane | 0.50 |
| Water | Water (Aqua) | Ad 100 |
| Carbopol ® Ultrez 21 | Acrylates/C10-30 Alkyl Acrylate Crosspolymer | 0.20 |
| Keltrol ® CG-RD | Xanthan gum | 0.10 |
| Glycerol 85 P. | Glycerol | 3.00 |
| DragoBetaGlucan | Water (Aqua), Butylene Glycol, Glycerol, *Avena Sativa* (Oat) Kernel Extract | 1.50 |
| Potassium Sorbate | Potassium Sorbate | 0.10 |
| Sodium Hydroxide 10% solution | Sodium Hydroxide | 0.50 |
| Hydrolite ® 5 | 1,2-Pentanediol | 0.20 |
| Euxyl ® K300 | Methyl-, butyl-, ethyl-, propyl-, isobutylparaben, phenoxyethanol | 0.30 |
| Cooling agent 8 | | 1.00 |

TABLE F29

| Face cream (quantities in wt.-%) | | |
|---|---|---|
| Components | INCI | Quantity |
| Emulsiphos ® | Potassium Cetyl Phosphate, Hydrogenated Palm Glycerides | 1.50 |
| Cutina ® GMS-V | Glyceryl Stearate | 1.70 |
| Lanette ® O | Cetearyl Alcohol | 3.00 |
| Tegosoft ® MM | Myristyl Myristate | 1.00 |
| PCL Liquid 100 | Cetearyl Ethylhexanoate | 1.00 |
| Isodragol ® | Triisononanoin | 3.00 |
| Dragoxat ® 89 | Ethylhexyl Isononanoate | 4.00 |

TABLE F29-continued

| Face cream (quantities in wt.-%) | | |
|---|---|---|
| Components | INCI | Quantity |
| Avocado Oil | *Persea Gratissima* (Avocado) Oil | 3.00 |
| Abil ® 350 | Dimethicone | 0.50 |
| Covi-ox ® T-70 | Tocopherol | 0.10 |
| Edeta ® BD | Disodium EDTA | 0.10 |
| Carbopol ® Ultrez 21 | Acrylates/C10-30 Alkyl Acrylate Crosspolymer | 0.30 |
| Keltrol ® CG-RD | Xanthan gum | 0.150 |
| Water | Water (Aqua) | Ad 100 |
| Glycerol 99.5 P. | Glycerol | 4.00 |
| Propylene Glycol-1.2 99 P GC | Propylene glycol | 3.00 |
| SymMatrix ® | Maltodextrin. *Rubus Fruticosus* (Blackberry) Leaf Extract | 0.50 |
| Sodium Hydroxide 10% solution | Sodium Hydroxide | 0.50 |
| Hydrolite ® 5 | 1,2-Pentanediol | 0.30 |
| Euxyl ® K712 | Sodium Benzoate, Potassium Sorbate | 0.20 |
| Cooling agent 9 | | 1.00 |

TABLE F30

| Moisturising cream (quantities in wt.-%) | |
|---|---|
| Ingredients (INCI) | Quantity |
| PEG-7 hydrogenated castor oil | 6.00 |
| Cetearyl ethyl hexanoate | 10.00 |
| Isopropyl myristate | 5.00 |
| Mineral oil | 7.00 |
| Shea Butter (*Butyrospermum parkii*) | 0.50 |
| Aluminum stearate | 0.50 |
| Magnesium stearate | 0.50 |
| Bisabolol | 0.20 |
| Quaternium-18 hectorite | 0.70 |
| Dipropylene glycol | 5.0 |
| Magnesium sulphate | 0.70 |
| 1,2-Pentanediol (Hydrolite ® 5) | 4.00 |
| Preservative (phenoxyethanol) | 0.20 |
| Cooling agent 1 | 1.00 |
| Aqua dem. | 58.90 |

TABLE F31

| Anti-wrinkle cream (quantities in wt.-%) | |
|---|---|
| Ingredients (INCI) | Quantity |
| Glyceryl Stearate Citrate | 1.00 |
| Glyceryl Laurate | 1.00 |
| Cetearyl Alcohol (and) Myristyl Myristate | 3.00 |
| Cetearyl Ethylhexanoate | 4.00 |
| Mineral oil | 4.00 |
| Cyclohexasiloxane | 0.50 |
| Acrylates/C10-30 Alkyl Acrylate Crosspolymer | 0.20 |
| Water | Ad 100 |
| 1,2-hexanediol | 2.00 |
| Sodium Hydroxide 10% solution | 0.10 |
| *Narcissus Tazetta* Bulb Extract | 1.00 |
| 1,2-Pentanediol (Hydrolite ® 5) | 0.30 |
| Preservative (phenoxyethanol) | 0.50 |
| Cooling agent 1 | 1.50 |

TABLE F32

| Disinfectant skin care oil (quantities in wt.-%) | | |
|---|---|---|
| Components | INCI | Quantity |
| Neutral Oil | Caprylic/Capric Triglyceride | Ad 100 |
| Sweet Almond Oil | *Prunus Dulcis* | 20.00 |
| Dragoxat ® 89 | Ethylhexyl Isononanoate | 4.00 |
| Isopropyl palmitate | Isopropyl palmitate | 6.00 |
| PCL Liquid 100 | Cetearyl Ethylhexanoate | 15.00 |
| Dragosantol ® 100 | Bisabolol | 0.20 |
| Retinyl Acetate In Oil (1 million 1e/G) | Retinyl Acetate | 0.50 |
| Vitamin E Acetate | Tocopheryl Acetate | 0.50 |
| Covi-ox ® T-70 | Tocopherol | 0.10 |
| Hydrolite ® 5 | 1,2-Pentanediol | 0.30 |
| Preservative | Methyl, butyl, ethyl, propyl paraben | 0.30 |
| Cooling agent 2 | | 1.00 |

TABLE F33

| Antiseptic wound cream (quantities in wt.-%) | |
|---|---|
| Ingredients (INCI) | Quantity |
| Sorbitan Isostearate, Hydrogenated Castor Oil, Ceresin, Beeswax (*Cera Alba*) | 6.00 |
| Petrolatum | 21.00 |
| *Cera Alba* | 5.00 |
| Cetearyl Alcohol | 7.00 |
| *Prunus Dulcis* | 7.00 |
| Lanolin | 5.00 |
| *Paraffinum Liquidum* | 12.00 |
| Water (Aqua) | Ad 100 |
| Panthenol | 7.00 |
| Magnesium sulphate | 0.70 |

TABLE F33-continued

| Antiseptic wound cream (quantities in wt.-%) | |
|---|---|
| Ingredients (INCI) | Quantity |
| 1,2-Pentanediol (Hydrolite ® 5) | 1.00 |
| Tocopheryl Acetate | 1.00 |
| Octenidine dihydrochloride | 0.10 |
| Phenoxyethanol | 0.50 |
| Cooling agent 3 | 1.50 |

TABLE F34

| Moisturising mask (quantities in wt.-%) | | |
|---|---|---|
| Components | INCI | Quantity |
| Water | Water (Aqua) | Ad 100 |
| Stabileze QM | PVM/MA Decadiene Crosspolymer | 0.50 |
| Biotive ® L-Arginine | Arginine | 0.75 |
| Actipone ® Laminaria Saccharina GW | Glycerol, Water (Aqua), Laminaria Saccharina Extract | 1.00 |
| Extrapone ® Cucumber | Water (Aqua), Propylene Glycol, *Cucumis Sativus* (Cucumber) Juice | 1.00 |
| Glycerol 99.5 P. | Glycerol | 7.00 |
| Neo Actipone ® Soap Nutshell | Sapindus Mukurossi Peel Extract | 0.50 |
| Colour I | Colour | 0.01 |
| Hydrolite ® 5 | Pentylene glycol | 5.00 |
| Solubilizer | PEG-40 Hydrogenated Castor Oil, Trideceth-9, Water (Aqua) | 0.60 |
| Hydrolite ® 5 | 1,2-Pentanediol | 0.08 |
| Preservative | Phenoxyethanol | 0.40 |
| Cooling agent 4 | | 1.00 |

TABLE F35

| Sprayable disinfectant gel (quantities in wt.-%) | | |
|---|---|---|
| Components | INCI | Quantity |
| Water | Water (Aqua) | Ad 100 |
| Stabileze QM | PVM/MA Decadiene Crosspolymer | 0.25 |
| Sodium Hydroxide 10% solution | Sodium Hydroxide | 0.40 |
| Caffeine pure | Caffeine | 0.50 |
| Extrapone ® Horse Chestnut | Propylene Glycol, Water (Aqua), Glucose, Aesculus Hippocastanum (Horse Chestnut) Seed Extract, Lactic Acid | 1.00 |
| Hydrolite ® 5 | 1,2-Pentanediol | 3.00 |
| 1,3-Butylene Glycol | Butylene glycol | 5.00 |
| Biotive ® Esculin Sesquihydrate | Esculin | 0.30 |
| Ethanol 96% | Alcohol Denat. | 10.00 |
| Solubilizer | PEG-40 Hydrogenated Castor Oil, Trideceth-9, Water (Aqua) | 0.50 |
| Octenidine dihydrochloride | | 0.10 |
| Preservative | Phenoxyethanol | 0.70 |
| Cooling agent 5 | | 1.00 |

TABLE F36

| Mineral washing and cleansing gel (quantities in wt.-%) | | |
|---|---|---|
| Components | INCI | Quantity |
| Water | Water (Aqua) | Ad 100 |
| Pionier ® NP 37 G | Sodium carbomer | 1.50 |
| SymSol ® PF-3 | Water (Aqua), Pentylene Glycol, Sodium Lauryl Sulfoacetate, Sodium Oleoyl Sarcosinate, Sodium Chloride, Disodium Sulfoacetate, SodiumOleate, Sodium Sulfate | 5.00 |

TABLE F36-continued

| Mineral washing and cleansing gel (quantities in wt.-%) | | |
|---|---|---|
| Components | INCI | Quantity |
| Hydroviton ® 24 | Water (Aqua), Pentylene Glycol, Glycerol, Sodium Lactate, Lactic Acid, Serine, Urea, Sorbitol, Sodium Chloride, Allantoin | 1.00 |
| Extrapone ® Silk GW | Water (Aqua), Glycerol, Hydrolyzed Silk | 1.00 |
| Hydrolite ® 5 Green | Hydrolite ® 5 Green | 4.00 |
| Actipearls Red Star # DH10402/6 | Water (Aqua), Propylene Glycol, Algin, Gellan Gum, Xanthan Gum, Calcium Chloride, CI 12490 (Pigment Red 5), Mica (CI 77019), Titanium Dioxide (CI 77891) | 1.00 |
| 1,2-Pentanediol (Hydrolite ® 5) | 1,2-Pentanediol | 0.50 |
| 3-Phenylpropanol | | 0.70 |
| Cooling agent 6 | | 0.30 |

TABLE F37

| Anti-acne wash (quantities in wt.-%) | |
|---|---|
| Ingredients (INCI) | Quantity |
| Water (Aqua) | 45.70 |
| Polyquaternium-7 | 0.50 |
| Cocamidopropyl Betaine 9,000 | 9.00 |
| Coco Glucoside 2.000 | 2.00 |
| Polysorbate 80, Glycerol, *Gossypium Herbaceum*, (Cotton) Seed Oil, Water (Aqua) | 1.00 |
| Trideceth-9, PEG-5 Ethylhexanoate, Water (Aqua) | 1.00 |
| Glycereth-90 Isostearate, Laureth-2 | 0.50 |
| Sodium Laureth Sulfate 37,000 | 37.00 |
| Glycerol, *Triticum Vulgare* (Wheat) Gluten, Water (Aqua) | 1.00 |
| Sodium Chloride | 0.30 |
| 1,2-Pentanediol (Hydrolite ® 5) | 1.00 |
| Phenoxyethanol, methylparaben, ethylparaben, butylparaben, propylparaben, isobutylparaben | 0.30 |
| Cooling agent 7 | 1.50 |

TABLE F38

| Sunscreen formulation (quantities in wt.-%) | |
|---|---|
| Ingredients (INCI) | Quantity |
| Ethylhexyl cinnamic acid | 7.50 |
| Benzophenone-3 | 2.00 |
| Polyglyceryl dimer soyate | 0.80 |
| Sorbitan stearate | 1.00 |
| Tocopheryl acetate | 0.50 |
| Glyceryl stearate, PEG-100 stearate | 3.00 |
| PEG-40, hydrogenated castor oil | 1.00 |
| Titanium dioxide, Aluminum oxide hydrate, Dimethicone/Methicone Copolymer | 3.00 |
| *Butyrospermum parkii* (Shea Butter) | 1.00 |
| C12-15 alkyl benzoate | 6.50 |
| Butylene glycol | 5.00 |
| Xanthan gum | 0.30 |
| Disodium EDTA | 0.10 |
| Allantoin | 0.10 |
| Polyacrylic amide, C13-14 isoparaffin, Laureth-7 | 1.00 |
| 1,2-Pentanediol (Hydrolite ® 5) | 5.00 |
| 4-t Butylcyclohexanol | 1.00 |
| PreservativePreservatives (methyl-, butyl-, ethyl-, propylparaben, phenoxyethanol). | 0.30 |
| Cooling agent 8 | 2.00 |
| Aqua dem. | Ad 100 |

TABLE F39

| Sunscreen spray (quantities in wt.-%) | | |
|---|---|---|
| Components | INCI | Quantity |
| Water, demineral. | Water (aqua) | 69.50 |
| Glycerol | Glycerol | 4.00 |
| 1,3-Butylene glycol | Butylene glycol | 5.00 |
| D-Panthenol | Panthenol | 0.50 |
| Lara Care A-200 | Galactoarabinan | 0.25 |
| Baysilone oil M 10 | Dimethicone | 1.00 |
| Edeta BD | Disodium EDTA | 0.10 |
| Copherol 1250 | Tocopheryl acetate | 0.50 |
| Cetiol OE | Dicaprylyl ether | 3.00 |
| Neo Heliopan ® HMS | Homosalate | 5.00 |
| Neo Heliopan ® AV | Ethylhexyl methoxycinnamate | 6.00 |
| Neo Heliopan ® 357 | Butyl methoxydibenzoylmethane | 1.00 |
| Corapan TQ | Diethylhexylnaphthalate | 2.00 |
| Alpha Bisabolol | Bisabolol | 0.10 |
| Pemulen TR-2 | Acrylates/C10-30 alkyl acrylate crosspolymer | 0.25 |
| NaOH, 10% | Sodium hydroxide | 0.60 |
| Hydrolite ® 5 | 1,2-Pentanediol | 0.20 |
| Phenoxyethanol | Phenoxyethanol | 0.40 |
| Solbrol M | Methylparaben | 0.10 |
| Solbrol P | Propylparaben | 0.10 |
| Cooling agent 9 | | 1.00 |

TABLE F40

| Sunscreen spray O/W, SPE 15-20 (quantities in wt.-%) | | |
|---|---|---|
| Components | INCI | Quantity |
| Dracorin ® GOC | Glyceryl Oleate Citrate, Caprylic/Capric Triglyceride | 2.00 |
| Corapan ® TQ | Diethylhexyl 2,6-naphthalates | 3.00 |
| Neo Heliopan ® HMS | Homosalate | 7.00 |
| Neo Heliopan ® OS | Ethylhexyl Salicylate | 5.00 |
| Neo Heliopan ® 357 | Butyl Methoxydibenzoylmethane | 3.00 |
| Isoadipate | Diisopropyl adipate | 6.00 |
| Baysilone ® Oil M10 | Dimethicone | 1.00 |
| Edeta ® BD | Disodium EDTA | 0.10 |
| Vitamin E Acetate | Tocopheryl Acetate | 0.50 |
| Dragosantol ® 100 | Bisabolol | 0.10 |
| Pemulen ® TR-2 | Acrylates/C10-30 Alkyl Acrylate Crosspolymer | 0.25 |
| Water | Water (Aqua) | Ad 100 |
| Glycerol 99.5 P. | Glycerol | 4.00 |
| Butylene glycol | Butylene glycol | 5.00 |
| Neo Heliopan ® Hydro (103089), used as 25% aq. solution | Phenylbenzimidazole Sulfonic Acid | 8.00 |
| Biotive ® L-Arginine | Arginine | 0.55 |
| Hydrolite ® 5 | 1,2-Pentanediol | 0.40 |
| Sobrol M | Methylparaben | 0.30 |
| Cooling agent 1 | | 1.00 |

TABLE F41

| Sunscreen soft cream (W/O), SPF 40 (quantities in wt.-%) | | |
|---|---|---|
| Components | INCI | Quantity |
| Dehymuls PGPH | Polyglyceryl-2-dipolyhydroxystearate | 5.00 |
| Copherol 1250 | Tocopheryl acetate | 0.50 |
| Permulgin 3220 | Ozocerite | 0.50 |
| Zinc stearate | Zinc stearate | 0.50 |
| Tegosoft TN | C12-15 alkyl benzoate | 10.00 |
| Neo Heliopan ® E1000 | Isoamyl-p-methoxycinnamate | 2.00 |
| Neo Heliopan ® 303 | Octocrylene | 5.00 |
| Neo Heliopan ® MBC | 4-Methylbenzylidene camphor | 3.00 |
| Zinc oxide, neutral | Zinc oxide | 5.00 |

TABLE F41-continued

| Sunscreen soft cream (W/O), SPF 40 (quantities in wt.-%) | | |
|---|---|---|
| Components | INCI | Quantity |
| Water. distilled | Water (aqua) | Ad 100 |
| EDETA BD | Disodium EDTA | 0.10 |
| Glycerol | Glycerol | 4.00 |
| Magnesium sulphate | Magnesium sulphate | 0.50 |
| Hydrolite ® 5 | 1,2-pentanediol | 0.30 |
| Symdiol ® 68 | 1,2-hexanediol, caprylylglycol | 0.30 |
| Cooling agent 1 | | 1.00 |

TABLE F42

| Sunscreen milk (W/O) (quantities in wt.-%) | | |
|---|---|---|
| Components | INCI | Quantity |
| Dehymuls PGPH | Polyglyceryl-2 dipolyhydroxystearate | 3.00 |
| Beeswax 8100 | Beeswax | 1.00 |
| Monomuls 90-0-18 | Glyceryl oleate | 1.00 |
| Zinc stearate | Zinc stearate | 1.00 |
| Cetiol SN | Cetearyl isononanoate | 5.00 |
| Cetiol OE | Dicaprylyl ether | 5.00 |
| Tegosoft TN | C12-15 alkyl benzoate | 4.00 |
| Vitamin E | Tocopherol | 0.50 |
| Neo Heliopan ® OS | Ethylhexyl salicylate | 5.00 |
| Neo Heliopan ® AV | Ethylhexyl methoxycinnamate | 7.50 |
| Uvinul ® T150 | Ethylhexyl triazone | 1.50 |
| Water, distilled | Water (Aqua) | Ad 100 |
| Trilon BD | Disodium EDTA | 0.10 |
| Glycerol | Glycerol | 5.00 |
| Neo Heliopan ® AP 10% solution. neutralized with NaOH | Disodium phenyl dibenzimidazole tetrasulfonate | 15.00 |
| Hydrolite ® 5 | 1,2-Pentanediol | 0.25 |
| Alpha bisabolol | Bisabolol | 0.10 |
| SymOcide ® PT | Phenoxyethanol, Tropolone | 0.25 |
| Cooling agent 2 | | 1.00 |

TABLE F43

| After Sun Gel (quantities in wt.-%) | | |
|---|---|---|
| Components | INCI | Quantity |
| SymSol ® PF-3 | Water (Aqua), Pentylene Glycol, Sodium Lauryl Sulfoacetate, Sodium Oleoyl Sarcosinate, Sodium Chloride, Disodium Sulfoacetate, Sodium Oleate, Sodium Sulfate | 3.000 |
| Glycerol 99.5 P. | Glycerol | 5.000 |
| SymHelios ® 1031 | Benzylidene dimethoxydimethylin danone | 0.100 |
| Water | Water (Aqua) | Ad 100 |
| Pemulen ® TR-2 | Acrylates/C10-30 Alkyl Acrylate Crosspolymer | 1.000 |
| D-Panthenol 75 W | Panthenol | 0.500 |
| SymFinity ® 1298 | Echinacea Purpurea Extract | 0.100 |
| Extrapone ® Pearl GW | Water (Aqua), Glycerol, Hydrolyzed Pearl, Xanthan Gum | 1.000 |
| Sodium Hydroxide 10% solution | Sodium Hydroxide | 2.500 |
| Ethanol 96% | Alcohol Denat. | 15.000 |
| Hydrolite ® 5 | 1,2-Pentanediol | 0.20 |
| SymOcide ® PS | Phenoxyethanol, 1,2-hexanediol, decyleneglycol | 0.50 |
| Cooling agent 3 | | 1.00 |

TABLE F44

| After Sun Lotion (quantities in wt.-%) | |
|---|---|
| Ingredients (INCI) | Quantity |
| Acrylates/C10-30 alkyl acrylates crosspolymer | 0.4 |
| Cetearylethyl hexanoate | 15.0 |
| Bisabolol | 0.2 |
| Tocopheryl acetate | 1.0 |
| Panthenol | 1.0 |
| Alcohol | 15.0 |
| Glycerol | 3.0 |
| 1,2-hexanediol | 0.60 |
| Cooling agent 4 | 1.50 |
| 1,2-Pentanediol (Hydrolite ® 5) | 4.0 |
| Aqua dem. | Ad 100 |
| Triethanolamine | 0.2 |

TABLE F45

| Hair Styling Gel (quantities in wt.-%) | |
|---|---|
| Ingredients (INCI) | Quantity |
| Water | Ad 100 |
| PVM/MA Decadiene Crosspolymer | 0.60 |
| PVP | 3.00 |
| Isocetyl stearate | 4.00 |
| Ethylhexyl Methoxycinnamate | 0.50 |
| Aminomethyl propanol | 0.40 |
| 1,2-Pentanediol (Hydrolite ® 5) | 0.60 |
| SymDiol ® 68T (1,2-hexanediol, 1,2-octanediol, tropolone) | 0.30 |
| Phenoxyethanol | 0.20 |
| Cooling agent 5 | 1.50 |

TABLE F46

| Silicone emulsion (quantities in wt.-%) | |
|---|---|
| Components | Quantity |
| Potassium Cetyl Phosphate, Hydrogenated Palm Glycerides | 1.00 |
| Cyclohexasiloxane | 4.00 |
| Cetearyl Alcohol | 1.50 |
| Phenyl trimethicone | 3.00 |
| Stearyl Heptanoate, Stearyl Caprylate | 3.00 |
| Dimethicone | 1.00 |
| Xanthan gum | 0.20 |
| Isoamyl p-methoxycinnamate | 5.00 |
| Water | Ad 100 |
| Methylpropanediol | 3.00 |
| 1,2-Pentanediol (Hydrolite ® 5) | 0.30 |
| Diazolidinyl urea | 0.10 |
| Cooling agent 6 | 1.50 |

TABLE F47

| Microemulsion gel (quantities in wt.-%) | |
|---|---|
| Ingredients (INCI) | Quantity |
| Glycerol isostearate | 1.80 |
| Octoxyglycerol | 1.00 |
| Ceteareth-15 | 5.20 |
| PEG-150 Distearate | 1.00 |
| Aluminium chlorohydrate | 5.00 |
| Isotridecylisononanoate | 3.30 |
| Cyclomethicone | 6.60 |
| 1,2-Pentanediol (Hydrolite ® 5) | 0.70 |
| Euxyl ® K145 (Methylchloroisothiazolinone, Methylisothiazlinone, Bronopol) | 0.10 |
| Cooling agent 7 | 1.00 |
| Water | Ad 100 |

TABLE F48

| Air freshener in gel form (quantities in wt.-%) | |
|---|---|
| Ingredients (INCI) | Quantity |
| Demineralised water | Ad 100 |
| Genugel ® X-6424 (carrageenan) | 2.00 |
| Arkopal ® N 100 or Tergitol ® NP 10 (emulsifier) | 3.50 |
| 1,2-Pentanediol (Hydrolite ® 5) | 0.60 |
| Preventol ® D 7 (5-chloro-2-methyl-4-isothiazolin-3-one, 2-methyl-2H-isothiazol-3-one) | 0.10 |
| Cooling agent 8 | 1.00 |

TABLE F49

| Textile cleaners (quantities in wt.-%) | |
|---|---|
| Ingredients (INCI) | Quantity |
| Aqua | 72.10 |
| Dialkyl ester ammonium methosulfate | 16.60 |
| Polydimethylsiloxane | 0.30 |
| Magnesium chloride | 10.00 |
| 1,2-Pentanediol (Hydrolite ® 5) | 0.60 |
| Mixture of 5-Chloro-2-methyl-2H-isothiazol-3-one and 2-Methyl-2H-isothiazol-3-one | 0.10 |
| Cooling agent 9 (encapsulated) | 0.40 |

TABLE F50

| Toothpaste (quantities in wt.-%) | |
|---|---|
| Ingredients (INCI) | Quantity |
| Deionised water | 27.52 |
| Sorbitol 70% | 45.00 |
| Solbrol ® M Na salt (p-hydroxybenzoic acid alkyl ester) | 0.15 |
| Trisodium phosphate | 0.10 |
| Saccharin, 450-fold | 0.20 |
| Sodium monofluorophosphate | 1.12 |
| Polyethylene glycol PEG 1500 | 5.00 |
| Sident 9 (abrasive silica) | 10.00 |
| Sident 22 S (thickening silicon dioxide) | 8.00 |
| Sodium carboxymethyl cellulose | 0.90 |
| Titanium dioxide | 0.50 |
| Sodium lauryl sulphate (SLS) | 1.50 |
| Cooling agent 4 | 0.01 |

TABLE F51

| Mouthwash (quantities in wt.-%) | |
|---|---|
| Ingredients (INCI) | Quantity |
| Ethanol | 10.00 |
| Cremophor ® CO 40 (BASF, detergent) | 1.00 |
| Benzoic acid | 0.12 |
| Peppermint-lemon balm flavouring containing 0.4 wt.-% of pellitorin and 10 wt.-% of cooling agent 4 | 0.25 |
| demineralised water | 83.46 |
| Sorbitol, 70% | 5.00 |
| Sodium saccharin 450 | 0.07 |
| L-Blue 5000 e.c., 1% in water (dye) | 0.10 |

TABLE F52

| Toothpaste against plaque with efficacy against bad breath (quantities in wt.-%) | |
|---|---|
| Ingredients (INCI) | Quantity |
| Na-carboxymethylcellulose | 1.00 |
| Glycerol | 12.50 |
| Sorbitol 70%, in water | 29.00 |
| Na-saccharinate | 0.20 |
| Na-fluoride | 0.22 |
| Azacycloheptane-2,2-diphosphoic acid, di-sodium salt | 1.00 |
| Bromochlorophene | 0.10 |
| Peppermint flavour | 0.90 |
| Cooling agent 1 | 0.10 |
| Parsley seed oil | 0.15 |
| Abrasive silica | 15.00 |
| Thickening silica | 5.00 |
| Sodium dodecyl sulphate (SDS) | 1.50 |
| Water dist. | Ad 100.00 |

TABLE F53

| Toothpaste and mouthwash as 2-in-1 product (quantities in wt.-%) | |
|---|---|
| Ingredients (INCI) | Quantity |
| Sorbitol | 40.00 |
| Glycerol | 20.00 |
| Ethanol | 5.00 |
| Water | Ad 100.00 |
| Solbrol M, Na salt (Methylparaben, Na salt) | 0.15 |

TABLE F53-continued

| Toothpaste and mouthwash as 2-in-1 product (quantities in wt.-%) | |
|---|---|
| Ingredients (INCI) | Quantity |
| Na-monofluorophosphate | 0.75 |
| Saccharin | 0.20 |
| Sident 9 (abrasive silica) | 20.00 |
| Sident 22 S (thickening silicon dioxide) | 2.00 |
| Sodium carboxymethyl cellulose | 0.30 |
| Sodium lauryl sulphate (SDS) | 1.20 |
| Colour (1% in water) | 0.50 |
| Cooling agent 1 | 1.00 |

TABLE F54

| Other toothpaste formulation (quantities in wt.-%) | |
|---|---|
| Ingredient | Quantity |
| demineralised water | 22.00 |
| Sorbitol (70%) | 45.00 |
| Solbrol ® M, sodium salt (Bayer AG, p-hydroxybenzoic acid alkyl ester) | 0.15 |
| Trisodium phosphate | 0.10 |
| Saccharin, 450 times | 0.20 |
| Sodium monofluorophosphate | 1.12 |
| Polyethylene glycol 1500 | 5.00 |
| Sident 9 (abrasive silica) | 10.00 |
| Sident 22 S (thickening silicon dioxide) | 8.00 |
| Sodium carboxymethyl cellulose | 0.90 |
| Titanium dioxide | 0.50 |
| demineralised water | 4.53 |
| Sodium lauryl sulphate | 1.50 |
| Cooling agent 1 | 1.00 |

Formulation Examples for Food Preparations

The following formulation examples F55 to F63 show a wide variety of formulations for cosmetic and pharmaceutical preparations. Cooling agent 1 means here the cooling agent according to the invention according to compound 1, cooling agent 2 means compound 8, cooling agent 3 means compound 14, cooling agent 4 means compound 27, cooling agent 5 means compound 39, cooling agent 6 means compound 40, cooling agent 7 means compound 41, cooling agent 8 means compound 42, cooling agent 9 means compound 51.

TABLE F55

| Chewing gum (quantities in wt.-%) | |
|---|---|
| Ingredients (INCI) | Quantity |
| Chewing gum base (“gum-base”) | 15-25 |
| Glucose syrup | 20-30 |
| Powdered sugar | 50-60 |
| Cooling agent 1 | 0.001-10 |
| Plasticiser (e.g. glycerol) | 1-2 |
| Water | 3-6 |

TABLE F56

| Other chewing gum formulations (quantities in wt.-%) | | | |
|---|---|---|---|
| Ingredients (INCI) | Quantity I | Quantity II | Quantity III |
| Chewing gum base K2 (28.5% terpene resin, 33.9% polyvinyl acetate (MW = 14000), 16.25% hydrogenated vegetable oil, 5.5% mono- and diglycerides, 0.5% polyisobutene (MW 75000), 2.0% butyl rubber (isobutene-isoprenecopolymer), 4.6% amorphous silicon dioxide (water content approx. 2.5%), 0.05% antioxidant tert-butylhydroxy-toluene (BHT), 0.2% lecithin, and 8.5% calcium carbonate). | 25.30 | 27.30 | 26.30 |
| Sorbitol | 61.48 | 59.48 | 61.48 |
| Glycerol | 2.40 | 2.40 | 2.40 |
| Lecithin | 7.00 | 7.00 | 7.00 |
| Aspartame | 0.14 | 0.14 | 0.14 |
| Encapsulated aspartame | 0.68 | 0.68 | 0.68 |
| Menthol, spray-dried | 0.50 | — | |
| Cherry flavour, spray-dried | — | 1.20 | |
| Cooling agent 1 | 2.50 | 1.80 | 1.68 |

TABLE F57

| Sugar-free chewing gum (quantities in wt.-%) | | |
|---|---|---|
| Ingredients (INCI) | Quantity I | Quantity II |
| Chewing gum base, “Jagum T” Company | 30.00 | 30.00 |
| Sorbitol, powdered | 39.00 | 39.00 |
| Isomalt ® (Palatinit GmbH) | 9.50 | 9.50 |
| Xylitol | 2.00 | 2.00 |
| Mannitol | 3.00 | 3.00 |
| Aspartam ® | 0.10 | 0.10 |
| Acesulfam ® K | 0.10 | 0.10 |
| Emulgum ® (Colloides Naturels, Inc.) | 0.30 | 0.30 |
| Sorbitol, 70% | 14.00 | 14.00 |
| Glycerol | 1.00 | 1.00 |
| Spearmint-peppermint-eucalyptus flavouring containing 5% by weight of cooling agent 2 | 1.00 | — |
| Cooling agent 2, pure | — | 1.20 |

TABLE F58

| Pudding, recipe (for 100 ml) (quantities in grams) | |
|---|---|
| Ingredients (INCI) | Quantity |
| Fat free dry milk | 10.715 |
| Sucrose | 5.000 |
| Novelose Starch, National Starch | 7.000 |
| Vegetable oil mixture | 2.200 |
| Carrageenan | 0.016 |
| Vanilla flavouring | 0.500 |
| Sodium stearoyl-2-lactylate | 0.095 |
| Yellow dye | 0.189 |
| Magnesium phosphate | 0.165 |
| Vitamin premix | 1.840 |
| Trace element premix | 0.015 |
| Cooling agent 3 | 0.500 |
| Water | 81.940 |

TABLE 59

| Chewy sweets (quantities in wt.-%) | |
|---|---|
| Ingredients (INCI) | Quantity |
| Water | 7.80 |
| Sugar (refined C4) | 42.10 |
| Glucose syrup (dextrose 40) | 37.30 |
| hardened vegetable fat, melting point 32-36° C. | 6.60 |
| Lecithin (emulsifier, soya lecithin) | 0.30 |
| Gelatine (pork gelatine) | 0.80 |
| Fondant type - S30 | 4.80 |
| Raspberry flavour | 0.22 |
| Cooling agent 4 | 0.08 |

TABLE 60

| Fruit gums (quantities in wt.-%) | |
|---|---|
| Ingredients (INCI) | Quantity |
| Water | 23.60 |
| Sucrose | 34.50 |
| Glucose syrup, DE 40 | 31.89 |
| Iso Syrup C* Tru Sweet 01750 (Cerestar GmbH) | 1.50 |
| Gelatine 240 Bloom | 8.20 |
| Yellow and red dye | 0.01 |
| Citric acid | 0.20 |
| Cooling agent 5 | 0.10 |

TABLE 61

| Gelatine capsule for direct consumption (quantities in wt.-%) | |
|---|---|
| Ingredients (INCI) | Quantity |
| Gelatine shell: | |
| Glycerol | 2.014 |
| Gelatine 240 Bloom | 7.91 |
| Sucralose | 0.065 |
| Allura Red | 0.006 |
| Brilliant blue | 0.005 |
| Core composition: | |
| Vegetable oil triglyceride (coconut oil - fraction) | 79.39 |
| Cinnamon anise flavour | 10.00 |
| Neotame and aspartame | 0.01 |
| Sucralose | 0.22 |
| Cooling agent 6 | 0.33 |
| Vanillin | 0.05 |

TABLE 62

| Non-stick chewing gum (quantities in wt.-%) | | | |
|---|---|---|---|
| Ingredients (INCI) | Quantity I | Quantity II | Quantity III |
| Chewing gum base K1 (2.0% butyl rubber (isobutene-isoprene copolymer, MW 400000), 6.0% polyisobutene (MW = 43800), 43.5% polyvinyl acetate (MW = 12000), 31.5% polyvinyl acetate (MW = 47000), 6.75% triacetin and 10.25% calcium carbonate) | 26.00 | 26.00 | 26.00 |
| Triacetin | 0.25 | 0.25 | 0.25 |
| Lecithin | 0.50 | 0.50 | 0.50 |

TABLE 62-continued

| Non-stick chewing gum (quantities in wt.-%) | | | |
|---|---|---|---|
| Ingredients (INCI) | Quantity I | Quantity II | Quantity III |
| Sorbitol, crystalline | Ad 100 | Ad 100 | Ad 100 |
| Mannitol | 15.30 | 15.20 | 15.10 |
| Glycerol | 12.10 | 12.00 | 11.80 |
| Aspartame | 0.17 | 0.17 | 0.17 |
| Encapsulated aspartame | 1.08 | 1.08 | 1.08 |
| Amorphous silica | 1.00 | 1.00 | 1.00 |
| Cottonseed oil | 0.05 | 0.05 | 0.05 |
| Polyoxyethylene sorbitan monolaurate (E-432) | 1.00 | 1.00 | 1.00 |
| Encapsulated spearmint flavouring (contains I-carvone) | 0.20 | 0.10 | 0.20 |
| Encapsulated wintergreen flavouring (containsmethyl salicylate) | — | 0.20 | — |
| Cooling agent 7 | 1.00 | 1.40 | 1.70 |

TABLE F63

| Throat sweets with liquid viscous centre filling (centrefilled hard candy) ((quantities in wt.-%) | | |
|---|---|---|
| Ingredients (INCI) | Quantity I | Quantity II |
| Mixture A (shell) (80% of the sweets) | | |
| Sugar (sucrose) | 58.12 | 49.39 |
| Mixture A (shell) (80% of the sweets) | | |
| Glucose syrup (solids content 80%) | 41.51 | 49.37 |
| Cooling agent 1 | 0.17 | 0.25 |
| I-Menthol | 0.10 | — |
| Lemon oil | 0.10 | 0.10 |
| Citric acid | — | 0.91 |
| Total: | 100 | 100 |
| Mixture B (core) (20% of the sweets) | | |
| High fructose corn syrup (content of solid sugars 85%, just under 15% water) | 84.38 | 84.36 |
| Glycerol | 15.00 | 15.00 |
| Lecithin | 0.02 | 0.02 |
| Cinnamon oil | — | 0.32 |
| Spearmint oil | 0.28 | — |
| Capsaicin | 0.05 | — |
| Vanillyl alcohol-n-butyl ether | — | 0.10 |
| Red dye, as 5 % aqueous solution | 0.20 | 0.20 |
| Vanillin | 0.07 | — |
| Total: | 100 | 100 |

The invention claimed is:

1. Physiological cooling agent of the general formula (I)

(I)

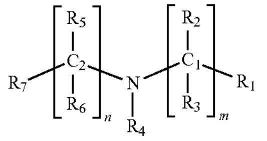

in which the residues R1 to R7 can each be identical or different and, independently of one another, have the following meanings:

R1 optionally substituted cycloalkyl group or optionally substituted aryl group or optionally substituted heterocycloalkyl group or is an optionally substituted heteroaryl group;

R2 H or
- $SiR_3$ or
- a group Q or
- optionally substituted linear or branched alkyl group or
- optionally substituted linear or branched alkenyl group or
- optionally substituted linear or branched alkynyl group or
- optionally substituted linear or branched alkoxy group or
- optionally substituted linear or branched alkylthio group or
- optionally substituted acyl group R(C═O)— or
- optionally substituted cycloalkyl group or
- optionally substituted aryl group or
- optionally substituted heterocycloalkyl group or
- is an optionally substituted heteroaryl group;

R3 H or
- $SiR_3$ or
- a group Q or
- optionally substituted linear or branched alkyl group or
- optionally substituted linear or branched alkenyl group or
- optionally substituted linear or branched alkynyl group, or
- optionally substituted linear or branched alkoxy group or
- optionally substituted linear or branched alkylthio group or
- optionally substituted acyl group R(C═O)— or
- optionally substituted cycloalkyl group or
- optionally substituted aryl group or
- optionally substituted heterocycloalkyl group or
- is an optionally substituted heteroaryl group;

R4 H or
- optionally substituted linear or branched alkyl group or
- optionally substituted linear or branched alkenyl group or
- optionally substituted linear or branched alkynyl group or
- optionally substituted cycloalkyl group or
- optionally substituted aryl group or
- optionally substituted heterocycloalkyl group or
- is an optionally substituted heteroaryl group;

R5 H or
- $SiR_3$ or
- a group Q or
- optionally substituted linear or branched alkyl group or
- optionally substituted linear or branched alkenyl group or
- optionally substituted linear or branched alkynyl group, or
- optionally substituted linear or branched alkoxy group or
- optionally substituted linear or branched alkylthio group or
- optionally substituted acyl group R(C═O)— or
- optionally substituted cycloalkyl group or
- optionally substituted aryl group or
- optionally substituted heterocycloalkyl group or
- is an optionally substituted heteroaryl group or
- R2 and R5 together with the $C_1$ and $C_2$ atom to which they are attached and the N atom between the $C_1$ and $C_2$ atom, form an optionally substituted heterocycloalkyl ring or optionally substituted heteroaryl ring;

R6 H or
- $SiR_3$ or
- a group Q or
- optionally substituted linear or branched alkyl group or
- optionally substituted linear or branched alkenyl group or
- optionally substituted linear or branched alkynyl group or
- optionally substituted linear or branched alkoxy group or
- optionally substituted linear or branched alkylthio group or
- optionally substituted acyl group R(C═O)— or
- optionally substituted cycloalkyl group or
- optionally substituted aryl group or
- optionally substituted heterocycloalkyl group or
- is an optionally substituted heteroaryl group or
- R3 and R6 together with the $C_1$ and $C_2$ atom to which they are attached and the N atom between the $C_1$ and $C_2$ atom, form an optionally substituted heterocycloalkyl ring or optionally substituted heteroaryl ring;

R7 optionally substituted cycloalkyl group or
- optionally substituted aryl group or
- optionally substituted heterocycloalkyl group or
- is an optionally substituted heteroaryl group;

m is 0 to 4; provided that
- if m=0, $C_1$, R2 and R3 are omitted;
- if m=1, $C_1$, R2 and R3 each occur once;
- if m=2, $C_1$, R2 and R3 each occur twice;
- if m=3, $C_1$, R2 and R3 each occur three times; and
- if m=4, $C_1$, R2 and R3 each occur four times;
- with the proviso that when m=2, 3 or 4, the bond between the $C_1$ atoms may be a single bond or a double bond and when the bond between the C atoms is a double bond, either R2 or R3 is absent at the corresponding C atoms; and where R2 and R3 can each be selected independently of each other;

n is 0 to 4; provided that
- if n=0, $C_2$, R5 and R6 are omitted;
- if n=1, $C_2$, R5 and R6 each occur once;
- if n=2, $C_2$, R5 and R6 each occur twice;
- if n=3, $C_2$, R5 and R6 each occur three times; and
- if n=4, $C_2$, R5 and R6 each occur four times;
- with the proviso that when n=2, 3 or 4, the bond between the $C_2$ atoms may be a single bond or a double bond and when the bond between the C atoms is a double bond, either R5 or R6 is absent at the corresponding C atoms; and where R5 and R6 can each be selected independently of each other;

where the group Q is a residue selected from the group consisting of: halogen, ═O, —OY, —SY, ═S, —NZZ, =NY, ═N—OY, —$CF_3$, —CN, —OCN, —SCN, —NO, —$NO_2$, —$S(O)_2Y$, —$S(O)_2OY$, —$OS(O)_2Y$, —$OS(O)_2OY$, —$P(O)(OY)_2$, —P(O)(OY)(OY), —C(O)Y, —C(S)Y, —C(NY)Y, —C(O)OY, —C(S)OY, —C(O)NZZ, —C(NY)NZZ, —OC(O)Y, —OC(S)Y, —OC(O)OY, —OC(S)OY, —NYC(O)Y, —NYC(S)Y, —NYC(O)OY, —NYC(S)OY, —NYC(O)NZZ, —NYC(NY)Y and —NYC(NY)NZZ;

where

Y is selected from the group consisting of: hydrogen,
optionally substituted alkyl group,
optionally substituted alkoxy group,
optionally substituted alkylthio group,
optionally substituted cycloalkyl group,
optionally substituted aryl group, optionally substituted heterocycloalkyl group, optionally substituted heteroaryl group; and/or Z represents Y or alternatively, two Z's together with the nitrogen atom to which they are attached represent a four, five, six or seven membered heterocycloalkyl ring or heteroaryl ring, wherein the heterocycloalkyl ring or heteroaryl ring may comprise one, two, three or four of the same or different heteroatoms selected from the group consisting of nitrogen, oxygen and sulphur;

the optionally substituted alkyl group is an optionally substituted $C_1$- to $C_{10}$-alkyl group;

the optionally substituted alkenyl group is an optionally substituted $C_1$- to $C_{10}$-alkenyl group;

the optionally substituted alkynyl group is an optionally substituted $C_1$- to $C_{10}$-alkynyl group;

the optionally substituted alkoxy group is an optionally substituted $C_1$- to $C_{10}$-alkoxy group;

the optionally substituted alkylthio group is an optionally substituted $C_1$- to $C_{10}$-alkylthio group;

in the acyl group R—(C═O)— the residue R represents hydrogen or an optionally substituted $C_1$- to $C_{10}$-alkyl group;

in the group $SiR_3$ the residue R represents hydrogen or an optionally substituted $C_1$- to $C_{10}$-alkyl group;

the optionally substituted cycloalkyl group is an optionally substituted four- to ten-membered monocyclic cycloalkyl group or an optionally substituted nine- to twelve-membered polycyclic cycloalkyl group;

the optionally substituted aryl group is an optionally substituted four- to ten-membered monocyclic aryl group or an optionally substituted nine- to twelve-membered polycyclic aryl group;

the optionally substituted heterocycloalkyl group is an optionally substituted four-, five-, six- or seven-membered monocyclic heterocycloalkyl group or an optionally substituted nine- to twelve-membered polycyclic;

the optionally substituted heteroaryl group is an optionally substituted four-, five-, six- or seven-membered monocyclic heteroaryl group or an optionally substituted nine- to twelve-membered polycyclic;

wherein the substituents are each independently selected; and salts thereof, where the cooling agents may be present in stereoisomerically pure form or as mixtures of different stereoisomers.

2. Physiological cooling agent according to claim 1 represented by the general formula (II)

(II)

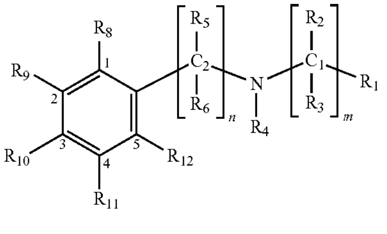

in which the residues R1 to R6 and R8 to R12 can be identical or different and have the following meanings independently of one another:

R1 as defined in claim 1;

R2 as defined in claim 1;

R3 as defined in claim 1;

R4 as defined in claim 1;

R5 as defined in claim 1;

R6 as defined in claim 1;

R8 H or $SiR_3$ or a group Q or optionally substituted linear or branched alkyl group or optionally substituted linear or branched alkenyl group or optionally substituted linear or branched alkynyl group or optionally substituted linear or branched alkoxy group or optionally substituted linear or branched alkylthio group or optionally substituted acyl group R(C═O)— or optionally substituted cycloalkyl group or optionally substituted aryl group or optionally substituted heterocycloalkyl group or is an optionally substituted heteroaryl group or R8 with the adjacent R9, together with the carbon atoms to which they are attached, forms an optionally substituted four, five, six or seven membered cycloalkyl or aryl ring or forms an optionally substituted four, five, six or seven membered heterocycloalkyl or heteroaryl ring, wherein the heterocycloalkyl or heteroaryl ring may comprise one, two, three or four identical or different heteroatoms selected from the group consisting of nitrogen, oxygen and sulphur;

R9 H or $SiR_3$ or a group Q or optionally substituted linear or branched alkyl group or optionally substituted linear or branched alkenyl group or optionally substituted linear or branched alkynyl group, or optionally substituted linear or branched alkoxy group or optionally substituted linear or branched alkylthio group or optionally substituted acyl group R(C═O)— or optionally substituted cycloalkyl group or optionally substituted aryl group or optionally substituted heterocycloalkyl group or is an optionally substituted heteroaryl group or R9 with the adjacent R8 or R10, together with the carbon atoms to which they are attached, forms an optionally substituted four, five, six or seven membered cycloalkyl or aryl ring or forms an optionally substituted four, five, six or seven membered heterocycloalkyl or heteroaryl ring, wherein the heterocycloalkyl or heteroaryl ring may comprise one, two, three or four identical or different heteroatoms selected from the group consisting of nitrogen, oxygen and sulphur;

R10 H or $SiR_3$ or a group Q or optionally substituted linear or branched alkyl group or optionally substituted linear or branched alkenyl group or optionally substituted linear or branched alkynyl group or optionally substituted linear or branched alkoxy group or optionally substituted linear or branched alkylthio group or optionally substituted acyl group R(C═O)— or
optionally substituted cycloalkyl group or
optionally substituted aryl group or
optionally substituted heterocycloalkyl group or
is an optionally substituted heteroaryl group or
R10 with the adjacent R9 or R11, together with the carbon atoms to which they are attached, forms an optionally substituted four, five, six or seven membered cycloalkyl or aryl ring or forms an optionally substituted four, five, six or seven membered heterocycloalkyl or heteroaryl ring, wherein the heterocycloalkyl or heteroaryl ring may comprise one, two, three or four identical or different heteroatoms selected from the group consisting of nitrogen, oxygen and sulphur;

R11 H or
$SiR_3$ or
a group Q or
optionally substituted linear or branched alkyl group or
optionally substituted linear or branched alkenyl group or
optionally substituted linear or branched alkynyl group, or
optionally substituted linear or branched alkoxy group or
optionally substituted linear or branched alkylthio group or
optionally substituted acyl group R(C═O)— or
optionally substituted cycloalkyl group or
optionally substituted aryl group or
optionally substituted heterocycloalkyl group or
is an optionally substituted heteroaryl group or
R11 with the adjacent R10 or R12, together with the carbon atoms to which they are attached, forms an optionally substituted four, five, six or seven membered cycloalkyl or aryl ring or forms an optionally substituted four, five, six or seven membered heterocycloalkyl or heteroaryl ring, wherein the heterocycloalkyl or heteroaryl ring may comprise one, two, three or four identical or different heteroatoms selected from the group consisting of nitrogen, oxygen and sulphur;

R12 H or
$SiR_3$ or
a group Q or
optionally substituted linear or branched alkyl group or
optionally substituted linear or branched alkenyl group or
optionally substituted linear or branched alkynyl group or
optionally substituted linear or branched alkoxy group or
optionally substituted linear or branched alkylthio group or
optionally substituted acyl group R(C═O)— or
optionally substituted cycloalkyl group or
optionally substituted aryl group or
optionally substituted heterocycloalkyl group or
is an optionally substituted heteroaryl group or
R12 with the adjacent R11, together with the carbon atoms to which they are attached, forms an optionally substituted four, five, six or seven membered cycloalkyl or aryl ring or forms an optionally substituted four, five, six or seven membered heterocycloalkyl or heteroaryl ring, wherein the heterocycloalkyl or heteroaryl ring may comprise one, two, three or four identical or different heteroatoms selected from the group consisting of nitrogen, oxygen and sulphur;

m as defined in claim 1;
n as defined in claim 1;
where
the group Q is a residue selected from the group consisting of: halogen, ═O, —OY, —SY, ═S, —NZZ, =NY, ═N—OY, $—CF_3$, —CN, —OCN, —SCN, —NO, $—NO_2$, $—S(O)_2Y$, $—S(O)_2OY$, $—OS(O)_2Y$, $—OS(O)_2OY$, $—P(O)(OY)_2$, —P(O)(OY)(OY), —C(O)Y, —C(S)Y, —C(NY)Y, —C(O)OY, —C(S)OY, —C(O)NZZ, —C(NY)NZZ, —OC(O)Y, —OC(S)Y, —OC(O)OY, —OC(S)OY, —NYC(O)Y, —NYC(S)Y, —NYC(O)OY, —NYC(S)OY, —NYC(O)NZZ, —NYC(NY)Y or —NYC(NY)NZZ;
where
Y is selected from the group consisting of: hydrogen,
optionally substituted alkyl group,
optionally substituted alkoxy group,
optionally substituted alkylthio group,
optionally substituted cycloalkyl group,
optionally substituted aryl group,
optionally substituted heterocycloalkyl group,
optionally substituted heteroaryl group; and/or
Z represents Y or alternatively, two Z's together with the nitrogen atom to which they are attached represent a four, five, six or seven membered heterocycloalkyl ring or heteroaryl ring, wherein the heterocycloalkyl ring or heteroaryl ring may comprise one, two, three or four of the same or different heteroatoms selected from the group consisting of nitrogen, oxygen and sulphur;
the optionally substituted alkyl group is an optionally substituted $C_1$- to $C_{10}$-alkyl group;
the optionally substituted alkenyl group is an optionally substituted $C_1$- to $C_{10}$-alkenyl group;
the optionally substituted alkynyl group is an optionally substituted $C_1$- to $C_{10}$-alkynyl group;
the optionally substituted alkoxy group is an optionally substituted $C_1$- to $C_{10}$-alkoxy group;
the optionally substituted alkylthio group is an optionally substituted $C_1$- to $C_{10}$-alkylthio group;
in the acyl group R—(C═O)— the residue R represents hydrogen or an optionally substituted $C_1$- to $C_{10}$-alkyl group;
in the group $SiR_3$ the residue R represents hydrogen or an optionally substituted $C_1$- to $C_{10}$-alkyl group;
the optionally substituted cycloalkyl group is an optionally substituted four- to ten-membered monocyclic cycloalkyl group or an optionally substituted nine- to twelve-membered polycyclic cycloalkyl group;
the optionally substituted aryl group is an optionally substituted four- to ten-membered monocyclic aryl group or an optionally substituted nine- to twelve-membered polycyclic aryl group;
the optionally substituted heterocycloalkyl group is an optionally substituted four-, five-, six- or seven-membered monocyclic heterocycloalkyl group or an optionally substituted nine- to twelve-membered polycyclic heterocycloalkyl group, wherein the heterocycloalkyl group may comprise one, two, three or four identical or different heteroatoms selected from the group consisting of nitrogen, oxygen and sulphur;
the optionally substituted heteroaryl group is an optionally substituted four-, five-, six- or seven-membered monocyclic heteroaryl group or an optionally substituted nine- to twelve-membered polycyclic heteroaryl group, wherein the heteroaryl group may comprise one, two, three or four identical or different heteroatoms selected from the group consisting of nitrogen, oxygen and sulphur;

wherein the substituents are each independently selected;

wherein optionally one, two, three, four or five carbon atom(s) in position 1, 2, 3, 4 or 5 of the benzene ring at the $C_2$ atom of the general formula (II) is/are each replaced by a nitrogen atom;

and salts thereof, where the cooling agents may be present in stereoisomerically pure form or as mixtures of different stereoisomers.

3. The physiological cooling agent of claim 1, further wherein the optionally substituted groups have one or more substituents such that:

(i) when in the substituted groups the substitution occurs on a saturated carbon, the substituent on the saturated carbon is selected from the group consisting of: —X, halogen, =O, —OY, —$SiR_3$, —SY, =S, —NZZ, —NY, —N—OY, —$CF_3$, —CN, —OCN, —SCN, —NO, —$NO_2$, —$S(O)_2Y$, —$S(O)_2OY$, —$OS(O)_2Y$, —$OS(O)_2OY$, —$P(O)(OY)_2$, —P(O)(OY)(OY), —C(O)Y, —C(S)Y, —C(NY)Y, —C(O)OY, —C(S)OY, —C(O)NZZ, —C(NY)NZZ, —OC(O)Y, —OC(S)Y, —OC(O)OY, —OC(S)OY, —NYC(O)Y, —NYC(S)Y, —NYC(O)OY, —NYC(S)OY, —NYC(O)NZZ, —NYC(NY)Y and —NYC(NY)NZZ;

(ii) when in the substituted groups the substitution occurs on an unsaturated carbon, the substituent on the unsaturated carbon is selected from the group consisting of: —X, halogen, —OY, —$SiR_3$, —SY, —NZZ, —$CF_3$, —CN, —OCN, —SCN, —NO, —$NO_2$, —$S(O)_2Y$, —$S(O)_2OY$, —$OS(O)_2Y$, —$OS(O)_2OY$, —$P(O)(OY)_2$, —P(O)(OY)(OY), —C(O)Y, —C(S)Y, —C(NY)Y, —C(O)OY, —C(S)OY, —C(O)NZZ, —C(NY)NZZ, —OC(O)Y, —OC(S)Y, —OC(O)OY, —OC(S)OY, —NYC(O)Y, —NYC(S)Y, —NYC(O)OY, —NYC(S)OY, —NYC(O)NZZ, —NYC(NY)Y and —NYC(NY)NZZ;

(iii) when in the substituted groups the substitution occurs on a nitrogen atom, the substituent on the nitrogen atom is selected from the group consisting of: —X, —OY, —SY, —NZZ, —$CF_3$, —CN, —OCN, —SCN, —NO, —$NO_2$, —$S(O)_2Y$, —$S(O)_2OY$, —$OS(O)_2Y$, —$OS(O)_2OY$, —$P(O)(OY)_2$, —P(O)(OY)(OY), —C(O)Y, —C(S)Y, —C(NY)Y, —C(O)OY, —C(S)OY, —C(O)NZZ, —C(NY)NZZ, —OC(O)Y, —OC(S)Y, —OC(O)OY, —OC(S)OY, —NYC(O)Y, —NYC(S)Y, —NYC(O)OY, —NYC(S)OY, —NYC(O)NZZ, —NYC(NY)Y and —NYC(NY)NZZ;

wherein in cases (i), (ii) and (iii)

X is selected from the group consisting of: optionally substituted alkyl group, optionally substituted alkoxy group,
optionally substituted alkylthio group,
optionally substituted cycloalkyl group,
optionally substituted aryl group,
optionally substituted heterocycloalkyl group,
optionally substituted heteroaryl group; and/or Y is selected from the group consisting of: hydrogen or X; and/or Z represents Y or alternatively two Z's together with the nitrogen atom to which they are attached represent a four, five, six or seven membered heterocycloalkyl ring or heteroaryl ring, wherein the heterocycloalkyl ring or heteroaryl ring may comprise one, two, three or four of the same or different heteroatoms selected from the group consisting of nitrogen, oxygen and sulphur.

4. The physiological cooling agent of claim 1, wherein R1 stands for a optionally substituted phenyl group,
optionally substituted benzyl group,
optionally substituted tolyl group,
optionally substituted xylolyl group,
optionally substituted phenol group,
optionally substituted dihydroxybenzene group,
optionally substituted pyridinyl group,
optionally substituted piperidinyl group,
optionally substituted tetrahydropyranyl group,
optionally substituted pyrollyl group,
optionally substituted imidazolyl group,
optionally substituted pyrimidinyl group,
optionally substituted oxazolyl group,
optionally substituted indolyl group,
optionally substituted benzothiophenyl group,
optionally substituted furanyl group,
optionally substituted benzofuranyl group,
optionally substituted thiophenyl group,
optionally substituted 1,3-benzodioxolyl group,
optionally substituted benzodioxanyl group,
optionally substituted morpholinyl group or
optionally substituted quinolinyl group, and/or R7 stands for a optionally substituted phenyl group,
optionally substituted benzyl group,
optionally substituted tolyl group,
optionally substituted xylolyl group,
optionally substituted phenol group,
optionally substituted dihydroxybenzene group,
optionally substituted pyridinyl group,
optionally substituted piperidinyl group,
optionally substituted tetrahydropyranyl group,
optionally substituted pyrollyl group,
optionally substituted imidazolyl group,
optionally substituted pyrimidinyl group,
optionally substituted oxazolyl group,
optionally substituted indolyl group,
optionally substituted benzothiophenyl group,
optionally substituted furanyl group,
optionally substituted benzofuranyl group,
optionally substituted thiophenyl group,
optionally substituted 1,3-benzodioxolyl group,
optionally substituted benzodioxanyl group,
optionally substituted morpholinyl group or optionally substituted quinolinyl group.

5. The physiological cooling agent of claim 4, further wherein the optionally substituted groups R1 and/or R7 themselves have one or more substituents selected from the group consisting of:

optionally substituted piperidinyl group,
optionally substituted morpholinyl group,
optionally substituted hexamethyleneiminyl group,
optionally substituted pyridinyl group,
optionally substituted tetrahydropyrrolyl group,
optionally substituted alkyl piperidinyl group,
optionally substituted thiomorpholinyl group,
optionally substituted pyrollyl group,
optionally substituted thioalkoxy group,
optionally substituted alkoxy group, and
optionally substituted phenyl group.

6. The physiological cooling agent of claim 1, selected from the group consisting of:

| Structure | Compound |
|---|---|
| 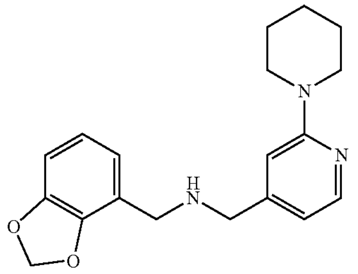 [SMILES: c1cc(CNCc2ccnc(N3CCCCC3)c2)c2c(c1)OCO2] | Compound 1 |
| 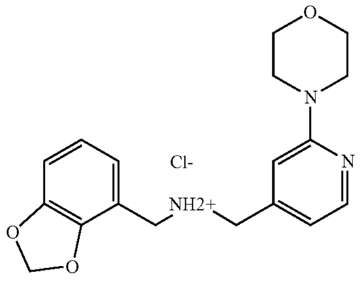 [SMILES: c1cc(C[NH2+]Cc2ccnc(N3CCOCC3)c2)c2c(c1)OCO2 ; [Cl-]] | Compound 2 |
| 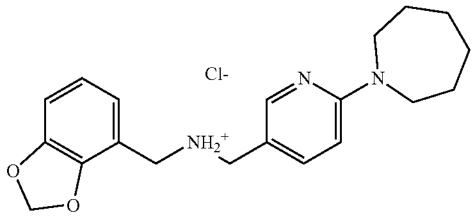 | Compound 3 |
| 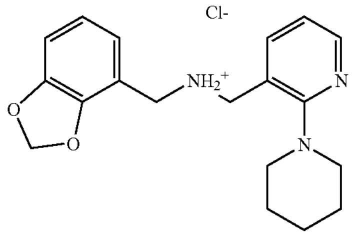 [SMILES: [Cl-] ; c1cnc(N2CCCCC2)c(C[NH2+]Cc2cccc3c2OCO3)c1] | Compound 4 |
| 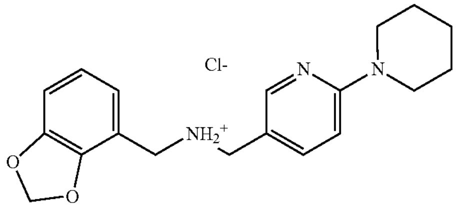 [SMILES: c1cc(C[NH2+]Cc2ccc(N3CCCCC3)nc2)c2c(c1)OCO2 ; [Cl-]] | Compound 5 |
| 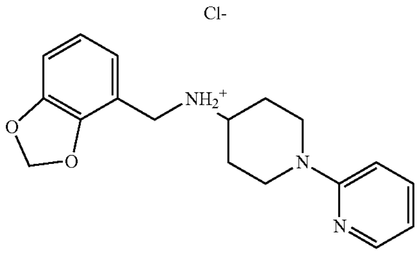 [SMILES: [Cl-] ; c1ccc(N2CCC([NH2+]Cc3cccc4c3OCO4)CC2)nc1] | Compound 6 |

-continued
| Structure | Compound |
|---|---|
| 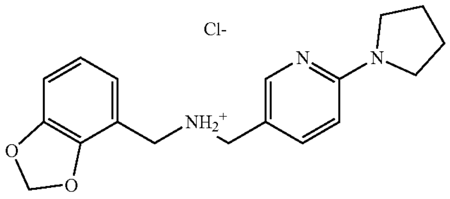 [SMILES: c1cc(C[NH2+]Cc2ccc(N3CCCC3)nc2)c2c(c1)OCO2 ; [Cl-]] | Compound 7 |
| 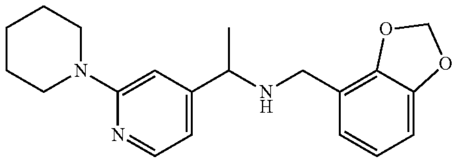 | Compound 8 |
| 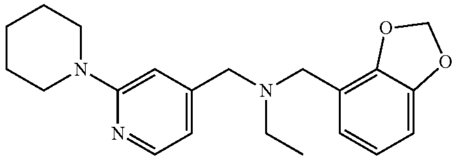 [SMILES: CCN(Cc1ccnc(N2CCCCC2)c1)Cc1cccc2c1OCO2] | Compound 9 |
| 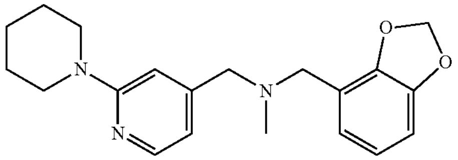 | Compound 10 |
| 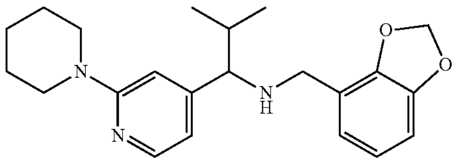 [SMILES: CC(C)C(NCc1cccc2c1OCO2)c1ccnc(N2CCCCC2)c1] | Compound 11 |
| 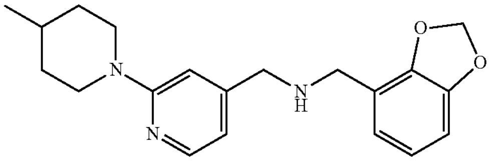 [SMILES: CC1CCN(c2cc(CNCc3cccc4c3OCO4)ccn2)CC1] | Compound 12 |
| 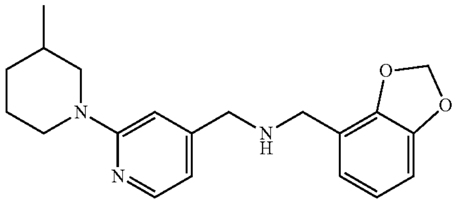 [SMILES: CC1CCCN(c2cc(CNCc3cccc4c3OCO4)ccn2)C1] | Compound 13 |
| 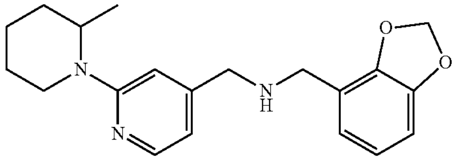 [SMILES: CC1CCCCN1c1cc(CNCc2cccc3c2OCO3)ccn1] | Compound 14 |

-continued
| Structure | Compound |
|---|---|
| 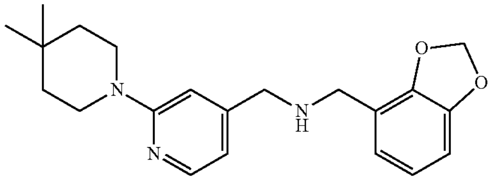 [SMILES: CC1(C)CCN(c2cc(CNCc3cccc4c3OCO4)ccn2)CC1] | Compound 15 |
| 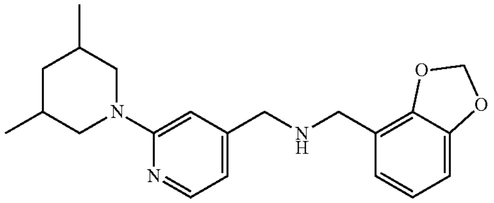 [SMILES: CC1CC(C)CN(c2cc(CNCc3cccc4c3OCO4)ccn2)C1] | Compound 16 |
| 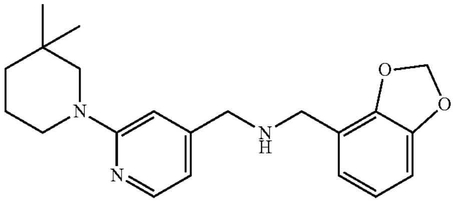 [SMILES: CC1(C)CCCN(c2cc(CNCc3cccc4c3OCO4)ccn2)C1] | Compound 17 |
| 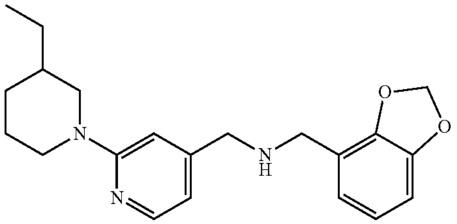 [SMILES: CCC1CCCN(c2cc(CNCc3cccc4c3OCO4)ccn2)C1] | Compound 18 |
| 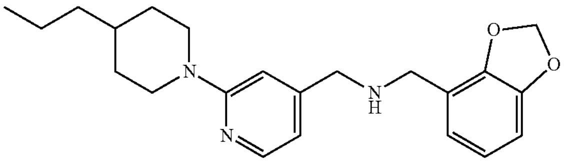 [SMILES: CCCC1CCN(c2cc(CNCc3cccc4c3OCO4)ccn2)CC1] | Compound 18 a |
| 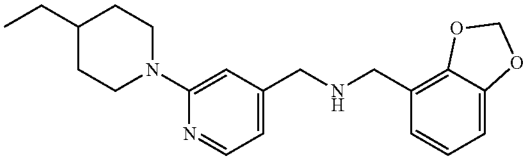 [SMILES: CCC1CCN(c2cc(CNCc3cccc4c3OCO4)ccn2)CC1] | Compound 19 |
| 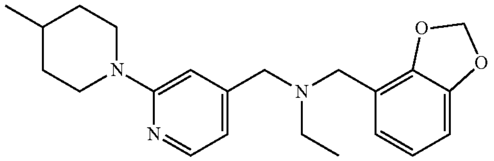 [SMILES: CCN(Cc1ccnc(N2CCC(C)CC2)c1)Cc1cccc2c1OCO2] | Compound 19 a |
| 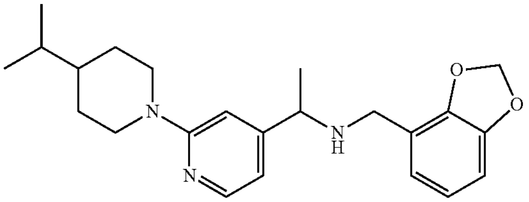 [SMILES: CC(NCc1cccc2c1OCO2)c1ccnc(N2CCC(C(C)C)CC2)c1] | Compound 20 |

-continued
| Structure | Compound |
| --- | --- |
| 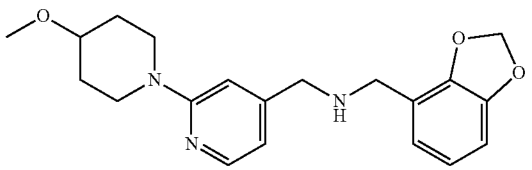 [SMILES: COC1CCN(c2cc(CNCc3cccc4c3OCO4)ccn2)CC1] | Compound 21 |
| 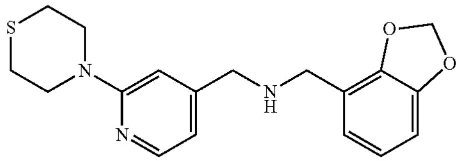 [SMILES: c1cc(CNCc2ccnc(N3CCSCC3)c2)c2c(c1)OCO2] | Compound 22 |
| 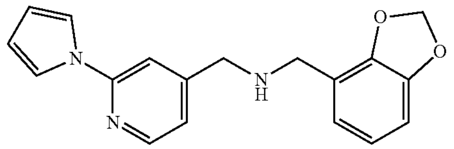 [SMILES: c1cc(CNCc2ccnc(-n3cccc3)c2)c2c(c1)OCO2] | Compound 22 a |
| 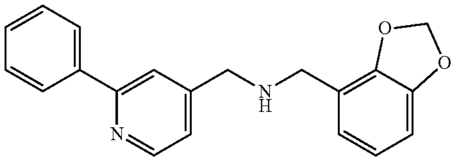 | Compound 22 b |
| 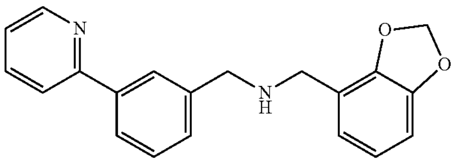 | Compound 22 c |
| 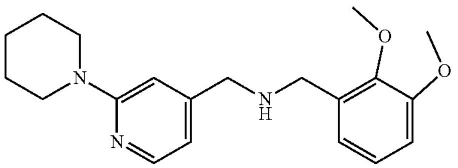 [SMILES: COc1cccc(CNCc2ccnc(N3CCCCC3)c2)c1OC] | Compound 23 |
| 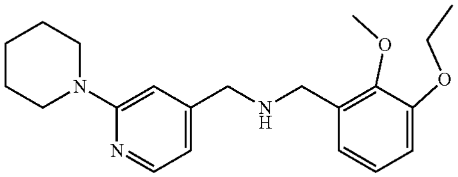 [SMILES: CCOc1cccc(CNCc2ccnc(N3CCCCC3)c2)c1OC] | Compound 24 |
| 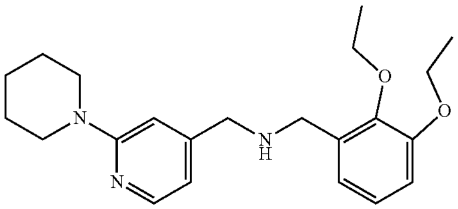 [SMILES: CCOc1cccc(CNCc2ccnc(N3CCCCC3)c2)c1OCC] | Compound 25 |

-continued
| Structure | Compound |
|---|---|
| 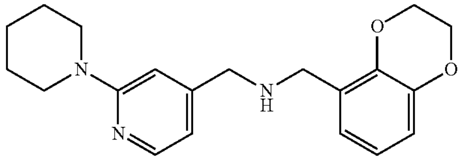 [SMILES: c1cc(CNCc2ccnc(N3CCCCC3)c2)c2c(c1)OCCO2] | Compound 26 |
| 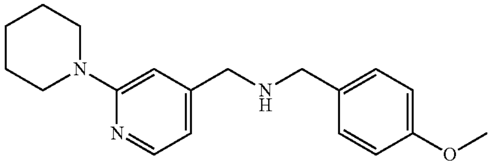 [SMILES: COc1ccc(CNCc2ccnc(N3CCCCC3)c2)cc1] | Compound 27 |
| 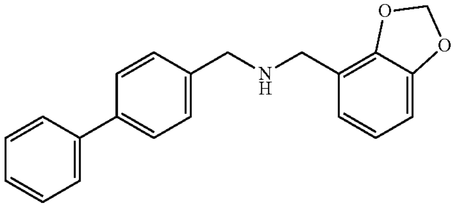 [SMILES: c1ccc(-c2ccc(CNCc3cccc4c3OCO4)cc2)cc1] | Compound 28 |
| 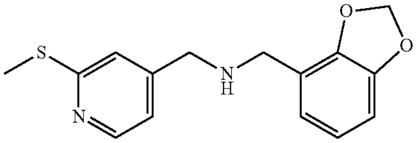 [SMILES: CSc1cc(CNCc2cccc3c2OCO3)ccn1] | Compound 29 |
| 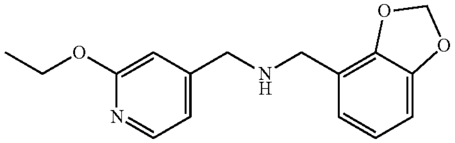 [SMILES: CCOc1cc(CNCc2cccc3c2OCO3)ccn1] | Compound 30 |
| 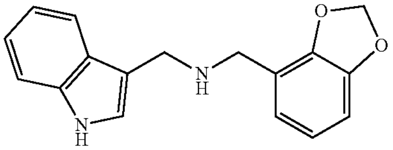 [SMILES: c1cc(CNCc2c[nH]c3ccccc23)c2c(c1)OCO2] | Compound 31 |
| 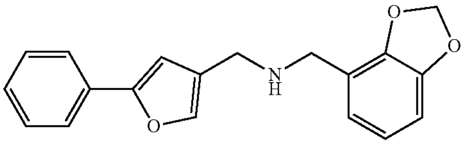 | Compound 31 a |
| 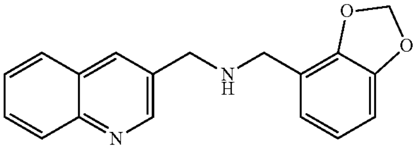 [SMILES: c1cc(CNCc2cnc3ccccc3c2)c2c(c1)OCO2] | Compound 32 |
| 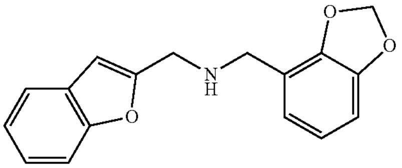 | Compound 32 a |

-continued
| Structure | Compound |
|---|---|
| 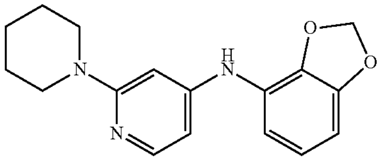 [SMILES: c1cc(Nc2ccnc(N3CCCCC3)c2)c2c(c1)OCO2] | Compound 33 |
| 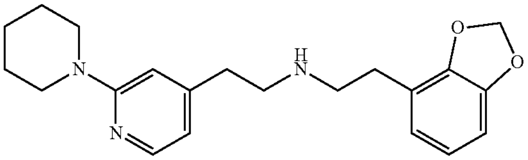 [SMILES: c1cc(CCNCCc2ccnc(N3CCCCC3)c2)c2c(c1)OCO2] | Compound 34 |
| 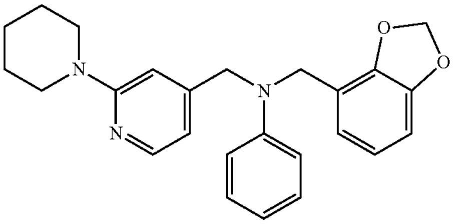 [SMILES: c1ccc(N(Cc2ccnc(N3CCCCC3)c2)Cc2cccc3c2OCO3)cc1] | Compound 35 |
| 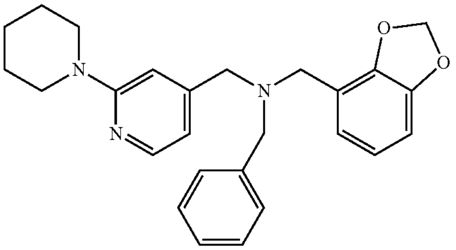 [SMILES: c1ccc(CN(Cc2ccnc(N3CCCCC3)c2)Cc2cccc3c2OCO3)cc1] | Compound 36 |
| 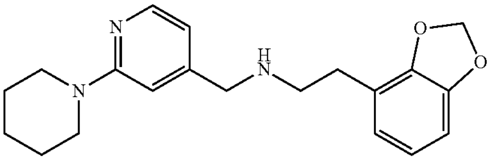 [SMILES: c1cc(CCNCc2ccnc(N3CCCCC3)c2)c2c(c1)OCO2] | Compound 37 |
| 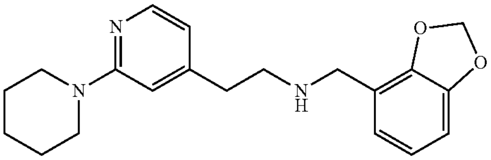 [SMILES: c1cc(CNCCc2ccnc(N3CCCCC3)c2)c2c(c1)OCO2] | Compound 38 |
| 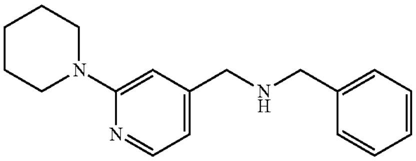 [SMILES: c1ccc(CNCc2ccnc(N3CCCCC3)c2)cc1] | Compound 39 |
| 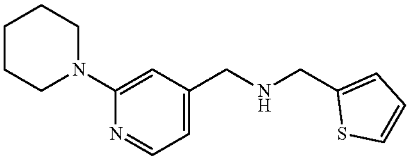 [SMILES: c1csc(CNCc2ccnc(N3CCCCC3)c2)c1] | Compound 40 |

-continued
| Structure | Compound |
| --- | --- |
| 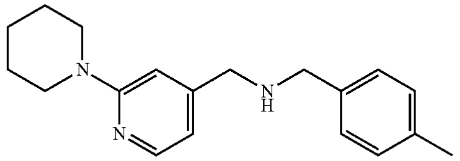 [SMILES: Cc1ccc(CNCc2ccnc(N3CCCCC3)c2)cc1] | Compound 41 |
| 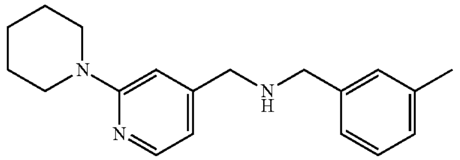 [SMILES: Cc1cccc(CNCc2ccnc(N3CCCCC3)c2)c1] | Compound 42 |
| 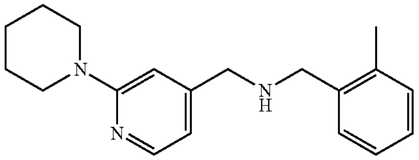 [SMILES: Cc1ccccc1CNCc1ccnc(N2CCCCC2)c1] | Compound 43 |
| 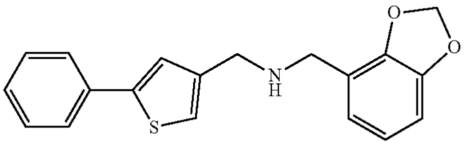 | Compound 43 a |
| 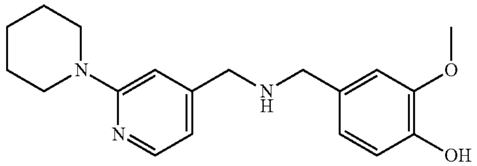 [SMILES: COc1cc(CNCc2ccnc(N3CCCCC3)c2)ccc1O] | Compound 44 |
| 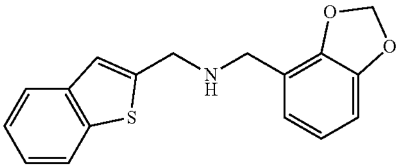 [SMILES: c1cc(CNCc2cc3ccccc3s2)c2c(c1)OCO2] | Compound 45 |
| 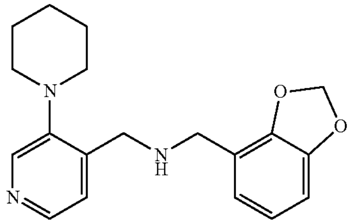 | Compound 46 |
| 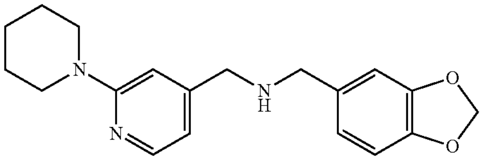 [SMILES: c1cc(CNCc2ccc3c(c2)OCO3)cc(N2CCCCC2)n1] | Compound 47 |

-continued
| Structure | Compound |
|---|---|
| 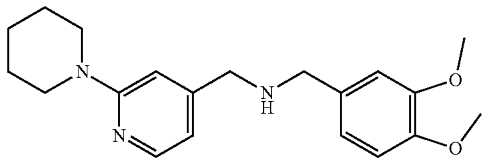 [SMILES: COc1ccc(CNCc2ccnc(N3CCCCC3)c2)cc1OC] | Compound 48 |
| 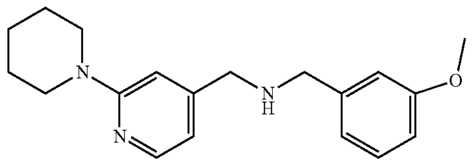 [SMILES: COc1cccc(CNCc2ccnc(N3CCCCC3)c2)c1] | Compound 49 |
| 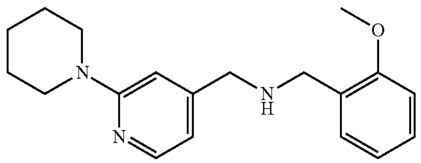 [SMILES: COc1ccccc1CNCc1ccnc(N2CCCCC2)c1] | Compound 50 |
| 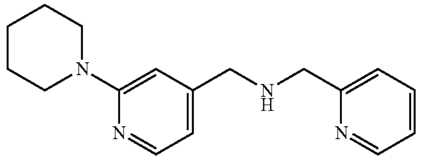 [SMILES: c1ccc(CNCc2ccnc(N3CCCCC3)c2)nc1] | Compound 51 |
| 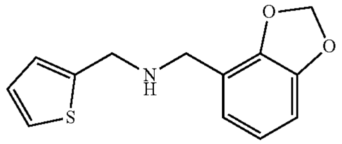 [SMILES: c1csc(CNCc2cccc3c2OCO3)c1] | Compound 52 |
| 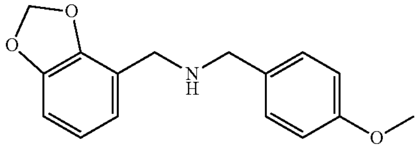 [SMILES: COc1ccc(CNCc2cccc3c2OCO3)cc1] | Compound 53 |
| 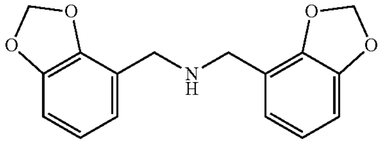 [SMILES: c1cc(CNCc2cccc3c2OCO3)c2c(c1)OCO2] | Compound 54 |
| 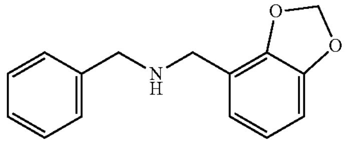 [SMILES: c1ccc(CNCc2cccc3c2OCO3)cc1] | Compound 55 |
| 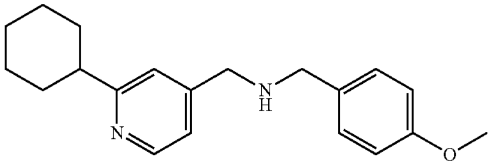 | Compound 56 |

-continued
| Structure | Compound |
| --- | --- |
| 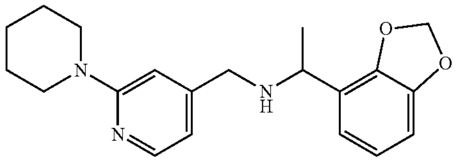 | Compound 57 |
| 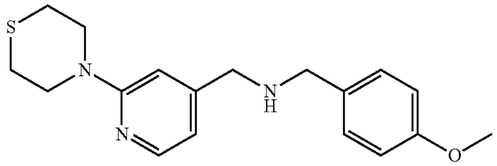 [SMILES: COc1ccc(CNCc2ccnc(N3CCSCC3)c2)cc1] | Compound 58 |
| 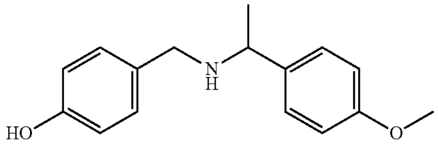 [SMILES: COc1ccc(C(C)NCc2ccc(O)cc2)cc1] | Compound 60 |
| 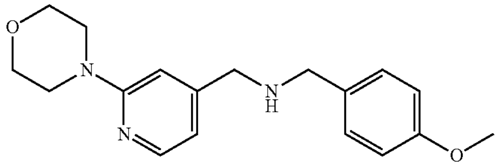 [SMILES: COc1ccc(CNCc2ccnc(N3CCOCC3)c2)cc1] | Compound 61 |
| 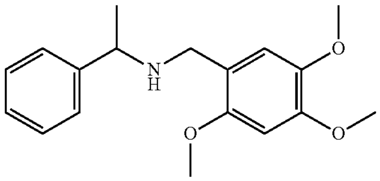 [SMILES: COc1cc(OC)c(OC)cc1CNC(C)c1ccccc1] | Compound 62 |
| 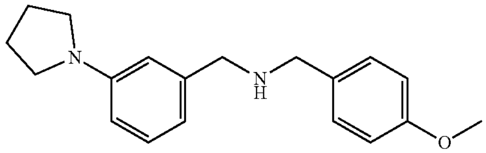 [SMILES: COc1ccc(CNCc2cccc(N3CCCC3)c2)cc1] | Compound 64 |
| 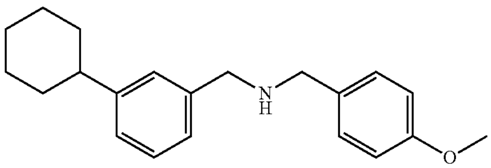 | Compound 65 |
| 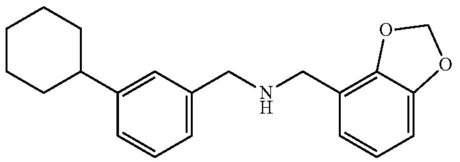 | Compound 66 |

-continued
| Structure | Compound |
|---|---|
| 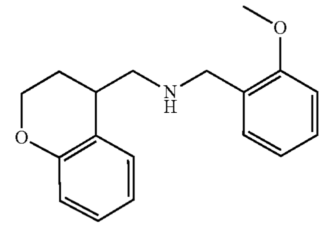 [SMILES: COc1ccccc1CNCC1CCOc2ccccc21] | Compound 67 |
| 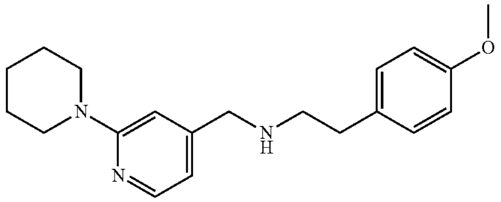 [SMILES: COc1ccc(CCNCc2ccnc(N3CCCCC3)c2)cc1] | Compound 70 |
| 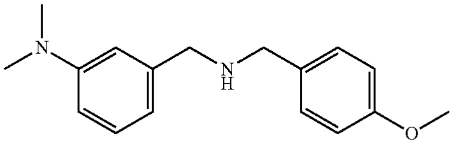 | Compound 71 |
| 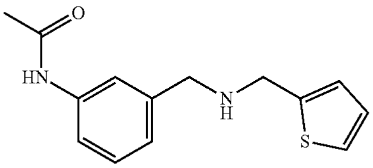 [SMILES: CC(=O)Nc1cccc(CNCc2cccs2)c1] | Compound 72 |
| 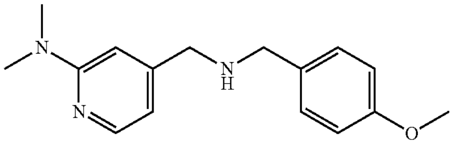 | Compound 75 |
| 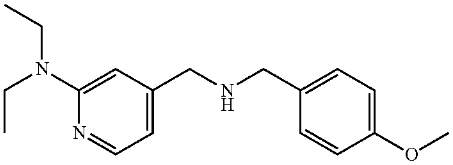 [SMILES: CCN(CC)c1cc(CNCc2ccc(OC)cc2)ccn1] | Compound 76 |
| 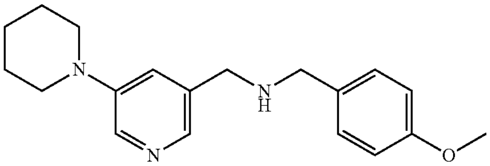 | Compound 77 |
| 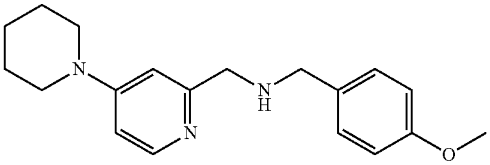 | Compound 79 |

-continued
| Structure | Compound |
| --- | --- |
| 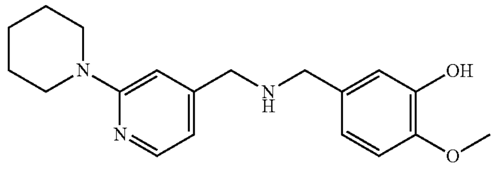 [SMILES: COc1ccc(CNCc2ccnc(N3CCCCC3)c2)cc1O] | Compound 80 |
| 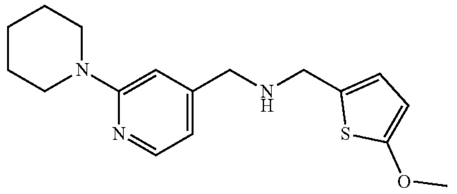 [SMILES: COc1ccc(CNCc2ccnc(N3CCCCC3)c2)s1] | Compound 81 |
| 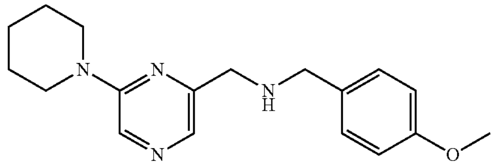 | Compound 82 |
| 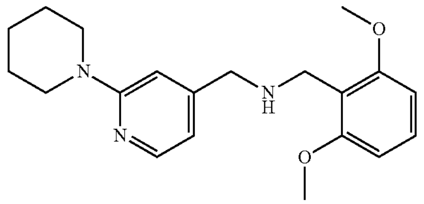 [SMILES: COc1cccc(OC)c1CNCc1ccnc(N2CCCCC2)c1] | Compound 83 |
| 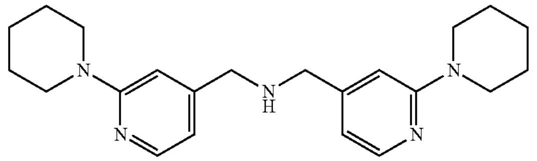 [SMILES: c1cc(CNCc2ccnc(N3CCCCC3)c2)cc(N2CCCCC2)n1] | Compound 84 |
| 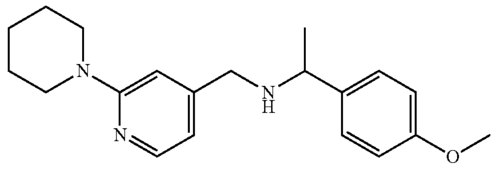 | Compound 85 |
| 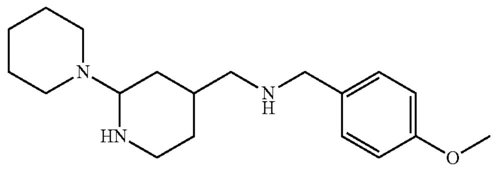 [SMILES: COc1ccc(CNCC2CCNC(N3CCCCC3)C2)cc1] | Compound 86 |
| 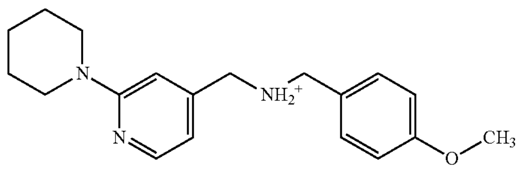 | Compound 87 |

-continued

| Structure | Compound |
|---|---|
| 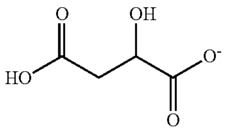 | |
| 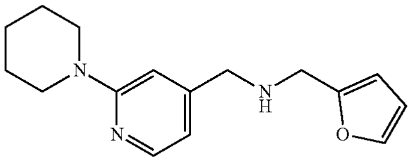 | Compound 88 |
| 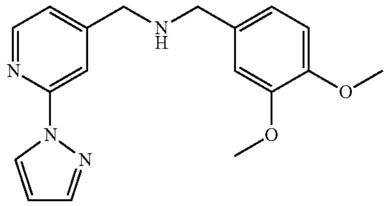 [SMILES: COc1ccc(CNCc2ccnc(-n3cccn3)c2)cc1OC] | Compound 89 |
| 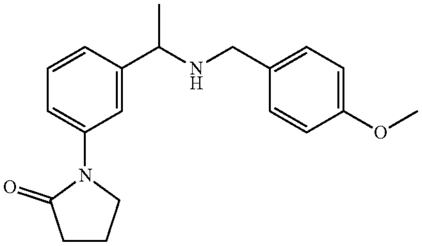 [SMILES: COc1ccc(CNC(C)c2cccc(N3CCCC3=O)c2)cc1] | Compound 90 |

and salts thereof, where the coolants may be present in stereoisomerically pure form or as mixtures of different stereoisomers.

7. The physiological cooling agent of claim 1, wherein the salt of the cooling agent is selected from the group consisting of (1) acid addition salts formed with inorganic acids or formed with organic acids; or (2) salts formed when an acidic proton present in the parent compound is replaced by a metal ion, or coordinated with an organic base.

8. A physiological cooling agent mixture comprising:

(a) one, two, three or more cooling agent(s) according to claim 1; and optionally (b) at least one further physiological cooling agent; and/or optionally (c) at least one solvent.

9. The physiological cooling agent mixture of claim 8, wherein the physiological cooling agent of component (b) is selected from the group consisting of: menthol, menthol methyl ether (FEMA GRAS 4054), monomenthyl glutamate (FEMA GRAS 4006), menthoxy-1,2-propanediol (FEMA GRAS 3784), dimenthyl glutarate (FEMA GRAS 4604), hydroxymethylcyclohexylethanone (FEMA GRAS 4742), 2-(4-ethylphenoxy)-N-(1H-pyrazol-3-yl)-N-(thiophen-2-ylmethyl) acetamide (FEMA GRAS 4880), WS-23 (2-isopropyl-N,2,3-trimethylbutyramide, FEMA GRAS 3804), N-(4-(cyanomethyl)phenyl)-2-isopropyl-5,5-dimethylcyclohexane carboxamide (FEMA GRAS 4882), N-(3-hydroxy-4-methoxyphenyl)-2-isopropyl-5,5-dimethylcyclohexane carboxamide (FEMA GRAS 4881), N-(2-hydroxy-2-phenylethyl)-2-isopropyl-5,5-dimethylcyclohexane-1-carboxamide (FEMA GRAS 4896), 3,4-methylenedioxy cinnamic acid, (E)-3-benzo[1,3]dioxol-5-yl-N,N-diphenyl-2-propenamide (FEMA GRAS 4788), menthol propylene glycol carbonate (FEMA GRAS 3806), menthyl N-ethyloxamate, monomethyl succinate (FEMA GRAS 3810), WS-3 (N-ethyl-p-menthane-3-carboxamide, FEMA GRAS 3455), menthol ethylene glycol carbonate (FEMA GRAS 3805), WS-5 (ethyl 3-(p-menthane-3-carboxamido)acetate, FEMA GRAS 4309), WS-12 (1R,2S,5R)-N-(4-methoxyphenyl)-p-menthane carboxamide (FEMA GRAS 4681), WS-27 (N-ethyl-2,2-diisopropylbutanamide, FEMA GRAS 4557), N-cyclopropyl-5-methyl-2-isopropylcyclohexanecarboxamide (FEMA GRAS 4693), WS-116 (N-(1,1-dimethyl-2-hydroxyethyl)-2,2-diethylbutanamide, FEMA GRAS 4603), menthoxyethanol (FEMA GRAS 4154), N-(4-cyanomethylphenyl)-p-menthanecarboxamide (FEMA GRAS 4496), N-(2-(pyridin-2-yl)ethyl)-3-p-menthanecarboxamide (FEMA GRAS 4549), N-(2-hydroxyethyl)-2-isopropy-1-2,3-dimethylbutanamide (FEMA GRAS 4602), (2S,5R)-N-[4-(2-amino-2-oxoethyl)phenyl]-p-menthanecarboxamide (FEMA GRAS 4684), N-cyclopropyl-5-methyl-2-isopropylcyclohexanecarboxamide (FEMA GRAS 4693), 2-[(2-p-menthoxy)ethoxy]ethanol (FEMA GRAS 4718), (2,6-diethyl-5-isopropyl-2-methyltetrahydropyran (FEMA GRAS 4680), trans-4-tert-butylcyclohexanol (FEMA GRAS 4724), 2-(p-tolyloxy)-N-(1H-pyrazol-5-yl)-N-((thiophen-2-yl)methyl) acetamide (FEMA GRAS 4809), menthone glycerol ketal (FEMA GRAS 3807 and 3808), (−)-menthoxypropane-1,2-diol, 3-(1-menthoxy)-2-methylpropane-1,2-diol (FEMA GRAS 3849), isopulegol, (+)-cis and (−)-trans-p-menthane-3,8-diol (62:38, FEMA GRAS 4053), 2,3-dihydroxy-p-menthane, 3,3,5-trimethylcyclohexanone glycerol ketal, menthyl pyrrolidone carboxylate, (1R,3R,4S)-3-menthyl-3,6-dioxaheptanoate, (1R,2S,5R)-3-menthyl methoxyacetate, (1R,2S,5R)-3-menthyl-3,6,9-trioxadecanoate, (1R,2S,5R)-3-menthyl-3,6,9-trioxadecanoate, (1R,2S,5R)-3-menthyl-(2-hydroxyethoxy)acetate, (1R,2S,5R)-menthyl-11-hydroxy-3,6,9-trioxaundecanoate, cubebol (FEMA GRAS 4497), 2-isopropyl-5-methylcyclohexyl-4-(dimethylamino)-4-oxobutanoate (FEMA GRAS 4230), menthyl lactate (FEMA GRAS 3748), 6-isopropyl-3,9-dimethyl-1,4-dioxaspiro[4.5]decan-2-one (FEMA GRAS 4285), N-benzo[1,3]dioxol-5-yl-3-p-menthane carboxamide, N-(1-isopropyl-1,2-dimethylpropyl)-1,3-benzodioxole-5-carboxamide, N-(R)-2-oxotetrahydrofuran-3-yl-(1R,2S,5R)-p-menthane-3-carboxamide, mixture of 2,2,5,6,6-pentamethyl-2,3,6,6a-tetrahydropentalen-3a (1H)-ol and 5-(2-hydroxy-2-methylpropyl)-3,4,4-trimethylcyclopent-2-en-1-one; (2S,5R)-2-isopropyl-5-methyl-N-(2-(pyridin-4-yl)ethyl) cyclohexanecarboxamide; (1S,2S,5R)-N-(4-(cyanomethyl)phenyl)-2-isopropyl-5-methylcyclohexanecarboxamide, 1,7-isopropyl-4,5-methyl-bicyclo[2.2.2]oct-5-ene derivatives, 4-methoxy-N-phenyl-N-[2-(pyridin-2-yl)ethyl]benzamide, 4-methoxy-N-phenyl-N-[2-(pyridin-2-yl)ethyl]benzenesulfonamide, 4-chloro-N-phenyl-N-[2-(pyridin-2-yl)ethyl]benzenesulfonamide, 4-cyano-N-phenyl-N-[2-(pyridin-2-yl)ethyl]benzenesulfonamide, 4-((benzhydrylamino)methyl)-2-methoxyphenol, 4-((bis(4-methoxyphenyl)methylamino) methyl)-2-methoxyphenol, 4-((1,2-diphenylethylamino)methyl)-2-methoxyphenol, 4-((benzhydryloxy)methyl)-2-methoxyphenol, 4-((9H-fluoren-9-ylamino)methyl)-2-methoxyphenol, 4-((benzhydrylamino)methyl)-2-ethoxyphenol, 1-(4-methoxyphenyl)-2-(1-methyl-1H-benzo[d]imidazol-2-yl) vinyl-4-methoxybenzoate, 2-(1-isopropyl-6-methyl-1H-benzo[d]imidazol-2-yl)-1-(4-methoxyphenyl) vinyl-4-methoxybenzoate, (Z)-2-(1-isopropyl-5-methyl-1H-benzo[d]imidazol-2-yl)-1-(4-methoxyphenyl) vinyl-4-methoxybenzoate, 3-alkyl-p-methan-3-ol derivatives, derivatives of fenchyl, D-bornyl, L-bornyl, exo-norbornyl, 2-methylisobornyl, 2-ethylfenchyl, 2-methylbornyl, cis-pinan-2-yl, verbanyl and isobornyl, menthyloxamate derivatives, menthyl 3-oxocarboxylic acid esters, N-alpha-(menthancarbonyl) amino acid amides, p-menthane carboxamide and WS-23 analogues, (−)-(1R,2R,4S)-dihydroumbellulol, p-menthane alkyloxyamide, cyclohexane derivatives, butanone derivatives, mixture of 3-menthoxy-1-propanol and 1-menthoxy-2-propanol, 1-[2-ydroxyphenyl]-4-[2-nitrophenyl]-1,2,3,6-tetrahydropyrimidin-2-one, 4-methyl-3-(1-pyrrolidinyl)-2-[5H]-furanone, and the components according to the following table:

| Structure | Name |
|---|---|
| 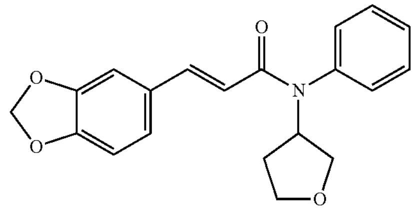 [SMILES: O=C(/C=C/c1ccc2c(c1)OCO2)N(c1ccccc1)C1CCOC1] | (E)-3-(1,3-benzodioxol-5-yl)-N-phenyl-N-tetrahydrofuran-3-yl-prop-2-enamide |
| 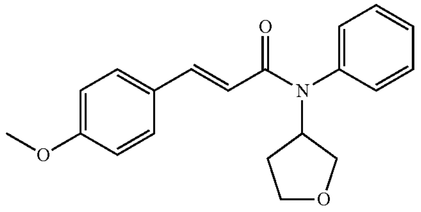 [SMILES: COc1ccc(/C=C/C(=O)N(c2ccccc2)C2CCOC2)cc1] | (E)-3-(4-methoxyphenyl)-N-phenyl-N-tetrahydrofuran-3-yl-prop-2-enamide |
| 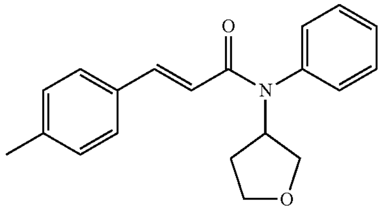 [SMILES: Cc1ccc(/C=C/C(=O)N(c2ccccc2)C2CCOC2)cc1] | (E)-N-phenyl-3-(p-tolyl)-N-tetrahydrofuran-3-yl-prop-2-enamide |
| 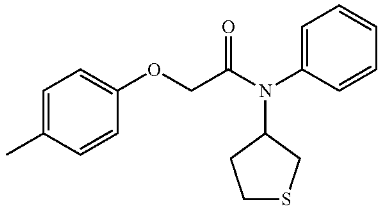 [SMILES: Cc1ccc(OCC(=O)N(c2ccccc2)C2CCSC2)cc1] | 2-(4-methylphenoxy)-N-phenyl-N-tetrahydrothiophen-3-yl-acetamide |

-continued

| Structure | Name |
|---|---|
| 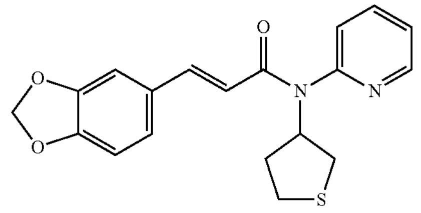 [SMILES: O=C(/C=C/c1ccc2c(c1)OCO2)N(c1ccccn1)C1CCSC1] | (E)-3-(1,3-benzodioxol-5-yl)-N-(2-pyridyl)-N-tetrahydrothiophen-3-yl-prop-2-enamide |
| 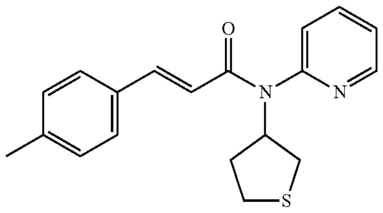 [SMILES: Cc1ccc(/C=C/C(=O)N(c2ccccn2)C2CCSC2)cc1] | (E)-3-(p-tolyl)-N-(2-pyridyl)-N-tetrahydrothiophen-3-yl-prop-2-enamide |
| 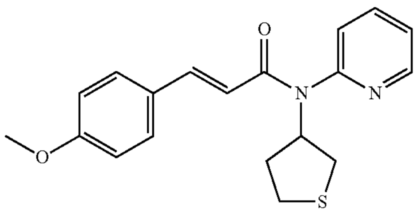 [SMILES: COc1ccc(/C=C/C(=O)N(c2ccccn2)C2CCSC2)cc1] | (E)-3-(4-methoxyphenyl)-N-(2-pyridyl)-N-tetrahydrothiophen-3-yl-prop-2-enamide |
| 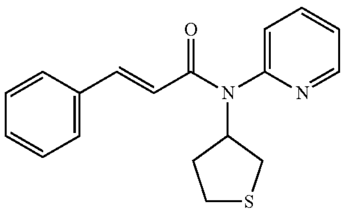 [SMILES: O=C(/C=C/c1ccccc1)N(c1ccccn1)C1CCSC1] | (E)-3-phenyl-N-(2-pyridyl)-N-tetrahydrothiophen-3-yl-prop-2-enamide |
| 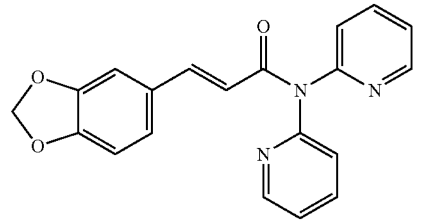 [SMILES: O=C(/C=C/c1ccc2c(c1)OCO2)N(c1ccccn1)c1ccccn1] | (E)-3-(1,3-benzodioxol-5-yl)-N,N-bis(2-pyridyl)prop-2-enamide |
| 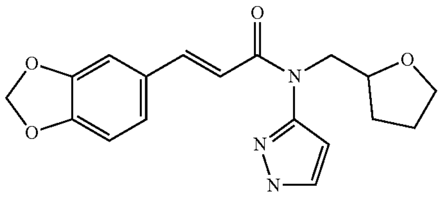 | (E)-3-(1,3-benzodioxol-5-yl)-N-(1H-pyrazol-3-yl)-N-(tetrahydrofuran-2-ylmethyl)prop-2-enamide |
| 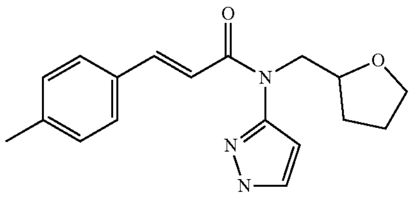 | (E)-3-(p-tolyl)-N-(1H-pyrazol-3-yl)-N-(tetrahydrofuran-2-ylmethyl)prop-2-enamide |

-continued

| Structure | Name |
| --- | --- |
| 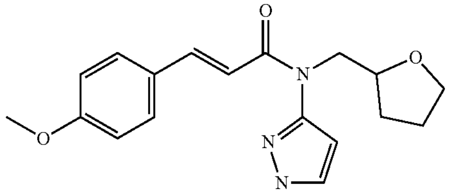 | (E)-3-(4-methoxyphenyl)-N-(1H-pyrazol-3-yl)-N-(tetrahydrofuran-2-ylmethyl)prop-2-enamide |
| 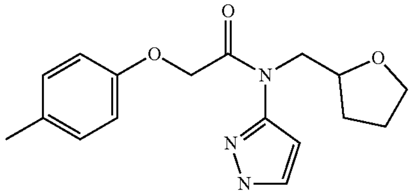 [SMILES: Cc1ccc(OCC(=O)N(CC2CCCO2)c2cc[nH]n2)cc1] | 2-(4-methylphenoxy)-N-(1H-pyrazol-3-yl)-N-(tetrahydrofuran-2-ylmethyl)acetamide |
| 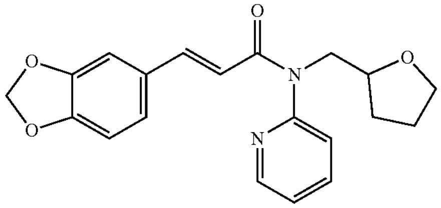 [SMILES: O=C(/C=C/c1ccc2c(c1)OCO2)N(CC1CCCO1)c1ccccn1] | (E)-3-(1,3-benzodioxol-5-yl)-N-(2-pyridyl)-N-(tetrahydrofuran-2-ylmethyl)prop-2-enamide |
| 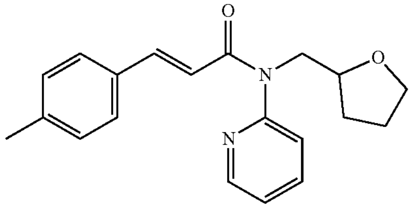 [SMILES: Cc1ccc(/C=C/C(=O)N(CC2CCCO2)c2ccccn2)cc1] | (E)-3-(p-tolyl)-N-(2-pyridyl)-N-(tetrahydrofuran-2-ylmethyl)prop-2-enamide |
| 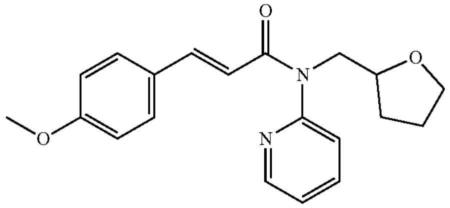 [SMILES: COc1ccc(/C=C/C(=O)N(CC2CCCO2)c2ccccn2)cc1] | (E)-3-(4-methoxyphenyl)-N-(2-pyridyl)-N-(tetrahydrofuran-2-ylmethyl)prop-2-enamide |
| 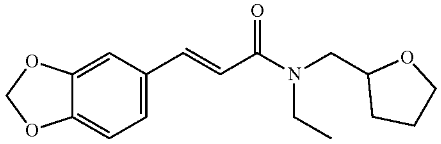 [SMILES: CCN(CC1CCCO1)C(=O)/C=C/c1ccc2c(c1)OCO2] | (E)-3-(1,3-benzodioxol-5-yl)-N-ethyl-N-(tetrahydrofuran-2-ylmethyl)prop-2-enamide |
| 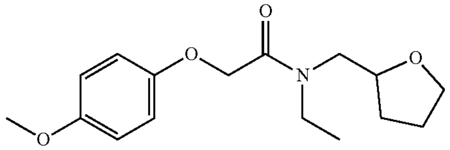 [SMILES: CCN(CC1CCCO1)C(=O)COc1ccc(OC)cc1] | N-ethyl-2-(4-methoxyphenoxy)-N-(tetrahydrofuran-2-ylmethyl)acetamide |
| 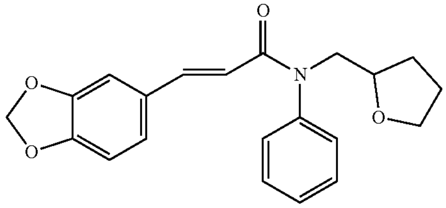 [SMILES: O=C(/C=C/c1ccc2c(c1)OCO2)N(CC1CCCO1)c1ccccc1] | (E)-3-(1,3-benzodioxol-5-yl)-N-phenyl-N-(tetrahydrofuran-2-ylmethyl)prop-2-enamide |

-continued

| Structure | Name |
|---|---|
| 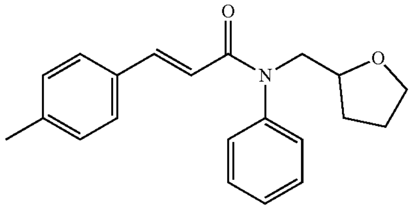 [SMILES: Cc1ccc(/C=C/C(=O)N(CC2CCCO2)c2ccccc2)cc1] | (E)-N-phenyl-3-(p-tolyl)-N-(tetrahydrofuran-2-ylmethyl)prop-2-enamide |
| 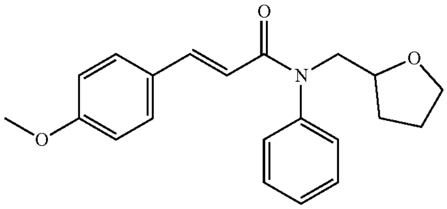 [SMILES: COc1ccc(/C=C/C(=O)N(CC2CCCO2)c2ccccc2)cc1] | (E)-3-(4-methoxyphenyl)-N-phenyl-N-(tetrahydrofuran-2-ylmethyl)prop-2-enamide |
| 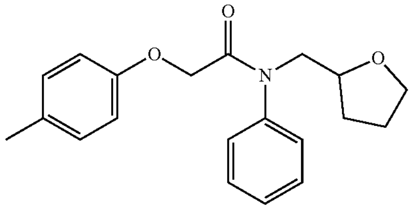 [SMILES: Cc1ccc(OCC(=O)N(CC2CCCO2)c2ccccc2)cc1] | 2-(4-methylphenoxy)-N-phenyl-N-(tetrahydrofuran-2-ylmethyl)acetamide |
| 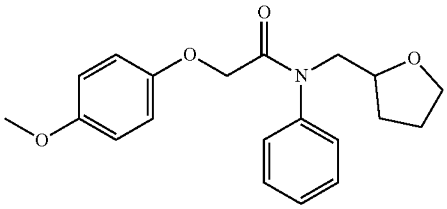 [SMILES: COc1ccc(OCC(=O)N(CC2CCCO2)c2ccccc2)cc1] | 2-(4-methoxyphenoxy)-N-phenyl-N-(tetrahydrofuran-2-ylmethyl)acetamide |
| 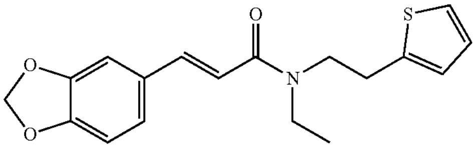 [SMILES: CCN(CCc1cccs1)C(=O)/C=C/c1ccc2c(c1)OCO2] | (E)-3-(1,3-benzodioxol-5-yl)-N-ethyl-N-[2-(2-thienyl)ethyl]prop-2-enamid |
| 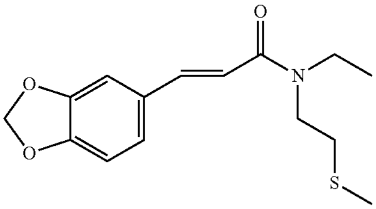 [SMILES: CCN(CCSC)C(=O)/C=C/c1ccc2c(c1)OCO2] | (E)-3-(1,3-benzodioxol-5-yl)-N-ethyl-N-(2-methylsulfanylethyl)prop-2-enamide |
| 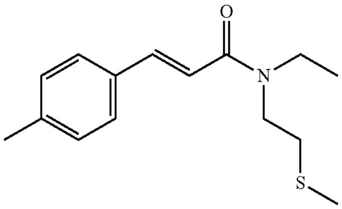 | (E)-N-ethyl-N-(2-methylsulfanylethyl)-3-(p-tolyl)prop-2-enamide |

-continued

| Structure | Name |
| --- | --- |
| 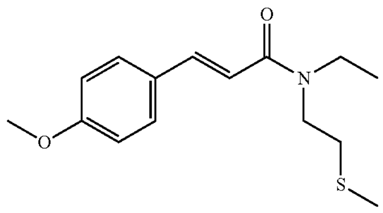 | (E)-N-ethyl-3-(4-methoxyphenyl)-N-(2-methylsulfanylethyl)prop-2-enamide |
| 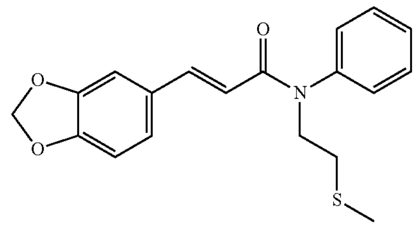 | (E)-3-(1,3-benzodioxol-5-yl)-N-(2-methylsulfanylethyl)-N-phenyl-prop-2-enamide |
| 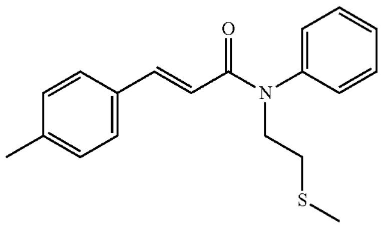 [SMILES: CSCCN(C(=O)/C=C/c1ccc(C)cc1)c1ccccc1] | (E)-N-(2-methylsulfanylethyl)-N-phenyl-3-(p-tolyl)prop-2-enamide |
| 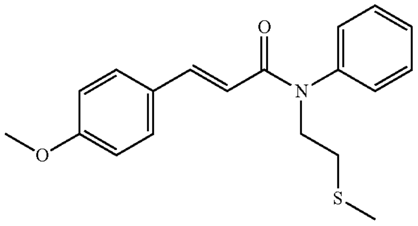 [SMILES: COc1ccc(/C=C/C(=O)N(CCSC)c2ccccc2)cc1] | (E)-3-(4-methoxyphenyl)-N-(2-methylsulfanylethyl)-N-phenyl-prop-2-enamide |
| 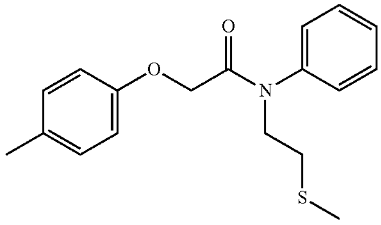 [SMILES: CSCCN(C(=O)COc1ccc(C)cc1)c1ccccc1] | 2-(4-methylphenoxy)-N-(2-methylsulfanylethyl)-N-phenyl-acetamide |
| 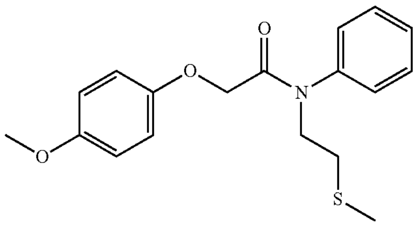 [SMILES: COc1ccc(OCC(=O)N(CCSC)c2ccccc2)cc1] | 2-(4-methoxyphenoxy)-N-(2-methylsulfanylethyl)-N-phenyl-acetamide |

-continued

| Structure | Name |
|---|---|
| 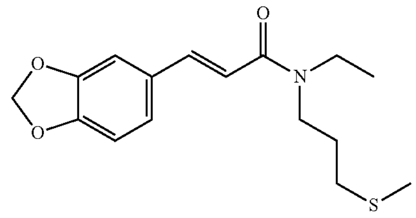 [SMILES: CCN(CCCSC)C(=O)/C=C/c1ccc2c(c1)OCO2] | (E)-3-(1,3-benzodioxol-5-yl)-N-ethyl-N-(3-methylsulfanylpropyl)prop-2-enamide |
| 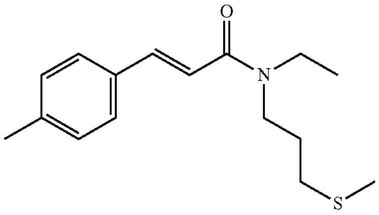 | (E)-N-ethyl-N-(3-methylsulfanylpropyl)-3-(p-tolyl)prop-2-enamide |
| 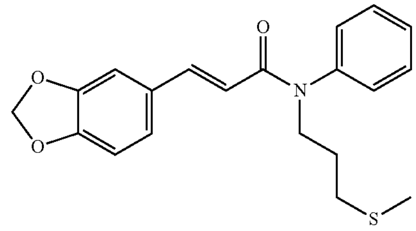 [SMILES: CSCCCN(C(=O)/C=C/c1ccc2c(c1)OCO2)c1ccccc1] | (E)-3-(1,3-benzodioxol-5-yl)-N-(3-methylsulfanylpropyl)-N-phenyl-prop-2-enamide |
| 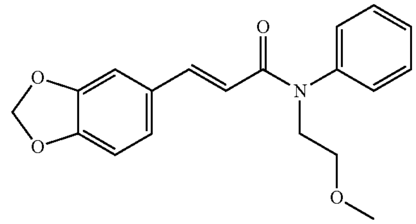 [SMILES: COCCN(C(=O)/C=C/c1ccc2c(c1)OCO2)c1ccccc1] | (E)-3-(1,3-benzodioxol-5-yl)-N-(2-methoxyethyl)-N-phenyl-prop-2-enamide |
| 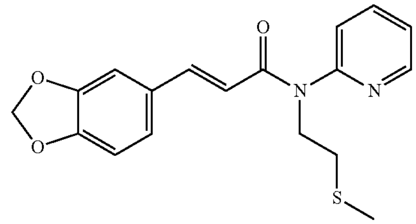 [SMILES: CSCCN(C(=O)/C=C/c1ccc2c(c1)OCO2)c1ccccn1] | (E)-3-(1,3-benzodioxol-5-yl)-N-(2-methylsulfanylethyl)-N-(2-pyridyl)prop-2-enamide |
| 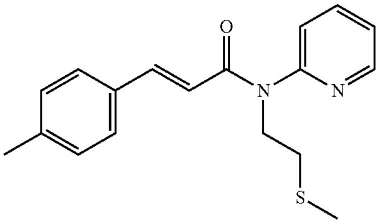 [SMILES: CSCCN(C(=O)/C=C/c1ccc(C)cc1)c1ccccn1] | (E)-N-(2-methylsulfanylethyl)-3-(p-tolyl)-N-(2-pyridyl)prop-2-enamide |

-continued

| Structure | Name |
| --- | --- |
| 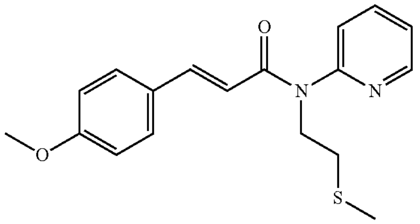 [SMILES: COc1ccc(/C=C/C(=O)N(CCSC)c2ccccn2)cc1] | (E)-3-(4-methoxyphenyl)-N-(2-methylsulfanylethyl)-N-(2-pyridyl)prop-2-enamide |
| 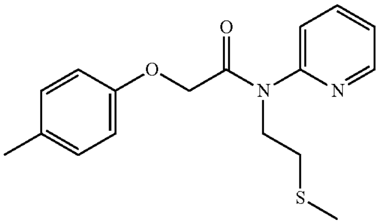 [SMILES: CSCCN(C(=O)COc1ccc(C)cc1)c1ccccn1] | 2-(4-Methylphenoxy)-N-(2-methylsulfanylethyl)-N-(2-pyridyl)acetamide |
| 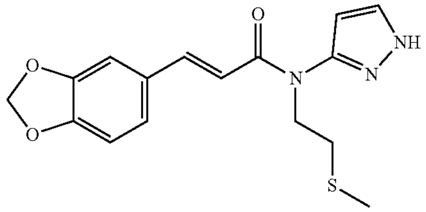 [SMILES: CSCCN(C(=O)/C=C/c1ccc2c(c1)OCO2)c1cc[nH]n1] | (E)-3-(1,3-benzodioxol-5-yl)-N-(2-methylsulfanylethyl)-N-(1H-pyrazol-3-yl)prop-2-enamide |
| 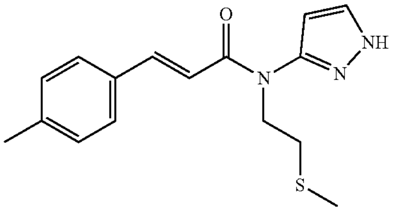 [SMILES: CSCCN(C(=O)/C=C/c1ccc(C)cc1)c1cc[nH]n1] | (E)-N-(2-methylsulfanylethyl)-3-(p-tolyl)-N-(1H-pyrazol-3-yl)prop-2-enamide |
| 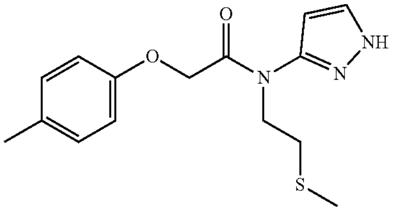 [SMILES: CSCCN(C(=O)COc1ccc(C)cc1)c1cc[nH]n1] | 2-(4-Methylphenoxy)-N-(2-methylsulfanylethyl)-N-(1H-pyrazol-3-yl)acetamide |
| 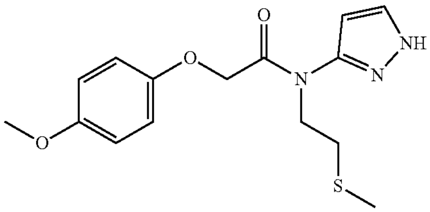 [SMILES: COc1ccc(OCC(=O)N(CCSC)c2cc[nH]n2)cc1] | 2-(4-Methoxyphenoxy)-N-(2-methylsulfanylethyl)-N-(1H-pyrazol-3-yl)acetamide |

and mixtures thereof.

10. The physiological cooling agent mixture of claim 8, wherein component (a) and component (b) are contained in a weight ratio of from about 0.1:99 to about 99:0.1.

11. The physiological cooling agent mixture of claim 8, wherein the solvent is selected from the group consisting of: benzyl alcohol, 2-phenylethanol, benzyl benzoate, diethyl succinate, triethyl citrate, triacetin, ethanol, peppermint oil, anethole, optamint, propylene glycol, phenoxyethanol, and mixtures thereof.

12. Aroma preparation comprising (d) one, two, three or more cooling agent(s) according to claim 1; and (e) at least one flavouring.

13. The aroma preparation according to claim 12, wherein the flavouring substance forming component (e) is selected from the group consisting of: acetophenone, allyl capronate, alpha ionone, beta ionone, anisaldehyde, anisyl acetate, anisyl formate, anethole, benzaldehyde, benzothiazole, benzyl acetate, benzyl alcohol, benzyl benzoate, beta ionone, butyl butyrate, butyl capronate, butylidene phthalide, carvone, camphene, caryophyllene, cineole, cinnamyl acetate, citral, citronellol, citronellal, citronellyl acetate, cyclohexyl acetate, cymene, damascone, decalactone, dihydrocoumarin, dimethyl anthranilate, dimethyl anthranilate, dodecalactone, ethoxyethyl acetate, ethyl butyric acid, ethyl butyrate, ethyl caprinate, ethyl capronate, ethyl crotonate, ethyl furaneol, ethyl guaiacol, ethyl isobutyrate, ethyl isovalerate, ethyl lactate, ethyl methyl butyrate, ethyl propionate, eucalyptol, eugenol, ethyl heptylate, 4-(p-hydroxyphenyl)-2-butanone, gamma-decalactone, geraniol, geranyl acetate, geranyl acetate, grapefruit aldehyde, methyl dihydrojasmonate, heliotropin, 2-heptanone, 3-heptanone, 4-heptanone, trans-2-heptenal, cis-4-heptenal, trans-2-hexenal, cis-3-hexenol, trans-2-hexenoic acid, trans-3-hexenoic acid, cis-2-hexenyl acetate, cis-3-hexenyl acetate, cis-3-hexenyl capronate, trans-2-hexenyl capronate, cis-3-hexenyl formate, cis-2-hexyl acetate, cis-3-hexyl acetate, trans-2-hexyl acetate, cis-3-hexyl formate, para-hydroxybenzylacetone, isoamyl alcohol, isoamyl isovalerate, isobutyl butyrate, isobutyraldehyde, isoeugenol methyl ether, isopropyl methyl thiazole, lauric acid, leavulinic acid, linalool, linalool oxide, linalyl acetate, menthol, menthofuran, methyl anthranilate, methyl butanol, methyl butyric acid, 2-methyl butyl acetate, methyl capronate, methyl cinnamate, 5-methyl furfural, 3,2,2-methylcyclopentenolone, 6,5,2-methyl heptenone, methyl dihydro jasmonate, methyl jasmonate, 2-methyl methyl butyrate, 2-methyl 2-pentenoic acid, methyl thiobutyrate, 3,1-methyl thiohexanol, 3-methyl thiohexyl acetate, nerol, nerylacetate, trans,trans-2,4-nonadienal, 2,4-nonadienol, 2,6-nonadienol, 2,4-nonadienol, nootkatone, delta octalactone, gamma octalactone, 2-octanol, 3-octanol, 1,3-octenol, 1-octyl acetate, 3-octyl acetate, palmitic acid, paraldehyde, phellandrene, pentanedione, phenyl ethyl acetate, phenyl ethyl alcohol, phenyl ethyl alcohol, phenyl ethyl isovalerate, piperonal, propionaldehyde, propyl butyrate, pulegone, pulegol, sinensal, sulfurol, terpinene, terpineol, terpinolene, 8,3-thiomenthanone, 4,4,2-thiomethylpentanone, thymol, delta-undecalactone, gamma-undecalactone, valencene, valeric acid, vanillin, acetoin, ethylvanillin, ethylvanillin isobutyrate (=3-ethoxy-4-isobutyryloxybenzaldehyde), 2,5-dimethyl-4-hydroxy-3 (2H)-furanone and its derivatives, homofuronol (=2-ethyl-5-methyl-4-hydroxy-3 (2H)-furanone and 5-ethyl-2-methyl-4-hydroxy-3 (2H)-furanone), maltol and maltol-derivatives, coumarin and coumarin derivatives, gamma-lactones, delta-lactones, methyl sorbate, divanilline, 4-hydroxy-2 (or 5)-ethyl-5 (or 2)-methyl-3 (2H)-furanone, 2-hydroxy-3-methyl-2-cyclopentenone, 3-hydroxy-4,5-dimethyl-2 (5H)-furanone, acetic acid isoamyl ester, butyric acid ethyl ester, butyric acid n-butyl ester, butyric acid isoamyl ester, 3-methyl butyric acid ethyl ester, n-hexanoic acid ethyl ester, n-hexanoic acid allyl ester, n-hexanoic acid n-butyl ester, n-octanoic acid ethyl ester, ethyl 3-methyl-3-phenylglycidate, ethyl 2-trans-4-cis-decadienoate, 4-(p-hydroxyphenyl)-2-butanone, 1,1-dimethoxy-2,2,5-trimethyl-4-hexane, 2,6-dimethyl-5-hepten-1-al and phenylacetaldehyde, 2-methyl-3-(methylthio) furan, 2-methyl-3-furanthiol, bis(2-methyl-3-furyl)disulphide, furfuryl mercaptan, methional, 2-acetyl-2-thiazoline, 3-mercapto-2-pentanone, 2,5-dimethyl-3-furanthiol, 2,4,5-trimethylthiazole, 2-acetylthiazole, 2,4-dimethyl-5-ethylthiazole, 2-acetyl-1-pyrroline, 2-methyl-3-ethylpyrazine, 2-ethyl-3,5-dimethylpyrazine, 2-ethyl-3,6-dimethylpyrazine, 2,3-diethyl-5-methylpyrazine, 3-isopropyl-2-methoxypyrazine, 3-isobutyl-2-methoxypyrazine, 2-acetylpyrazine, 2-pentylpyridine, (E,E)-2,4-decadienal, (E,E)-2,4-nonadienal, (E)-2-octenal, (E)-2-nonenal, 2-undecenal, 12-methyltridecanal, 1-penten-3-one, 4-hydroxy-2,5-dimethyl-3 (2H)-furanone, guaiacol, 3-hydroxy-4,5-dimethyl-2 (5H)-furanone, 3-hydroxy-4-methyl-5-ethyl-2 (5H)-furanone, cinnamaldehyde, cinnamalcohol, methyl salicylate, and isopulegol as well as stereoisomers, enantiomers, positional isomers, diastereomers, cis/trans isomers or epimers of these substances; and/or wherein the flavouring agent forming component (e) is selected from the group consisting of: erythritol, threitol, arabitol, ribotol, xylitol, sorbitol, mannitol, dulcitol, lactitol, miraculin, monellin, thaumatin, curculin, brazzein, magap, sodium cyclamate, Acesulfame K, neohesperidin dihydrochalcone, saccharin sodium salt, Aspartame, Superaspartame, Neotame, Alitame, sucralose, steviosides, rebaudiosides, Lugduname, Carrelame, Sucrononate, Sucrooctate, Monatin, Phenylodulcin, glycine, D-leucine, D-threonine, D-asparagine, D-phenylalanine, D-tryptophane, L-proline, hernandulcin, dihydrochalcone glycosides, glycyrrhizin, glycerrhetinic acid, their derivatives and salts, extracts of liquorice (*Glycyrrhiza glabra* ssp.), *Lippia dulcis* extracts, *Momordica* ssp. extracts, mogrosides, *Hydrangea dulcis* and steviosides and mixtures thereof.

14. The aroma preparation according to claim 12, wherein component (d) and component (e) are contained in a weight ratio of from about 1:99 to about 99:1.

15. The physiological cooling agent according to claim 1, wherein the physiological cooling agent is in an encapsulated form.

16. A method for producing a physiological cooling effect on skin or mucous membrane in humans or animals, comprising contacting the skin or mucous membrane with the physiological cooling agent of claim 1, with a package containing the physiological cooling agent of claim 1, or with a textile containing the physiological cooling agent of claim 1.

17. A method for improving the taste properties of flavouring substances comprising formulating the flavouring substances with the physiological cooling agent of claim 1.

18. A foodstuff, food supplement, cosmetic or pharmaceutical preparation, animal feed, textile, packaging or tobacco product, comprising the physiological cooling agent according to claim 1, wherein the pharmaceutical preparation optionally further comprises active ingredients selected from the group consisting of: Aspirin, Minoxidil, Erythromycin, Fenistil, Betamethasone, Ibuprofen, Ketoprofen, Dicyclofenac, Metronidazole, Acyclovir, Imiquimod, Terbafin, Cyclopiroxolamine, Paracetamol, and other pharmaceutical non-steroidal anti-inflammatory drug (NSAID) agents and mixtures thereof.

19. A method for preventing or treating pain and inflammatory conditions of the skin and mucous membranes, for treating inflammatory conditions of the skin and mucous membranes and joints, for treating prostate or bladder carcinomas, or for treating bladder weakness in a patient in need thereof comprising administering the pharmaceutical preparation of claim 18 to the patient.

20. A method for modulating the cold menthol receptor TRPM8, for producing a physiological cooling effect on skin or mucous membrane, or for improving the flavour properties of flavouring substances comprising the following steps:

(i) providing at least one physiological cooling agent according to claim 1; and (ii) contacting the receptor TRPM8 with the physiological cooling agent of (i) to modulate the receptor TRPM8; or contacting human skin or mucosa with the physiological cooling agent of (i) to produce a physiological cooling effect on the skin or mucous membrane; or incorporating the physiological cooling agent of (i) and at least one flavouring agent, wherein the physiological cooling agent of (i) and the at least one flavouring agent have been mixed together, into an oral formulation to improve the flavour properties of flavouring substances.

* * * * *